US012781224B2

(12) United States Patent
Calamini et al.

(10) Patent No.: US 12,781,224 B2
(45) Date of Patent: Nov. 3, 2026

(54) MAPT RNA INTERFERENCE AGENTS

(71) Applicant: Eli Lilly and Company, Indianapolis, IN (US)

(72) Inventors: Barbara Calamini, Acton, MA (US); Sarah Katharina Fritschi, Frankfurt am Main (DE); Rebecca Ruth Miles, Pendleton, IN (US); Andrew Peter McCarthy, Arlington, MA (US); Douglas Raymond Perkins, New Palestine, IN (US); Keith Geoffrey Phillips, Newburyport, MA (US); Kaushambi Roy, North Chelmsford, MA (US); Isabel Cristina Gonzalez Valcarcel, Indianapolis, IN (US); Jibo Wang, Carmel, IN (US); Shih-Ying Wu, Needham, MA (US); Jeremy S. York, Noblesville, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 710 days.

(21) Appl. No.: 18/064,391

(22) Filed: Dec. 12, 2022

(65) Prior Publication Data

US 2023/0212576 A1 Jul. 6, 2023

Related U.S. Application Data

(60) Provisional application No. 63/288,846, filed on Dec. 13, 2021.

(51) Int. Cl.
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/351* (2013.01); *C12N 2320/32* (2013.01)

(58) Field of Classification Search
CPC .............. C12N 15/113; C12N 2310/14; A61K 31/7088; A61P 25/28
See application file for complete search history.

(56) References Cited

U.S. PATENT DOCUMENTS

| | | | |
|---|---|---|---|
| 2016/0145617 A1 | 5/2016 | Kordasiewicz et al. | |
| 2021/0363523 A1 | 11/2021 | Khvorova et al. | |

FOREIGN PATENT DOCUMENTS

| | | | |
|---|---|---|---|
| WO | 2004058940 A2 | 7/2004 | |
| WO | WO2016/151523 A1 | 9/2016 | |
| WO | 2017109679 A1 | 6/2017 | |
| WO | 2020007892 A1 | 1/2020 | |
| WO | WO202/188626 A1 | 9/2021 | |
| WO | WO2021/202511 A2 | 10/2021 | |
| WO | WO2023/064707 A1 | 4/2023 | |

OTHER PUBLICATIONS

Egli, Martin et al., “Critical Reviews and Perspectives, Chemistry, structure and function of approved oligonucleotide therapeutics.” Nucleic Acids Research, vol. 51, No. 6. Mar. 7, 2023, pp. 2529-2573.
Easton, et al, “Identification and characterization of a MAPT-targeting locked nucleic acid antisense oligonucleotide therapeutic for tauopathies”, Molecular Therapy, Nucleic Acids, vol. 29, Sep. 2022, p. 625-642.
Jadhav, et al, “A walk through tau therapeutic strategies”, Acta Neurophathologica Communications (2019) 7:22, p. 1-31.
Robbins, et al, “Synaptic tau: A pathological or physiological phenomenon?”, Acta Neuropathologica Communications (2021) 9:149, p. 1-30.
Leveille Etinne et al: “Tau and MAPT Genetics in Tauopathies and Synucleinopathies”, Parkinsonism and Related Disorders, vol. 90, Sep. 1, 2021 pp. 142-154.
Hu Bo, et al: “Therapeutic siRNA: State of the Art”. Signal Transduction and Targeted Therapy, vol. 5, No. 1, 101, Dec. 1, 2020, pp. 1-25.
Stoyka et al. 8(3) ENEURO.0458029.2021, 1-15 (2021).
Xu et al. “Taul Silencing by siRNA in the P301S Mouse Model of Tauopathy” Current Gene Therapy 14, 343-351 (2014).

*Primary Examiner* — J. E. Angell
(74) *Attorney, Agent, or Firm* — Jessica L. Roberts

(57) ABSTRACT

Provided herein are MAPT RNAi agents and compositions comprising a MAPT RNAi agent. Also provided herein are methods of using the MAPT RNAi agents or compositions comprising a MAPT RNAi agent for reducing MAPT expression and/or treating tauopathy in a subject.

33 Claims, No Drawings

Specification includes a Sequence Listing.

SEQUENCE LISTING

```
Sequence total quantity: 119
SEQ ID NO: 1             moltype = RNA  length = 21
FEATURE                  Location/Qualifiers
misc_feature             1..21
                         note = Description of Artificial Sequence: Synthetic
                          oligonucleotide
source                   1..21
                         mol_type = other RNA
                         organism = synthetic construct
SEQUENCE: 1
acaagctgac cttccgcgag a                                              21

SEQ ID NO: 2             moltype = RNA  length = 23
FEATURE                  Location/Qualifiers
misc_feature             1..23
                         note = Description of Artificial Sequence: Synthetic
                          oligonucleotide
source                   1..23
                         mol_type = other RNA
                         organism = synthetic construct
SEQUENCE: 2
tctcgcggaa ggtcagcttg tgg                                            23

SEQ ID NO: 3             moltype = RNA  length = 21
FEATURE                  Location/Qualifiers
misc_feature             1..21
                         note = Description of Artificial Sequence: Synthetic
                          oligonucleotide
source                   1..21
```

```
                       mol_type = other RNA
                       organism = synthetic construct
SEQUENCE: 3
agattgaaac ccacaagctg a                                       21

SEQ ID NO: 4           moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 4
tcagcttgtg ggtttcaatc ttt                                     23

SEQ ID NO: 5           moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 5
aataaaaaga ttgaaaccca a                                       21

SEQ ID NO: 6           moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 6
ttgggtttca atctttttat ttc                                     23

SEQ ID NO: 7           moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 7
ggaaataaaa agattgaaac a                                       21

SEQ ID NO: 8           moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 8
tgtttcaatc tttttatttc ctc                                     23

SEQ ID NO: 9           moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 9
ggcggaggaa ataaaaagat a                                       21

SEQ ID NO: 10          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
```

```
SEQUENCE: 10
tatcttttta tttcctccgc cag                                         23

SEQ ID NO: 11          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 11
gaagtaaaat ctgagaagct a                                           21

SEQ ID NO: 12          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 12
tagcttctca gattttactt cca                                         23

SEQ ID NO: 13          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 13
ggaagtaaaa tctgagaagc a                                           21

SEQ ID NO: 14          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 14
tgcttctcag attttacttc cac                                         23

SEQ ID NO: 15          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 15
gtggaagtaa aatctgagaa a                                           21

SEQ ID NO: 16          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 16
tttctcagat tttacttcca cct                                         23

SEQ ID NO: 17          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 17
ccaggtggaa gtaaaatctg a                                           21
```

-continued

```
SEQ ID NO: 18          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 18
tcagatttta cttccacctg gcc                                          23

SEQ ID NO: 19          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 19
caagtccaag atcggctcca a                                            21

SEQ ID NO: 20          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 20
ttggagccga tcttggactt gac                                          23

SEQ ID NO: 21          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 21
tctggtgaac ctccaaaatc a                                            21

SEQ ID NO: 22          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 22
tgattttgga ggttcaccag agc                                          23

SEQ ID NO: 23          moltype = RNA  length = 21
FEATURE                Location/Qualifiers
misc_feature           1..21
                       note = Description of Artificial Sequence: Synthetic
                        oligonucleotide
source                 1..21
                       mol_type = other RNA
                       organism = synthetic construct
SEQUENCE: 23
caggtggaag taaaatctga a                                            21

SEQ ID NO: 24          moltype = RNA  length = 23
FEATURE                Location/Qualifiers
misc_feature           1..23
                       note = Description of Artificial Sequence: Synthetic
                        oligonucleotide
source                 1..23
                       mol_type = other RNA
                       organism = synthetic construct
SEQUENCE: 24
ttcagatttt acttccacct ggc                                          23

SEQ ID NO: 25          moltype = RNA  length = 21
```

-continued

```
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 25
acaagctgac cttccgcgag a                                          21

SEQ ID NO: 26           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
misc_feature            7
                        note = 2'-OMe modified nucleotide
misc_feature            8
```

```
                     note = 2'-OMe modified nucleotide
misc_feature         9
                     note = 2'-OMe modified nucleotide
misc_feature         10
                     note = 2'-OMe modified nucleotide
misc_feature         11
                     note = 2'-OMe modified nucleotide
misc_feature         12
                     note = 2'-OMe modified nucleotide
misc_feature         13
                     note = 2'-OMe modified nucleotide
misc_feature         14
                     note = 2'-F modified nucleotide
misc_feature         15
                     note = 2'-OMe modified nucleotide
misc_feature         16
                     note = 2'-F modified nucleotide
misc_feature         17
                     note = 2'-OMe modified nucleotide
misc_feature         18
                     note = 2'-OMe modified nucleotide
misc_feature         19
                     note = 2'-OMe modified nucleotide
misc_feature         20
                     note = 2'-OMe modified nucleotide
misc_feature         21
                     note = 2'-OMe modified nucleotide with a
                      3'-phosphorothioate linkage
misc_feature         22
                     note = 2'-OMe modified nucleotide with a
                      3'-phosphorothioate linkage
misc_feature         23
                     note = 2'-OMe modified nucleotide
source               1..23
                     mol_type = other RNA
                     organism = synthetic construct
SEQUENCE: 26
tctcgcggaa ggtcagcttg tgg                                             23

SEQ ID NO: 27        moltype = RNA  length = 21
FEATURE              Location/Qualifiers
misc_feature         1..21
                     note = Description of Artificial Sequence: Synthetic
                      oligonucleotide
misc_feature         1
                     note = 2'-OMe modified nucleotide with a
                      3'-phosphorothioate linkage
misc_feature         2
                     note = 2'-OMe modified nucleotide with a
                      3'-phosphorothioate linkage
misc_feature         3
                     note = 2'-OMe modified nucleotide
misc_feature         4
                     note = 2'-OMe modified nucleotide
misc_feature         5
                     note = 2'-OMe modified nucleotide
misc_feature         6
                     note = 2'-OMe modified nucleotide
misc_feature         7
                     note = 2'-F modified nucleotide
misc_feature         8
                     note = 2'-OMe modified nucleotide
misc_feature         9
                     note = 2'-F modified nucleotide
misc_feature         10
                     note = 2'-F modified nucleotide
misc_feature         11
                     note = 2'-F modified nucleotide
misc_feature         12
                     note = 2'-OMe modified nucleotide
misc_feature         13
                     note = 2'-OMe modified nucleotide
misc_feature         14
                     note = 2'-OMe modified nucleotide
misc_feature         15
                     note = 2'-OMe modified nucleotide
misc_feature         16
                     note = 2'-OMe modified nucleotide
misc_feature         17
```

```
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 27
agattgaaac ccacaagctg a                                                  21

SEQ ID NO: 28           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
misc_feature            7
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 28
tcagcttgtg ggtttcaatc ttt                                                23
```

```
SEQ ID NO: 29           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 29
aataaaaaga ttgaaaccca a                                              21

SEQ ID NO: 30           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
misc_feature            7
                        note = 2'-OMe modified nucleotide
```

-continued

```
misc_feature          8
                      note = 2'-OMe modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
                      note = 2'-OMe modified nucleotide
source                1..23
                      mol_type = other RNA
                      organism = synthetic construct
SEQUENCE: 30
ttgggtttca atctttttat ttc                                          23

SEQ ID NO: 31         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-F modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
```

-continued

```
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 31
ggaaataaaa agattgaaac a                                          21

SEQ ID NO: 32         moltype = RNA  length = 23
FEATURE               Location/Qualifiers
misc_feature          1..23
                      note = Description of Artificial Sequence: Synthetic
                       oligonucleotide
misc_feature          1
                      note = 2'-OMe modified nucleotide with a
                       3'-phosphorothioate linkage and a 5'-vinylphosphonate
                       substitution
misc_feature          2
                      note = 2'-F modified nucleotide with a 3'-phosphorothioate
                       linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-F modified nucleotide
misc_feature          7
                      note = 2'-OMe modified nucleotide
misc_feature          8
                      note = 2'-OMe modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
                      note = 2'-OMe modified nucleotide
source                1..23
                      mol_type = other RNA
                      organism = synthetic construct
SEQUENCE: 32
tgtttcaatc tttttatttc ctc                                        23
```

```
SEQ ID NO: 33           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 33
ggcggaggaa ataaaaagat a                                              21

SEQ ID NO: 34           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
misc_feature            7
```

```
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 34
tatcttttta tttcctccgc cag                                            23

SEQ ID NO: 35           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
```

```
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 35
gaagtaaaat ctgagaagct a                                             21

SEQ ID NO: 36           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
misc_feature            7
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 36
```

```
tagcttctca gattttactt cca                                             23

SEQ ID NO: 37           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 37
ggaagtaaaa tctgagaagc a                                               21

SEQ ID NO: 38           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
```

```
misc_feature            7
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 38
tgcttctcag attttacttc cac                                            23

SEQ ID NO: 39           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
```

```
misc_feature           16
                       note = 2'-OMe modified nucleotide
misc_feature           17
                       note = 2'-OMe modified nucleotide
misc_feature           18
                       note = 2'-OMe modified nucleotide
misc_feature           19
                       note = 2'-OMe modified nucleotide with a
                        3'-phosphorothioate linkage
misc_feature           20
                       note = 2'-OMe modified nucleotide with a
                        3'-phosphorothioate linkage
misc_feature           21
                       note = 2'-OMe modified nucleotide
source                 1..21
                       mol_type = other RNA
                       organism = synthetic construct
SEQUENCE: 39
gtggaagtaa aatctgagaa a                                            21

SEQ ID NO: 40          moltype = RNA  length = 23
FEATURE                Location/Qualifiers
misc_feature           1..23
                       note = Description of Artificial Sequence: Synthetic
                        oligonucleotide
misc_feature           1
                       note = 2'-OMe modified nucleotide with a
                        3'-phosphorothioate linkage and a 5'-vinylphosphonate
                        substitution
misc_feature           2
                       note = 2'-F modified nucleotide with a 3'-phosphorothioate
                        linkage
misc_feature           3
                       note = 2'-OMe modified nucleotide
misc_feature           4
                       note = 2'-OMe modified nucleotide
misc_feature           5
                       note = 2'-OMe modified nucleotide
misc_feature           6
                       note = 2'-F modified nucleotide
misc_feature           7
                       note = 2'-OMe modified nucleotide
misc_feature           8
                       note = 2'-OMe modified nucleotide
misc_feature           9
                       note = 2'-OMe modified nucleotide
misc_feature           10
                       note = 2'-OMe modified nucleotide
misc_feature           11
                       note = 2'-OMe modified nucleotide
misc_feature           12
                       note = 2'-OMe modified nucleotide
misc_feature           13
                       note = 2'-OMe modified nucleotide
misc_feature           14
                       note = 2'-F modified nucleotide
misc_feature           15
                       note = 2'-OMe modified nucleotide
misc_feature           16
                       note = 2'-F modified nucleotide
misc_feature           17
                       note = 2'-OMe modified nucleotide
misc_feature           18
                       note = 2'-OMe modified nucleotide
misc_feature           19
                       note = 2'-OMe modified nucleotide
misc_feature           20
                       note = 2'-OMe modified nucleotide
misc_feature           21
                       note = 2'-OMe modified nucleotide with a
                        3'-phosphorothioate linkage
misc_feature           22
                       note = 2'-OMe modified nucleotide with a
                        3'-phosphorothioate linkage
misc_feature           23
                       note = 2'-OMe modified nucleotide
source                 1..23
                       mol_type = other RNA
                       organism = synthetic construct
```

```
SEQUENCE: 40
tttctcagat tttacttcca cct                                          23

SEQ ID NO: 41           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 41
ccaggtggaa gtaaaatctg a                                            21

SEQ ID NO: 42           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
```

-continued

```
                        note = 2'-F modified nucleotide
misc_feature            7
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 42
tcagatttta cttccacctg gcc                                          23

SEQ ID NO: 43           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
```

```
                     note = 2'-OMe modified nucleotide
misc_feature         16
                     note = 2'-OMe modified nucleotide
misc_feature         17
                     note = 2'-OMe modified nucleotide
misc_feature         18
                     note = 2'-OMe modified nucleotide
misc_feature         19
                     note = 2'-OMe modified nucleotide with a
                      3'-phosphorothioate linkage
misc_feature         20
                     note = 2'-OMe modified nucleotide with a
                      3'-phosphorothioate linkage
misc_feature         21
                     note = 2'-OMe modified nucleotide
source               1..21
                     mol_type = other RNA
                     organism = synthetic construct
SEQUENCE: 43
caagtccaag atcggctcca a                                          21

SEQ ID NO: 44        moltype = RNA  length = 23
FEATURE              Location/Qualifiers
misc_feature         1..23
                     note = Description of Artificial Sequence: Synthetic
                      oligonucleotide
misc_feature         1
                     note = 2'-OMe modified nucleotide with a
                      3'-phosphorothioate linkage and a 5'-vinylphosphonate
                      substitution
misc_feature         2
                     note = 2'-F modified nucleotide with a 3'-phosphorothioate
                      linkage
misc_feature         3
                     note = 2'-OMe modified nucleotide
misc_feature         4
                     note = 2'-OMe modified nucleotide
misc_feature         5
                     note = 2'-OMe modified nucleotide
misc_feature         6
                     note = 2'-F modified nucleotide
misc_feature         7
                     note = 2'-OMe modified nucleotide
misc_feature         8
                     note = 2'-OMe modified nucleotide
misc_feature         9
                     note = 2'-OMe modified nucleotide
misc_feature         10
                     note = 2'-OMe modified nucleotide
misc_feature         11
                     note = 2'-OMe modified nucleotide
misc_feature         12
                     note = 2'-OMe modified nucleotide
misc_feature         13
                     note = 2'-OMe modified nucleotide
misc_feature         14
                     note = 2'-F modified nucleotide
misc_feature         15
                     note = 2'-OMe modified nucleotide
misc_feature         16
                     note = 2'-F modified nucleotide
misc_feature         17
                     note = 2'-OMe modified nucleotide
misc_feature         18
                     note = 2'-OMe modified nucleotide
misc_feature         19
                     note = 2'-OMe modified nucleotide
misc_feature         20
                     note = 2'-OMe modified nucleotide
misc_feature         21
                     note = 2'-OMe modified nucleotide with a
                      3'-phosphorothioate linkage
misc_feature         22
                     note = 2'-OMe modified nucleotide with a
                      3'-phosphorothioate linkage
misc_feature         23
                     note = 2'-OMe modified nucleotide
source               1..23
                     mol_type = other RNA
```

-continued

```
                        organism = synthetic construct
SEQUENCE: 44
ttggagccga tcttggactt gac                                           23

SEQ ID NO: 45           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 45
tctggtgaac ctccaaaatc a                                             21

SEQ ID NO: 46           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
```

```
misc_feature           6
                       note = 2'-F modified nucleotide
misc_feature           7
                       note = 2'-OMe modified nucleotide
misc_feature           8
                       note = 2'-OMe modified nucleotide
misc_feature           9
                       note = 2'-OMe modified nucleotide
misc_feature           10
                       note = 2'-OMe modified nucleotide
misc_feature           11
                       note = 2'-OMe modified nucleotide
misc_feature           12
                       note = 2'-OMe modified nucleotide
misc_feature           13
                       note = 2'-OMe modified nucleotide
misc_feature           14
                       note = 2'-F modified nucleotide
misc_feature           15
                       note = 2'-OMe modified nucleotide
misc_feature           16
                       note = 2'-F modified nucleotide
misc_feature           17
                       note = 2'-OMe modified nucleotide
misc_feature           18
                       note = 2'-OMe modified nucleotide
misc_feature           19
                       note = 2'-OMe modified nucleotide
misc_feature           20
                       note = 2'-OMe modified nucleotide
misc_feature           21
                       note = 2'-OMe modified nucleotide with a
                        3'-phosphorothioate linkage
misc_feature           22
                       note = 2'-OMe modified nucleotide with a
                        3'-phosphorothioate linkage
misc_feature           23
                       note = 2'-OMe modified nucleotide
source                 1..23
                       mol_type = other RNA
                       organism = synthetic construct
SEQUENCE: 46
tgattttgga ggttcaccag agc                                          23

SEQ ID NO: 47          moltype = RNA  length = 21
FEATURE                Location/Qualifiers
misc_feature           1..21
                       note = Description of Artificial Sequence: Synthetic
                        oligonucleotide
misc_feature           1
                       note = 2'-OMe modified nucleotide with a
                        3'-phosphorothioate linkage
misc_feature           2
                       note = 2'-OMe modified nucleotide with a
                        3'-phosphorothioate linkage
misc_feature           3
                       note = 2'-OMe modified nucleotide
misc_feature           4
                       note = 2'-OMe modified nucleotide
misc_feature           5
                       note = 2'-OMe modified nucleotide
misc_feature           6
                       note = 2'-OMe modified nucleotide
misc_feature           7
                       note = 2'-F modified nucleotide
misc_feature           8
                       note = 2'-OMe modified nucleotide
misc_feature           9
                       note = 2'-F modified nucleotide
misc_feature           10
                       note = 2'-F modified nucleotide
misc_feature           11
                       note = 2'-F modified nucleotide
misc_feature           12
                       note = 2'-OMe modified nucleotide
misc_feature           13
                       note = 2'-OMe modified nucleotide
misc_feature           14
                       note = 2'-OMe modified nucleotide
```

-continued

```
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 47
caggtggaag taaaatctga a                                           21

SEQ ID NO: 48         moltype = RNA  length = 23
FEATURE               Location/Qualifiers
misc_feature          1..23
                      note = Description of Artificial Sequence: Synthetic
                       oligonucleotide
misc_feature          1
                      note = 2'-OMe modified nucleotide with a
                       3'-phosphorothioate linkage and a 5'-vinylphosphonate
                       substitution
misc_feature          2
                      note = 2'-F modified nucleotide with a 3'-phosphorothioate
                       linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-F modified nucleotide
misc_feature          7
                      note = 2'-OMe modified nucleotide
misc_feature          8
                      note = 2'-OMe modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
                      note = 2'-OMe modified nucleotide
source                1..23
```

-continued

```
                        mol_type = other RNA
                        organism = synthetic construct
SEQUENCE: 48
ttcagatttt acttccacct ggc                                          23

SEQ ID NO: 49           moltype = DNA  length = 6644
FEATURE                 Location/Qualifiers
source                  1..6644
                        mol_type = genomic DNA
                        organism = Homo sapiens
SEQUENCE: 49
gcagtcaccg ccacccacca gctccggcac caacagcagc gccgctgcca ccgcccacct  60
tctgccgccg ccaccacagc caccttctcc tcctccgctg tcctctcccg tcctcgcctc  120
tgtcgactat caggtgaact ttgaaccagg atggctgagc ccgccagga gttcgaagtg  180
atggaagatc acgctgggac gtacgggttg gggacagga aagatcaggg gggctacacc  240
atgcaccaag accaagaggg tgacacggac gctggcctga aagaatctcc cctgcagacc  300
cccactgagg acggatctga ggaaccgggc tctgaaacct ctgatgctaa gagcactcca  360
acagcggaag atgtgacagc acccttagtg gatgagggag ctcccggcaa gcaggctgcc  420
gcgcagcccc acacggagat cccagaagga accacagctg aagaagcagg cattggagac  480
acccccagcc tggaagacga agctgctggt cacgtgaccc aagagcctga aagtggtaag  540
gtggtccagg aaggcttcct ccgagagcca ggcccccag gtctgagcca ccagctcatg  600
tccggcatgc ctggggctcc cctcctgcct gagggcccca gagaggccac acgccaacct  660
tcggggacag gacctgagga cacagagggc ggccgccacg cccctgagct gctcaagcac  720
cagcttctag gagacctgca ccaggagggg ccgccgctga agggggcagg gggcaaagag  780
aggccgggga gcaaggagga ggtggatgaa gaccgcgacg tcgatgagtc ctcccccaa  840
gactcccctc cctccaaggc ctccccagcc caagatgggc ggcctcccca gacagccgcc  900
agagaagcca ccagcatccc aggcttccca gcggagggtg ccatccccct ccctgtggat  960
ttcctctcca aagtttccac agagatccca gcctcagagc ccgacgggcc cagtgtaggg  1020
cgggccaaag ggcaggatgc ccccctggag ttcacgtttc acgtggaaat cacacccaac  1080
gtgcagaagg agcaggcgca ctcggaggag catttgggaa gggctgcatt tccaggggcc  1140
cctggagagg ggccagaggc ccggggcccc tctttgggag aggacacaaa agaggctgac  1200
cttccagagc cctctgaaaa gcagcctgct gctgctccgc gggggaagcc cgtcagccgg  1260
gtccctcaac tcaaagctcg catggtcagt aaaagcaaag acgggactgg aagcgatgac  1320
aaaaaagcca agacatccac acgttcctct gctaaaacct tgaaaaatag gccttgcctt  1380
agccccaaac accccactcc tggtagctca gaccctctga tccaaccctc cagccctgct  1440
gtgtgcccag agccaccttc ctctcctaaa tacgtctctt ctgtcacttc ccgaactggc  1500
agttctggag caaaggagat gaaactcaag gggggctgatg gtaaaacgaa gatcgccaca  1560
ccgcggggag cagcccctcc aggccagaag ggccaggcca acgccaccag gattccagca  1620
aaaaccccgc ccgctccaaa gacaccaccc agctctgcga ctaagcaagt ccagagaaga  1680
ccaccccctg cagggcccag atctgagaga ggtgaacctc caaaatcagg ggatcgcagc  1740
ggctacagca gccccggctc cccaggcact cccggcagcc gctcccgcac cccgtccctt  1800
ccaaccccac ccacccggga gcccaagaag gtggcagtgg tccgtactcc acccaagtcg  1860
ccgtcttccg ccaagagccg cctgcagaca gccccgtgc ccatgccaga cctgaagaat  1920
gtcaagtcca agatcggctc cactgagaac ctgaagcacc agccgggagg cgggaaggtg  1980
cagataatta ataagaagct ggatcttagc aacgtccagt ccaagtgtgg ctcaaaggat  2040
aatatcaaac acgtcccggg aggcggcagt gtgcaaatag tctacaaacc agttgacctg  2100
agcaaggtga cctccaagtg tggctcatta ggcaacatcc atcataaacc aggaggtggc  2160
caggtggaag taaaatctga gaagcttgac ttcaaggaca gagtccagtc gaagattggg  2220
tccctggaca atatcaccca cgtccctggc ggaggaaata aaaagattga aacccacaag  2280
ctgaccttcc gcgagaacgc caaagccaag acagaccacg gggcggagat cgtgtacaag  2340
tcgccagtgg tgtctgggga cacgtctcca cggcatctca gcaatgtctc ctccaccggc  2400
agcatcgaca tggtagactc gccccagctc gccacgctag ctgacgaggt gtctgcctcc  2460
ctggccaagc agggtttgtg atcaggcccc tggggcggtc aataattgtg gagaggagag  2520
aatgagagag tgtggaaaaa aaaagaataa tgacccggcc cccgccctct gcccccagct  2580
gctcctcgca gttcggttaa ttggttaatc acttaacctg cttttgtcac tcggctttgg  2640
ctcgggactt caaaatcagt gatgggagta agagcaaatt tcatctttcc aaattgatgg  2700
gtgggctagt aataaaatat ttaaaaaaaa acattcaaaa acatggccac atccaacatt  2760
tcctcaggca attccttttg attctttttt cttcccctc catgtagaag agggagaagg  2820
agaggctctg aaagctgctt ctgggggatt tcaagggact gggggtgcca accacctctg  2880
gccctgttgt gggggtgtca cagaggcagt ggcagcaaca aaggatttga aacttggtgt  2940
gttcgtggag ccacaggcag acgatgtcaa ccttgtgtga gtgtgacggg ggttggggtg  3000
gggcgggagg ccacggggga ggccgaggca ggggctgggc agaggggaga ggaagcacaa  3060
gaagtgggag tgggagagga agccacgtgc tggagagtag acatccccct ccttgccgct  3120
gggagagcca aggcctatgc cacctgcagc gtctgagcgg ccgcctgtcc ttggtggccg  3180
ggggtggggg cctgctgtgg gtcagtgtgc caccctctgc agggcagcct gtgggagaag  3240
ggacagcggg taaaaagaga aggcaagctg gcaggagggt ggcacttcgt ggatgacctc  3300
cttagaaaag actgaccttg atgtcttgag agcgctggcc tcttcctccc tccctgcagg  3360
gtagggggcc tgagttgagg ggcttccctc tgctccacag aaaccctgtt ttattgagtt  3420
ctgaaggttg gaactgctgc catgattttg gccactttgc agacctggga ctttagggct  3480
aaccagttct ctttgtaagg acttgtgcct cttgggagac gtccacccgt ttccaagcct  3540
gggccactgg catctctgga gtgtgtgggg gtctgggagg caggtcccga gccccctgtc  3600
cttcccacgg ccactgcagt caccccgtct gcgccgctgt gctgttgtct gccgtgagag  3660
cccaatcact gcctataccc ctcatcacac gtcacaatgt cccgaattcc cagcctcacc  3720
accccttctc agtaatgacc ctggttggtt gcaggaggta cctactccat actgagggtg  3780
aaattaaggg aaggcaaagt ccaggcacaa gagtgggacc ccagcctctc actctcagtt  3840
ccactcatcc aactgggacc ctcaccacga atctcatgat ctgattcggt tccctgtctc  3900
ctcctcccgt cacagatgtg agccagggca ctgctcagct gtgaccctag gtgtttctgc  3960
cttgttgaca tggagagagc cctttcccct gagaaggcct ggccccttcc tgtgctgagc  4020
ccacagcagc aggctgggtg tcttggttgt cagtggtggc accaggatgg aagggcaagg  4080
```

```
cacccagggc aggcccacag tcccgctgtc ccccacttgc accctagctt gtagctgcca  4140
acctcccaga cagcccagcc cgctgctcag ctccacatgc atagtatcag ccctccacac  4200
ccgacaaagg ggaacacacc cccttggaaa tggttctttt cccccagtcc cagctggaag  4260
ccatgctgtc tgttctgctg gagcagctga acatatacat agatgttgcc ctgccctccc  4320
catctgcacc ctgttgagtt gtagttggat ttgtctgttt atgcttggat tcaccagagt  4380
gactatgata gtgaaaagaa aaaaaaaaaa aaaaaaggac gcatgtatct tgaaatgctt  4440
gtaaagaggt ttctaaccca ccctcacgag gtgtctctca cccccacact gggactcgtg  4500
tggcctgtgt ggtgccaccc tgctggggcc tcccaagttt tgaaaggctt tcctcagcac  4560
ctgggaccca acagagacca gcttctagca gctaaggagg ccgttcagct gtgacgaagg  4620
cctgaagcac aggattagga ctgaagcgat gatgtcccct tccctacttc cccttggggc  4680
tccctgtgtc agggcacaga ctaggtcttg tggctggtct ggcttgcggc gcgaggatgg  4740
ttctctctgg tcatagcccg aagtctcatg gcagtcccaa aggaggctta caactcctgc  4800
atcacaagaa aaaggaagcc actgccagct ggggggatct gcagctccca gaagctccgt  4860
gagcctcagc cacccctcag actgggttcc tctccaagct cgccctctgg aggggcagcg  4920
cagcctccca ccaagggccc tgcgaccaca gcagggattg ggatgaattg cctgtcctgg  4980
atctgctcta gaggcccaag ctgcctgcct gaggaaggat gacttgacaa gtcaggagac  5040
actgttccca aagccttgac cagagcacct cagcccgctg accttgcaca aactccatct  5100
gctgccatga gaaaagggaa gccgcctttg caaaacattg ctgcctaaag aaactcagca  5160
gcctcaggcc caattctgcc acttctggtt tgggtacagt taaaggcaac cctgagggac  5220
ttggcagtag aaatccaggg cctcccctgg ggctggcagc ttcgtgtgca gctagagctt  5280
tacctgaaag gaagtctctg ggcccagaac tctccaccaa gagcctccct gccgttcgct  5340
gagtcccagc aattctccta agttgaaggg atctgagaag gagaaggaaa tgtggggtag  5400
atttggtggt ggttagagat atgccccccct cattactgcc aacagtttcg gctgcatttc  5460
ttcacgcacc tcggttcctc ttcctgaagt tcttgtgccc tgctcttcag caccatgggc  5520
cttcttatac ggaaggctct gggatctccc ccttgtgggg caggctcttg gggccagcct  5580
aagatcatgg tttagggtga tcagtgctgg cagataaatt gaaaaggcac gctggcttgt  5640
gatcttaaat gaggacaatc cccccagggc tgggcactcc tcccctcccc tcacttctcc  5700
cacctgcaga gccagtgtcc ttgggtgggc tagataggat atactgtatg ccggctcctt  5760
caagctgctg actcacttta tcaatagttc catttaaatt gacttcagtg gtgagactgt  5820
atcctgtttg ctattgcttg ttgtgctatg gggggagggg ggaggaatgt gtaagatagt  5880
taacatgggc aaagggagat cttggggtgc agcacttaaa ctgcctcgta acccttttca  5940
tgatttcaac cacatttgct agagggaggg agcagccacg gagttagagg cccttggggt  6000
ttctcttttc cactgacagg ctttcccagg cagctggcta gttcattccc tccccagcca  6060
ggtgcaggcg taggaatatg gacatctggt tgctttggcc tgctgccctc tttcaggggt  6120
cctaagccca caatcatgcc tccctaagac cttggcatcc ttccctctaa gccgttggca  6180
cctctgtgcc acctctcaca ctggctccag acacacagcc tgtgcttttg gagctgagat  6240
cactcgcttc accctcctca tctttgttct ccaagtaaag ccacgaggtc ggggcgaggg  6300
cagaggtgat cacctgcgtg tcccatctac agacctgcag cttcataaaa cttctgattt  6360
ctcttcagct ttgaaaaggg ttaccctggg cactggccta gagcctcacc tcctaataga  6420
cttagcccca tgagtttgcc atgttgagca ggactatttc tggcacttgc aagtcccatg  6480
atttcttcgg taattctgag ggtgggggga gggacatgaa atcatcttag cttagctttc  6540
tgtctgtgaa tgtctatata gtgtattgtg tgttttaaca aatgatttac actgactgtt  6600
gctgtaaaag tgaatttgga aataaagtta ttactctgat taaa                  6644

SEQ ID NO: 50          moltype = AA  length = 776
FEATURE                Location/Qualifiers
source                 1..776
                       mol_type = protein
                       organism = Homo sapiens
SEQUENCE: 50
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQEPESGK VVQEGFLREP GPPGLSHQLM SGMPGAPLLP EGPREATRQP SGTGPEDTEG  180
GRHAPELLKH QLLGDLHQEG PPLKGAGGKE RPGSKEEVDE DRDVDESSPQ DSPPSKASPA  240
QDGRPPQTAA REATSIPGFP AEGAIPLPVD FLSKVSTEIP ASEPDGPSVG RAKGQDAPLE  300
FTFHVEITPN VQKEQAHSEE HLGRAAFPGA PGEGPEARGP SLGEDTKEAD LPEPSEKQPA  360
AAPRGKPVSR VPQLKARMVS KSKDGTGSDD KKAKTSTRSS AKTLKNRPCL SPKHPTPGSS  420
DPLIQPSSPA VCPEPPSSPK YVSSVTSRTG SSGAKEMKLK GADGKTKIAT PRGAAPPGQK  480
GQANATRIPA KTPPAPKTPP SSATKQVQRR PPPAGPRSER GEPPKSGDRS GYSSPGSPGT  540
PGSRSRTPSL PTPPTREPKK VAVVRTPPKS PSSAKSRLQT APVPMPDLKN VKSKIGSTEN  600
LKHQPGGGKV QIINKKLDLS NVQSKCGSKD NIKHVPGGGS VQIVYKPVDL SKVTSKCGSL  660
GNIHHKPGGG QVEVKSEKLD FKDRVQSKIG SLDNITHVPG GGNKKIETHK LTFRENAKAK  720
TDHGAEIVYK SPVVSGDTSP RHLSNVSSTG SIDMVDSPQL ATLADEVSAS LAKQGL      776

SEQ ID NO: 51          moltype = DNA  length = 5552
FEATURE                Location/Qualifiers
source                 1..5552
                       mol_type = genomic DNA
                       organism = Homo sapiens
SEQUENCE: 51
gcagtcaccg ccacccacca gctccggcac caacagcagc gccgctgcca ccgcccacct  60
tctgccgccg ccaccacagc caccttctcc tcctccgctg tcctctcccg tcctcgcctc  120
tgtcgactat caggtgaact ttgaaccagg atggctgagc ccgccagga gttcgaagtg  180
atggaagatc acgctgggac gtacgggttg ggggacagga aagatcaggg gggctacacc  240
atgcaccaag accaagaggg tgacacggac gctggcctga aagaatctcc cctgcagacc  300
cccactgagg acggatctga ggaaccgggc tctgaaacct ctgatgctaa gagcactcca  360
acagcggaag ctgaagaagc aggcattgga gacaccccca gcctggaaga cgaagctgct  420
ggtcacgtga cccaagctcg catggtcagt aaaagcaaag acgggactgg aagcgatgac  480
aaaaaagcca agggggctga tggtaaaacg aagatcgcca caccgcgggg agcagcccct  540
```

-continued

```
ccaggccaga agggccaggc caacgccacc aggattccag caaaaacccc gcccgctcca  600
aagacaccac ccagctctgg tgaacctcca aaatcagggg atcgcagcgg ctacagcagc  660
cccggctccc caggcactcc cggcagccgc tcccgcaccc cgtcccttcc aaccccaccc  720
acccgggagc ccaagaaggt ggcagtggtc cgtactccac ccaagtcgcc gtcttccgcc  780
aagagccgcc tgcagacagc cccgtgccc atgccagacc tgaagaatgt caagtccaag  840
atcggctcca ctgagaacct gaagcaccag ccgggaggcg ggaaggtgca gataattaat  900
aagaagctgg atcttagcaa cgtccagtcc aagtgtggct caaaggataa tatcaaacac  960
gtcccgggag gcggcagtgt gcaaatagtc tacaaaccag ttgacctgag caaggtgacc  1020
tccaagtgtg gctcattagg caacatccat cataaaccag gaggtggcca ggtggaagta  1080
aaatctgaga agcttgactt caaggacaga gtccagtcga agattgggtc cctggacaat  1140
atcacccacg tccctggcgg aggaaataaa aagattgaaa cccacaagct gaccttccgc  1200
gagaacgcca aagccaagac agaccacggg gcggagatcg tgtacaagtc gccagtggtg  1260
tctggggaca cgtctccacg gcatctcagc aatgtctcct ccaccggcag catcgacatg  1320
gtagactcgc cccagctcgc cacgctagct gacgaggtgt ctgcctccct ggccaagcag  1380
ggtttgtgat caggcccctg gggcggtcaa taattgtgga gaggagagaa tgagagagtg  1440
tggaaaaaaa aagaataatg acccggcccc cgccctctgc ccccagctgc tcctcgcagt  1500
tcggttaatt ggttaatcac ttaacctgct tttgtcactc ggctttggct cgggacttca  1560
aaatcagtga tgggagtaag agcaaatttc atctttccaa attgatgggt gggctagtaa  1620
taaaatattt aaaaaaaaac attcaaaaac atggccacat ccaacatttc ctcaggcaat  1680
tccttttgat tcttttttct tccccctcca tgtagaagag ggagaaggag aggctctgaa  1740
agctgcttct gggggatttc aagggactgg gggtgccaac cacctctggc cctgttgtgg  1800
gggtgtcaca gaggcagtgg cagcaacaaa ggatttgaaa cttggtgtgt tcgtggagcc  1860
acaggcagac gatgtcaacc ttgtgtgagt gtgacggggg ttggggtggg gcgggaggcc  1920
acgggggagg ccgaggcagg ggctgggcag aggggagagg aagcacaaga agtgggagtg  1980
ggagaggaag ccacgtgctg gagagtagac atccccctcc ttgccgctgg gagagccaag  2040
gcctatgcca cctgcagcgt ctgagcggcc gcctgtcctt ggtggccggg ggtgggggcc  2100
tgctgtgggt cagtgtgcca ccctctgcag ggcagcctgt gggagaaggg acagcgggta  2160
aaaagagaag gcaagctggc aggagggtgg cacttcgtgg atgacctcct tagaaaagac  2220
tgaccttgat gtcttgagag cgctggcctc ttcctccctc cctgcagggt agggggcctg  2280
agttgagggg cttccctctg ctccacagaa accctgtttt attgagttct gaaggttgga  2340
actgctgcca tgattttggc cactttgcag acctgggact ttagggctaa ccagttctct  2400
ttgtaaggac ttgtgcctct tgggagacgt ccacccgttt ccaagcctgg gccactggca  2460
tctctggagt gtgtgggggt ctgggaggca ggtcccgagc cccctgtcct tcccacggcc  2520
actgcagtca ccccgtctgc gccgctgtgc tgttgtctgc cgtgagagcc caatcactgc  2580
ctataccccct catcacacgt cacaatgtcc cgaattccca gcctcaccac cccttctcag  2640
taatgaccct ggttggttgc aggaggtacc tactccatac tgagggtgaa attaagggaa  2700
ggcaaagtcc aggcacaaga gtgggacccc agcctctcac tctcagttcc actcatccaa  2760
ctgggaccct caccacgaat ctcatgatct gattcggttc cctgtctcct cctcccgtca  2820
cagatgtgag ccagggcact gctcagctgt gaccctaggt gtttctgcct tgttgacatg  2880
gagagagccc tttcccctga gaaggcctgg ccccttcctg tgctgagccc acagcagcag  2940
gctgggtgtc ttggttgtca gtggtggcac caggatggaa gggcaaggca cccagggcag  3000
gcccacagtc ccgctgtccc ccacttgcac cctagcttgt agctgccaac ctcccagaca  3060
gcccagcccg ctgctcagct ccacatgcat agtatcagcc ctccacaccc gacaaagggg  3120
aacacacccc cttggaaatg gttcttttcc cccagtccca gctggaagcc atgctgtctg  3180
ttctgctgga gcagctgaac atatacatag atgttgccct gccctcccca tctgcaccct  3240
gttgagttgt agttggattt gtctgtttat gcttggattc accagagtga ctatgatagt  3300
gaaaagaaaa aaaaaaaaaa aaaaggacgc atgtatcttg aaatgcttgt aaagaggttt  3360
ctaacccacc ctcacgaggt gtctctcacc cccacactgg gactcgtgtg gcctgtgtgg  3420
tgccaccctg ctggggcctc ccaagttttg aaaggctttc ctcagcacct gggacccaac  3480
agagaccagc ttctagcagc taaggaggcc gttcagctgt gacgaaggcc tgaagcacag  3540
gattaggact gaagcgatga tgtccccttc cctacttccc cttggggctc cctgtgtcag  3600
ggcacagact aggtcttgtg gctggtctgg cttgcggcgc gaggatggtt ctctctggtc  3660
atagcccgaa gtctcatggc agtcccaaag gaggcttaca actcctgcat cacaagaaaa  3720
aggaagccac tgccagctgg ggggatctgc agctcccaga agctccgtga gcctcagcca  3780
cccctcagac tgggttcctc tccaagctcg ccctctggag gggcagcgca gcctcccacc  3840
aagggccctg cgaccacagc agggattggg atgaattgcc tgtcctggat ctgctctaga  3900
ggcccaagct gcctgcctga ggaaggatga cttgacaagt caggagacac tgttcccaaa  3960
gccttgacca gagcacctca gcccgctgac cttgcacaaa ctccatctgc tgccatgaga  4020
aaagggaagc cgcctttgca aaacattgct gcctaaagaa actcagcagc ctcaggccca  4080
attctgccac ttctggtttg ggtacagtta aaggcaaccc tgagggactt ggcagtagaa  4140
atccagggcc tcccctgggg ctggcagctt cgtgtgcagc tagagcttta cctgaaagga  4200
agtctctggg cccagaactc tccaccaaga gcctccctgc cgttcgctga gtcccagcaa  4260
ttctcctaag ttgaagggat ctgagaagga gaaggaaatg tggggtagat ttggtggtgg  4320
ttagagatat gccccctca ttactgccaa cagtttcggc tgcatttctt cacgcacctc  4380
ggttcctctt cctgaagttc ttgtgccctg ctcttcagca ccatgggcct tcttatacgg  4440
aaggctctgg gatctccccc ttgtggggca ggctcttggg gccagcctaa gatcatggtt  4500
tagggtgatc agtgctggca gataaattga aaaggcacgc tggcttgtga tcttaaatga  4560
ggacaatccc cccagggctg ggcactcctc ccctcccctc acttctccca cctgcagagc  4620
cagtgtcctt gggtgggcta gataggatat actgtatgcc ggctccttca agctgctgac  4680
tcactttatc aatagttcca tttaaattga cttcagtggt gagactgtat cctgtttgct  4740
attgcttgtt gtgctatggg gggagggggg aggaatgtgt aagatagtta acatgggcaa  4800
agggagatct tggggtgcag cacttaaact gcctcgtaac ccttttcatg atttcaacca  4860
catttgctag agggagggag cagccacgga gttagaggcc cttggggttt ctcttttcca  4920
ctgacaggct ttcccaggca gctggctagt tcattccctc cccagccagg tgcaggcgta  4980
ggaatatgga catctggttg ctttggcctg ctgccctctt tcaggggtcc taagcccaca  5040
atcatgcctc cctaagacct tggcatcctt ccctctaagc cgttggcacc tctgtgccac  5100
ctctcacact ggctccagac acacagcctg tgcttttgga gctgagatca ctcgcttcac  5160
cctcctcatc tttgttctcc aagtaaagcc acgaggtcgg ggcgagggca gaggtgatca  5220
cctgcgtgtc ccatctacag acctgcagct tcataaaact tctgatttct cttcagcttt  5280
```

-continued

```
gaaaagggtt accctgggca ctggcctaga gcctcacctc ctaatagact tagccccatg  5340
agtttgccat gttgagcagg actatttctg gcacttgcaa gtcccatgat ttcttcggta  5400
attctgaggg tgggggaggg gacatgaaat catcttagct tagctttctg tctgtgaatg  5460
tctatatagt gtattgtgtg ttttaacaaa tgatttacac tgactgttgc tgtaaaagtg  5520
aatttggaaa taaagttatt actctgatta aa                              5552

SEQ ID NO: 52           moltype = AA  length = 412
FEATURE                 Location/Qualifiers
source                  1..412
                        mol_type = protein
                        organism = Homo sapiens
SEQUENCE: 52
MAEPRQEFEV MEDHAGTYGL GDRKDQGGYT MHQDQEGDTD AGLKESPLQT PTEDGSEEPG  60
SETSDAKSTP TAEAEEAGIG DTPSLEDEAA GHVTQARMVS KSKDGTGSDD KKAKGADGKT  120
KIATPRGAAP PGQKGQANAT RIPAKTPPAP KTPPSSGEPP KSGDRSGYSS PGSPGTPGSR  180
SRTPSLPTPP TREPKKVAVV RTPPKSPSSA KSRLQTAPVP MPDLKNVKSK IGSTENLKHQ  240
PGGGKVQIIN KKLDLSNVQS KCGSKDNIKH VPGGGSVQIV YKPVDLSKVT SKCGSLGNIH  300
HKPGGGQVEV KSEKLDFKDR VQSKIGSLDN ITHVPGGGNK KIETHKLTFR ENAKAKTDHG  360
AEIVYKSPVV SGDTSPRHLS NVSSTGSIDM VDSPQLATLA DEVSASLAKQ GL          412

SEQ ID NO: 53           moltype = DNA  length = 5372
FEATURE                 Location/Qualifiers
source                  1..5372
                        mol_type = genomic DNA
                        organism = Homo sapiens
SEQUENCE: 53
gcagtcaccg ccacccacca gctccggcac caacagcagc gccgctgcca ccgcccacct  60
tctgccgccg ccaccacagc caccttctcc tcctccgctg tcctctcccg tcctcgcctc  120
tgtcgactat caggtgaact ttgaaccagg atggctgagc cccgccagga gttcgaagtg  180
atggaagatc acgctgggac gtacgggttg ggggacagga aagatcaggg gggctacacc  240
atgcaccaag accaagaggg tgacacggac gctggcctga aagctgaaga agcaggcatt  300
ggagacaccc ccagcctgga agacgaagct gctggtcacg tgacccaagc tcgcatggtc  360
agtaaaagca aagacgggac tggaagcgat gacaaaaaag ccaagggggc tgatggtaaa  420
acgaagatcg ccacaccgcg gggagcagcc cctccaggcc agaagggcca ggccaacgcc  480
accaggattc cagcaaaaac cccgcccgct ccaaagacac cacccagctc tggtgaacct  540
ccaaaatcag gggatcgcag cggctacagc agccccggct ccccaggcac tcccggcagc  600
cgctcccgca ccccgtccct tccaacccca cccacccggg agcccaagaa ggtggcagtg  660
gtccgtactc cacccaagtc gccgtcttcc gccaagagcc gcctgcagac agcccccgtg  720
cccatgccag acctgaagaa tgtcaagtcc aagatcggct ccactgagaa cctgaagcac  780
cagccgggag gcgggaaggt gcaaatagtc tacaaaccag ttgacctgag caaggtgacc  840
tccaagtgtg gctcattagg caacatccat cataaaccag gaggtggcca ggtggaagta  900
aaatctgaga agcttgactt caaggacaga gtccagtcga agattgggtc cctggacaat  960
atcacccacg tccctggcgg aggaaataaa aagattgaaa cccacaagct gaccttccgc  1020
gagaacgcca aagccaagac agaccacggg gcggagatcg tgtacaagtc gccagtggtg  1080
tctggggaca cgtctccacg gcatctcagc aatgtctcct ccaccggcag catcgacatg  1140
gtagactcgc cccagctcgc cacgctagct gacgaggtgt ctgcctccct ggccaagcag  1200
ggtttgtgat caggcccctg gggcggtcaa taattgtgga gaggagagaa tgagagagtg  1260
tggaaaaaaa aagaataatg acccggcccc cgccctctgc cccagctgc tcctcgcagt  1320
tcggttaatt ggttaatcac ttaacctgct tttgtcactc ggctttggct cgggacttca  1380
aaatcagtga tgggagtaag agcaaatttc atctttccaa attgatgggt gggctagtaa  1440
taaaatattt aaaaaaaaac attcaaaaac atggccacat ccaacatttc ctcaggcaat  1500
tcctttgat tcttttttct tccccctcca tgtagaagag ggagaaggag aggctctgaa  1560
agctgcttct gggggatttc aagggactgg gggtgccaac cacctctggc cctgttgtgg  1620
gggtgtcaca gaggcagtgg cagcaacaaa ggatttgaaa cttggtgtgt tcgtggagcc  1680
acaggcagac gatgtcaacc ttgtgtgagt gtgacggggg ttggggtggg gcgggaggcc  1740
acgggggagg ccgaggcagg ggctgggcag aggggagagg aagcacaaga agtgggagtg  1800
ggagaggaag ccacgtgctg gagagtagac atcccctcc ttgccgctgg gagagccaag  1860
gcctatgcca cctgcagcgt ctgagcggcc gcctgtcctt ggtggccggg ggtgggggcc  1920
tgctgtgggt cagtgtgcca ccctctgcag ggcagcctgt gggagaaggg acagcgggta  1980
aaaagagaag gcaagctggc aggagggtgg cacttcgtgg atgacctcct tagaaaagac  2040
tgaccttgat gtcttgagag cgctggcctc ttcctccctc cctgcagggt agggggcctg  2100
agttgagggg cttccctctg ctccacagaa accctgtttt attgagttct gaaggttgga  2160
actgctgcca tgattttggc cactttgcag acctgggact ttagggctaa ccagttctct  2220
ttgtaaggac ttgtgcctct tgggagacgt ccacccgttt ccaagcctgg gccactggca  2280
tctctggagt gtgtgggggt ctgggaggca ggtcccgagc cccctgtcct tcccacggcc  2340
actgcagtca ccccgtctgc gccgctgtgc tgttgtctgc cgtgagagcc caatcactgc  2400
ctatacccct catcacacgt cacaatgtcc cgaattccca gcctcaccac cccttctcag  2460
taatgaccct ggttggttgc aggaggtacc tactccatac tgagggtgaa attaagggaa  2520
ggcaaagtcc aggcacaaga gtgggacccc agcctctcac tctcagttcc actcatccaa  2580
ctgggaccct caccacgaat ctcatgatct gattcggttc cctgtctcct cctcccgtca  2640
cagatgtgag ccagggcact gctcagctgt gaccctaggt gtttctgcct tgttgacatg  2700
gagagagccc tttcccctga gaaggcctgg ccccttcctg tgctgagccc acagcagcag  2760
gctgggtgtc ttggttgtca gtggtggcac caggatggaa gggcaaggca cccagggcag  2820
gcccacagtc ccgctgtccc ccacttgcac cctagcttgt agctgccaac ctcccagaca  2880
gcccagcccg ctgctcagct ccacatgcat agtatcagcc ctccacaccc gacaaagggg  2940
aacacacccc cttggaaatg gttcttttcc cccagtccca gctggaagcc atgctgtctg  3000
ttctgctgga gcagctgaac atatacatag atgttgccct gccctcccca tctgcaccct  3060
gttgagttgt agttggattt gtctgtttat gcttggattc accagagtga ctatgatagt  3120
gaaaagaaaa aaaaaaaaaa aaaaggacgc atgtatcttg aaatgcttgt aaagaggttt  3180
```

-continued

```
ctaacccacc ctcacgaggt gtctctcacc cccacactgg gactcgtgtg gcctgtgtgg  3240
tgccaccctg ctggggcctc ccaagttttg aaaggctttc ctcagcacct gggacccaac  3300
agagaccagc ttctagcagc taaggaggcc gttcagctgt gacgaaggcc tgaagcacag  3360
gattaggact gaagcgatga tgtccccttc cctacttccc cttggggctc cctgtgtcag  3420
ggcacagact aggtcttgtg gctggtctgg cttgcggcgc gaggatggtt ctctctggtc  3480
atagcccgaa gtctcatggc agtcccaaag gaggcttaca actcctgcat cacaagaaaa  3540
aggaagccac tgccagctgg ggggatctgc agctcccaga agctccgtga gcctcagcca  3600
cccctcagac tgggttcctc tccaagctcg ccctctggag gggcagcgca gcctccccacc  3660
aagggccctg cgaccacagc agggattggg atgaattgcc tgtcctggat ctgctctaga  3720
ggcccaagct gcctgcctga ggaaggatga cttgacaagt caggagacac tgttcccaaa  3780
gccttgacca gagcacctca gcccgctgac cttgcacaaa ctccatctgc tgccatgaga  3840
aaagggaagc cgcctttgca aaacattgct gcctaaagaa actcagcagc ctcaggccca  3900
attctgccac ttctggtttg ggtacagtta aaggcaaccc tgagggactt ggcagtagaa  3960
atccagggcc tcccctgggg ctggcagctt cgtgtgcagc tagagcttta cctgaaagga  4020
agtctctggg cccagaactc tccaccaaga gcctccctgc cgttcgctga gtcccagcaa  4080
ttctcctaag ttgaagggat ctgagaagga gaaggaaatg tggggtagat ttggtggtgg  4140
ttagagatat gccccctca ttactgccaa cagtttcggc tgcatttctt cacgcacctc  4200
ggttcctctt cctgaagttc ttgtgccctg ctcttcagca ccatgggcct tcttatacgg  4260
aaggctctgg gatctccccc ttgtggggca ggctcttggg gccagcctaa gatcatggtt  4320
tagggtgatc agtgctggca gataaattga aaaggcacgc tggcttgtga tcttaaatga  4380
ggacaatccc cccagggctg ggcactcctc ccctcccctc acttctccca cctgcagagc  4440
cagtgtcctt gggtgggcta gataggatat actgtatgcc ggctccttca agctgctgac  4500
tcactttatc aatagttcca tttaaattga cttcagtggt gagactgtat cctgtttgct  4560
attgcttgtt gtgctatggg gggagggggg aggaatgtgt aagatagtta acatgggcaa  4620
agggagatct tggggtgcag cacttaaact gcctcgtaac ccttttcatg atttcaacca  4680
catttgctag agggagggag cagccacgga gttagaggcc cttggggttt ctcttttcca  4740
ctgacaggct ttcccaggca gctggctagt tcattccctc cccagccagg tgcaggcgta  4800
ggaatatgga catctggttg ctttggcctg ctgccctctt tcaggggtcc taagcccaca  4860
atcatgcctc cctaagacct tggcatcctt ccctctaagc cgttggcacc tctgtgccac  4920
ctctcacact ggctccagac acacagcctg tgcttttgga gctgagatca ctcgcttcac  4980
cctcctcatc tttgttctcc aagtaaagcc acgaggtcgg ggcgagggca gaggtgatca  5040
cctgcgtgtc ccatctacag acctgcagct tcataaaact tctgatttct cttcagcttt  5100
gaaaagggtt accctgggca ctggcctaga gcctcacctc ctaatagact tagccccatg  5160
agtttgccat gttgagcagg actatttctg gcacttgcaa gtcccatgat ttcttcggta  5220
attctgaggg tgggggggagg gacatgaaat catcttagct tagctttctg tctgtgaatg  5280
tctatatagt gtattgtgtg ttttaacaaa tgatttacac tgactgttgc tgtaaaagtg  5340
aatttggaaa taaagttatt actctgatta aa                                5372

SEQ ID NO: 54          moltype = AA  length = 352
FEATURE                Location/Qualifiers
source                 1..352
                       mol_type = protein
                       organism = Homo sapiens
SEQUENCE: 54
MAEPRQEFEV MEDHAGTYGL GDRKDQGGYT MHQDQEGDTD AGLKAEEAGI GDTPSLEDEA  60
AGHVTQARMV SKSKDGTGSD DKKAKGADGK TKIATPRGAA PPGQKGQANA TRIPAKTPPA  120
PKTPPSSGEP PKSGDRSGYS SPGSPGTPGS RSRTPSLPTP PTREPKKVAV VRTPPKSPSS  180
AKSRLQTAPV PMPDLKNVKS KIGSTENLKH QPGGGKVQIV YKPVDLSKVT SKCGSLGNIH  240
HKPGGGQVEV KSEKLDFKDR VQSKIGSLDN ITHVPGGGNK KIETHKLTFR ENAKAKTDHG  300
AEIVYKSPVV SGDTSPRHLS NVSSTGSIDM VDSPQLATLA DEVSASLAKQ GL          352

SEQ ID NO: 55          moltype = RNA  length = 21
FEATURE                Location/Qualifiers
misc_feature           1..21
                       note = Description of Artificial Sequence: Synthetic
                        oligonucleotide
misc_feature           10
                       note = n is an abasic nucleotide
source                 1..21
                       mol_type = other RNA
                       organism = synthetic construct
SEQUENCE: 55
gtggaagtan aatctgagaa a                                            21

SEQ ID NO: 56          moltype = RNA  length = 21
FEATURE                Location/Qualifiers
misc_feature           1..21
                       note = Description of Artificial Sequence: Synthetic
                        oligonucleotide
misc_feature           9
                       note = n is an abasic nucleotide
source                 1..21
                       mol_type = other RNA
                       organism = synthetic construct
SEQUENCE: 56
gtggaagtna aatctgagaa a                                            21

SEQ ID NO: 57          moltype = RNA  length = 21
FEATURE                Location/Qualifiers
```

```
misc_feature          1..21
                      note = Description of Artificial Sequence: Synthetic
                       oligonucleotide
source                1..21
                      mol_type = other RNA
                      organism = synthetic construct
SEQUENCE: 57
ccaagtgtgg ctcattaggc a                                            21

SEQ ID NO: 58         moltype = RNA  length = 23
FEATURE               Location/Qualifiers
misc_feature          1..23
                      note = Description of Artificial Sequence: Synthetic
                       oligonucleotide
source                1..23
                      mol_type = other RNA
                      organism = synthetic construct
SEQUENCE: 58
tgcctaatga gccacacttg gag                                          23

SEQ ID NO: 59         moltype = RNA  length = 21
FEATURE               Location/Qualifiers
misc_feature          1..21
                      note = Description of Artificial Sequence: Synthetic
                       oligonucleotide
misc_feature          9
                      note = n is an abasic nucleotide
source                1..21
                      mol_type = other RNA
                      organism = synthetic construct
SEQUENCE: 59
ccaagtgtng ctcattaggc a                                            21

SEQ ID NO: 60         moltype = RNA  length = 21
FEATURE               Location/Qualifiers
misc_feature          1..21
                      note = Description of Artificial Sequence: Synthetic
                       oligonucleotide
misc_feature          9
                      note = n is an abasic nucleotide
source                1..21
                      mol_type = other RNA
                      organism = synthetic construct
SEQUENCE: 60
tgcaaatant ctacaaacca a                                            21

SEQ ID NO: 61         moltype = RNA  length = 23
FEATURE               Location/Qualifiers
misc_feature          1..23
                      note = Description of Artificial Sequence: Synthetic
                       oligonucleotide
source                1..23
                      mol_type = other RNA
                      organism = synthetic construct
SEQUENCE: 61
ttggtttgta gactatttgc acc                                          23

SEQ ID NO: 62         moltype = RNA  length = 21
FEATURE               Location/Qualifiers
misc_feature          1..21
                      note = Description of Artificial Sequence: Synthetic
                       oligonucleotide
source                1..21
                      mol_type = other RNA
                      organism = synthetic construct
SEQUENCE: 62
tgcaaatagt ctacaaacca a                                            21

SEQ ID NO: 63         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
```

```
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-F modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 63
gtggaagtaa aatctgagaa a                                            21

SEQ ID NO: 64         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
```

```
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 64
gtggaagtaa aatctgagaa a                                            21

SEQ ID NO: 65         moltype = RNA  length = 23
FEATURE               Location/Qualifiers
misc_feature          1..23
                      note = Description of Artificial Sequence: Synthetic
                       oligonucleotide
misc_feature          1
                      note = 2'-OMe modified nucleotide with a
                       3'-phosphorothioate linkage and a 5'-vinylphosphonate
                       substitution
misc_feature          2
                      note = 2'-F modified nucleotide with a 3'-phosphorothioate
                       linkage
misc_feature          3
                      note = 2'-OMe modified nucleotide
misc_feature          4
                      note = 2'-OMe modified nucleotide
misc_feature          5
                      note = 2'-F modified nucleotide
misc_feature          6
                      note = 2'-OMe modified nucleotide
misc_feature          7
                      note = 2'-OMe modified nucleotide
misc_feature          8
                      note = 2'-F modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
```

```
                        note = 2'-OMe modified nucleotide
source                  1..23
                        mol_type = other RNA
                        organism = synthetic construct
SEQUENCE: 65
tttctcagat tttacttcca cct                                          23

SEQ ID NO: 66           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-O-C16 alkyl modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 66
gtggaagtaa aatctgagaa a                                            21

SEQ ID NO: 67           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
```

-continued

```
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified nucleotide
misc_feature          10
                      note = n is an abasic nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 67
gtggaagtan aatctgagaa a                                                21

SEQ ID NO: 68         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          8
                      note = 2'-OMe modified nucleotide
misc_feature          9
                      note = 2'-F modified nucleotide
misc_feature          10
                      note = n is an abasic nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
misc_feature          14
                      note = 2'-OMe modified nucleotide
misc_feature          15
                      note = 2'-OMe modified nucleotide
misc_feature          16
                      note = 2'-OMe modified nucleotide
```

```
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 68
gtggaagtan aatctgagaa a                                    21

SEQ ID NO: 69         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = n is an abasic nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 69
gtggaagtna aatctgagaa a                                    21

SEQ ID NO: 70         moltype = RNA  length = 23
FEATURE               Location/Qualifiers
misc_feature          1..23
                      note = Description of Artificial Sequence: Synthetic
```

```
                        oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-F modified nucleotide
misc_feature            7
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-F modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-F modified nucleotide
misc_feature            19
                        note = 2'-OMe modified nucleotide
misc_feature            20
                        note = 2'-F modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 70
tttctcagat tttacttcca cct                                           23

SEQ ID NO: 71           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
```

```
misc_feature           8
                       note = 2'-OMe modified nucleotide
misc_feature           9
                       note = 2'-F modified nucleotide
misc_feature           10
                       note = 2'-F modified nucleotide
misc_feature           11
                       note = 2'-F modified nucleotide
misc_feature           12
                       note = 2'-OMe modified nucleotide
misc_feature           13
                       note = 2'-O-C16 alkyl modified nucleotide
misc_feature           14
                       note = 2'-OMe modified nucleotide
misc_feature           15
                       note = 2'-F modified nucleotide
misc_feature           16
                       note = 2'-OMe modified nucleotide
misc_feature           17
                       note = 2'-OMe modified nucleotide
misc_feature           18
                       note = 2'-OMe modified nucleotide
misc_feature           19
                       note = 2'-OMe modified nucleotide with a
                        3'-phosphorothioate linkage
misc_feature           20
                       note = 2'-OMe modified nucleotide with a
                        3'-phosphorothioate linkage
misc_feature           21
                       note = 2'-OMe modified nucleotide
source                 1..21
                       mol_type = other RNA
                       organism = synthetic construct
SEQUENCE: 71
gtggaagtaa aatctgagaa a                                            21

SEQ ID NO: 72          moltype = RNA  length = 23
FEATURE                Location/Qualifiers
misc_feature           1..23
                       note = Description of Artificial Sequence: Synthetic
                        oligonucleotide
misc_feature           1
                       note = 2'-OMe modified nucleotide with a
                        3'-phosphorothioate linkage and a 5'-vinylphosphonate
                        substitution
misc_feature           2
                       note = 2'-F modified nucleotide with a 3'-phosphorothioate
                        linkage
misc_feature           3
                       note = 2'-OMe modified nucleotide
misc_feature           4
                       note = 2'-OMe modified nucleotide
misc_feature           5
                       note = 2'-F modified nucleotide
misc_feature           6
                       note = 2'-OMe modified nucleotide
misc_feature           7
                       note = 2'-F modified nucleotide
misc_feature           8
                       note = 2'-OMe modified nucleotide
misc_feature           9
                       note = 2'-OMe modified nucleotide
misc_feature           10
                       note = 2'-OMe modified nucleotide
misc_feature           11
                       note = 2'-OMe modified nucleotide
misc_feature           12
                       note = 2'-OMe modified nucleotide
misc_feature           13
                       note = 2'-OMe modified nucleotide
misc_feature           14
                       note = 2'-F modified nucleotide
misc_feature           15
                       note = 2'-OMe modified nucleotide
misc_feature           16
                       note = 2'-F modified nucleotide
misc_feature           17
                       note = 2'-OMe modified nucleotide
misc_feature           18
```

-continued

```
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 72
tttctcagat tttacttcca cct                                            23

SEQ ID NO: 73           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-F modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-F modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 73
```

-continued

```
tttctcagat tttacttcca cct                                         23

SEQ ID NO: 74           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-F modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 74
tttctcagat tttacttcca cct                                         23

SEQ ID NO: 75           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
```

```
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-O-C16 alkyl modified nucleotide
misc_feature            13
                        note = 2'-F modified nucleotide
misc_feature            14
                        note = 2'-OMe modified nucleotide
misc_feature            15
                        note = 2'-F modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 75
gtggaagtaa aatctgagaa a                                            21

SEQ ID NO: 76           moltype = RNA  length = 21
FEATURE                 Location/Qualifiers
misc_feature            1..21
                        note = Description of Artificial Sequence: Synthetic
                         oligonucleotide
misc_feature            1
                        note = 2'-O-C16 alkyl modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
```

```
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 76
gtggaagtaa aatctgagaa a                                              21

SEQ ID NO: 77         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-O-C16 alkyl modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 77
gtggaagtaa aatctgagaa a                                              21

SEQ ID NO: 78         moltype = RNA  length = 21
FEATURE               Location/Qualifiers
```

```
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-O-C16 alkyl modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 78
gtggaagtaa aatctgagaa a                                              21

SEQ ID NO: 79         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-O-C16 alkyl modified nucleotide
misc_feature          7
                      note = 2'-OMe modified nucleotide
misc_feature          8
                      note = 2'-OMe modified nucleotide
misc_feature          9
```

```
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 79
gtggaagtaa aatctgagaa a                                               21

SEQ ID NO: 80           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-O-C16 alkyl modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
```

-continued

```
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 80
gtggaagtaa aatctgagaa a                                            21

SEQ ID NO: 81           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-O-C16 alkyl modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 81
gtggaagtaa aatctgagaa a                                            21

SEQ ID NO: 82           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
```

```
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified nucleotide
misc_feature          10
                      note = 2'-O-C16 alkyl modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 82
gtggaagtaa aatctgagaa a                                            21

SEQ ID NO: 83         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
```

```
misc_feature         14
                     note = 2'-OMe modified nucleotide
misc_feature         15
                     note = 2'-O-C16 alkyl modified nucleotide
misc_feature         16
                     note = 2'-OMe modified nucleotide
misc_feature         17
                     note = 2'-OMe modified nucleotide
misc_feature         18
                     note = 2'-OMe modified nucleotide
misc_feature         19
                     note = 2'-OMe modified nucleotide with a
                      3'-phosphorothioate linkage
misc_feature         20
                     note = 2'-OMe modified nucleotide with a
                      3'-phosphorothioate linkage
misc_feature         21
                     note = 2'-OMe modified nucleotide
source               1..21
                     mol_type = other RNA
                     organism = synthetic construct
SEQUENCE: 83
gtggaagtaa aatctgagaa a                                            21

SEQ ID NO: 84        moltype = RNA  length = 21
FEATURE              Location/Qualifiers
misc_feature         1..21
                     note = Description of Artificial Sequence: Synthetic
                      oligonucleotide
misc_feature         1
                     note = 2'-OMe modified nucleotide with a
                      3'-phosphorothioate linkage
misc_feature         2
                     note = 2'-OMe modified nucleotide with a
                      3'-phosphorothioate linkage
misc_feature         3
                     note = 2'-OMe modified nucleotide
misc_feature         4
                     note = 2'-OMe modified nucleotide
misc_feature         5
                     note = 2'-OMe modified nucleotide
misc_feature         6
                     note = 2'-OMe modified nucleotide
misc_feature         7
                     note = 2'-OMe modified nucleotide
misc_feature         8
                     note = 2'-OMe modified nucleotide
misc_feature         9
                     note = 2'-F alkyl modified nucleotide
misc_feature         10
                     note = 2'-F modified nucleotide
misc_feature         11
                     note = 2'-F modified nucleotide
misc_feature         12
                     note = 2'-OMe modified nucleotide
misc_feature         13
                     note = 2'-OMe modified nucleotide
misc_feature         14
                     note = 2'-OMe modified nucleotide
misc_feature         15
                     note = 2'-OMe modified nucleotide
misc_feature         16
                     note = 2'-OMe modified nucleotide
misc_feature         17
                     note = 2'-OMe modified nucleotide
misc_feature         18
                     note = 2'-OMe modified nucleotide
misc_feature         19
                     note = 2'-O-C16 alkyl modified nucleotide with a
                      3'-phosphorothioate linkage
misc_feature         20
                     note = 2'-OMe modified nucleotide with a
                      3'-phosphorothioate linkage
misc_feature         21
                     note = 2'-OMe modified nucleotide
source               1..21
                     mol_type = other RNA
                     organism = synthetic construct
SEQUENCE: 84
```

```
gtggaagtaa aatctgagaa a                                              21

SEQ ID NO: 85          moltype = RNA  length = 21
FEATURE                Location/Qualifiers
misc_feature           1..21
                       note = Description of Artificial Sequence: Synthetic
                        oligonucleotide
misc_feature           1
                       note = 2'-OMe modified nucleotide with a
                        3'-phosphorothioate linkage
misc_feature           2
                       note = 2'-OMe modified nucleotide with a
                        3'-phosphorothioate linkage
misc_feature           3
                       note = 2'-OMe modified nucleotide
misc_feature           4
                       note = 2'-OMe modified nucleotide
misc_feature           5
                       note = 2'-OMe modified nucleotide
misc_feature           6
                       note = 2'-OMe modified nucleotide
misc_feature           7
                       note = 2'-OMe modified nucleotide
misc_feature           8
                       note = 2'-OMe modified nucleotide
misc_feature           9
                       note = 2'-F modified nucleotide
misc_feature           10
                       note = 2'-F modified nucleotide
misc_feature           11
                       note = 2'-F modified nucleotide
misc_feature           12
                       note = 2'-OMe modified nucleotide
misc_feature           13
                       note = 2'-OMe modified nucleotide
misc_feature           14
                       note = 2'-OMe modified nucleotide
misc_feature           15
                       note = 2'-OMe modified nucleotide
misc_feature           16
                       note = 2'-OMe modified nucleotide
misc_feature           17
                       note = 2'-OMe modified nucleotide
misc_feature           18
                       note = 2'-OMe modified nucleotide
misc_feature           19
                       note = 2'-OMe modified nucleotide with a
                        3'-phosphorothioate linkage
misc_feature           20
                       note = 2'-O-C16 alkyl modified nucleotide with a
                        3'-phosphorothioate linkage
misc_feature           21
                       note = 2'-OMe modified nucleotide
source                 1..21
                       mol_type = other RNA
                       organism = synthetic construct
SEQUENCE: 85
gtggaagtaa aatctgagaa a                                              21

SEQ ID NO: 86          moltype = RNA  length = 21
FEATURE                Location/Qualifiers
misc_feature           1..21
                       note = Description of Artificial Sequence: Synthetic
                        oligonucleotide
misc_feature           1
                       note = 2'-OMe modified nucleotide with a
                        3'-phosphorothioate linkage
misc_feature           2
                       note = 2'-OMe modified nucleotide with a
                        3'-phosphorothioate linkage
misc_feature           3
                       note = 2'-OMe modified nucleotide
misc_feature           4
                       note = 2'-OMe modified nucleotide
misc_feature           5
                       note = 2'-OMe modified nucleotide
misc_feature           6
                       note = 2'-OMe modified nucleotide
misc_feature           7
```

-continued

```
                        note = 2'-OMe modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-O-C16 alkyl modified nucleotide
source                  1..21
                        mol_type = other RNA
                        organism = synthetic construct
SEQUENCE: 86
gtggaagtaa aatctgagaa a                                             21

SEQ ID NO: 87           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-O-C16 alkyl modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
```

```
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 87
ccaagtgtgg ctcattaggc a                                             21

SEQ ID NO: 88           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-F modified nucleotide
misc_feature            6
                        note = 2'-OMe modified nucleotide
misc_feature            7
                        note = 2'-OMe modified nucleotide
misc_feature            8
                        note = 2'-F modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 88
tgcctaatga gccacacttg gag                                           23

SEQ ID NO: 89           moltype = RNA  length = 21
FEATURE                 Location/Qualifiers
```

```
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = n is an abasic nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 89
ccaagtgtng ctcattaggc a                                              21

SEQ ID NO: 90         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
```

```
                        note = n is an abasic mucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-O-C16 alkyl modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 90
tgcaaatant ctacaaacca a                                             21

SEQ ID NO: 91           moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-F modified nucleotide
misc_feature            6
                        note = 2'-OMe modified nucleotide
misc_feature            7
                        note = 2'-OMe modified nucleotide
misc_feature            8
                        note = 2'-F modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
```

-continued

```
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 91
ttggtttgta gactatttgc acc                                            23

SEQ ID NO: 92           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified mucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-O-C16 alkyl modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 92
tgcaaatagt ctacaaacca a                                              21

SEQ ID NO: 93           moltype = RNA  length = 21
FEATURE                 Location/Qualifiers
misc_feature            1..21
                        note = Description of Artificial Sequence: Synthetic
                         oligonucleotide
misc_feature            1
```

```
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-O-C16 alkyl modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified mucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 93
gtggaagtaa aatctgagaa a                                              21

SEQ ID NO: 94           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-O-C16 alkyl modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified mucleotide
misc_feature            10
                        note = 2'-F modified nucleotide
misc_feature            11
```

```
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 94
gtggaagtaa aatctgagaa a                                          21

SEQ ID NO: 95         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-O-C16 alkyl modified nucleotide
misc_feature          8
                      note = 2'-OMe modified nucleotide
misc_feature          9
                      note = 2'-F modified mucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
```

```
                         note = 2'-OMe modified nucleotide
source                   1..21
                         mol_type = other RNA
                         organism = synthetic construct
SEQUENCE: 95
gtggaagtaa aatctgagaa a                                              21

SEQ ID NO: 96            moltype = RNA  length = 21
FEATURE                  Location/Qualifiers
misc_feature             1..21
                         note = Description of Artificial Sequence: Synthetic
                          oligonucleotide
misc_feature             1
                         note = 2'-OMe modified nucleotide with a
                          3'-phosphorothioate linkage
misc_feature             2
                         note = 2'-OMe modified nucleotide with a
                          3'-phosphorothioate linkage
misc_feature             3
                         note = 2'-OMe modified nucleotide
misc_feature             4
                         note = 2'-OMe modified nucleotide
misc_feature             5
                         note = 2'-OMe modified nucleotide
misc_feature             6
                         note = 2'-OMe modified nucleotide
misc_feature             7
                         note = 2'-OMe modified nucleotide
misc_feature             8
                         note = 2'-OMe modified nucleotide
misc_feature             9
                         note = 2'-F modified mucleotide
misc_feature             10
                         note = 2'-F modified nucleotide
misc_feature             11
                         note = 2'-O-C16 alkyl modified nucleotide
misc_feature             12
                         note = 2'-OMe modified nucleotide
misc_feature             13
                         note = 2'-OMe modified nucleotide
misc_feature             14
                         note = 2'-OMe modified nucleotide
misc_feature             15
                         note = 2'-OMe modified nucleotide
misc_feature             16
                         note = 2'-OMe modified nucleotide
misc_feature             17
                         note = 2'-OMe modified nucleotide
misc_feature             18
                         note = 2'-OMe modified nucleotide
misc_feature             19
                         note = 2'-OMe modified nucleotide with a
                          3'-phosphorothioate linkage
misc_feature             20
                         note = 2'-OMe modified nucleotide with a
                          3'-phosphorothioate linkage
misc_feature             21
                         note = 2'-OMe modified nucleotide
source                   1..21
                         mol_type = other RNA
                         organism = synthetic construct
SEQUENCE: 96
gtggaagtaa aatctgagaa a                                              21

SEQ ID NO: 97            moltype = RNA  length = 21
FEATURE                  Location/Qualifiers
misc_feature             1..21
                         note = Description of Artificial Sequence: Synthetic
                          oligonucleotide
misc_feature             1
                         note = 2'-OMe modified nucleotide with a
                          3'-phosphorothioate linkage
misc_feature             2
                         note = 2'-OMe modified nucleotide with a
                          3'-phosphorothioate linkage
misc_feature             3
                         note = 2'-OMe modified nucleotide
misc_feature             4
                         note = 2'-OMe modified nucleotide
```

```
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified mucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-O-C16 alkyl modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 97
gtggaagtaa aatctgagaa a                                              21

SEQ ID NO: 98           moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified mucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
```

```
misc_feature          16
                      note = 2'-O-C16 alkyl modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 98
gtggaagtaa aatctgagaa a                                            21

SEQ ID NO: 99         moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified mucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-O-C16 alkyl modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 99
gtggaagtaa aatctgagaa a                                            21

SEQ ID NO: 100        moltype = RNA  length = 21
FEATURE               Location/Qualifiers
```

-continued

```
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified mucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-O-C16 alkyl modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 100
gtggaagtaa aatctgagaa a                                              21

SEQ ID NO: 101        moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
```

```
                         note = 2'-F modified mucleotide
misc_feature             10
                         note = 2'-F modified nucleotide
misc_feature             11
                         note = 2'-F modified nucleotide
misc_feature             12
                         note = 2'-OMe modified nucleotide
misc_feature             13
                         note = 2'-O-C16 alkyl modified nucleotide
misc_feature             14
                         note = 2'-OMe modified nucleotide
misc_feature             15
                         note = 2'-OMe modified nucleotide
misc_feature             16
                         note = 2'-OMe modified nucleotide
misc_feature             17
                         note = 2'-OMe modified nucleotide
misc_feature             18
                         note = 2'-OMe modified nucleotide
misc_feature             19
                         note = 2'-OMe modified nucleotide with a
                          3'-phosphorothioate linkage
misc_feature             20
                         note = 2'-OMe modified nucleotide with a
                          3'-phosphorothioate linkage
misc_feature             21
                         note = 2'-OMe modified nucleotide
source                   1..21
                         mol_type = other RNA
                         organism = synthetic construct
SEQUENCE: 101
ccaggtggaa gtaaaatctg a                                          21

SEQ ID NO: 102           moltype = RNA  length = 23
FEATURE                  Location/Qualifiers
misc_feature             1..23
                         note = Description of Artificial Sequence: Synthetic
                          oligonucleotide
misc_feature             1
                         note = 2'-OMe modified nucleotide with a
                          3'-phosphorothioate linkage and a 5'-vinylphosphonate
                          substitution
misc_feature             2
                         note = 2'-F modified nucleotide with a 3'-phosphorothioate
                          linkage
misc_feature             3
                         note = 2'-OMe modified nucleotide
misc_feature             4
                         note = 2'-OMe modified nucleotide
misc_feature             5
                         note = 2'-F modified nucleotide
misc_feature             6
                         note = 2'-OMe modified nucleotide
misc_feature             7
                         note = 2'-OMe modified nucleotide
misc_feature             8
                         note = 2'-F modified nucleotide
misc_feature             9
                         note = 2'-OMe modified nucleotide
misc_feature             10
                         note = 2'-OMe modified nucleotide
misc_feature             11
                         note = 2'-OMe modified nucleotide
misc_feature             12
                         note = 2'-OMe modified nucleotide
misc_feature             13
                         note = 2'-OMe modified nucleotide
misc_feature             14
                         note = 2'-F modified nucleotide
misc_feature             15
                         note = 2'-OMe modified nucleotide
misc_feature             16
                         note = 2'-F modified nucleotide
misc_feature             17
                         note = 2'-OMe modified nucleotide
misc_feature             18
                         note = 2'-OMe modified nucleotide
misc_feature             19
                         note = 2'-OMe modified nucleotide
```

```
misc_feature          20
                      note = 2'-OMe modified nucleotide
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
                      note = 2'-OMe modified nucleotide
source                1..23
                      mol_type = other RNA
                      organism = synthetic construct
SEQUENCE: 102
tcagatttta cttccacctg gcc                                          23

SEQ ID NO: 103        moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-F modified mucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-O-C16 alkyl modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide
source                1..21
                      mol_type = other RNA
                      organism = synthetic construct
SEQUENCE: 103
ggaagtaaaa tctgagaagc a                                            21

SEQ ID NO: 104        moltype = RNA  length = 23
FEATURE               Location/Qualifiers
misc_feature          1..23
                      note = Description of Artificial Sequence: Synthetic
                       oligonucleotide
misc_feature          1
```

-continued

```
                         note = 2'-OMe modified nucleotide with a
                          3'-phosphorothioate linkage and a 5'-vinylphosphonate
                          substitution
misc_feature             2
                         note = 2'-F modified nucleotide with a 3'-phosphorothioate
                          linkage
misc_feature             3
                         note = 2'-OMe modified nucleotide
misc_feature             4
                         note = 2'-OMe modified nucleotide
misc_feature             5
                         note = 2'-F modified nucleotide
misc_feature             6
                         note = 2'-OMe modified nucleotide
misc_feature             7
                         note = 2'-OMe modified nucleotide
misc_feature             8
                         note = 2'-F modified nucleotide
misc_feature             9
                         note = 2'-OMe modified nucleotide
misc_feature             10
                         note = 2'-OMe modified nucleotide
misc_feature             11
                         note = 2'-OMe modified nucleotide
misc_feature             12
                         note = 2'-OMe modified nucleotide
misc_feature             13
                         note = 2'-OMe modified nucleotide
misc_feature             14
                         note = 2'-F modified nucleotide
misc_feature             15
                         note = 2'-OMe modified nucleotide
misc_feature             16
                         note = 2'-F modified nucleotide
misc_feature             17
                         note = 2'-OMe modified nucleotide
misc_feature             18
                         note = 2'-OMe modified nucleotide
misc_feature             19
                         note = 2'-OMe modified nucleotide
misc_feature             20
                         note = 2'-OMe modified nucleotide
misc_feature             21
                         note = 2'-OMe modified nucleotide with a
                          3'-phosphorothioate linkage
misc_feature             22
                         note = 2'-OMe modified nucleotide with a
                          3'-phosphorothioate linkage
misc_feature             23
                         note = 2'-OMe modified nucleotide
source                   1..23
                         mol_type = other RNA
                         organism = synthetic construct
SEQUENCE: 104
tgcttctcag attttacttc cac                                             23

SEQ ID NO: 105           moltype = RNA  length = 21
FEATURE                  Location/Qualifiers
misc_feature             1..21
                         note = Description of Artificial Sequence: Synthetic
                          oligonucleotide
misc_feature             1
                         note = 2'-OMe modified nucleotide with a
                          3'-phosphorothioate linkage
misc_feature             2
                         note = 2'-OMe modified nucleotide with a
                          3'-phosphorothioate linkage
misc_feature             3
                         note = 2'-OMe modified nucleotide
misc_feature             4
                         note = 2'-OMe modified nucleotide
misc_feature             5
                         note = 2'-OMe modified nucleotide
misc_feature             6
                         note = 2'-OMe modified nucleotide
misc_feature             7
                         note = 2'-F modified nucleotide
misc_feature             8
                         note = 2'-OMe modified nucleotide
```

```
misc_feature          9
                      note = 2'-F modified mucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide with a
                       3'-phosphorothioate linkage
misc_feature          21
                      note = 2'-OMe modified nucleotide with a
                       3'-phosphorothioate linkage
source                1..21
                      mol_type = other RNA
                      organism = synthetic construct
SEQUENCE: 105
gtggaagtaa aatctgagaa a                                          21

SEQ ID NO: 106        moltype = RNA  length = 23
FEATURE               Location/Qualifiers
misc_feature          1..23
                      note = Description of Artificial Sequence: Synthetic
                       oligonucleotide
misc_feature          1
                      note = 2'-OMe modified nucleotide with a
                       3'-phosphorothioate linkage and a 5'-vinylphosphonate
                       substitution
misc_feature          2
                      note = 2'-F modified nucleotide with a 3'-phosphorothioate
                       linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-OMe modified nucleotide
misc_feature          8
                      note = 2'-OMe modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide
misc_feature          18
                      note = 2'-OMe modified nucleotide
misc_feature          19
```

-continued

```
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 106
tttctcagat tttacttcca cct                                          23

SEQ ID NO: 107          moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-F modified nucleotide
misc_feature            5
                        note = 2'-OMe modified nucleotide
misc_feature            6
                        note = 2'-F modified nucleotide
misc_feature            7
                        note = 2'-F modified nucleotide
misc_feature            8
                        note = 2'-OMe modified nucleotide
misc_feature            9
                        note = 2'-F modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 107
tttctcagat tttacttcca cct                                          23
```

-continued

```
SEQ ID NO: 108          moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
misc_feature            3
                        note = 2'-OMe modified nucleotide
misc_feature            4
                        note = 2'-OMe modified nucleotide
misc_feature            5
                        note = 2'-F modified nucleotide
misc_feature            6
                        note = 2'-F modified nucleotide
misc_feature            7
                        note = 2'-F modified nucleotide
misc_feature            8
                        note = 2'-F modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-F modified nucleotide
misc_feature            15
                        note = 2'-OMe modified nucleotide
misc_feature            16
                        note = 2'-F modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide
misc_feature            21
                        note = 2'-OMe modified nucleotide with a
                         3'-phosphorothioate linkage
misc_feature            22
                        note = 2'-OMe modified nucleotide with a
                         3'-phosphorothioate linkage
misc_feature            23
                        note = 2'-OMe modified nucleotide
source                  1..23
                        mol_type = other RNA
                        organism = synthetic construct
SEQUENCE: 108
tttctcagat tttacttcca cct                                          23

SEQ ID NO: 109          moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
```

```
misc_feature          6
                      note = 2'-OMe modified nucleotide
misc_feature          7
                      note = 2'-F modified nucleotide
misc_feature          8
                      note = 2'-OMe modified nucleotide
misc_feature          9
                      note = 2'-F modified mucleotide
misc_feature          10
                      note = n is an abasic nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide with a
                       3'-phosphorothioate linkage
misc_feature          21
                      note = 2'-OMe modified nucleotide with a
                       3'-phosphorothioate linkage
source                1..21
                      mol_type = other RNA
                      organism = synthetic construct
SEQUENCE: 109
gtggaagtan aatctgagaa a                                             21

SEQ ID NO: 110        moltype = RNA  length = 21
FEATURE               Location/Qualifiers
misc_feature          1..21
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-F modified nucleotide
misc_feature          8
                      note = 2'-OMe modified nucleotide
misc_feature          9
                      note = 2'-F modified nucleotide
misc_feature          10
                      note = 2'-F modified nucleotide
misc_feature          11
                      note = 2'-F modified nucleotide
misc_feature          12
                      note = 2'-OMe modified nucleotide
misc_feature          13
                      note = 2'-OMe modified nucleotide
misc_feature          14
                      note = 2'-OMe modified nucleotide
misc_feature          15
                      note = 2'-OMe modified nucleotide
misc_feature          16
                      note = 2'-OMe modified nucleotide
```

```
misc_feature            17
                        note = 2'-OMe modified nucleotide
misc_feature            18
                        note = 2'-OMe modified nucleotide
misc_feature            19
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
source                  1..21
                        mol_type = other RNA
                        organism = synthetic construct
SEQUENCE: 110
gtggaagtaa aatctgagaa g                                            21

SEQ ID NO: 111          moltype = RNA  length = 17
FEATURE                 Location/Qualifiers
misc_feature            1..17
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-F modified nucleotide
misc_feature            4
                        note = 2'-OMe modified nucleotide
misc_feature            5
                        note = 2'-F modified nucleotide
misc_feature            6
                        note = 2'-F modified nucleotide
misc_feature            7
                        note = 2'-F modified nucleotide
misc_feature            8
                        note = 2'-OMe modified nucleotide
misc_feature            9
                        note = 2'-OMe modified nucleotide
misc_feature            10
                        note = 2'-OMe modified nucleotide
misc_feature            11
                        note = 2'-OMe modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide with a
                         3'-phosphorothioate linkage
misc_feature            16
                        note = 2'-OMe modified nucleotide with a
                         3'-phosphorothioate linkage
misc_feature            17
                        note = 2'-OMe modified nucleotide
source                  1..17
                        mol_type = other RNA
                        organism = synthetic construct
SEQUENCE: 111
aagtaaaatc tgagaaa                                                 17

SEQ ID NO: 112          moltype = RNA  length = 23
FEATURE                 Location/Qualifiers
misc_feature            1..23
                        note = Description of Artificial Sequence: Synthetic
                         oligonucleotide
misc_feature            1
                        note = 2'-OMe modified nucleotide with a
                         3'-phosphorothioate linkage and a 5'-vinylphosphonate
                         substitution
misc_feature            2
                        note = 2'-F modified nucleotide with a 3'-phosphorothioate
                         linkage
```

```
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-F modified nucleotide
misc_feature          7
                      note = 2'-OMe modified nucleotide
misc_feature          8
                      note = 2'-OMe modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide with a
                       3'-phosphorothioate linkage
misc_feature          18
                      note = 2'-OMe modified nucleotide with a
                       3'-phosphorothioate linkage
misc_feature          19
                      note = 2'-OMe modified nucleotide with a
                       3'-phosphorothioate linkage
misc_feature          20
                      note = 2'-OMe modified nucleotide with a
                       3'-phosphorothioate linkage
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
                      note = 2'-OMe modified nucleotide
source                1..23
                      mol_type = other RNA
                      organism = synthetic construct
SEQUENCE: 112
tttctcagat tttacttcca cct                                         23

SEQ ID NO: 113        moltype = RNA  length = 23
FEATURE               Location/Qualifiers
misc_feature          1..23
                      note = Description of Artificial Sequence: Synthetic
                       oligonucleotide
misc_feature          1
                      note = 2'-OMe modified nucleotide with a
                       3'-phosphorothioate linkage
misc_feature          2
                      note = 2'-OMe modified nucleotide with a
                       3'-phosphorothioate linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-OMe modified nucleotide
misc_feature          7
                      note = 2'-F modified nucleotide
misc_feature          8
                      note = 2'-OMe modified nucleotide
misc_feature          9
                      note = 2'-F modified nucleotide
```

```
misc_feature           10
                       note = 2'-F modified nucleotide
misc_feature           11
                       note = 2'-F modified nucleotide
misc_feature           12
                       note = 2'-OMe modified nucleotide
misc_feature           13
                       note = 2'-OMe modified nucleotide
misc_feature           14
                       note = 2'-OMe modified nucleotide
misc_feature           15
                       note = 2'-OMe modified nucleotide
misc_feature           16
                       note = 2'-OMe modified nucleotide
misc_feature           17
                       note = 2'-OMe modified nucleotide
misc_feature           18
                       note = 2'-OMe modified nucleotide
misc_feature           19
                       note = 2'-OMe modified nucleotide
misc_feature           20
                       note = 2'-OMe modified nucleotide
misc_feature           21
                       note = 2'-OMe modified nucleotide
misc_feature           22
                       note = t is thymine
misc_feature           23
                       note = t is thymine with a 3'-phosphorothioate linkage
source                 1..23
                       mol_type = other RNA
                       organism = synthetic construct
SEQUENCE: 113
gtggaagtaa aatctgagaa att                                          23

SEQ ID NO: 114         moltype = RNA  length = 23
FEATURE                Location/Qualifiers
misc_feature           1..23
                       note = Description of Artificial Sequence: Synthetic
                        oligonucleotide
misc_feature           1
                       note = 2'-OMe modified nucleotide with a
                        3'-phosphorothioate linkage and a 5'-vinylphosphonate
                        substitution
misc_feature           2
                       note = 2'-F modified nucleotide with a 3'-phosphorothioate
                        linkage
misc_feature           3
                       note = 2'-OMe modified nucleotide
misc_feature           4
                       note = 2'-OMe modified nucleotide
misc_feature           5
                       note = 2'-OMe modified nucleotide
misc_feature           6
                       note = 2'-F modified nucleotide
misc_feature           7
                       note = 2'-OMe modified nucleotide
misc_feature           8
                       note = 2'-OMe modified nucleotide
misc_feature           9
                       note = 2'-OMe modified nucleotide
misc_feature           10
                       note = 2'-OMe modified nucleotide
misc_feature           11
                       note = 2'-OMe modified nucleotide
misc_feature           12
                       note = 2'-OMe modified nucleotide
misc_feature           13
                       note = 2'-OMe modified nucleotide
misc_feature           14
                       note = 2'-F modified nucleotide
misc_feature           15
                       note = 2'-OMe modified nucleotide
misc_feature           16
                       note = 2'-F modified nucleotide
misc_feature           17
                       note = 2'-OMe modified nucleotide
misc_feature           18
                       note = 2'-OMe modified nucleotide
misc_feature           19
```

```
                        note = 2'-OMe modified nucleotide with a
                         3'-phosphorothioate linkage
misc_feature            20
                        note = 2'-OMe modified nucleotide with a
                         3'-phosphorothioate linkage
misc_feature            21
                        note = 2'-OMe modified nucleotide
misc_feature            22
                        note = t is thymine
misc_feature            23
                        note = t is thymine
source                  1..23
                        mol_type = other RNA
                        organism = synthetic construct
SEQUENCE: 114
tttctcagat tttacttcca ctt                                           23

SEQ ID NO: 115          moltype = RNA  length = 21
FEATURE                 Location/Qualifiers
misc_feature            1..21
                        note = Description of Artificial Sequence: Synthetic
                         oligonucleotide
misc_feature            1
                        note = 2'-OMe modified nucleotide with a
                         3'-phosphorothioate linkage
misc_feature            2
                        note = 2'-OMe modified nucleotide with a
                         3'-phosphorothioate linkage
misc_feature            3
                        note = 2'-OMe modified nucleotide
misc_feature            4
                        note = 2'-OMe modified nucleotide
misc_feature            5
                        note = 2'-OMe modified nucleotide
misc_feature            6
                        note = 2'-OMe modified nucleotide
misc_feature            7
                        note = 2'-OMe modified nucleotide
misc_feature            8
                        note = 2'-OMe modified nucleotide
misc_feature            9
                        note = 2'-F modified nucleotide
misc_feature            10
                        note = 2'-F modified nucleotide
misc_feature            11
                        note = 2'-F modified nucleotide
misc_feature            12
                        note = 2'-OMe modified nucleotide
misc_feature            13
                        note = 2'-OMe modified nucleotide
misc_feature            14
                        note = 2'-OMe modified nucleotide
misc_feature            15
                        note = 2'-OMe modified nucleotide
misc_feature            16
                        note = 2'-OMe modified nucleotide
misc_feature            17
                        note = 2'-OMe modified nucleotide
misc_feature            18
                        note = 2'-OMe modified nucleotide
misc_feature            19
                        note = 2'-OMe modified nucleotide
misc_feature            20
                        note = 2'-OMe modified nucleotide with a
                         3'-phosphorothioate linkage
misc_feature            21
                        note = 2'-OMe modified nucleotide with a
                         3'-phosphorothioate linkage
source                  1..21
                        mol_type = other RNA
                        organism = synthetic construct
SEQUENCE: 115
gtggaagtaa aatctgagaa a                                             21

SEQ ID NO: 116          moltype = RNA  length = 23
FEATURE                 Location/Qualifiers
misc_feature            1..23
                        note = Description of Artificial Sequence: Synthetic
                         oligonucleotide
```

```
misc_feature          1
                      note = 2'-OMe modified nucleotide with a
                       3'-phosphorothioate linkage and a 5'-vinylphosphonate
                       substitution
misc_feature          2
                      note = 2'-F modified nucleotide with a 3'-phosphorothioate
                       linkage
misc_feature          3
                      note = 2'-OMe modified nucleotide
misc_feature          4
                      note = 2'-OMe modified nucleotide
misc_feature          5
                      note = 2'-OMe modified nucleotide
misc_feature          6
                      note = 2'-F modified nucleotide
misc_feature          7
                      note = 2'-OMe modified nucleotide
misc_feature          8
                      note = 2'-OMe modified nucleotide
misc_feature          9
                      note = 2'-OMe modified nucleotide
misc_feature          10
                      note = 2'-OMe modified nucleotide
misc_feature          11
                      note = 2'-OMe modified nucleotide
misc_feature          12
                      note = 2'-OMe modified nucleotide
misc_feature          13
                      note = 2'-OMe modified nucleotide
misc_feature          14
                      note = 2'-F modified nucleotide
misc_feature          15
                      note = 2'-OMe modified nucleotide
misc_feature          16
                      note = 2'-F modified nucleotide
misc_feature          17
                      note = 2'-OMe modified nucleotide
misc_feature          18
                      note = 2'-OMe modified nucleotide
misc_feature          19
                      note = 2'-OMe modified nucleotide
misc_feature          20
                      note = 2'-OMe modified nucleotide with a
                       3'-phosphorothioate linkage
misc_feature          21
                      note = 2'-OMe modified nucleotide with a
                       3'-phosphorothioate linkage
misc_feature          22
                      note = 2'-OMe modified nucleotide with a
                       3'-phosphorothioate linkage
misc_feature          23
                      note = 2'-OMe modified nucleotide
source                1..23
                      mol_type = other RNA
                      organism = synthetic construct
SEQUENCE: 116
tttctcagat tttacttcca cct                                         23

SEQ ID NO: 117        moltype = RNA  length = 23
FEATURE               Location/Qualifiers
misc_feature          1..23
                      note = Description of Artificial Sequence: Synthetic
                       oligonucleotide
misc_feature          22
                      note = t is thymine
misc_feature          23
                      note = t is thymine
source                1..23
                      mol_type = other RNA
                      organism = synthetic construct
SEQUENCE: 117
gtggaagtaa aatctgagaa att                                         23

SEQ ID NO: 118        moltype = RNA  length = 23
FEATURE               Location/Qualifiers
misc_feature          1..23
                      note = Description of Artificial Sequence: Synthetic
                       oligonucleotide
misc_feature          22
```

-continued

```
                           note = t is thymine
misc_feature               23
                           note = t is thymine
source                     1..23
                           mol_type = other RNA
                           organism = synthetic construct
SEQUENCE: 118
tttctcagat tttacttcca ctt                                      23

SEQ ID NO: 119             moltype = RNA  length = 21
FEATURE                    Location/Qualifiers
misc_feature               1..21
                           note = Description of Artificial Sequence: Synthetic
                            oligonucleotide
source                     1..21
                           mol_type = other RNA
                           organism = synthetic construct
SEQUENCE: 119
gtggaagtaa aatctgagaa g                                        21
```

MAPT RNA INTERFERENCE AGENTS

SEQUENCE LISTING

The present application is being filed along with a Sequence Listing in ST.26 XML format. The Sequence Listing is provided as a file titled "30170" created 2 Nov. 2022 and is 835 kilobytes in size. The Sequence Listing information in the ST.26 XML format is incorporated herein by reference in its entirety.

BACKGROUND

Microtubule associated protein Tau is encoded by the MAPT gene located on chromosome 17. Tau protein interacts with tubulin to stabilize the microtubules and promote tubulin assembly into microtubules. MAPT transcripts are differentially expressed throughout the body, predominantly in the central and peripheral nervous system.

The MAPT gene consists of 16 exons. Alternative mRNA splicing gives rise to multiple MAPT isoforms. At least six Tau isoforms exist in human brain, ranging from 352 to 441 amino acids long. Alternative splicing of exons 2 and/or 3 leads to inclusion of zero, one, or two copies of the N-terminal acidic domain, which are referred to as 0N, 1N, or 2N Tau, respectively. The Tau isoforms that include exon 10, which encodes an additional microtubule-binding domain, are referred to as "4R Tau", as it has four microtubule-binding domains. The Tau isoforms without exon 10 are referred to as "3R Tau", as it has three microtubule-binding domains.

Mutations in MAPT and hyperphosphorylation of Tau protein can cause aggregation and deposition of Tau in pathogenic neurofibrillary tangles, causing progressive neurodegenerative disorders such as Alzheimer's disease, frontotemporal dementia (FTD), progressive supranuclear palsy (PSP), and other tauopathies.

RNA interference (RNAi) is a highly conserved regulatory mechanism in which RNA molecules are involved in sequence-specific suppression of gene expression by double-stranded RNA molecules (dsRNA) (Fire et al., Nature 391:806-811, 1998).

There are currently no FDA-approved disease-modifying therapeutic agents specifically for reducing MAPT and treating tauopathies. Aducanumab, which targets amyloid beta protein (AB), is the only disease-modifying medication currently approved to treat Alzheimer's disease. Accordingly, there remains a need for therapeutic agents that can inhibit or adjust the expression of the MAPT gene for treating tauopathies, e.g., by utilizing RNAi.

SUMMARY OF INVENTION

Provided herein are MAPT RNAi agents and compositions comprising a MAPT RNAi agent. Also provided herein are methods of using the MAPT RNAi agents or compositions comprising a MAPT RNAi agent for reducing MAPT expression and/or treating tauopathy in a subject.

In one aspect, provided herein are MAPT RNAi agents having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence having at least 95% sequence identity to SEQ ID NO: 1, and the antisense strand comprises a second nucleic acid sequence having at least 95% sequence identity to SEQ ID NO: 2;

(b) the sense strand comprises a first nucleic acid sequence having at least 95% sequence identity to SEQ ID NO: 3, and the antisense strand comprises a second nucleic acid sequence having at least 95% sequence identity to SEQ ID NO: 4;

(c) the sense strand comprises a first nucleic acid sequence having at least 95% sequence identity to SEQ ID NO: 5, and the antisense strand comprises a second nucleic acid sequence having at least 95% sequence identity to SEQ ID NO: 6;

(d) the sense strand comprises a first nucleic acid sequence having at least 95% sequence identity to SEQ ID NO: 7, and the antisense strand comprises a second nucleic acid sequence having at least 95% sequence identity to SEQ ID NO: 8;

(e) the sense strand comprises a first nucleic acid sequence having at least 95% sequence identity to SEQ ID NO: 9, and the antisense strand comprises a second nucleic acid sequence having at least 95% sequence identity to SEQ ID NO: 10;

(f) the sense strand comprises a first nucleic acid sequence having at least 95% sequence identity to SEQ ID NO: 11, and the antisense strand comprises a second nucleic acid sequence having at least 95% sequence identity to SEQ ID NO: 12;

(g) the sense strand comprises a first nucleic acid sequence having at least 95% sequence identity to SEQ ID NO:13, and the antisense strand comprises a second nucleic acid sequence having at least 95% sequence identity to SEQ ID NO: 14;

(h) the sense strand comprises a first nucleic acid sequence having at least 95% sequence identity to SEQ ID NO:15, and the antisense strand comprises a second nucleic acid sequence having at least 95% sequence identity to SEQ ID NO: 16;

(i) the sense strand comprises a first nucleic acid sequence having at least 95% sequence identity to SEQ ID NO:17, and the antisense strand comprises a second nucleic acid sequence having at least 95% sequence identity to SEQ ID NO: 18;

(j) the sense strand comprises a first nucleic acid sequence having at least 95% sequence identity to SEQ ID NO:19, and the antisense strand comprises a second nucleic acid sequence having at least 95% sequence identity to SEQ ID NO: 20;

(k) the sense strand comprises a first nucleic acid sequence having at least 95% sequence identity to SEQ ID NO:21, and the antisense strand comprises a second nucleic acid sequence having at least 95% sequence identity to SEQ ID NO: 22; and (l) the sense strand comprises a first nucleic acid sequence having at least 95% sequence identity to SEQ ID NO:23, and the antisense strand comprises a second nucleic acid sequence having at least 95% sequence identity to SEQ ID NO: 24;

(m) the sense strand comprises a first nucleic acid sequence having at least 95% sequence identity to SEQ ID NO: 55, and the antisense strand comprises a second nucleic acid sequence having at least 95% sequence identity to SEQ ID NO: 16;

(n) the sense strand comprises a first nucleic acid sequence having at least 95% sequence identity to SEQ ID NO: 56, and the antisense strand comprises a second nucleic acid sequence having at least 95% sequence identity to SEQ ID NO: 16;

(o) the sense strand comprises a first nucleic acid sequence having at least 95% sequence identity to SEQ ID NO: 57, and the antisense strand comprises a second nucleic acid sequence having at least 95% sequence identity to SEQ ID NO: 58;

(p) the sense strand comprises a first nucleic acid sequence having at least 95% sequence identity to SEQ ID NO: 59, and the antisense strand comprises a second nucleic acid sequence having at least 95% sequence identity to SEQ ID NO: 58;

(q) the sense strand comprises a first nucleic acid sequence having at least 95% sequence identity to SEQ ID NO: 60, and the antisense strand comprises a second nucleic acid sequence having at least 95% sequence identity to SEQ ID NO: 61;

(r) the sense strand comprises a first nucleic acid sequence having at least 95% sequence identity to SEQ ID NO: 62, and the antisense strand comprises a second nucleic acid sequence having at least 95% sequence identity to SEQ ID NO: 61;

(s) the sense strand comprises a first nucleic acid sequence having at least 95% sequence identity to SEQ ID NO: 117, and the anti sense strand comprises a second nucleic acid sequence having at least 95% sequence identity to SEQ ID NO: 118; and (t) the sense strand comprises a first nucleic acid sequence having at least 95% sequence identity to SEQ ID NO: 119, and the antisense strand comprises a second nucleic acid sequence having at least 95% sequence identity to SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, the sense strand and the antisense strand of the MAPT RNAi agent described herein comprise a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12;

(g) the sense strand comprises a first nucleic acid sequence of SEQ ID NO:13, and the antisense strand comprises a second nucleic acid sequence of SEQ ID NO: 14;

(h) the sense strand comprises a first nucleic acid sequence of SEQ ID NO:15, and the antisense strand comprises a second nucleic acid sequence of SEQ ID NO: 16;

(i) the sense strand comprises a first nucleic acid sequence of SEQ ID NO:17, and the antisense strand comprises a second nucleic acid sequence of SEQ ID NO: 18;

(j) the sense strand comprises a first nucleic acid sequence of SEQ ID NO:19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118; and (t) the sense strand comprises a first nucleic acid sequence of SEQ ID NO: 119, and the antisense strand comprises a second nucleic acid sequence of SEQ ID NO: 16.

In some embodiments, the sense strand and the antisense strand of the MAPT RNAi agent described herein have a pair of nucleic acid sequences selected from the group consisting of:

(a) the sense strand has a first nucleic acid sequence of SEQ ID NO: 1, and the antisense strand has a second nucleic acid sequence of SEQ ID NO: 2;

(b) the sense strand has a first nucleic acid sequence of SEQ ID NO: 3, and the antisense strand has a second nucleic acid sequence of SEQ ID NO: 4;

(c) the sense strand has a first nucleic acid sequence of SEQ ID NO: 5, and the antisense strand has a second nucleic acid sequence of SEQ ID NO: 6;

(d) the sense strand has a first nucleic acid sequence of SEQ ID NO: 7, and the antisense strand has a second nucleic acid sequence of SEQ ID NO: 8;

(e) the sense strand has a first nucleic acid sequence of SEQ ID NO: 9, and the antisense strand has a second nucleic acid sequence of SEQ ID NO: 10;
(f) the sense strand has a first nucleic acid sequence of SEQ ID NO: 11, and the antisense strand has a second nucleic acid sequence of SEQ ID NO: 12;
(g) the sense strand has a first nucleic acid sequence of SEQ ID NO:13, and the antisense strand has a second nucleic acid sequence of SEQ ID NO: 14;
(h) the sense strand has a first nucleic acid sequence of SEQ ID NO:15, and the antisense strand has a second nucleic acid sequence of SEQ ID NO: 16;
(i) the sense strand has a first nucleic acid sequence of SEQ ID NO:17, and the antisense strand has a second nucleic acid sequence of SEQ ID NO: 18;
(j) the sense strand has a first nucleic acid sequence of SEQ ID NO:19, and the antisense strand has a second nucleic acid sequence of SEQ ID NO: 20;
(k) the sense strand has a first nucleic acid sequence of SEQ ID NO:21, and the antisense strand has a second nucleic acid sequence of SEQ ID NO: 22;
(l) the sense strand has a first nucleic acid sequence of SEQ ID NO:23, and the antisense strand has a second nucleic acid sequence of SEQ ID NO: 24;
(m) the sense strand has a first nucleic acid sequence of SEQ ID NO: 55, and the antisense strand has a second nucleic acid sequence of SEQ ID NO: 16;
(n) the sense strand has a first nucleic acid sequence of SEQ ID NO: 56, and the antisense strand has a second nucleic acid sequence of SEQ ID NO: 16;
(o) the sense strand has a first nucleic acid sequence of SEQ ID NO: 57, and the antisense strand has a second nucleic acid sequence of SEQ ID NO: 58;
(p) the sense strand has a first nucleic acid sequence of SEQ ID NO: 59, and the antisense strand has a second nucleic acid sequence of SEQ ID NO: 58;
(q) the sense strand has a first nucleic acid sequence of SEQ ID NO: 60, and the antisense strand has a second nucleic acid sequence of SEQ ID NO: 61;
(r) the sense strand has a first nucleic acid sequence of SEQ ID NO: 62, and the antisense strand has a second nucleic acid sequence of SEQ ID NO: 61;
(s) the sense strand has a first nucleic acid sequence of SEQ ID NO: 117, and the antisense strand has a second nucleic acid sequence of SEQ ID NO: 118; and
(t) the sense strand has a first nucleic acid sequence of SEQ ID NO: 119, and the antisense strand has a second nucleic acid sequence of SEQ ID NO: 16.

The MAPT RNAi agents described herein may include modifications. The modifications can be made to one or more nucleotides of the sense strand and/or antisense strand or to the internucleotide linkages. In some embodiments, one or more nucleotides of the sense strand are modified nucleotides. In some embodiments, each nucleotide of the sense strand is a modified nucleotide. In some embodiments, one or more nucleotides of the antisense strand are modified nucleotides. In some embodiments, each nucleotide of the antisense strand is a modified nucleotide. In some embodiments, the modified nucleotide is a 2'-fluoro modified nucleotide, 2'-O-methyl modified nucleotide, or 2'-O-alkyl modified nucleotide, e.g., 2'-O—C16 alkyl modified nucleotide. In some embodiments, the sense strand has four 2'-fluoro modified nucleotides at positions 7, 9, 10, 11 from the 5' end of the sense strand. In some embodiments, nucleotides at positions other than positions 7, 9, 10, and 11 of the sense strand are 2'-O-methyl modified nucleotides or 2'-O—C16 alkyl modified nucleotides. In some embodiments, the antisense strand has four 2'-fluoro modified nucleotides at positions 2, 6, 14, 16 from the 5' end of the antisense strand. In some embodiments, nucleotides at positions other than positions 2, 6, 14 and 16 of the antisense strand are 2'-O-methyl modified nucleotides or 2'-O—C16 alkyl modified nucleotides. In some embodiments, the sense strand has three 2'-fluoro modified nucleotides, e.g., at positions 9, 10, 11 from the 5' end of the sense strand. In some embodiments, the other nucleotides of the sense strand are 2'-O-methyl modified nucleotides. In some embodiments, the antisense strand has five 2'-fluoro modified nucleotides, e.g., at positions 2, 5, 7, 14, 16 from the 5' end of the antisense strand. In some embodiments, the antisense strand has five 2'-fluoro modified nucleotides, e.g., at positions 2, 5, 8, 14, 16 from the 5' end of the antisense strand. In some embodiments, the antisense strand has five 2'-fluoro modified nucleotides, e.g., at positions 2, 3, 7, 14, 16 from the 5' end of the antisense strand. In some embodiments, the other nucleotides of the antisense strand are 2'-O-methyl modified nucleotides. In some embodiments, the sense strand comprises an abasic moiety or inverted abasic moiety.

In some embodiments, the first nucleotide from the 5' end of the antisense strand is a modified nucleotide that has a phosphate analog, e.g., a 5'-vinylphosphonate. In some embodiments, the sense strand comprises an abasic moiety or inverted abasic moiety. In some embodiments, the sense strand and the antisense strand have one or more modified internucleotide linkages, e.g., phosphorothioate linkage. In some embodiments, the sense strand has four or five phosphorothioate linkages. In some embodiments, the antisense strand has four or five phosphorothioate linkages. In some embodiments, the sense strand has four phosphorothioate linkages and the antisense strand has four phosphorothioate linkages.

In some embodiments, provided herein are MAPT RNAi agents having a sense strand and an antisense strand, wherein the sense strand and the antisense strand form a duplex, wherein the sense strand and the antisense strand comprise a pair of nucleic acid sequences selected from the group consisting of:
(a) the sense strand comprises a first nucleic acid sequence of SEQ ID NO: 25, and the antisense strand comprises a second nucleic acid sequence of SEQ ID NO: 26;
(b) the sense strand comprises a first nucleic acid sequence of SEQ ID NO: 27, and the antisense strand comprises a second nucleic acid sequence of SEQ ID NO: 28;
(c) the sense strand comprises a first nucleic acid sequence of SEQ ID NO: 29, and the antisense strand comprises a second nucleic acid sequence of SEQ ID NO: 30;
(d) the sense strand comprises a first nucleic acid sequence of SEQ ID NO: 31, and the antisense strand comprises a second nucleic acid sequence of SEQ ID NO: 32;
(e) the sense strand comprises a first nucleic acid sequence of SEQ ID NO: 33, and the antisense strand comprises a second nucleic acid sequence of SEQ ID NO: 34;
(f) the sense strand comprises a first nucleic acid sequence of SEQ ID NO: 35, and the antisense strand comprises a second nucleic acid sequence of SEQ ID NO: 36;
(g) the sense strand comprises a first nucleic acid sequence of SEQ ID NO: 37, and the antisense strand comprises a second nucleic acid sequence of SEQ ID NO: 38;

(h) the sense strand comprises a first nucleic acid sequence of SEQ ID NO: 39, and the antisense strand comprises a second nucleic acid sequence of SEQ ID NO: 40;
(i) the sense strand comprises a first nucleic acid sequence of SEQ ID NO: 41, and the antisense strand comprises a second nucleic acid sequence of SEQ ID NO: 42;
(j) the sense strand comprises a first nucleic acid sequence of SEQ ID NO: 43, and the antisense strand comprises a second nucleic acid sequence of SEQ ID NO: 44;
(k) the sense strand comprises a first nucleic acid sequence of SEQ ID NO: 45, and the antisense strand comprises a second nucleic acid sequence of SEQ ID NO: 46;
(l) the sense strand comprises a first nucleic acid sequence of SEQ ID NO: 47, and the antisense strand comprises a second nucleic acid sequence of SEQ ID NO: 48;
(m) the sense strand comprises a first nucleic acid sequence of SEQ ID NO: 63, and the antisense strand comprises a second nucleic acid sequence of SEQ ID NO: 40;
(n) the sense strand comprises a first nucleic acid sequence selected from any one of SEQ ID NOs: 64, 66-69, 71, 75-86, 93-100, and the antisense strand comprises a second nucleic acid sequence of SEQ ID NO: 65;
(o) the sense strand comprises a first nucleic acid sequence of SEQ ID NO: 64, and the antisense strand comprises a second nucleic acid sequence selected from any one of SEQ ID NOs: 70, 72-74;
(p) the sense strand comprises a first nucleic acid sequence selected from SEQ ID NO: 87 or 89, and the antisense strand comprises a second nucleic acid sequence of SEQ ID NO: 88;
(q) the sense strand comprises a first nucleic acid sequence selected from SEQ ID NO: 90 or 92, and the antisense strand comprises a second nucleic acid sequence of SEQ ID NO: 91;
(r) the sense strand comprises a first nucleic acid sequence of SEQ ID NO: 101, and the antisense strand comprises a second nucleic acid sequence of SEQ ID NO: 102;
(s) the sense strand comprises a first nucleic acid sequence of SEQ ID NO: 103, and the antisense strand comprises a second nucleic acid sequence of SEQ ID NO: 104;
(t) the sense strand comprises a first nucleic acid sequence of SEQ ID NO: 105, and the antisense strand comprises a second nucleic acid sequence selected from any one of SEQ ID NOs: 65, 106-108;
(u) the sense strand comprises a first nucleic acid sequence of SEQ ID NO: 109, and the antisense strand comprises a second nucleic acid sequence of SEQ ID NO: 65;
(v) the sense strand comprises a first nucleic acid sequence of SEQ ID NO: 110, and the antisense strand comprises a second nucleic acid sequence of SEQ ID NO: 40;
(w) the sense strand comprises a first nucleic acid sequence of SEQ ID NO: 111, and the antisense strand comprises a second nucleic acid sequence of SEQ ID NO: 112;
(x) the sense strand comprises a first nucleic acid sequence of SEQ ID NO: 113, and the antisense strand comprises a second nucleic acid sequence of SEQ ID NO: 114; and (y) the sense strand comprises a first nucleic acid sequence of SEQ ID NO: 115, and the antisense strand comprises a second nucleic acid sequence of SEQ ID NO: 116.

In some embodiments, provided herein are MAPT RNAi agents having a sense strand and an antisense strand, wherein the sense strand and the antisense strand form a duplex, wherein the sense strand and the antisense strand have a pair of nucleic acid sequences selected from the group consisting of:
(a) the sense strand has a first nucleic acid sequence of SEQ ID NO: 25, and the antisense strand has a second nucleic acid sequence of SEQ ID NO: 26;
(b) the sense strand has a first nucleic acid sequence of SEQ ID NO: 27, and the antisense strand has a second nucleic acid sequence of SEQ ID NO: 28;
(c) the sense strand has a first nucleic acid sequence of SEQ ID NO: 29, and the antisense strand has a second nucleic acid sequence of SEQ ID NO: 30;
(d) the sense strand has a first nucleic acid sequence of SEQ ID NO: 31, and the antisense strand has a second nucleic acid sequence of SEQ ID NO: 32;
(e) the sense strand has a first nucleic acid sequence of SEQ ID NO: 33, and the antisense strand has a second nucleic acid sequence of SEQ ID NO: 34;
(f) the sense strand has a first nucleic acid sequence of SEQ ID NO: 35, and the antisense strand has a second nucleic acid sequence of SEQ ID NO: 36;
(g) the sense strand has a first nucleic acid sequence of SEQ ID NO: 37, and the antisense strand has a second nucleic acid sequence of SEQ ID NO: 38;
(h) the sense strand has a first nucleic acid sequence of SEQ ID NO: 39, and the antisense strand has a second nucleic acid sequence of SEQ ID NO: 40;
(i) the sense strand has a first nucleic acid sequence of SEQ ID NO: 41, and the antisense strand has a second nucleic acid sequence of SEQ ID NO: 42;
(j) the sense strand has a first nucleic acid sequence of SEQ ID NO: 43, and the antisense strand has a second nucleic acid sequence of SEQ ID NO: 44;
(k) the sense strand has a first nucleic acid sequence of SEQ ID NO: 45, and the antisense strand has a second nucleic acid sequence of SEQ ID NO: 46;
(l) the sense strand has a first nucleic acid sequence of SEQ ID NO: 47, and the antisense strand has a second nucleic acid sequence of SEQ ID NO: 48;
(m) the sense strand has a first nucleic acid sequence of SEQ ID NO: 63, and the antisense strand has a second nucleic acid sequence of SEQ ID NO: 40;
(n) the sense strand has a first nucleic acid sequence selected from any one of SEQ ID NOs: 64, 66-69, 71, 75-86, 93-100, and the antisense strand has a second nucleic acid sequence of SEQ ID NO: 65;
(o) the sense strand has a first nucleic acid sequence of SEQ ID NO: 64, and the antisense strand has a second nucleic acid sequence selected from any one of SEQ ID NOs: 70, 72-74;
(p) the sense strand has a first nucleic acid sequence selected from SEQ ID NO: 87 or 89, and the antisense strand has a second nucleic acid sequence of SEQ ID NO: 88;
(q) the sense strand has a first nucleic acid sequence selected from SEQ ID NO: 90 or 92, and the antisense strand has a second nucleic acid sequence of SEQ ID NO: 91;
(r) the sense strand has a first nucleic acid sequence of SEQ ID NO: 101, and the antisense strand has a second nucleic acid sequence of SEQ ID NO: 102;
(s) the sense strand has a first nucleic acid sequence of SEQ ID NO: 103, and the antisense strand has a second nucleic acid sequence of SEQ ID NO: 104;

(t) the sense strand has a first nucleic acid sequence of SEQ ID NO: 105, and the antisense strand has a second nucleic acid sequence selected from any one of SEQ ID NOs: 65, 106-108;

(u) the sense strand has a first nucleic acid sequence of SEQ ID NO: 109, and the antisense strand has a second nucleic acid sequence of SEQ ID NO: 65;

(v) the sense strand has a first nucleic acid sequence of SEQ ID NO: 110, and the antisense strand has a second nucleic acid sequence of SEQ ID NO: 40;

(w) the sense strand has a first nucleic acid sequence of SEQ ID NO: 111, and the antisense strand has a second nucleic acid sequence of SEQ ID NO: 112;

(x) the sense strand has a first nucleic acid sequence of SEQ ID NO: 113, and the antisense strand has a second nucleic acid sequence of SEQ ID NO: 114; and (y) the sense strand has a first nucleic acid sequence of SEQ ID NO: 115, and the antisense strand has a second nucleic acid sequence of SEQ ID NO: 116.

In some embodiments, the sense strand of the MAPT RNAi agent has a delivery moiety. In some embodiments, the sense strand of the MAPT RNAi agent has a delivery moiety conjugated to the 5' or 3' end of the sense strand. In some embodiments, the sense strand of the MAPT RNAi agent has a delivery moiety conjugated to a nucleotide of the sense strand. In some embodiments, the delivery moiety is α-tocopherol or palmitic acid. In some embodiments, the delivery moiety is conjugated to the 5' or 3' end of the sense stand via a linker, e.g., a linker of Table 5.

In a further aspect, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprises a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12;

(g) the sense strand comprises a first nucleic acid sequence of SEQ ID NO:13, and the antisense strand comprises a second nucleic acid sequence of SEQ ID NO: 14;

(h) the sense strand comprises a first nucleic acid sequence of SEQ ID NO:15, and the antisense strand comprises a second nucleic acid sequence of SEQ ID NO: 16;

(i) the sense strand comprises a first nucleic acid sequence of SEQ ID NO:17, and the antisense strand comprises a second nucleic acid sequence of SEQ ID NO: 18;

(j) the sense strand comprises a first nucleic acid sequence of SEQ ID NO:19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118; and (t) the sense strand comprises a first nucleic acid sequence of SEQ ID NO: 119, and the antisense strand comprises a second nucleic acid sequence of SEQ ID NO: 16, wherein optionally one or more nucleotides of the sense strand and the anti sense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a dsRNA having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 1, and the antisense strand has a second nucleic acid sequence of SEQ ID NO: 2;

(b) the sense strand has a first nucleic acid sequence of SEQ ID NO: 3, and the antisense strand has a second nucleic acid sequence of SEQ ID NO: 4;

(c) the sense strand has a first nucleic acid sequence of SEQ ID NO: 5, and the antisense strand has a second nucleic acid sequence of SEQ ID NO: 6;

(d) the sense strand has a first nucleic acid sequence of SEQ ID NO: 7, and the antisense strand has a second nucleic acid sequence of SEQ ID NO: 8;

(e) the sense strand has a first nucleic acid sequence of SEQ ID NO: 9, and the antisense strand has a second nucleic acid sequence of SEQ ID NO: 10;

(f) the sense strand has a first nucleic acid sequence of SEQ ID NO: 11, and the antisense strand has a second nucleic acid sequence of SEQ ID NO: 12;

(g) the sense strand has a first nucleic acid sequence of SEQ ID NO:13, and the antisense strand has a second nucleic acid sequence of SEQ ID NO: 14;

(h) the sense strand has a first nucleic acid sequence of SEQ ID NO:15, and the antisense strand has a second nucleic acid sequence of SEQ ID NO: 16;

(i) the sense strand has a first nucleic acid sequence of SEQ ID NO:17, and the antisense strand has a second nucleic acid sequence of SEQ ID NO: 18;

(j) the sense strand has a first nucleic acid sequence of SEQ ID NO:19, and the antisense strand has a second nucleic acid sequence of SEQ ID NO: 20;

(k) the sense strand has a first nucleic acid sequence of SEQ ID NO:21, and the antisense strand has a second nucleic acid sequence of SEQ ID NO: 22;

(l) the sense strand has a first nucleic acid sequence of SEQ ID NO:23, and the antisense strand has a second nucleic acid sequence of SEQ ID NO: 24;

(m) the sense strand has a first nucleic acid sequence of SEQ ID NO: 55, and the antisense strand has a second nucleic acid sequence of SEQ ID NO: 16;

(n) the sense strand has a first nucleic acid sequence of SEQ ID NO: 56, and the antisense strand has a second nucleic acid sequence of SEQ ID NO: 16;

(o) the sense strand has a first nucleic acid sequence of SEQ ID NO: 57, and the antisense strand has a second nucleic acid sequence of SEQ ID NO: 58;

(p) the sense strand has a first nucleic acid sequence of SEQ ID NO: 59, and the antisense strand has a second nucleic acid sequence of SEQ ID NO: 58;

(q) the sense strand has a first nucleic acid sequence of SEQ ID NO: 60, and the antisense strand has a second nucleic acid sequence of SEQ ID NO: 61;

(r) the sense strand has a first nucleic acid sequence of SEQ ID NO: 62, and the antisense strand has a second nucleic acid sequence of SEQ ID NO: 61;

(s) the sense strand has a first nucleic acid sequence of SEQ ID NO: 117, and the antisense strand has a second nucleic acid sequence of SEQ ID NO: 118; and (t) the sense strand has a first nucleic acid sequence of SEQ ID NO: 119, and the antisense strand has a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a dsRNA having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprise a pair of nucleic acid sequences selected from the group consisting of:

(a) the sense strand comprises a first nucleic acid sequence of SEQ ID NO: 25, and the antisense strand comprises a second nucleic acid sequence of SEQ ID NO: 26;

(b) the sense strand comprises a first nucleic acid sequence of SEQ ID NO: 27, and the antisense strand comprises a second nucleic acid sequence of SEQ ID NO: 28;

(c) the sense strand comprises a first nucleic acid sequence of SEQ ID NO: 29, and the antisense strand comprises a second nucleic acid sequence of SEQ ID NO: 30;

(d) the sense strand comprises a first nucleic acid sequence of SEQ ID NO: 31, and the antisense strand comprises a second nucleic acid sequence of SEQ ID NO: 32;

(e) the sense strand comprises a first nucleic acid sequence of SEQ ID NO: 33, and the antisense strand comprises a second nucleic acid sequence of SEQ ID NO: 34;

(f) the sense strand comprises a first nucleic acid sequence of SEQ ID NO: 35, and the antisense strand comprises a second nucleic acid sequence of SEQ ID NO: 36;

(g) the sense strand comprises a first nucleic acid sequence of SEQ ID NO: 37, and the antisense strand comprises a second nucleic acid sequence of SEQ ID NO: 38;

(h) the sense strand comprises a first nucleic acid sequence of SEQ ID NO: 39, and the antisense strand comprises a second nucleic acid sequence of SEQ ID NO: 40;

(i) the sense strand comprises a first nucleic acid sequence of SEQ ID NO: 41, and the antisense strand comprises a second nucleic acid sequence of SEQ ID NO: 42;

(j) the sense strand comprises a first nucleic acid sequence of SEQ ID NO: 43, and the antisense strand comprises a second nucleic acid sequence of SEQ ID NO: 44;

(k) the sense strand comprises a first nucleic acid sequence of SEQ ID NO: 45, and the antisense strand comprises a second nucleic acid sequence of SEQ ID NO: 46;

(l) the sense strand comprises a first nucleic acid sequence of SEQ ID NO: 47, and the antisense strand comprises a second nucleic acid sequence of SEQ ID NO: 48;

(m) the sense strand comprises a first nucleic acid sequence of SEQ ID NO: 105, and the antisense strand comprises a second nucleic acid sequence selected from SEQ ID NO: 65, 106-108;

(n) the sense strand comprises a first nucleic acid sequence of SEQ ID NO: 109, and the antisense strand comprises a second nucleic acid sequence of SEQ ID NO: 65;

(o) the sense strand comprises a first nucleic acid sequence of SEQ ID NO: 110, and the antisense strand comprises a second nucleic acid sequence of SEQ ID NO: 40;

(p) the sense strand comprises a first nucleic acid sequence of SEQ ID NO: 111, and the antisense strand comprises a second nucleic acid sequence of SEQ ID NO: 112;

(q) the sense strand comprises a first nucleic acid sequence of SEQ ID NO: 113, and the antisense strand comprises a second nucleic acid sequence of SEQ ID NO: 114; and (r) the sense strand comprises a first nucleic acid sequence of SEQ ID NO: 115, and the antisense strand comprises a second nucleic acid sequence of SEQ ID NO: 116.

In some embodiments, provided herein are MAPT RNAi agents of Formula (I): R-L-D, wherein R is a dsRNA having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 25, and the antisense strand has a second nucleic acid sequence of SEQ ID NO: 26;

(b) the sense strand has a first nucleic acid sequence of SEQ ID NO: 27, and the antisense strand has a second nucleic acid sequence of SEQ ID NO: 28;

(c) the sense strand has a first nucleic acid sequence of SEQ ID NO: 29, and the antisense strand has a second nucleic acid sequence of SEQ ID NO: 30;

(d) the sense strand has a first nucleic acid sequence of SEQ ID NO: 31, and the antisense strand has a second nucleic acid sequence of SEQ ID NO: 32;

(e) the sense strand has a first nucleic acid sequence of SEQ ID NO: 33, and the antisense strand has a second nucleic acid sequence of SEQ ID NO: 34;

(f) the sense strand has a first nucleic acid sequence of SEQ ID NO: 35, and the antisense strand has a second nucleic acid sequence of SEQ ID NO: 36;

(g) the sense strand has a first nucleic acid sequence of SEQ ID NO: 37, and the antisense strand has a second nucleic acid sequence of SEQ ID NO: 38;

(h) the sense strand has a first nucleic acid sequence of SEQ ID NO: 39, and the antisense strand has a second nucleic acid sequence of SEQ ID NO: 40;

(i) the sense strand has a first nucleic acid sequence of SEQ ID NO: 41, and the antisense strand has a second nucleic acid sequence of SEQ ID NO: 42;

(j) the sense strand has a first nucleic acid sequence of SEQ ID NO: 43, and the antisense strand has a second nucleic acid sequence of SEQ ID NO: 44;

(k) the sense strand has a first nucleic acid sequence of SEQ ID NO: 45, and the antisense strand has a second nucleic acid sequence of SEQ ID NO: 46;

(l) the sense strand has a first nucleic acid sequence of SEQ ID NO: 47, and the antisense strand has a second nucleic acid sequence of SEQ ID NO: 48;

(m) the sense strand has a first nucleic acid sequence of SEQ ID NO: 105, and the antisense strand has a second nucleic acid sequence selected from SEQ ID NO: 65, 106-108;

(n) the sense strand has a first nucleic acid sequence of SEQ ID NO: 109, and the antisense strand has a second nucleic acid sequence of SEQ ID NO: 65;

(o) the sense strand has a first nucleic acid sequence of SEQ ID NO: 110, and the antisense strand has a second nucleic acid sequence of SEQ ID NO: 40;

(p) the sense strand has a first nucleic acid sequence of SEQ ID NO: 111, and the antisense strand has a second nucleic acid sequence of SEQ ID NO: 112;

(q) the sense strand has a first nucleic acid sequence of SEQ ID NO: 113, and the antisense strand has a second nucleic acid sequence of SEQ ID NO: 114; and (r) the sense strand has a first nucleic acid sequence of SEQ ID NO: 115, and the antisense strand has a second nucleic acid sequence of SEQ ID NO: 116.

In another aspect, provided herein are pharmaceutical compositions comprising a MAPT RNAi agent described herein and a pharmaceutically acceptable carrier. Also provided herein are pharmaceutical compositions comprising a means for reducing MAPT expression in a cell and a pharmaceutically acceptable carrier.

In another aspect, provided herein are methods of reducing MAPT expression in a patient in need thereof, and such method comprises administering to the patient an effective amount of a MAPT RNAi agent or a pharmaceutical composition described herein.

In another aspect, provided herein are methods of treating a tauopathy in a patient in need thereof, and such method comprises administering to the patient an effective amount of the MAPT RNAi agent or a pharmaceutical composition described herein.

Also provided herein are methods of reducing MAPT expression in a cell (e.g., a neuron), and such methods can include introducing a MAPT RNAi agent described herein into the cell; and incubating the cell for a time sufficient for degradation of MAPT mRNA, thereby reducing MAPT expression in the cell.

In another aspect, provided herein are MAPT RNAi agents or pharmaceutical compositions comprising a MAPT RNAi agent for use in reducing MAPT expression. Also provided herein are MAPT RNAi agents or the pharmaceutical composition comprising a MAPT RNAi agent for use in a therapy. Also provided herein are MAPT RNAi agents or pharmaceutical compositions comprising a MAPT RNAi agent for use in the treatment of a tauopathy. Also provided herein are uses of MAPT RNAi agents in the manufacture of a medicament for the treatment of a tauopathy.

DETAILED DESCRIPTION

Provided herein are MAPT RNAi agents and compositions comprising a MAPT RNAi agent. Also provided herein are methods of using the MAPT RNAi agents or compositions comprising a MAPT RNAi agent for reducing MAPT expression and/or treating tauopathy in a subject.

In some embodiments, provided herein are MAPT RNAi agents having a sense strand and an antisense strand, and the sense strand and the antisense strand form a duplex. The antisense strand is complimentary to a region of MAPT mRNA. In a further embodiment, the sense strand and the antisense strand are each 15-30 nucleotides in length, e.g., 20-25 nucleotides in length. In some embodiments, provided herein are MAPT RNAi agents having a sense strand of 21 nucleotides and an antisense strand of 23 nucleotides. In some embodiments, the sense strand and antisense strand of the MAPT RNAi agent may have overhangs at either the 5' end or the 3' end (i.e., 5' overhang or 3' overhang). For example, the sense strand and the antisense strand may have 5' or 3' overhangs of 1 to 5 nucleotides or 1 to 3 nucleotides. In some embodiments, the antisense strand comprises a 3' overhang of two nucleotides. In some embodiments, the sense strand and antisense strand sequences of the MAPT RNAi agents are provided in Table 1.

Provided herein are MAPT RNAi agents having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 1, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 2;

(b) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 3, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 4;

(c) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 5, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 6;

(d) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 7, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 8;

(e) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 9, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 10;

(f) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 11, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 12;

(g) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:13, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 14;

(h) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:15, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16;

(i) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:17, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 18;

(j) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:19, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 20;

(k) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:21, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 22; and (l) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO:23, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 24;

(m) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 55, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16;

(n) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 56, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16;

(o) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 57, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 58;

(p) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 59, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 58;

(q) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 60, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 61;

(r) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 62, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 61;

(s) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 117, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 118;

(t) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 119, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 1, and the anti sense strand comprises a second nucleic acid sequence having at least 95% (e.g., about 95%, about 96%, about 97%, about 98%, about 99%, or about 100%) sequence identity to SEQ ID NO: 2, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 3, and the antisense strand comprises a second nucleic acid sequence having at least 95% (e.g., about 95%, about 96%, about 97%, about 98%, about 99%, or about 100%) sequence identity to SEQ ID NO: 4, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 5, and the antisense strand comprises a second nucleic acid sequence having at least 95% (e.g., about 95%, about 96%, about 97%, about 98%, about 99%, or about 100%) sequence identity to SEQ ID NO: 6, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 7, and the antisense strand comprises a second nucleic acid sequence having at least 95% (e.g., about 95%, about 96%, about 97%, about 98%, about 99%, or about 100%) sequence identity to SEQ ID NO: 8, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 9, and the antisense strand comprises a second nucleic acid sequence having at least 95% (e.g., about 95%, about 96%, about 97%, about 98%, about 99%, or about 100%) sequence identity to SEQ ID NO: 10, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 11, and the antisense strand comprises a second nucleic acid sequence having at least 95% (e.g., about 95%, about 96%, about 97%, about 98%, about 99%, or about 100%) sequence identity to SEQ ID NO: 12, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 13, and the antisense strand comprises a second nucleic acid sequence having at least 95% (e.g., about 95%, about 96%, about 97%, about 98%, about 99%, or about 100%) sequence identity to SEQ ID NO: 14, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 15, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 17, and the antisense strand comprises a second nucleic acid sequence having at least 95% (e.g., about 95%, about 96%, about 97%, about 98%, about 99%, or about 100%) sequence identity to SEQ ID NO: 18, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 19, and the antisense strand comprises a second nucleic acid sequence having at least 95% (e.g., about 95%, about 96%, about 97%, about 98%, about 99%, or about 100%) sequence identity to SEQ ID NO: 20, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 21, and the antisense strand comprises a second nucleic acid sequence having at least 95% (e.g., about 95%, about 96%, about 97%, about 98%, about 99%, or about 100%) sequence identity to SEQ ID NO: 22, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 23, and the antisense strand comprises a second nucleic acid sequence having at least 95% (e.g., about 95%, about 96%, about 97%, about 98%, about 99%, or about 100%) sequence identity to SEQ ID NO: 24, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 55, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 56, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 57, and the antisense strand comprises a second nucleic acid sequence having at least 95% (e.g., about 95%, about 96%, about 97%, about 98%, about 99%, or about 100%) sequence identity to SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 59, and the antisense strand comprises a second nucleic acid sequence having at least 95% (e.g., about 95%, about 96%, about 97%, about 98%, about 99%, or about 100%) sequence identity to SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 60, and the antisense strand comprises a second nucleic acid sequence having at least 95% (e.g., about 95%, about 96%, about 97%, about 98%, about 99%, or about 100%) sequence identity to SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 62, and the antisense strand comprises a second nucleic acid sequence having at least 95% (e.g., about 95%, about 96%, about 97%, about 98%, about 99%, or about 100%) sequence identity to SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 117, and the antisense strand comprises a second nucleic acid sequence having at least 95% (e.g., about 95%, about 96%, about 97%, about 98%, about 99%, or about 100%) sequence identity to SEQ ID NO: 118, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence having at least 95% (e.g., about 95%, about 96%, about 97%, about 98%, about 99%, or about 100%) sequence identity to SEQ ID NO: 119, and the antisense strand comprises a second nucleic acid sequence having at least 95% (e.g., about 95%, about 96%, about 97%, about 98%, about 99%, or about 100%) sequence identity to SEQ ID NO: 16, wherein one or more nucleotides of the sense strand and the antisense strand are independently modified nucleotides, and wherein optionally one or more internucleotide linkages of the sense strand and the antisense strand are modified internucleotide linkages.

TABLE 1

Nucleic Acid Sequences of MAPT RNAi Agents

| MAPT RNAi Agent No. | Sense Strand (5' to 3') | SEQ ID NO | Start position of sense strand target region of human MAPT transcript NM_ 001123067.4 | Antisense Strand (5' to 3') | SEQ ID NO | Start position of antisense strand target region of human MAPT transcript NM_ 001123067.4 |
|---|---|---|---|---|---|---|
| 1 | ACAAGCUGACCUUCCG CGAGA | 1 | 1184 | UCUCGCGGAAGGUCAGCU UGUGG | 2 | 1182 |
| 2 | AGAUUGAAACCCACAA GCUGA | 3 | 1172 | UCAGCUUGUGGGUUUCAA UCUUU | 4 | 1170 |

TABLE 1-continued

Nucleic Acid Sequences of MAPT RNAi Agents

| MAPT RNAi Agent No. | Sense Strand (5' to 3') | SEQ ID NO | Start position of sense strand target region of human MAPT transcript NM_ 001123067.4 | Antisense Strand (5' to 3') | SEQ ID NO | Start position of antisense strand target region of human MAPT transcript NM_ 001123067.4 |
|---|---|---|---|---|---|---|
| 3 | AAUAAAAAGAUUGAA ACCCAA | 5 | 1165 | UUGGGUUUCAAUCUUUU UAUUUC | 6 | 1163 |
| 4 | GGAAAUAAAAAGAUU GAAACA | 7 | 1162 | UGUUUCAAUCUUUUUAU UUCCUC | 8 | 1160 |
| 5 | GGCGGAGGAAAUAAAA AGAUA | 9 | 1156 | UAUCUUUUUAUUUCCUCC GCCAG | 10 | 1154 |
| 6 | GAAGUAAAAUCUGAGA AGCUA | 11 | 1075 | UAGCUUCUCAGAUUUUAC UUCCA | 12 | 1073 |
| 7 | GGAAGUAAAAUCUGAG AAGCA | 13 | 1074 | UGCUUCUCAGAUUUUACU UCCAC | 14 | 1072 |
| 8 | GUGGAAGUAAAAUCUG AGAAA | 15 | 1072 | UUUCUCAGAUUUUACUUC CACCU | 16 | 1070 |
| 9 | CCAGGUGGAAGUAAAA UCUGA | 17 | 1068 | UCAGAUUUUACUUCCACC UGGCC | 18 | 1066 |
| 10 | CAAGUCCAAGAUCGGC UCCAA | 19 | 831 | UUGGAGCCGAUCUUGGAC UUGAC | 20 | 829 |
| 11 | UCUGGUGAACCUCCAA AAUCA | 21 | 616 | UGAUUUUGGAGGUUCACC AGAGC | 22 | 614 |
| 12 | CAGGUGGAAGUAAAAU CUGAA | 23 | 1069 | UUCAGAUUUUACUUCCAC CUGGC | 24 | 1067 |
| 25 | GUGGAAGUA(n)AAUCU GAGAAA, wherein (n) indicates an abasic moiety. | 55 | 1072 | UUUCUCAGAUUUUACUUC CACCU | 16 | 1070 |
| 26 | GUGGAAGU(n)AAAUCU GAGAAA, wherein (n) indicates an abasic moiety. | 56 | 1072 | UUUCUCAGAUUUUACUUC CACCU | 16 | 1070 |
| 27 | CCAAGUGUGGCUCAUU AGGCA | 57 | 1022 | UGCCUAAUGAGCCACACU UGGAG | 58 | 1020 |
| 28 | CCAAGUGU(n)GCUCAU UAGGCA, wherein (n) indicates an abasic moiety. | 59 | 1022 | UGCCUAAUGAGCCACACU UGGAG | 58 | 1020 |
| 29 | UGCAAAUA(n)UCUACA AACCAA, wherein (n) indicates an abasic moiety. | 60 | 980 | UUGGUUUGUAGACUAUU UGCACC | 61 | 978* |
| 30 | UGCAAAUAGUCUACAA ACCAA | 62 | 980 | UUGGUUUGUAGACUAUU UGCACC | 61 | 978* |
| 77 | GUGGAAGUAAAAUCUG AGAAATT | 117 | 1072 | UUUCUCAGAUUUUACUUC CACTT | 118 | 1070** |
| 78 | GUGGAAGUAAAAUCUG AGAAG | 119 | 1072 | UUUCUCAGAUUUUACUUC CACCU | 16 | 1070 |

*The last nucleotide does not match the transcript.
**The last two nucleotides do not match the transcript.

In some embodiments, the sense strand and the antisense strand of the MAPT RNAi agent described herein comprise a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12;

(g) the sense strand comprises a first nucleic acid sequence of SEQ ID NO:13, and the antisense strand comprises a second nucleic acid sequence of SEQ ID NO: 14;

(h) the sense strand comprises a first nucleic acid sequence of SEQ ID NO:15, and the antisense strand comprises a second nucleic acid sequence of SEQ ID NO: 16;

(i) the sense strand comprises a first nucleic acid sequence of SEQ ID NO:17, and the antisense strand comprises a second nucleic acid sequence of SEQ ID NO: 18;

(j) the sense strand comprises a first nucleic acid sequence of SEQ ID NO:19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118; and (t) the sense strand comprises a first nucleic acid sequence of SEQ ID NO: 119, and the antisense strand comprises a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 1, and the antisense strand comprises a second nucleic acid sequence of SEQ ID NO: 2, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 3, and the antisense strand comprises a second nucleic acid sequence of SEQ ID NO: 4, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 5, and the antisense strand comprises a second nucleic acid sequence of SEQ ID NO: 6, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 7, and the antisense strand comprises a second nucleic acid sequence of SEQ ID NO: 8, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 9, and the antisense strand comprises a second nucleic acid sequence of SEQ ID NO: 10, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 11, and the antisense strand comprises a second nucleic acid sequence of SEQ ID NO: 12, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 13, and the antisense strand comprises a second nucleic acid sequence of SEQ ID NO: 14, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 15, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 17, and the antisense strand comprises a second nucleic acid sequence of SEQ ID NO: 18, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 19, and the antisense strand comprises a second nucleic acid sequence of SEQ ID NO: 20, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 21, and the antisense strand comprises a second nucleic acid sequence of SEQ ID NO: 22, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 23, and the antisense strand comprises a second nucleic acid sequence of SEQ ID NO: 24, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 55, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 56, and the antisense strand comprises a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 57, and the antisense strand comprises a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 59, and the antisense strand comprises a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 57, and the antisense strand comprises a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 60, and the antisense strand comprises a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 62, and the antisense strand comprises a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 117, and the antisense strand comprises a second nucleic acid sequence of SEQ ID NO: 118, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 119, and the antisense strand comprises a second nucleic acid sequence of SEQ ID NO: 16, wherein one or more nucleotides of the sense strand and the anti sense strand are independently modified nucleotides, and wherein optionally one or more internucleotide linkages of the sense strand and the antisense strand are modified internucleotide linkages.

In some embodiments, the sense strand and the antisense strand of the MAPT RNAi agent described herein have a pair of nucleic acid sequences selected from the group consisting of:

(a) the sense strand has a first nucleic acid sequence of SEQ ID NO: 1, and the antisense strand has a second nucleic acid sequence of SEQ ID NO: 2;
(b) the sense strand has a first nucleic acid sequence of SEQ ID NO: 3, and the antisense strand has a second nucleic acid sequence of SEQ ID NO: 4;
(c) the sense strand has a first nucleic acid sequence of SEQ ID NO: 5, and the antisense strand has a second nucleic acid sequence of SEQ ID NO: 6;
(d) the sense strand has a first nucleic acid sequence of SEQ ID NO: 7, and the antisense strand has a second nucleic acid sequence of SEQ ID NO: 8;
(e) the sense strand has a first nucleic acid sequence of SEQ ID NO: 9, and the antisense strand has a second nucleic acid sequence of SEQ ID NO: 10;
(f) the sense strand has a first nucleic acid sequence of SEQ ID NO: 11, and the antisense strand has a second nucleic acid sequence of SEQ ID NO: 12;
(g) the sense strand has a first nucleic acid sequence of SEQ ID NO:13, and the antisense strand has a second nucleic acid sequence of SEQ ID NO: 14;
(h) the sense strand has a first nucleic acid sequence of SEQ ID NO:15, and the antisense strand has a second nucleic acid sequence of SEQ ID NO: 16;
(i) the sense strand has a first nucleic acid sequence of SEQ ID NO:17, and the antisense strand has a second nucleic acid sequence of SEQ ID NO: 18;
(j) the sense strand has a first nucleic acid sequence of SEQ ID NO:19, and the antisense strand has a second nucleic acid sequence of SEQ ID NO: 20;
(k) the sense strand has a first nucleic acid sequence of SEQ ID NO:21, and the antisense strand has a second nucleic acid sequence of SEQ ID NO: 22;
(l) the sense strand has a first nucleic acid sequence of SEQ ID NO:23, and the antisense strand has a second nucleic acid sequence of SEQ ID NO: 24;
(m) the sense strand has a first nucleic acid sequence of SEQ ID NO: 55, and the antisense strand has a second nucleic acid sequence of SEQ ID NO: 16;
(n) the sense strand has a first nucleic acid sequence of SEQ ID NO: 56, and the antisense strand has a second nucleic acid sequence of SEQ ID NO: 16;
(o) the sense strand has a first nucleic acid sequence of SEQ ID NO: 57, and the antisense strand has a second nucleic acid sequence of SEQ ID NO: 58;
(p) the sense strand has a first nucleic acid sequence of SEQ ID NO: 59, and the antisense strand has a second nucleic acid sequence of SEQ ID NO: 58;
(q) the sense strand has a first nucleic acid sequence of SEQ ID NO: 60, and the antisense strand has a second nucleic acid sequence of SEQ ID NO: 61;
(r) the sense strand has a first nucleic acid sequence of SEQ ID NO: 62, and the antisense strand has a second nucleic acid sequence of SEQ ID NO: 61;
(s) the sense strand has a first nucleic acid sequence of SEQ ID NO: 117, and the antisense strand has a second nucleic acid sequence of SEQ ID NO: 118; and
(t) the sense strand has a first nucleic acid sequence of SEQ ID NO: 119, and the antisense strand has a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 1, and the antisense strand has a second nucleic acid sequence of SEQ ID NO: 2, wherein one or more nucleotides of the sense strand and the anti sense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 3, and the antisense strand has a second nucleic acid sequence of SEQ ID NO: 4, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 5, and the antisense strand has a second nucleic acid sequence of SEQ ID NO: 6, wherein one or more nucleotides of the sense strand and the anti sense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 7, and the antisense strand has a second nucleic acid sequence of SEQ ID NO: 8, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 9, and the antisense strand has a second nucleic acid sequence of SEQ ID NO: 10, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 11, and the antisense strand has a second nucleic acid sequence of SEQ ID NO: 12, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 13, and the antisense strand has a second nucleic acid sequence of SEQ ID NO: 14, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 15, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 17, and the antisense strand has a second nucleic acid sequence of SEQ ID NO: 18, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 19, and the antisense strand has a second nucleic acid sequence of SEQ ID NO: 20, wherein one or more nucleotides of the sense strand and the anti sense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 21, and the antisense strand has a second nucleic acid sequence of SEQ ID NO: 22, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 23, and the antisense strand has a second nucleic acid sequence of SEQ ID NO: 24, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 55, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 56, and the antisense strand has a second nucleic acid sequence of SEQ ID NO: 16, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 57, and the antisense strand has a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 59, and the antisense strand has a second nucleic acid sequence of SEQ ID NO: 58, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 60, and the antisense strand has a second nucleic acid sequence of SEQ ID NO: 61, wherein one or more nucleotides of the sense strand and the anti sense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 62, and the antisense strand has a second nucleic acid sequence of SEQ ID NO: 61, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 117, and the antisense strand has a second nucleic acid sequence of SEQ ID NO: 118, wherein one or more nucleotides of the sense strand and the antisense strand are independently modified nucleotides, and wherein optionally one or more internucleotide linkages of the sense strand and the antisense strand are modified internucleotide linkages. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 119, and the antisense strand has a second nucleic acid sequence of SEQ ID NO: 16, wherein one or more nucleotides of the sense strand and the anti sense strand are independently modified nucleotides, and wherein optionally one or more internucleotide linkages of the sense strand and the antisense strand are modified internucleotide linkages.

In some embodiments, the MAPT RNAi agent described herein can comprise a sense strand that comprises a sequence that has 1, 2, or 3 differences from SEQ ID NO: 1, 3, 5, 7, 9, 11, 13, 15, 17, 19, 21, 23, 55, 56, 57, 59, 60, 62, 117, 119. In some embodiments, the MAPT RNAi agent described herein can comprise an antisense strand that comprises a sequence that has 1, 2, or 3 differences from SEQ ID NO: 2, 4, 6, 8, 10, 12, 14, 16, 18, 20, 22, 24, 58, 61, 118.

The MAPT RNAi agents described herein may include modifications. The modifications can be made to one or more nucleotides of the sense strand and/or antisense strand or to the internucleotide linkages, which are the bonds between two nucleotides in the sense or antisense strand. For example, some 2'-modifications of ribose or deoxyribose can increase RNA or DNA stability and half-life. Such 2'-modifications can be 2'-fluoro, 2'-O-methyl (i.e., 2'-methoxy), 2'-O-alkyl, e.g., 2'-O—C16 alkyl modified nucleotide, or 2'-O-methoxyethyl (2'-O-MOE).

In some embodiments, one or more nucleotides of the sense strand and/or the antisense strand are independently modified nucleotides, which means the sense strand and the antisense strand can have different modified nucleotides. In some embodiments, one or more nucleotides of the sense strand are modified nucleotides. In some embodiments, each nucleotide of the sense strand is a modified nucleotide. In some embodiments, one or more nucleotides of the antisense strand are modified nucleotides. In some embodiments, each nucleotide of the antisense strand is a modified nucleotide. In some embodiments, the modified nucleotide is a 2'-fluoro modified nucleotide, 2'-O-methyl modified nucleotide, or 2'-O-alkyl modified nucleotide, e.g., 2'-O—C16 alkyl modified nucleotide. In some embodiments, each nucleotide of the sense strand and the antisense strand is independently a modified nucleotide, e.g., a 2'-fluoro modified nucleotide, 2'-O-methyl modified nucleotide, or 2'-O-alkyl modified nucleotide, e.g., 2'-O—C16 alkyl modified nucleotide.

In some embodiments, the sense strand has four 2'-fluoro modified nucleotides, e.g., at positions 7, 9, 10, 11 from the 5' end of the sense strand. In some embodiments, nucleotides at positions other than positions 7, 9, 10, and 11 of the sense strand are 2'-O-methyl modified nucleotides or 2'-O—C16 alkyl modified nucleotides. In some embodiments, the antisense strand has four 2'-fluoro modified nucleotides, e.g., at positions 2, 6, 14, 16 from the 5' end of the antisense strand. In some embodiments, nucleotides at positions other than positions 2, 6, 14 and 16 of the antisense strand are 2'-O-methyl modified nucleotides or 2'-O—C16 alkyl modified nucleotides.

In some embodiments, the sense strand has three 2'-fluoro modified nucleotides, e.g., at positions 9, 10, 11 from the 5' end of the sense strand. In some embodiments, the other nucleotides of the sense strand are 2'-O-methyl modified nucleotides. In some embodiments, the antisense strand has five 2'-fluoro modified nucleotides, e.g., at positions 2, 5, 7, 14, 16 from the 5' end of the antisense strand. In some embodiments, the antisense strand has five 2'-fluoro modified nucleotides, e.g., at positions 2, 5, 8, 14, 16 from the 5' end of the antisense strand. In some embodiments, the antisense strand has five 2'-fluoro modified nucleotides, e.g., at positions 2, 3, 7, 14, 16 from the 5' end of the antisense strand. In some embodiments, the other nucleotides of the antisense strand are 2'-O-methyl modified nucleotides. In some embodiments, the sense strand comprises an abasic moiety or inverted abasic moiety.

In some embodiments, the modified nucleotide is a 2'-O-alkyl modified nucleotide, e.g., 2'-O—C16 alkyl modified nucleotide, which can serve as a delivery moiety. In some embodiments, the 2'-O-alkyl modified nucleotide is a 2'-O-hexadecyl uridine, 2'-O-hexadecyl cytidine, 2'-O-hexadecyl guanine, or 2'-O-hexadecyl adenosine. In some embodiments, 2'-O-hexadecyl uridine, 2'-O-hexadecyl cytidine, 2'-O-hexadecyl guanine, or 2'-O-hexadecyl adenosine is a modified nucleotide in the sense strand.

In some embodiments, the first nucleotide from the 5' end of the antisense strand is a modified nucleotide that has a phosphate analog, e.g., 5'-vinylphosphonate (5'-VP).

In some embodiments, the sense strand comprises an abasic moiety or inverted abasic moiety, e.g., a moiety shown in Table 3.

In some embodiments, the sense strand and the antisense strand have one or more modified internucleotide linkages. In some embodiments, the modified internucleotide linkage is phosphorothioate linkage. In some embodiments, the sense strand has four or five phosphorothioate linkages. In some embodiments, the antisense strand has four or five phosphorothioate linkages. In some embodiments, the sense strand and the antisense strand each has four or five phosphorothioate linkages. In some embodiments, the sense strand has four phosphorothioate linkages and the antisense strand has four phosphorothioate linkages.

In a further aspect, provided herein are MAPT RNAi agent having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 25, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 26;

(b) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 27, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 28;

(c) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 29, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 30;

(d) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 31, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 32;

(e) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 33, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 34;

(f) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 35, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 36;

(g) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 37, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 38;

(h) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 39, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 40;

(i) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 41, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 42;

(j) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 43, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 44;

(k) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 45, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 46;

(l) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 47, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 48;

(m) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 63, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 40;

(n) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to any one of SEQ ID NOs: 64, 66-69, 71, 75-86, 93-100, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 65;

(o) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 64, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to any one of SEQ ID NOs: 70, 72-74;

(p) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 87 or 89, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 88;

(q) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 90 or 92, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 91;

(r) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 101, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 102;

(s) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 103, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 104;

(t) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 105, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to any one of SEQ ID NOs: 65, 106-108;

(u) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 109, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 65;

(v) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 110, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 40;

(w) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 111, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 112;

(x) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 113, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 114; and (y) the sense strand comprises a first nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 115, and the antisense strand comprises a second nucleic acid sequence having at least 90% (e.g., about 90%, about 91%, about 92%, about 93%, about 94%, about 95%, about 96%, about 97%, about 98%, about 99%, or about 100%) sequence identity to SEQ ID NO: 116.

In some embodiments, provided herein are MAPT RNAi agent having a sense strand and an antisense strand, wherein the sense strand and the antisense strand form a duplex, wherein the sense strand and the antisense strand comprise a pair of nucleic acid sequences selected from the group consisting of:

(a) the sense strand comprises a first nucleic acid sequence of SEQ ID NO: 25, and the antisense strand comprises a second nucleic acid sequence of SEQ ID NO: 26;

(b) the sense strand comprises a first nucleic acid sequence of SEQ ID NO: 27, and the antisense strand comprises a second nucleic acid sequence of SEQ ID NO: 28;

(c) the sense strand comprises a first nucleic acid sequence of SEQ ID NO: 29, and the antisense strand comprises a second nucleic acid sequence of SEQ ID NO: 30;

(d) the sense strand comprises a first nucleic acid sequence of SEQ ID NO: 31, and the antisense strand comprises a second nucleic acid sequence of SEQ ID NO: 32;

(e) the sense strand comprises a first nucleic acid sequence of SEQ ID NO: 33, and the antisense strand comprises a second nucleic acid sequence of SEQ ID NO: 34;

(f) the sense strand comprises a first nucleic acid sequence of SEQ ID NO: 35, and the antisense strand comprises a second nucleic acid sequence of SEQ ID NO: 36;

(g) the sense strand comprises a first nucleic acid sequence of SEQ ID NO: 37, and the antisense strand comprises a second nucleic acid sequence of SEQ ID NO: 38;

(h) the sense strand comprises a first nucleic acid sequence of SEQ ID NO: 39, and the antisense strand comprises a second nucleic acid sequence of SEQ ID NO: 40;

(i) the sense strand comprises a first nucleic acid sequence of SEQ ID NO: 41, and the antisense strand comprises a second nucleic acid sequence of SEQ ID NO: 42;

(j) the sense strand comprises a first nucleic acid sequence of SEQ ID NO: 43, and the antisense strand comprises a second nucleic acid sequence of SEQ ID NO: 44;

(k) the sense strand comprises a first nucleic acid sequence of SEQ ID NO: 45, and the antisense strand comprises a second nucleic acid sequence of SEQ ID NO: 46;

(l) the sense strand comprises a first nucleic acid sequence of SEQ ID NO: 47, and the antisense strand comprises a second nucleic acid sequence of SEQ ID NO: 48;

(m) the sense strand comprises a first nucleic acid sequence of SEQ ID NO: 63, and the antisense strand comprises a second nucleic acid sequence of SEQ ID NO: 40;

(n) the sense strand comprises a first nucleic acid sequence selected from any one of SEQ ID NOs: 64, 66-69, 71, 75-86, 93-100, and the antisense strand comprises a second nucleic acid sequence of SEQ ID NO: 65;

(o) the sense strand comprises a first nucleic acid sequence of SEQ ID NO: 64, and the antisense strand comprises a second nucleic acid sequence selected from any one of SEQ ID NOs: 70, 72-74;

(p) the sense strand comprises a first nucleic acid sequence selected from SEQ ID NO: 87 or 89, and the antisense strand comprises a second nucleic acid sequence of SEQ ID NO: 88;

(q) the sense strand comprises a first nucleic acid sequence selected from SEQ ID NO: 90 or 92, and the antisense strand comprises a second nucleic acid sequence of SEQ ID NO: 91;

(r) the sense strand comprises a first nucleic acid sequence of SEQ ID NO: 101, and the antisense strand comprises a second nucleic acid sequence of SEQ ID NO: 102;

(s) the sense strand comprises a first nucleic acid sequence of SEQ ID NO: 103, and the antisense strand comprises a second nucleic acid sequence of SEQ ID NO: 104;

(t) the sense strand comprises a first nucleic acid sequence of SEQ ID NO: 105, and the antisense strand comprises a second nucleic acid sequence selected from any one of SEQ ID NOs: 65, 106-108;

(u) the sense strand comprises a first nucleic acid sequence of SEQ ID NO: 109, and the antisense strand comprises a second nucleic acid sequence of SEQ ID NO: 65;

(v) the sense strand comprises a first nucleic acid sequence of SEQ ID NO: 110, and the antisense strand comprises a second nucleic acid sequence of SEQ ID NO: 40;

(w) the sense strand comprises a first nucleic acid sequence of SEQ ID NO: 111, and the antisense strand comprises a second nucleic acid sequence of SEQ ID NO: 112;

(x) the sense strand comprises a first nucleic acid sequence of SEQ ID NO: 113, and the antisense strand comprises a second nucleic acid sequence of SEQ ID NO: 114; and (y) the sense strand comprises a first nucleic acid sequence of SEQ ID NO: 115, and the antisense strand comprises a second nucleic acid sequence of SEQ ID NO: 116.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 25, and the antisense strand comprises a second nucleic acid sequence of SEQ ID NO: 26. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 27, and the antisense strand comprises a second nucleic acid sequence of SEQ ID NO: 28. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 29, and the antisense strand comprises a second nucleic acid sequence of SEQ ID NO: 30. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 31, and the antisense strand comprises a second nucleic acid sequence of SEQ ID NO: 32. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 33, and the antisense strand comprises a second nucleic acid sequence of SEQ ID NO: 34. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 35, and the antisense strand comprises a second nucleic acid sequence of SEQ ID NO: 36. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 37, and the antisense strand comprises a second nucleic acid sequence of SEQ ID NO: 38. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 39, and the antisense strand comprises a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 41, and the antisense strand comprises a second nucleic acid sequence of SEQ ID NO: 42. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 43, and the antisense strand comprises a second nucleic acid sequence of SEQ ID NO: 44. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 45, and the antisense strand comprises a second nucleic acid sequence of SEQ ID NO: 46. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 47, and the antisense strand comprises a second nucleic acid sequence of SEQ ID NO: 48.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 63, and the antisense strand comprises a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand comprises a first nucleic acid sequence selected from any one of SEQ ID NOs: 64, 66-69, 71, 75-86, 93-100, and the antisense strand comprises a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 64, and the antisense strand comprises a second nucleic acid sequence selected from any one of SEQ ID NOs: 70, 72-74. In some embodiments, provided herein are MAPT RNAi agent having a sense strand and an antisense strand, wherein the sense strand and the antisense strand form a duplex, and wherein the sense strand comprises a first nucleic acid sequence selected from SEQ ID NO: 87 or 89, and the anti sense strand comprises a second nucleic acid sequence of SEQ ID NO: 88. In some embodiments, provided herein are MAPT RNAi agent having a sense strand and an antisense strand, wherein the sense strand and the antisense strand form a duplex, and wherein the sense strand comprises a first nucleic acid sequence selected from SEQ ID NO: 90 or 92, and the antisense strand comprises a second nucleic acid sequence of SEQ ID NO: 91. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 101, and the antisense strand comprises a second nucleic acid sequence of SEQ ID NO: 102. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 103, and the antisense strand comprises a second nucleic acid sequence of SEQ ID NO: 104.

In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 105, and the antisense strand comprises a second nucleic acid sequence selected from any one of SEQ ID NOs: 65, 106-108. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 109, and the antisense strand comprises a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 110, and the antisense strand comprises a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 111, and the antisense strand comprises a second nucleic acid sequence of SEQ ID NO: 112. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 113, and the antisense strand comprises a second nucleic acid sequence of SEQ ID NO: 114. In some embodiments, provided herein are MAPT RNAi agent having a sense strand and an antisense strand, wherein the sense strand and the antisense strand form a duplex, and wherein the sense strand comprises a first nucleic acid sequence of SEQ ID NO: 115, and the antisense strand comprises a second nucleic acid sequence of SEQ ID NO: 116.

In some embodiments, the MAPT RNAi agent described herein can comprise a sense strand that comprises a sequence that has 1, 2, or 3 differences from SEQ ID NO: 25, 27, 29, 31, 33, 35, 37, 39, 41, 43, 45, 47, 63, 64, 66-69, 71, 75-87, 89, 90, 92-101, 103, 105, 109-111, 113, 115. In some embodiments, the MAPT RNAi agent described herein can comprise an antisense strand that comprises a sequence that has 1, 2, or 3 differences from SEQ ID NO: 26, 28, 30, 32, 34, 36, 38, 40, 42, 44, 46, 48, 65, 70, 72-74, 88, 91, 102, 104, 106-108, 112, 114, 116.

In some embodiments, provided herein are MAPT RNAi agent having a sense strand and an antisense strand, wherein the sense strand and the antisense strand form a duplex, wherein the sense strand and the antisense strand have a pair of nucleic acid sequences selected from the group consisting of:

(a) the sense strand has a first nucleic acid sequence of SEQ ID NO: 25, and the antisense strand has a second nucleic acid sequence of SEQ ID NO: 26;

(b) the sense strand has a first nucleic acid sequence of SEQ ID NO: 27, and the antisense strand has a second nucleic acid sequence of SEQ ID NO: 28;

(c) the sense strand has a first nucleic acid sequence of SEQ ID NO: 29, and the antisense strand has a second nucleic acid sequence of SEQ ID NO: 30;

(d) the sense strand has a first nucleic acid sequence of SEQ ID NO: 31, and the antisense strand has a second nucleic acid sequence of SEQ ID NO: 32;

(e) the sense strand has a first nucleic acid sequence of SEQ ID NO: 33, and the antisense strand has a second nucleic acid sequence of SEQ ID NO: 34;

(f) the sense strand has a first nucleic acid sequence of SEQ ID NO: 35, and the antisense strand has a second nucleic acid sequence of SEQ ID NO: 36;

(g) the sense strand has a first nucleic acid sequence of SEQ ID NO: 37, and the antisense strand has a second nucleic acid sequence of SEQ ID NO: 38;

(h) the sense strand has a first nucleic acid sequence of SEQ ID NO: 39, and the antisense strand has a second nucleic acid sequence of SEQ ID NO: 40;

(i) the sense strand has a first nucleic acid sequence of SEQ ID NO: 41, and the antisense strand has a second nucleic acid sequence of SEQ ID NO: 42;

(j) the sense strand has a first nucleic acid sequence of SEQ ID NO: 43, and the antisense strand has a second nucleic acid sequence of SEQ ID NO: 44;

(k) the sense strand has a first nucleic acid sequence of SEQ ID NO: 45, and the antisense strand has a second nucleic acid sequence of SEQ ID NO: 46;

(l) the sense strand has a first nucleic acid sequence of SEQ ID NO: 47, and the antisense strand has a second nucleic acid sequence of SEQ ID NO: 48;

(m) the sense strand has a first nucleic acid sequence of SEQ ID NO: 63, and the antisense strand has a second nucleic acid sequence of SEQ ID NO: 40;

(n) the sense strand has a first nucleic acid sequence selected from any one of SEQ ID NOs: 64, 66-69, 71, 75-86, 93-100, and the antisense strand has a second nucleic acid sequence of SEQ ID NO: 65;

(o) the sense strand has a first nucleic acid sequence of SEQ ID NO: 64, and the antisense strand has a second nucleic acid sequence selected from any one of SEQ ID NOs: 70, 72-74;

(p) the sense strand has a first nucleic acid sequence selected from SEQ ID NO: 87 or 89, and the antisense strand has a second nucleic acid sequence of SEQ ID NO: 88;

(q) the sense strand has a first nucleic acid sequence selected from SEQ ID NO: 90 or 92, and the antisense strand has a second nucleic acid sequence of SEQ ID NO: 91;

(r) the sense strand has a first nucleic acid sequence of SEQ ID NO: 101, and the antisense strand has a second nucleic acid sequence of SEQ ID NO: 102;

(s) the sense strand has a first nucleic acid sequence of SEQ ID NO: 103, and the antisense strand has a second nucleic acid sequence of SEQ ID NO: 104;

(t) the sense strand has a first nucleic acid sequence of SEQ ID NO: 105, and the antisense strand has a second nucleic acid sequence selected from any one of SEQ ID NOs: 65, 106-108;

(u) the sense strand has a first nucleic acid sequence of SEQ ID NO: 109, and the antisense strand has a second nucleic acid sequence of SEQ ID NO: 65;

(v) the sense strand has a first nucleic acid sequence of SEQ ID NO: 110, and the antisense strand has a second nucleic acid sequence of SEQ ID NO: 40;

(w) the sense strand has a first nucleic acid sequence of SEQ ID NO: 111, and the antisense strand has a second nucleic acid sequence of SEQ ID NO: 112;

(x) the sense strand has a first nucleic acid sequence of SEQ ID NO: 113, and the antisense strand has a second nucleic acid sequence of SEQ ID NO: 114; and (y) the sense strand has a first nucleic acid sequence of SEQ ID NO: 115, and the antisense strand has a second nucleic acid sequence of SEQ ID NO: 116.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 25, and the antisense strand has a second nucleic acid sequence of SEQ ID NO: 26. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 27, and the antisense strand has a second nucleic acid sequence of SEQ ID NO: 28. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 29, and the antisense strand has a second nucleic acid sequence of SEQ ID NO: 30. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 31, and the antisense strand has a second nucleic acid sequence of SEQ ID NO: 32. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 33, and the antisense strand has a second nucleic acid sequence of SEQ ID NO: 34. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 35, and the antisense strand has a second nucleic acid sequence of SEQ ID NO: 36. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 37, and the antisense strand has a second nucleic acid sequence of SEQ ID NO: 38. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 39, and the antisense strand has a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 41, and the antisense strand has a second nucleic acid sequence of SEQ ID NO: 42. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 43, and the antisense strand has a second nucleic acid sequence of SEQ ID NO: 44. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 45, and the antisense strand has a second nucleic acid sequence of SEQ ID NO: 46. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 47, and the antisense strand has a second nucleic acid sequence of SEQ ID NO: 48.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 63, and the antisense strand has a second nucleic acid sequence of SEQ ID NO: 40. In some embodiments, provided herein are MAPT RNAi agent having a sense strand and an antisense strand, wherein the sense strand and the anti sense strand form a duplex, and wherein the sense strand has a first nucleic acid sequence selected from any one of SEQ ID NOs: 64, 66-69, 71, 75-86, 93-100, and the antisense strand has a second nucleic acid sequence of SEQ ID NO: 65. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 64, and the antisense strand has a second nucleic acid sequence selected from any one of SEQ ID NOs: 70, 72-74. In some embodiments, provided herein are MAPT RNAi agent having a sense strand and an antisense strand, wherein the sense strand and the anti sense strand form a duplex, and wherein the sense strand has a first nucleic acid sequence selected from SEQ ID NO: 87 or 89, and the antisense strand has a second nucleic acid sequence of SEQ ID NO: 88. In some embodiments, provided herein are MAPT RNAi agent having a sense strand and an antisense strand, wherein the sense strand and the antisense strand form a duplex, and wherein the sense strand has a first nucleic acid sequence selected from SEQ ID NO: 90 or 92, and the antisense strand has a second nucleic acid sequence of SEQ ID NO: 91. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 101, and the antisense strand has a second nucleic acid sequence of SEQ ID NO: 102. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 103, and the antisense strand has a second nucleic acid sequence of SEQ ID NO: 104.

In some embodiments, provided herein are MAPT RNAi agent having a sense strand and an antisense strand, wherein the sense strand and the antisense strand form a duplex, and wherein the sense strand has a first nucleic acid sequence of SEQ ID NO: 105, and the antisense strand has a second nucleic acid sequence selected from any one of SEQ ID NOs: 65, 106-108. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 109, and the antisense strand has a second nucleic acid sequence of SEQ ID NO: 65. In some embodiments, provided herein are MAPT RNAi agent having a sense strand and an antisense strand, wherein the sense strand and the anti sense strand form a duplex, and wherein the sense strand has a first nucleic acid sequence of SEQ ID NO: 110, and the antisense strand has a second nucleic acid sequence of SEQ ID NO: 40. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 111, and the antisense strand has a second nucleic acid sequence of SEQ ID NO: 112. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 113, and the antisense strand has a second nucleic acid sequence of SEQ ID NO: 114. In some embodiments, provided herein are MAPT RNAi agent having a sense strand and an antisense strand, wherein the sense strand and the antisense strand form a duplex, and wherein the sense strand has a first nucleic acid sequence of SEQ ID NO: 115, and the antisense strand has a second nucleic acid sequence of SEQ ID NO: 116.

TABLE 2

MAPT RNAi Agents with Modifications

| MAPT RNAi Agent No. | Strand | Sequence from 5' to 3' end | SEQ ID NO |
|---|---|---|---|
| 13 | S | mA*mC*mAmAmGmCfUmGfAfCfCmUmUmCmCmGmCmGmA*mG*mA | 25 |
| | AS | VPmU*fC*mUmCmGfCmGmGmAmAmGmGmUfCmAfGmCmUmUmGmU*mG*mG | 26 |
| 14 | S | mA*mG*mAmUmUmGfAmAfAfCfCmCmAmCmAmAmGmCmU*mG*mA | 27 |
| | AS | VPmU*fC*mAmGmCfUmUmGmUmGmGmGmUfUmUfCmAmAmUmCmU*mU*mU | 28 |
| 15 | S | mA*mA*mUmAmAmAfAmAfGfAfUmUmGmAmAmAmCmCmC*mA*mA | 29 |
| | AS | VPmU*fU*mGmGmGfUmUmUmCmAmAmUmCfUmUfUmUmUmAmUmU*mU*mC | 30 |
| 16 | S | mG*mG*mAmAmAmUfAmAfAfAfAmGmAmUmUmGmAmAmA*mC*mA | 31 |
| | AS | VPmU*fG*mUmUmUfCmAmAmUmCmUmUmUfUmUfAmUmUmUmCmC*mU*mC | 32 |
| 17 | S | mG*mG*mCmGmGmAfGmGfAfAfAmUmAmAmAmAmAmGmA*mU*mA | 33 |
| | AS | VPmU*fA*mUmCmUfUmUmUmUmAmUmUmUfCmCfUmCmCmGmCmC*mA*mG | 34 |

TABLE 2-continued

MAPT RNAi Agents with Modifications

| MAPT RNAi Agent No. | Strand | Sequence from 5' to 3' end | SEQ ID NO |
|---|---|---|---|
| 18 | S | mG*mA*mAmGmUmAfAmAfAfUfCmUmGmAmGmAmAmGmC*mU*mA | 35 |
| | AS | VPmU*fA*mGmCmUfUmCmUmCmAmGmAmUfUmUfUmAmCmUmUmC*mC*mA | 36 |
| 19 | S | mG*mG*mAmAmGmUfAmAfAfAfUmCmUmGmAmGmAmAmG*mC*mA | 37 |
| | AS | VPmU*fG*mCmUmUfCmUmCmAmGmAmUmUfUmUfAmCmUmUmCmC*mA*mC | 38 |
| 20 | S | mG*mU*mGmGmAmAfGmUfAfAfAmAmUmCmUmGmAmGmA*mA*mA | 39 |
| | AS | VPmU*fU*mUmCmUfCmAmGmAmUmUmUmUfAmCfUmUmCmCmAmC*mC*mU | 40 |
| 21 | S | mC*mC*mAmGmGmUfGmGfAfAfGmUmAmAmAmAmUmCmU*mG*mA | 41 |
| | AS | VPmU*fC*mAmGmAfUmUmUmUmAmCmUmUfCmCfAmCmCmUmGmG*mC*mC | 42 |
| 22 | S | mC*mA*mAmGmUmCfCmAfAfGfAmUmCmGmGmCmUmCmC*mA*mA | 43 |
| | AS | VPmU*fU*mGmGmAfGmCmCmGmAmUmCmUfUmGfGmAmCmUmUmG*mA*mC | 44 |
| 23 | S | mU*mC*mUmGmGmUfGmAfAfCfCmUmCmCmAmAmAmAmU*mC*mA | 45 |
| | AS | VPmU*fG*mAmUmUfUmUmGmGmAmGmGmUfUmCfAmCmCmAmGmA*mG*mC | 46 |
| 24 | S | mC*mA*mGmGmUmGfGmAfAfGfUmAmAmAmAmUmCmUmG*mA*mA | 47 |
| | AS | VPmU*fU*mCmAmGfAmUmUmUmUmAmCmUfUmCfCmAmCmCmUmG*mG*mC | 48 |
| 31 | S | mG*mU*mGmGmAmAfGmUfAfAfAmA(Uhd)mCmUmGmAmGmA*mA*mA | 63 |
| | AS | VPmU*fU*mUmCmUfCmAmGmAmUmUmUmUfAmCfUmUmCmCmAmC*mC*mU | 40 |
| 32 | S | mG*mU*mGmGmAmAmGmUfAfAfAmA(Uhd)mCmUmGmAmGmA*mA*mA | 64 |
| | AS | VPmU*fU*mUmCfUmCmAfGmAmUmUmUmUfAmCfUmUmCmCmAmC*mC*mU | 65 |
| 33 | S | mG*mU*mGmGmAmAmGmUfAfAfA(Ahd)mUmCmUmGmAmGmA*mA*mA | 66 |
| | AS | VPmU*fU*mUmCfUmCmAfGmAmUmUmUmUfAmCfUmUmCmCmAmC*mC*mU | 65 |
| 34 | S | mG*mU*mGmGmAmAmGmUfA(n)fAmA(Uhd)mCmUmGmAmGmA*mA*mA | 67 |
| | AS | VPmU*fU*mUmCfUmCmAfGmAmUmUmUmUfAmCfUmUmCmCmAmC*mC*mU | 65 |
| 35 | S | mG*mU*mGmGmAmAGmUfA(n)fAmA(Uhd)mCmUmGmAmGmA*mA*mA | 68 |
| | AS | VPmU*fU*mUmCfUmCmAfGmAmUmUmUmUfAmCfUmUmCmCmAmC*mC*mU | 65 |
| 36 | S | mG*mU*mGmGmAmAmGmU(n)fAfAmA(Uhd)mCmUmGmAmGmA*mA*mA | 69 |
| | AS | VPmU*fU*mUmCfUmCmAfGmAmUmUmUmUfAmCfUmUmCmCmAmC*mC*mU | 65 |
| 37 | S | mG*mU*mGmGmAmAmGmUfAfAfAmA(Uhd)mCmUmGmAmGmA*mA*mA | 64 |
| | AS | VPmU*fU*mUmCmUfCmAmGmAfUmUmUmUfAmCfUmUfCmCfAmC*mC*mU | 70 |
| 38 | S | mG*mU*mGmGmAmAmGmUfAfAfAmA(Uhd)mCfUmGmAmGmA*mA*mA | 71 |
| | AS | VPmU*fU*mUmCfUmCmAfGmAmUmUmUmUfAmCfUmUmCmCmAmC*mC*mU | 65 |
| 39 | S | mG*mU*mGmGmAmAmGmUfAfAfAmA(Uhd)mCmUmGmAmGmA*mA*mA | 64 |
| | AS | VPmU*fU*mUmCfUmCfAmGmAmUmUmUmUfAmCfUmUmCmCmAmC*mC*mU | 72 |
| 40 | S | mG*mU*mGmGmAmAmGmUfAfAfAmA(Uhd)mCmUmGmAmGmA*mA*mA | 64 |
| | AS | VPmU*fU*fUmCmUmCfAmGmAmUmUmUmUfAmCfUmUmCmCmAmC*mC*mU | 73 |
| 41 | S | mG*mU*mGmGmAmAmGmUfAfAfAmA(Uhd)mCmUmGmAmGmA*mA*mA | 64 |
| | AS | VPmU*fU*mUmCfUmCmAmGmAmUmUmUmUfAmCmUmUmCmCmAmC*mC*mU | 74 |
| 42 | S | mG*mU*mGmGmAmAmGmUfAfAfA(Uhd)fUmCfUmGmAmGmA*mA*mA | 75 |
| | AS | VPmU*fU*mUmCfUmCmAfGmAmUmUmUmUfAmCfUmUmCmCmAmC*mC*mU | 65 |
| 43 | S | (Ghd)*mU*mGmGmAmAmGmUfAfAfAmAmUmCmUmGmAmGmA*mA*mA | 76 |
| | AS | VPmU*fU*mUmCfUmCmAfGmAmUmUmUmUfAmCfUmUmCmCmAmC*mC*mU | 65 |
| 44 | S | mG*(Uhd)*mGmGmAmAmGmUfAfAfAmAmUmCmUmGmAmGmA*mA*mA | 77 |
| | AS | VPmU*fU*mUmCfUmCmAfGmAmUmUmUmUfAmCfUmUmCmCmAmC*mC*mU | 65 |
| 45 | S | mG*mU*(Ghd)mGmAmAmGmUfAfAfAmAmUmCmUmGmAmGmA*mA*mA | 78 |
| | AS | VPmU*fU*mUmCfUmCmAfGmAmUmUmUmUfAmCfUmUmCmCmAmC*mC*mU | 65 |
| 46 | S | mG*mU*mGmGmA(Ahd)mGmUfAfAfAmAmUmCmUmGmAmGmA*mA*mA | 79 |
| | AS | VPmU*fU*mUmCfUmCmAfGmAmUmUmUmUfAmCfUmUmCmCmAmC*mC*mU | 65 |

TABLE 2-continued

MAPT RNAi Agents with Modifications

| MAPT RNAi Agent No. | Strand | Sequence from 5' to 3' end | SEQ ID NO |
|---|---|---|---|
| 47 | S | mG*mU*mGmGmAmAmG(Uhd)fAfAfAmAmUmCmUmGmAmGmA*mA*mA | 80 |
| | AS | VPmU*fU*mUmCfUmCmAfGmAmUmUmUmUfAmCfUmUmCmCmAmC*mC*mU | 65 |
| 48 | S | mG*mU*mGmGmAmAmGmU(Ahd)fAfAmAmUmCmUmGmAmGmA*mA*mA | 81 |
| | AS | VPmU*fU*mUmCfUmCmAfGmAmUmUmUmUfAmCfUmUmCmCmAmC*mC*mU | 65 |
| 49 | S | mG*mU*mGmGmAmAmGmUfA(Ahd)fAmAmUmCmUmGmAmGmA*mA*mA | 82 |
| | AS | VPmU*fU*mUmCfUmCmAfGmAmUmUmUmUfAmCfUmUmCmCmAmC*mC*mU | 65 |
| 50 | S | mG*mU*mGmGmAmAmGmUfAfAfAmAmUmC(Uhd)mGmAmGmA*mA*mA | 83 |
| | AS | VPmU*fU*mUmCfUmCmAfGmAmUmUmUmUfAmCfUmUmCmCmAmC*mC*mU | 65 |
| 51 | S | mG*mU*mGmGmAmAmGmUfAfAfAmAmUmCmUmGmAmG(Ahd)*mA*mA | 84 |
| | AS | VPmU*fU*mUmCfUmCmAfGmAmUmUmUmUfAmCfUmUmCmCmAmC*mC*mU | 65 |
| 52 | S | mG*mU*mGmGmAmAmGmUfAfAfAmAmUmCmUmGmAmGmA*(Ahd)*mA | 85 |
| | AS | VPmU*fU*mUmCfUmCmAfGmAmUmUmUmUfAmCfUmUmCmCmAmC*mC*mU | 65 |
| 53 | S | mG*mU*mGmGmAmAmGmUfAfAfAmAmUmCmUmGmAmGmA*mA*(Ahd) | 86 |
| | AS | VPmU*fU*mUmCfUmCmAfGmAmUmUmUmUfAmCfUmUmCmCmAmC*mC*mU | 65 |
| 54 | S | mC*mC*mAmAmGmUmGmUfGfGfCmU(Chd)mAmUmUmAmGmG*mC*mA | 87 |
| | AS | VPmU*fG*mCmCfUmAmAfUmGmAmGmCmCfAmCfAmCmUmUmGmG*mA*mG | 88 |
| 55 | S | mC*mC*mAmAmGmUmGmU(n)fGfCmU(Chd)mAmUmUmAmGmG*mC*mA | 89 |
| | AS | VPmU*fG*mCmCfUmAmAfUmGmAmGmCmCfAmCfAmCmUmUmGmG*mA*mG | 88 |
| 56 | S | mU*mG*mCmAmAmAmUmA(n)fUfCmU(Ahd)mCmAmAmAmCmC*mA*mA | 90 |
| | AS | VPmU*fU*mGmGfUmUmUfGmUmAmGmAmCfUmAfUmUmUmGmCmA*mC*mC | 91 |
| 57 | S | mU*mG*mCmAmAmAmUmAfGfUfCmU(Ahd)mCmAmAmAmCmC*mA*mA | 92 |
| | AS | VPmU*fU*mGmGfUmUmUfGmUmAmGmAmCfUmAfUmUmUmGmCmA*mC*mC | 91 |
| 58 | S | mG*mU*mG(Ghd)mAmAmGmUfAfAfAmAmUmCmUmGmAmGmA*mA*mA | 93 |
| | AS | VPmU*fU*mUmCfUmCmAfGmAmUmUmUmUfAmCfUmUmCmCmAmC*mC*mU | 65 |
| 59 | S | mG*mU*mGmG(Ahd)mAmGmUfAfAfAmAmUmCmUmGmAmGmA*mA*mA | 94 |
| | AS | VPmU*fU*mUmCfUmCmAfGmAmUmUmUmUfAmCfUmUmCmCmAmC*mC*mU | 65 |
| 60 | S | mG*mU*mGmGmAmA(Ghd)mUfAfAfAmAmUmCmUmGmAmGmA*mA*mA | 95 |
| | AS | VPmU*fU*mUmCfUmCmAfGmAmUmUmUmUfAmCfUmUmCmCmAmC*mC*mU | 65 |
| 61 | S | mG*mU*mGmGmAmAmGmUfAfA(Ahd)mAmUmCmUmGmAmGmA*mA*mA | 96 |
| | AS | VPmU*fU*mUmCfUmCmAfGmAmUmUmUmUfAmCfUmUmCmCmAmC*mC*mU | 65 |
| 62 | S | mG*mU*mGmGmAmAmGmUfAfAfAmAmU(Chd)mUmGmAmGmA*mA*mA | 97 |
| | AS | VPmU*fU*mUmCfUmCmAfGmAmUmUmUmUfAmCfUmUmCmCmAmC*mC*mU | 65 |
| 63 | S | mG*mU*mGmGmAmAmGmUfAfAfAmAmUmCmU(Ghd)mAmGmA*mA*mA | 98 |
| | AS | VPmU*fU*mUmCfUmCmAfGmAmUmUmUmUfAmCfUmUmCmCmAmC*mC*mU | 65 |
| 64 | S | mG*mU*mGmGmAmAmGmUfAfAfAmAmUmCmUmG(Ahd)mGmA*mA*mA | 99 |
| | AS | VPmU*fU*mUmCfUmCmAfGmAmUmUmUmUfAmCfUmUmCmCmAmC*mC*mU | 65 |
| 65 | S | mG*mU*mGmGmAmAmGmUfAfAfAmAmUmCmUmGmA(Ghd)mA*mA*mA | 100 |
| | AS | VPmU*fU*mUmCfUmCmAfGmAmUmUmUmUfAmCfUmUmCmCmAmC*mC*mU | 65 |
| 66 | S | mC*mC*mAmGmGmUmGmGfAfAfGmU(Ahd)mAmAmAmUmCmU*mG*mA | 101 |
| | AS | VPmU*fC*mAmGfAmUmUfUmUmAmCmUmUfCmCfAmCmCmUmGmG*mC*mC | 102 |
| 67 | S | mG*mG*mAmAmGmUmAmAfAfAfUmC(Uhd)mGmAmGmAmAmG*mC*mA | 103 |
| | AS | VPmU*fG*mCmUfUmCmUfCmAmGmAmUmUfUmUfAmCmUmUmCmC*mA*mC | 104 |
| 68 | S | mG*mU*mGmGmAmAfGmUfAfAfAmAmUmCmUmGmAmGmAmA*mA* | 105 |
| | AS | VPmU*fU*mUmCmUmCmAmGmAmUmUmUmUfAmCfUmUmCmCmAmC*mC*mU | 106 |

TABLE 2-continued

| MAPT RNAi Agents with Modifications | | | |
|---|---|---|---|
| MAPT RNAi Agent No. | Strand | Sequence from 5' to 3' end | SEQ ID NO |
| 69 | S | mG*mU*mGmGmAmAfGmUfAfAfAmAmUmCmUmGmAmGmAmA*mA* | 105 |
| | AS | VPmU*fU*mUfCmUfCfAmGfAmUmUmUmUfAmCfUmUmCmCmAmC*mC*mU | 107 |
| 70 | S | mG*mU*mGmGmAmAfGmUfAfAfAmAmUmCmUmGmAmGmAmA*mA* | 105 |
| | AS | VPmU*fU*mUmCfUmCmAfGmAmUmUmUmUfAmCfUmUmCmCmAmC*mC*mU | 65 |
| 71 | S | mG*mU*mGmGmAmAfGmUfAfAfAmAmUmCmUmGmAmGmAmA*mA* | 105 |
| | AS | VPmU*fU*mUmCfUfCfAfGmAmUmUmUmUfAmCfUmUmCmCmAmC*mC*mU | 108 |
| 72 | S | mG*mU*mGmGmAmAfGmUfA(n)fAmAmUmCmUmGmAmGmAmA*mA* | 109 |
| | AS | VPmU*fU*mUmCfUmCmAfGmAmUmUmUmUfAmCfUmUmCmCmAmC*mC*mU | 65 |
| 73 | S | mG*mU*mGmGmAmAfGmUfAfAfAmAmUmCmUmGmAmGmA*mA*mG | 110 |
| | AS | VPmU*fU*mUmCmUfCmAmGmAmUmUmUmUfAmCfUmUmCmCmAmC*mC*mU | 40 |
| 74 | S | mA*mA*fGmUfAfAfAmAmUmCmUmGmAmGmA*mA*mA | 111 |
| | AS | VPmU*fU*mUmCmUfCmAmGmAmUmUmUmUfAmCfUmU*mC*mC*mA*mC* mC*mU | 112 |
| 75 | S | mG*mU*mGmGmAmAfGmUfAfAfAmAmUmCmUmGmAmGmAmAmAdTdT* | 113 |
| | AS | VPmU*fU*mUmCmUfCmAmGmAmUmUmUmUfAmCfUmUmCmC*mA*mCdTdT | 114 |
| 76 | S | mG*mU*mGmGmAmAmGmUfAfAfAmAmUmCmUmGmAmGmAmA*mA* | 115 |
| | AS | VPmU*fU*mUmCmUfCmAmGmAmUmUmUmUfAmCfUmUmCmA*mC*mC* mU | 116 |

Abbreviations
"m" indicates 2'-OMe;
"f" indicated 2'-fluoro;
"*" indicates phosphorothioate linkage;
"VP" indicates 5'-vinylphosphonate;
"Uhd" indicates 2'-O-hexadecyl uridine;
"Chd" indicates 2'-O-hexadecyl cytidine;
"Ahd" indicates 2'-O-hexadecyl adenosine;
"iAb" indicates inverted abasic moiety;
"n" indicates abasic moiety;
"S" means the sense strand;
"AS" means the antisense strand.

TABLE 3

| Abasic or inverted abasic (iAb) moieties | |
|---|---|
| | Structure |
| 1 (abasic) | 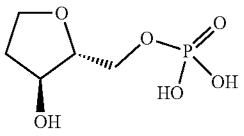 [SMILES: O=P(O)(O)OC[C@H]1OCC[C@@H]1O] |
| 2 (iAb) | 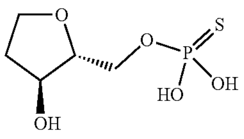 [SMILES: O[C@H]1CCO[C@@H]1COP(O)(O)=S] |

"5'" and "3'" indicate the 5' to 3' direction of the sequences

In some embodiments, the sense strand of the MAPT RNAi agent has a delivery moiety. In some embodiments, the sense strand of the MAPT RNAi agent has a delivery moiety conjugated to the 5' or 3' end of the sense strand. In some embodiments, the sense strand of the MAPT RNAi agent has a delivery moiety conjugated to a nucleotide of the sense strand. The delivery moiety can facilitate the entry of RNAi agent into the cells. In some embodiments, the delivery moiety is α-tocopherol or palmitic acid (see Table 4). In some embodiments, the delivery moiety is a known delivery moiety for delivering RNAi agent into a cell, e.g., a delivery moiety described in Hu et al., Signal Transduction and Targeted Therapy (2020) 5:101. Placement of a delivery moiety on the RNAi agent needs to overcome potential inefficient loading of AGO2 (Argonaute-2), or other hindrance of the RNA-induced silencing complex (RISC) complex activity.

In some embodiments, the delivery moiety is conjugated to the 5' or 3' end of the sense stand via a linker. In some embodiments, the linker is selected from Linker 1, Linker 2, Linker 3, or Linker 4 of Table 5. Other suitable linkers are known in the art. Exemplary linker-delivery moiety pairs are shown in Table 6. In some embodiments, the MAPT RNAi agent has a linker-delivery moiety pair of Table 6.

In some embodiments, the delivery moiety is conjugated to a nucleotide of the sense strand. In that case, the delivery moiety is a modified nucleotide located in the sense strand. In some embodiments, the modified nucleotide is 2'-O-hexadecyl uridine, 2'-O-hexadecyl cytidine, 2'-O-hexadecyl guanine, or 2'-O-hexadecyl adenosine (Table 4).

TABLE 4
| Delivery Moieties | |
|---|---|
| Delivery Moiety | Structure |
| 1 | α-Tocopherol<br>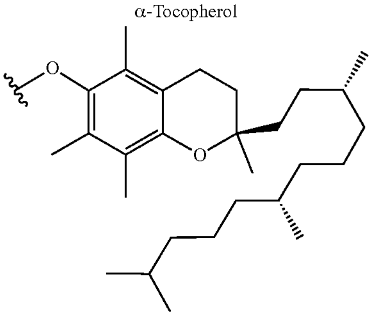 |
| 2 | Palmitic Acid<br>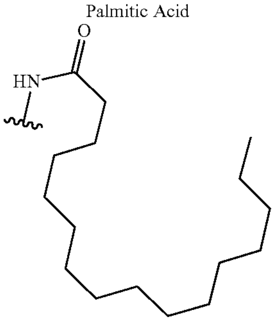 |
| 3 | Uhd (2'-O-hexadecyl uridine)<br>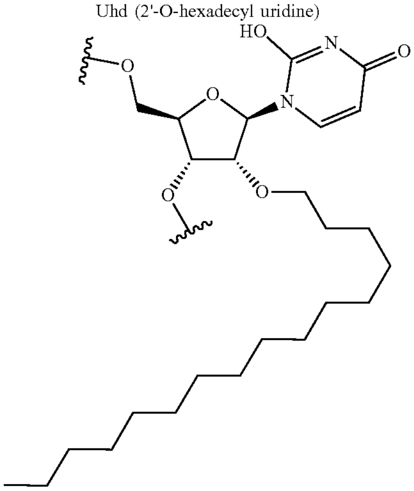 |
TABLE 4-continued
| Delivery Moieties | |
|---|---|
| Delivery Moiety | Structure |
| 4 | Ahd (2'-O-hexadecyl adenosine)<br>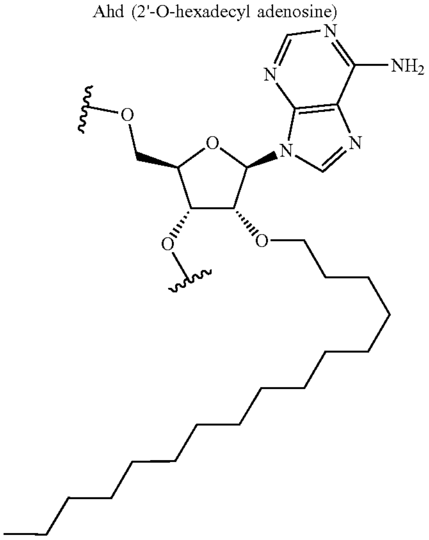 |
| 5 | Chd (2'-O-hexadecyl cytidine)<br>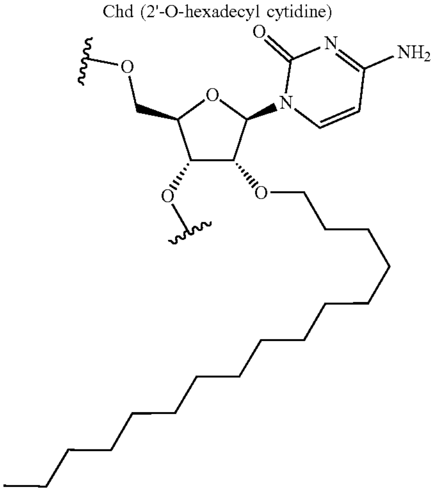 |

6
Ghd (2'-O-hexadecyl guanine)
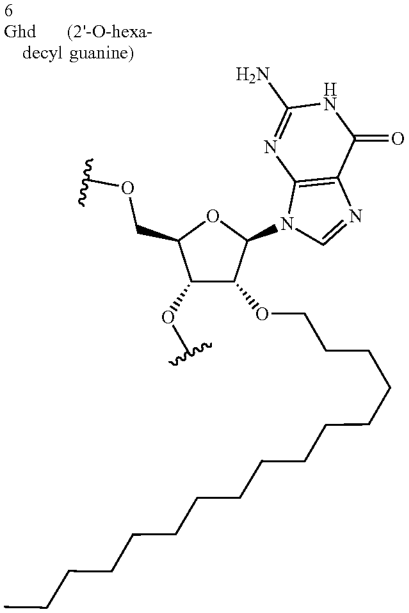
| Linkers | |
|---|---|
| Linker | Structure |
| 1 | Teg (tetraethylene glycol) linker 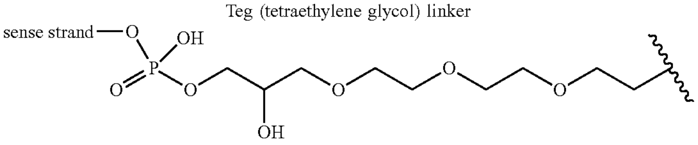 |
| 2 | Piperidinol-PEG linker 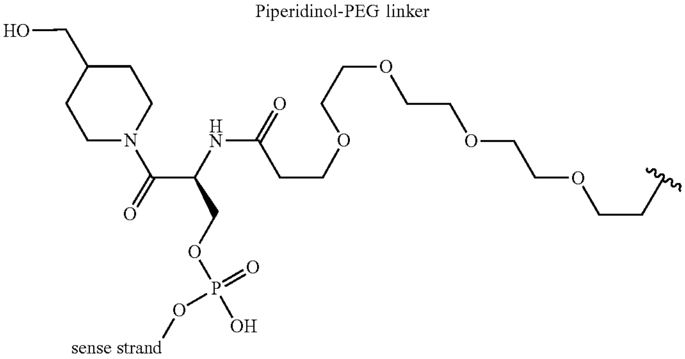 |
| 3 | Teg (tetraethylene glycol) linker PS 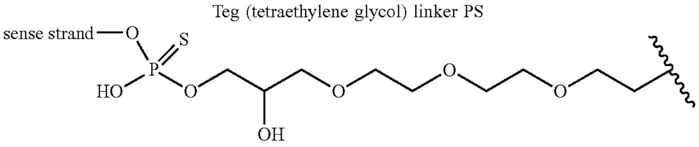 |

-continued
| Linkers | |
|---|---|
| **Linker** | **Structure** |
| 4 | Piperidinol-PEG linker PS<br>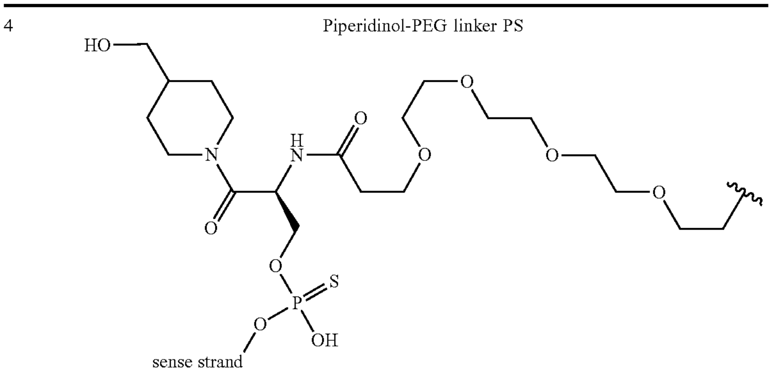 |
TABLE 6
| Linker Delivery Moiety Pairs (LDP) | | |
|---|---|---|
| **LDP** | **Linker** | **Delivery Moiety** |
| 1 | Teg (tetraethylene glycol) linker<br>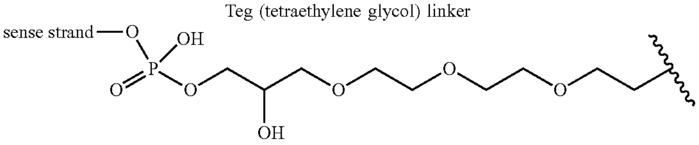 | α-Tocopherol<br>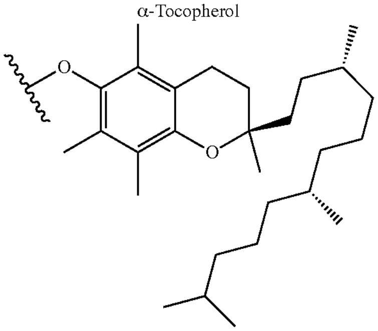 |
| 2 | Piperidinol-PEG linker<br>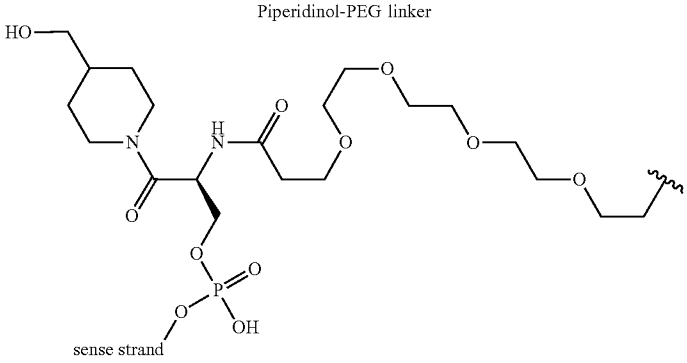 | α-Tocopherol<br>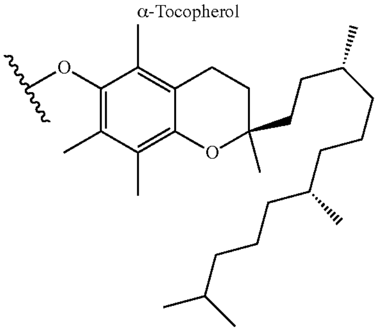 |

TABLE 6-continued
| Linker Delivery Moiety Pairs (LDP) | | |
|---|---|---|
| LDP | Linker | Delivery Moiety |
| 3 | Piperidinol-PEG linker 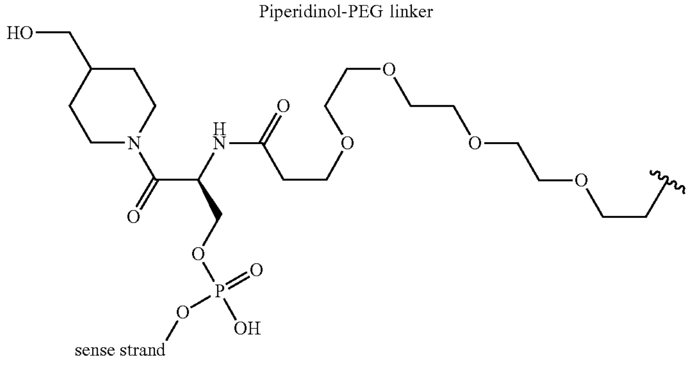 | Palmitic Acid 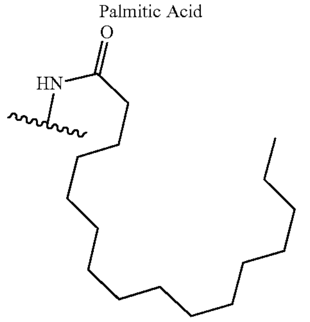 |
| 4 | None | Uhd 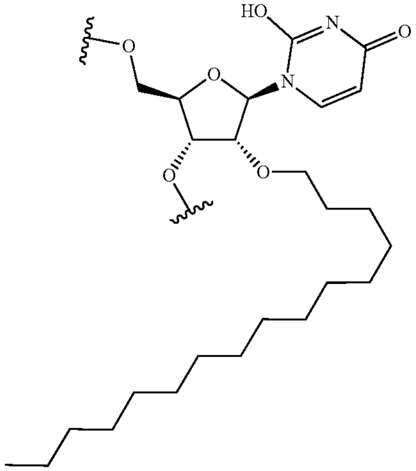 [SMILES: *OC[C@H]1O[C@@H](n2ccc(=O)nc2O)[C@H](OCCCCCCCCCCCCCCCC)[C@@H]1O*] |
| 5 | None | Ahd 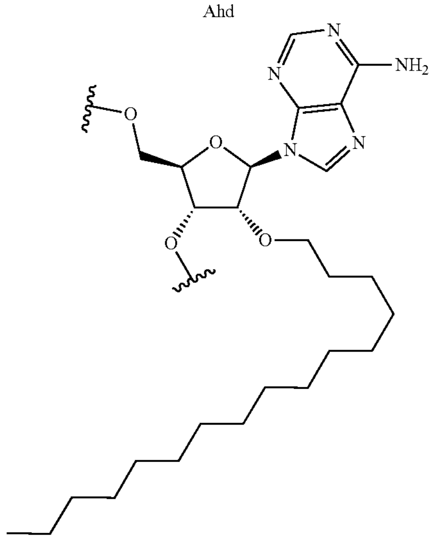 |

TABLE 6-continued

| Linker Delivery Moiety Pairs (LDP) | | |
|---|---|---|
| LDP | Linker | Delivery Moiety |
| 6 | None | Chd<br>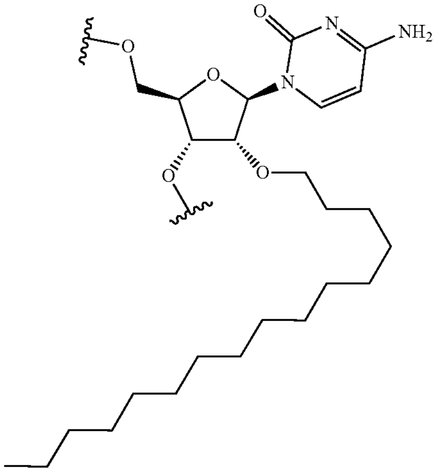 [SMILES: *OC[C@H]1O[C@@H](n2ccc(N)nc2=O)[C@H](OCCCCCCCCCCCCCCCC)[C@@H]1O*] |
| 7 | None | Ghd<br>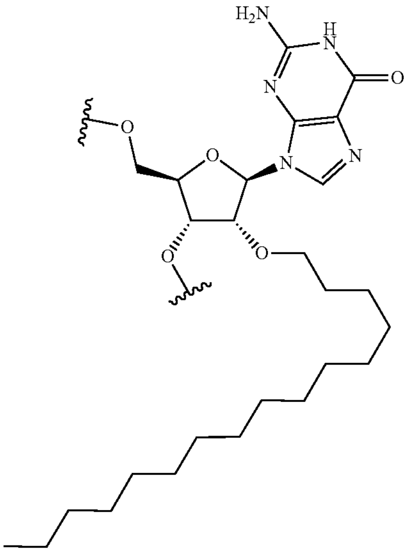 [SMILES: *OC[C@H]1O[C@@H](n2cnc3c(=O)[nH]c(N)nc32)[C@H](OCCCCCCCCCCCCCCCC)[C@@H]1O*] |

In a further aspect, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprise a pair of nucleic acid sequences selected from the group consisting of:

(a) the sense strand comprises a first nucleic acid sequence of SEQ ID NO: 1, and the antisense strand comprises a second nucleic acid sequence of SEQ ID NO: 2;

(b) the sense strand comprises a first nucleic acid sequence of SEQ ID NO: 3, and the antisense strand comprises a second nucleic acid sequence of SEQ ID NO: 4;

(c) the sense strand comprises a first nucleic acid sequence of SEQ ID NO: 5, and the antisense strand comprises a second nucleic acid sequence of SEQ ID NO: 6;

(d) the sense strand comprises a first nucleic acid sequence of SEQ ID NO: 7, and the antisense strand comprises a second nucleic acid sequence of SEQ ID NO: 8;

(e) the sense strand comprises a first nucleic acid sequence of SEQ ID NO: 9, and the antisense strand comprises a second nucleic acid sequence of SEQ ID NO: 10;

(f) the sense strand comprises a first nucleic acid sequence of SEQ ID NO: 11, and the antisense strand comprises a second nucleic acid sequence of SEQ ID NO: 12;

(g) the sense strand comprises a first nucleic acid sequence of SEQ ID NO:13, and the antisense strand comprises a second nucleic acid sequence of SEQ ID NO: 14;

(h) the sense strand comprises a first nucleic acid sequence of SEQ ID NO:15, and the antisense strand comprises a second nucleic acid sequence of SEQ ID NO: 16;

(i) the sense strand comprises a first nucleic acid sequence of SEQ ID NO:17, and the antisense strand comprises a second nucleic acid sequence of SEQ ID NO: 18;

(j) the sense strand comprises a first nucleic acid sequence of SEQ ID NO:19, and the antisense strand comprises a second nucleic acid sequence of SEQ ID NO: 20;

(k) the sense strand comprises a first nucleic acid sequence of SEQ ID NO:21, and the antisense strand comprises a second nucleic acid sequence of SEQ ID NO: 22;

(l) the sense strand comprises a first nucleic acid sequence of SEQ ID NO:23, and the antisense strand comprises a second nucleic acid sequence of SEQ ID NO: 24;

(m) the sense strand comprises a first nucleic acid sequence of SEQ ID NO: 55, and the antisense strand comprises a second nucleic acid sequence of SEQ ID NO: 16;

(n) the sense strand comprises a first nucleic acid sequence of SEQ ID NO: 56, and the antisense strand comprises a second nucleic acid sequence of SEQ ID NO: 16;

(o) the sense strand comprises a first nucleic acid sequence of SEQ ID NO: 57, and the antisense strand comprises a second nucleic acid sequence of SEQ ID NO: 58;

(p) the sense strand comprises a first nucleic acid sequence of SEQ ID NO: 59, and the antisense strand comprises a second nucleic acid sequence of SEQ ID NO: 58;

(q) the sense strand comprises a first nucleic acid sequence of SEQ ID NO: 60, and the antisense strand comprises a second nucleic acid sequence of SEQ ID NO: 61;

(r) the sense strand comprises a first nucleic acid sequence of SEQ ID NO: 62, and the antisense strand comprises a second nucleic acid sequence of SEQ ID NO: 61;

(s) the sense strand comprises a first nucleic acid sequence of SEQ ID NO: 117, and the antisense strand comprises a second nucleic acid sequence of SEQ ID NO: 118;

(t) the sense strand comprises a first nucleic acid sequence of SEQ ID NO: 119, and the antisense strand comprises a second nucleic acid sequence of SEQ ID NO: 16, wherein optionally one or more nucleotides of the sense strand and the anti sense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 1, and the antisense strand has a second nucleic acid sequence of SEQ ID NO: 2;

(b) the sense strand has a first nucleic acid sequence of SEQ ID NO: 3, and the antisense strand has a second nucleic acid sequence of SEQ ID NO: 4;

(c) the sense strand has a first nucleic acid sequence of SEQ ID NO: 5, and the antisense strand has a second nucleic acid sequence of SEQ ID NO: 6;

(d) the sense strand has a first nucleic acid sequence of SEQ ID NO: 7, and the antisense strand has a second nucleic acid sequence of SEQ ID NO: 8;

(e) the sense strand has a first nucleic acid sequence of SEQ ID NO: 9, and the antisense strand has a second nucleic acid sequence of SEQ ID NO: 10;

(f) the sense strand has a first nucleic acid sequence of SEQ ID NO: 11, and the antisense strand has a second nucleic acid sequence of SEQ ID NO: 12;

(g) the sense strand has a first nucleic acid sequence of SEQ ID NO:13, and the antisense strand has a second nucleic acid sequence of SEQ ID NO: 14;

(h) the sense strand has a first nucleic acid sequence of SEQ ID NO:15, and the antisense strand has a second nucleic acid sequence of SEQ ID NO: 16;

(i) the sense strand has a first nucleic acid sequence of SEQ ID NO:17, and the antisense strand has a second nucleic acid sequence of SEQ ID NO: 18;

(j) the sense strand has a first nucleic acid sequence of SEQ ID NO:19, and the antisense strand has a second nucleic acid sequence of SEQ ID NO: 20;

(k) the sense strand has a first nucleic acid sequence of SEQ ID NO:21, and the antisense strand has a second nucleic acid sequence of SEQ ID NO: 22;

(l) the sense strand has a first nucleic acid sequence of SEQ ID NO:23, and the antisense strand has a second nucleic acid sequence of SEQ ID NO: 24;

(m) the sense strand has a first nucleic acid sequence of SEQ ID NO: 55, and the antisense strand has a second nucleic acid sequence of SEQ ID NO: 16;

(n) the sense strand has a first nucleic acid sequence of SEQ ID NO: 56, and the antisense strand has a second nucleic acid sequence of SEQ ID NO: 16;

(o) the sense strand has a first nucleic acid sequence of SEQ ID NO: 57, and the antisense strand has a second nucleic acid sequence of SEQ ID NO: 58;

(p) the sense strand has a first nucleic acid sequence of SEQ ID NO: 59, and the antisense strand has a second nucleic acid sequence of SEQ ID NO: 58;

(q) the sense strand has a first nucleic acid sequence of SEQ ID NO: 60, and the antisense strand has a second nucleic acid sequence of SEQ ID NO: 61;

(r) the sense strand has a first nucleic acid sequence of SEQ ID NO: 62, and the antisense strand has a second nucleic acid sequence of SEQ ID NO: 61;

(s) the sense strand has a first nucleic acid sequence of SEQ ID NO: 117, and the antisense strand has a second nucleic acid sequence of SEQ ID NO: 118; and (t) the sense strand has a first nucleic acid sequence of SEQ ID NO: 119, and the antisense strand has a second nucleic acid sequence of SEQ ID NO: 16, wherein optionally one or more nucleotides of the sense strand and the antisense strand are independently modified nucleotides, and wherein optionally one or more internucleotide linkages of the sense strand and the antisense strand are modified internucleotide linkages.

In some embodiments, provided herein are MAPT RNAi agents of Formula (I): R-L-D, wherein R is a double stranded RNA (dsRNA) having a sense stand and an antisense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand comprise a pair of nucleic acid sequences selected from the group consisting of:

(a) the sense strand comprises a first nucleic acid sequence of SEQ ID NO: 25, and the antisense strand comprises a second nucleic acid sequence of SEQ ID NO: 26;
(b) the sense strand comprises a first nucleic acid sequence of SEQ ID NO: 27, and the antisense strand comprises a second nucleic acid sequence of SEQ ID NO: 28;
(c) the sense strand comprises a first nucleic acid sequence of SEQ ID NO: 29, and the antisense strand comprises a second nucleic acid sequence of SEQ ID NO: 30;
(d) the sense strand comprises a first nucleic acid sequence of SEQ ID NO: 31, and the antisense strand comprises a second nucleic acid sequence of SEQ ID NO: 32;
(e) the sense strand comprises a first nucleic acid sequence of SEQ ID NO: 33, and the antisense strand comprises a second nucleic acid sequence of SEQ ID NO: 34;
(f) the sense strand comprises a first nucleic acid sequence of SEQ ID NO: 35, and the antisense strand comprises a second nucleic acid sequence of SEQ ID NO: 36;
(g) the sense strand comprises a first nucleic acid sequence of SEQ ID NO: 37, and the antisense strand comprises a second nucleic acid sequence of SEQ ID NO: 38;
(h) the sense strand comprises a first nucleic acid sequence of SEQ ID NO: 39, and the antisense strand comprises a second nucleic acid sequence of SEQ ID NO: 40;
(i) the sense strand comprises a first nucleic acid sequence of SEQ ID NO: 41, and the antisense strand comprises a second nucleic acid sequence of SEQ ID NO: 42;
(j) the sense strand comprises a first nucleic acid sequence of SEQ ID NO: 43, and the antisense strand comprises a second nucleic acid sequence of SEQ ID NO: 44;
(k) the sense strand comprises a first nucleic acid sequence of SEQ ID NO: 45, and the antisense strand comprises a second nucleic acid sequence of SEQ ID NO: 46;
(l) the sense strand comprises a first nucleic acid sequence of SEQ ID NO: 47, and the antisense strand comprises a second nucleic acid sequence of SEQ ID NO: 48;
(m) the sense strand comprises a first nucleic acid sequence of SEQ ID NO: 105, and the antisense strand comprises a second nucleic acid sequence selected from SEQ ID NO: 65, 106-108;
(n) the sense strand comprises a first nucleic acid sequence of SEQ ID NO: 109, and the antisense strand comprises a second nucleic acid sequence of SEQ ID NO: 65;
(o) the sense strand comprises a first nucleic acid sequence of SEQ ID NO: 110, and the antisense strand comprises a second nucleic acid sequence of SEQ ID NO: 40;
(p) the sense strand comprises a first nucleic acid sequence of SEQ ID NO: 111, and the antisense strand comprises a second nucleic acid sequence of SEQ ID NO: 112;
(q) the sense strand comprises a first nucleic acid sequence of SEQ ID NO: 113, and the antisense strand comprises a second nucleic acid sequence of SEQ ID NO: 114; and
(r) the sense strand comprises a first nucleic acid sequence of SEQ ID NO: 115, and the antisense strand comprises a second nucleic acid sequence of SEQ ID NO: 116.

In some embodiments, provided herein are MAPT RNAi agents of Formula (I): R-L-D, wherein R is a double stranded RNA (dsRNA) having a sense stand and an anti-sense strand, wherein the sense strand and the antisense strand form a duplex; wherein D is a delivery means for delivering the dsRNA into a cell; and wherein L is a linking means for linking the dsRNA to the delivery means, or optionally absent, wherein the sense strand and the antisense strand have a pair of nucleic acid sequences selected from the group consisting of:

(a) the sense strand has a first nucleic acid sequence of SEQ ID NO: 25, and the antisense strand has a second nucleic acid sequence of SEQ ID NO: 26;
(b) the sense strand has a first nucleic acid sequence of SEQ ID NO: 27, and the antisense strand has a second nucleic acid sequence of SEQ ID NO: 28;
(c) the sense strand has a first nucleic acid sequence of SEQ ID NO: 29, and the antisense strand has a second nucleic acid sequence of SEQ ID NO: 30;
(d) the sense strand has a first nucleic acid sequence of SEQ ID NO: 31, and the antisense strand has a second nucleic acid sequence of SEQ ID NO: 32;
(e) the sense strand has a first nucleic acid sequence of SEQ ID NO: 33, and the antisense strand has a second nucleic acid sequence of SEQ ID NO: 34;
(f) the sense strand has a first nucleic acid sequence of SEQ ID NO: 35, and the antisense strand has a second nucleic acid sequence of SEQ ID NO: 36;
(g) the sense strand has a first nucleic acid sequence of SEQ ID NO: 37, and the antisense strand has a second nucleic acid sequence of SEQ ID NO: 38;
(h) the sense strand has a first nucleic acid sequence of SEQ ID NO: 39, and the antisense strand has a second nucleic acid sequence of SEQ ID NO: 40;
(i) the sense strand has a first nucleic acid sequence of SEQ ID NO: 41, and the antisense strand has a second nucleic acid sequence of SEQ ID NO: 42;
(j) the sense strand has a first nucleic acid sequence of SEQ ID NO: 43, and the antisense strand has a second nucleic acid sequence of SEQ ID NO: 44;
(k) the sense strand has a first nucleic acid sequence of SEQ ID NO: 45, and the antisense strand has a second nucleic acid sequence of SEQ ID NO: 46;
(l) the sense strand has a first nucleic acid sequence of SEQ ID NO: 47, and the antisense strand has a second nucleic acid sequence of SEQ ID NO: 48;
(m) the sense strand has a first nucleic acid sequence of SEQ ID NO: 105, and the antisense strand has a second nucleic acid sequence selected from SEQ ID NO: 65, 106-108;
(n) the sense strand has a first nucleic acid sequence of SEQ ID NO: 109, and the antisense strand has a second nucleic acid sequence of SEQ ID NO: 65;
(o) the sense strand has a first nucleic acid sequence of SEQ ID NO: 110, and the antisense strand has a second nucleic acid sequence of SEQ ID NO: 40;
(p) the sense strand has a first nucleic acid sequence of SEQ ID NO: 111, and the antisense strand has a second nucleic acid sequence of SEQ ID NO: 112;

(q) the sense strand has a first nucleic acid sequence of SEQ ID NO: 113, and the antisense strand has a second nucleic acid sequence of SEQ ID NO: 114; and (r) the sense strand has a first nucleic acid sequence of SEQ ID NO: 115, and the antisense strand has a second nucleic acid sequence of SEQ ID NO: 116.

In some embodiments, the delivery means is conjugated to the sense strand. In some embodiments, the delivery means is conjugated to the 5' or 3' end of the sense strand. In some embodiments, the delivery means is conjugated to a nucleotide of the sense strand. In some embodiments, the delivery means is palmitic acid or α-tocopherol. In some embodiments, the linking means is selected from the group consisting of Linker 1, Linker 2, Linker 3, and Linker 4 of Table 5.

The sense strand and antisense strand of MAPT RNAi agent can be synthesized using any nucleic acid polymerization methods known in the art, for example, solid-phase synthesis by employing phosphoramidite chemistry methodology (e.g., Current Protocols in Nucleic Acid Chemistry, Beaucage, S. L. et al. (Edrs.), John Wiley & Sons, Inc., New York, NY, USA), H-phosphonate, phosphortriester chemistry, or enzymatic synthesis. Automated commercial synthesizers can be used, for example, MerMade™ 12 from LGC Biosearch Technologies, or other synthesizers from BioAutomation or Applied Biosystems. Phosphorothioate linkages can be introduced using a sulfurizing reagent such as phenylacetyl disulfide or DDTT (((dimethyl aminomethylidene) amino)-3H-1,2,4-dithiazaoline-3-thione). It is well known to use similar techniques and commercially available modified amidites and controlled-pore glass (CPG) products to synthesize modified oligonucleotides or conjugated oligonucleotides.

Purification methods can be used to exclude the unwanted impurities from the final oligonucleotide product. Commonly used purification techniques for single stranded oligonucleotides include reverse-phase ion pair high performance liquid chromatography (RP-IP-HPLC), capillary gel electrophoresis (CGE), anion exchange HPLC (AX-HPLC), and size exclusion chromatography (SEC). After purification, oligonucleotides can be analyzed by mass spectrometry and quantified by spectrophotometry at a wavelength of 260 nm. The sense strand and anti sense strand can then be annealed to form a duplex.

In another aspect, provided herein are pharmaceutical compositions comprising a MAPT RNAi agent described herein and a pharmaceutically acceptable carrier. Also provided herein are pharmaceutical compositions comprising a means for reducing MAPT expression in a cell and a pharmaceutically acceptable carrier. Such pharmaceutical compositions can also comprise one or more pharmaceutically acceptable excipient, diluent, or carrier. Pharmaceutical compositions can be prepared by methods well known in the art (e.g., Remington: The Science and Practice of Pharmacy, 23rd edition (2020), A. Loyd et al., Academic Press).

In a further aspect, provided herein are methods of reducing MAPT expression in a cell (e.g., a neuron), such methods can include introducing a MAPT RNAi agent described herein into the cell; and incubating the cell for a time sufficient for degradation of MAPT mRNA, thereby reducing MAPT expression in the cell. The MAPT RNAi agent can be introduced into the cell (e.g., a neuron) using a method known in the art, e.g., transfection, electroporation, microinjection, or uptake by the cell via natural transport mechanisms.

In another aspect, provided herein are methods of reducing MAPT expression in a patient in need thereof, and such method comprises administering to the patient an effective amount of a MAPT RNAi agent or a pharmaceutical composition described herein. Aggregation of MAPT can be caused by overexpression of the MAPT protein or a mutation that affects the structure of the protein, resulting in an increased tendency of the MAPT protein to self-associate. Therefore, reducing MAPT expression level can be beneficial to the patient with tauopathy.

In another aspect, provided herein are methods of treating a tauopathy in a patient in need thereof, and such method comprises administering to the patient an effective amount of the MAPT RNAi agent or a pharmaceutical composition described herein. Exemplary tauopathy includes, but are not limited to, Alzheimer's disease (AD), frontotemporal dementia (FTD), frontotemporal dementia with parkinsonism linked to chromosome 17 (FTDP-17), frontotemporal lobar degeneration (FTLD), behavioral variant frontotemporal dementia (bvFTD), nonfluent variant primary progressive aphasia (nfvPPA), Parkinson's discase, Pick's disease (PiD), primary progressive aphasia-semantic (PPA-S), primary progressive aphasia-logopenic (PPA-L), multiple system tauopathy with presenile dementia (MSTD), neurofibrillary tangle (NFT) dementia, FTD with motor neuron disease, progressive supranuclear palsy (PSP), amyotrophic lateral sclerosis/parkinsonism-dementia complex (ALS-PDC), argyrophilic grain dementia (AGD), British type amyloid angiopathy, cerebral amyloid angiopathy, chronic traumatic encephalopathy (CTE), corticobasal degeneration (CBD), Creutzfeldt-Jakob disease (CJD), dementia pugilistica, diffuse neurofibrillary tangles with calcification, Down's syndrome, epilepsy, Gerstmann-Straussler-Scheinker disease, Hallervorden-Spatz disease, Huntington's disease, inclusion body myositis, lead encephalopathy, Lytico-Bodig disease (Parkinson-dementia complex of Guam), meningioangiomatosis, multiple system atrophy, myotonic dystrophy, Niemann-Pick disease type C (NP-C), non-Guamanian motor neuron disease with neurofibrillary tangles, postencephalitic parkinsonism, prion protein cerebral amyloid angiopathy, progressive subcortical gliosis, tangle only dementia, tangle-predominant dementia, ganglioglioma, gangliocytoma, subacute sclerosingpan encephalitis, tuberous sclerosis, lipofuscinosis, primary age-related tauopathy (PART), globular glial tauopathies (GGT). In some embodiments, the tauopathy is Alzheimer's disease (AD), frontotemporal dementia (FTD), or progressive supranuclear palsy (PSP).

The MAPT RNAi agent can be administered to the patient intrathecally, intracerebroventricularly, or via intracisternal *magna* injection. In some embodiments, the MAPT RNAi agent is administered to the patient intrathecally via a catheter.

RNAi dosage regimens may be adjusted to provide the optimum desired response (e.g., a therapeutic response). For example, a single bolus may be administered, several divided doses may be administered over time, or the dose may be proportionally reduced or increased as indicated by the exigencies of the therapeutic situation.

Dosage values may vary with the type and severity of the condition to be alleviated. It is further understood that for any particular subject, specific dosage regimens should be adjusted over time according to the individual need and the professional judgment of the person administering or supervising the administration of the compositions.

In another aspect, provided herein are MAPT RNAi agents or pharmaceutical compositions comprising a MAPT RNAi agent for use in reducing MAPT expression. Also provided herein are MAPT RNAi agents or the pharmaceutical composition comprising a MAPT RNAi agent for use in a therapy. Also provided herein are MAPT RNAi agents or pharmaceutical compositions comprising a MAPT RNAi agent for use in the treatment of a tauopathy. Also provided herein are uses of MAPT RNAi agents in the manufacture of a medicament for the treatment of a tauopathy.

As used herein, the terms “a,” “an,” “the,” and similar terms used in the context of the present disclosure (especially in the context of the claims) are to be construed to cover both the singular and plural unless otherwise indicated herein or clearly contradicted by the context.

As used herein, the term “alkyl” means saturated linear or branched-chain monovalent hydrocarbon radical, containing the indicated number of carbon atoms. For example, “$C_1$-$C_{20}$ alkyl” means a radical having 1-20 carbon atoms in a linear or branched arrangement.

As used herein, “antisense strand” means an oligonucleotide that is complementary to a region of a target sequence. Likewise, and as used herein, “sense strand” means an oligonucleotide that is complementary to a region of an antisense strand.

As used herein, “complementary” means a structural relationship between two nucleotides (e.g., on two opposing nucleic acids or on opposing regions of a single nucleic acid strand) that permits the two nucleotides to form base pairs with one another. For example, a purine nucleotide of one nucleic acid that is complementary to a pyrimidine nucleotide of an opposing nucleic acid may base pair together by forming hydrogen bonds with one another. Complementary nucleotides can base pair in the Watson-Crick manner or in any other manner that allows for the formation of stable duplexes. Likewise, two nucleic acids may have regions of multiple nucleotides that are complementary with each other to form regions of complementarity, as described herein.

As used herein, a “delivery moiety” refers to a chemical moiety that facilitates the entry of an oligonucleotide or RNAi agent into a cell. The delivery moiety can be lipid, cholesterol, vitamin E, carbohydrate, amino sugar, polypeptide or protein.

As used herein, “duplex,” in reference to nucleic acids or oligonucleotides, means a structure formed through complementary base pairing of two antiparallel sequences of nucleotides (i.e., in opposite directions), whether formed by two separate nucleic acid strands or by a single, folded strand (e.g., via a hairpin).

An “effective amount” refers to an amount necessary (for periods of time and for the means of administration) to achieve the desired therapeutic result. An effective amount of a RNAi agent may vary according to factors such as the disease state, age, sex, and weight of the individual, and the ability of the RNAi agent to elicit a desired response in the individual. An effective amount is also one in which any toxic or detrimental effects of the RNAi agent are outweighed by the therapeutically beneficial effects.

The term “have”, “having” or “has”, when referring to a sequence, means consists of or consists essentially of.

The term “knockdown” or “expression knockdown” refers to reduced mRNA or protein expression of a gene after treatment of a reagent, e.g., a RNAi agent.

As used herein, “modified internucleotide linkage” means an internucleotide linkage having one or more chemical modifications when compared with a reference internucleotide linkage having a phosphodiester bond. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc. In some embodiments, the modified internucleotide linkage is phosphorothioate linkage.

As used herein, “modified nucleotide” refers to a nucleotide having one or more chemical modifications when compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide, and thymidine deoxyribonucleotide. A modified nucleotide can have, for example, one or more chemical modification in its sugar, nucleobase, and/or phosphate group. Additionally, or alternatively, a modified nucleotide can have one or more chemical moieties conjugated to a corresponding reference nucleotide. In some embodiments, the modified nucleotide is a 2'-fluoro modified nucleotide, 2'-O-methyl modified nucleotide, or 2'-O-alkyl modified nucleotide, e.g., 2'-O—C16 alkyl modified nucleotide. In some embodiments, the modified nucleotide has a phosphate analog, e.g., 5'-vinylphosphonate. In some embodiments, the modified nucleotide is an abasic moiety or inverted abasic moiety, e.g., a moiety shown in Table 3.

As used herein, the term “tauopathy” refers to a disease associated with abnormal tau protein expression, secretion, phosphorylation, cleavage, and/or aggregation.

As used herein, “nucleotide” means an organic compound having a nucleoside (a nucleobase, e.g., adenine, cytosine, guanine, thymine, or uracil, and a pentose sugar, e.g., ribose or 2'-deoxyribose) linked to a phosphate group, which can serve as a monomeric unit of nucleic acid polymers such as deoxyribonucleic acid (DNA) and ribonucleic acid (RNA).

As used herein, “oligonucleotide” means a polymer of linked nucleotides, each of which can be modified or unmodified. An oligonucleotide is typically less than about 100 nucleotides in length.

As used herein, “overhang” means the unpaired nucleotide or nucleotides that protrude from the duplex structure of a double stranded oligonucleotide. An overhang may include one or more unpaired nucleotides extending from a duplex region at the 5' terminus or 3' terminus of a double stranded oligonucleotide. The overhang can be a 3' or 5' overhang on the antisense strand or sense strand of a double stranded oligonucleotide.

The term “patient”, as used herein, refers to a human patient.

As used herein, “phosphate analog” means a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. A 5' phosphate analog can include a phosphatase-resistant linkage. Examples of phosphate analogs include 5' methylene phosphonate (5'-MP) and 5'-(E)-vinylphosphonate (5'-VP). In some embodiments, the phosphate analog is 5'-VP.

The term “% sequence identity” or “percentage sequence identity” with respect to a reference nucleic acid sequence is defined as the percentage of nucleotides, nucleosides, or nucleobases in a candidate sequence that are identical with the nucleotides, nucleosides, or nucleobases in the reference nucleic acid sequence, after optimally aligning the sequences and introducing gaps or overhangs, if necessary, to achieve the maximum percent sequence identity. Alignment for purposes of determining percent nucleic acid sequence identity can be achieved in various ways that are within the skill in the art, for instance, using publicly available computer software programs, for example, those described in Current Protocols in Molecular Biology (Ausubel et al., eds., 1987, Supp. 30, section 7.7.18, Table 7.7.1), and including BLAST, BLAST-2, ALIGN, Clustal W2.0, Clustal X2.0, or Megalign (DNASTAR) software. Those skilled in the art can determine appropriate parameters for measuring alignment, including any algorithms needed to achieve maximal alignment over the full length of the sequences being compared. Percentage of "sequence identity" can be determined by comparing two optimally aligned sequences over a comparison window, where the fragment of the nucleic acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical nucleotide, nucleoside, or nucleobase occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

As used herein, "RNAi," "RNAi agent," "iRNA," "iRNA agent," and "RNA interference agent" means an agent that mediates sequence-specific degradation of a target mRNA by RNA interference, e.g., via RNA-induced silencing complex (RISC) pathway. In some embodiments, the RNAi agent has a sense strand and an antisense strand, and the sense strand and the antisense strand form a duplex. In some embodiments, the sense strand has a delivery moiety, e.g., a delivery moiety conjugated to the 5' or 3' end of the sense strand or a nucleotide of the sense strand.

As used herein, "strand" refers to a single, contiguous sequence of nucleotides linked together through internucleotide linkages (e.g., phosphodiester linkages or phosphorothioate linkages). A strand can have two free ends (e.g., a 5' end and a 3' end).

As used herein, "MAPT" refers to a human MAPT mRNA transcript, encoding a microtubule associated protein Tau. The nucleotide sequences of human MAPT transcript variants and amino acid sequences of human Tau protein isoforms can be found at:

i. MAPT transcript variant 1→Tau protein isoform 1: NM_016835.5 (nucleotide sequence)→NP_058519.3 (amino acid sequence);
ii. MAPT transcript variant 2→Tau protein isoform 2: NM_005910.6 (nucleotide sequence)→NP_005901.2 (amino acid sequence);
iii. MAPT transcript variant 3→Tau protein isoform 3: NM_016834.5 (nucleotide sequence)→NP_058518.1 (amino acid sequence);
iv. MAPT transcript variant 4→Tau protein isoform 4: NM_016841.5 (nucleotide sequence)→NP_058525.1 (amino acid sequence);
v. MAPT transcript variant 5→Tau protein isoform 5: NM_001123067.4 (nucleotide sequence)→NP_001116539.1 (amino acid sequence);
vi. MAPT transcript variant 6→Tau protein isoform 6: NM_001123066.4 (nucleotide sequence)→NP_001116538.2 (amino acid sequence);
vii. MAPT transcript variant 7→Tau protein isoform 7: NM_001203251.2 (nucleotide sequence)→NP_001190180.1 (amino acid sequence);
viii. MAPT transcript variant 8→Tau protein isoform 8: NM_001203252.2 (nucleotide sequence)→NP_001190181.1 (amino acid sequence);
ix. MAPT transcript variant 9→Tau protein isoform 9: NM_001377265.1 (nucleotide sequence)→NP_001364194.1 (amino acid sequence);
x. MAPT transcript variant 10→Tau protein isoform 10: NM_001377266.1 (nucleotide sequence)→NP_001364195.1 (amino acid sequence);
xi. MAPT transcript variant 11→Tau protein isoform 11: NM_001377267.1 (nucleotide sequence)→NP_001364196.1 (amino acid sequence);
xii. MAPT transcript variant 12→Tau protein isoform 4: NM_001377268.1 (nucleotide sequence)→NP_001364197.1 (amino acid sequence).

The nucleotide sequence of the human MAPT transcript variant 6 (encoding 2N4R Tau) can be found at NM_001123066.4:

(SEQ ID NO: 49)

```
  1 GCAGTCACCG CCACCCACCA GCTCCGGCAC CAACAGCAGC GCCGCTGCCA CCGCCCACCT

 61 TCTGCCGCCG CCACCACAGC CACCTTCTCC TCCTCCGCTG TCCTCTCCCG TCCTCGCCTC

121 TGTCGACTAT CAGGTGAACT TTGAACCAGG ATGGCTGAGC CCCGCCAGGA GTTCGAAGTG

181 ATGGAAGATC ACGCTGGGAC GTACGGGTTG GGGGACAGGA AAGATCAGGG GGGCTACACC

241 ATGCACCAAG ACCAAGAGGG TGACACGGAC GCTGGCCTGA AAGAATCTCC CCTGCAGACC

301 CCCACTGAGG ACGGATCTGA GGAACCGGGC TCTGAAACCT CTGATGCTAA GAGCACTCCA

361 ACAGCGGAAG ATGTGACAGC ACCCTTAGTG GATGAGGGAG CTCCCGGCAA GCAGGCTGCC

421 GCGCAGCCCC ACACGGAGAT CCCAGAAGGA ACCACAGCTG AAGAAGCAGG CATTGGAGAC

481 ACCCCCAGCC TGGAAGACGA AGCTGCTGGT CACGTGACCC AAGAGCCTGA AAGTGGTAAG

541 GTGGTCCAGG AAGGCTTCCT CCGAGAGCCA GGCCCCCCAG GTCTGAGCCA CCAGCTCATG

601 TCCGGCATGC CTGGGGCTCC CCTCCTGCCT GAGGGCCCCA GAGAGGCCAC ACGCCAACCT

661 TCGGGGACAG GACCTGAGGA CACAGAGGGC GGCCGCCACG CCCCTGAGCT GCTCAAGCAC

721 CAGCTTCTAG GAGACCTGCA CCAGGAGGGG CCGCCGCTGA AGGGGGCAGG GGGCAAAGAG
```

-continued

```
781 AGGCCGGGGA GCAAGGAGGA GGTGGATGAA GACCGCGACG TCGATGAGTC CTCCCCCCAA
841 GACTCCCCTC CCTCCAAGGC CTCCCCAGCC CAAGATGGGC GGCCTCCCCA GACAGCCGCC
901 AGAGAAGCCA CCAGCATCCC AGGCTTCCCA GCGGAGGGTG CCATCCCCCT CCCTGTGGAT
961 TTCCTCTCCA AAGTTTCCAC AGAGATCCCA GCCTCAGAGC CCGACGGGCC CAGTGTAGGG
1021 CGGGCCAAAG GGCAGGATGC CCCCCTGGAG TTCACGTTTC ACGTGGAAAT CACACCCAAC
1081 GTGCAGAAGG AGCAGGCGCA CTCGGAGGAG CATTTGGGAA GGGCTGCATT TCCAGGGGCC
1141 CCTGGAGAGG GGCCAGAGGC CCGGGGCCCC TCTTTGGGAG AGGACACAAA AGAGGCTGAC
1201 CTTCCAGAGC CCTCTGAAAA GCAGCCTGCT GCTGCTCCGC GGGGGAAGCC CGTCAGCCGG
1261 GTCCCTCAAC TCAAAGCTCG CATGGTCAGT AAAAGCAAAG ACGGGACTGG AAGCGATGAC
1321 AAAAAAGCCA AGACATCCAC ACGTTCCTCT GCTAAAACCT TGAAAAATAG GCCTTGCCTT
1381 AGCCCCAAAC ACCCCACTCC TGGTAGCTCA GACCCTCTGA TCCAACCCTC CAGCCCTGCT
1441 GTGTGCCCAG AGCCACCTTC CTCTCCTAAA TACGTCTCTT CTGTCACTTC CCGAACTGGC
1501 AGTTCTGGAG CAAAGGAGAT GAAACTCAAG GGGGCTGATG GTAAAACGAA GATCGCCACA
1561 CCGCGGGGAG CAGCCCCTCC AGGCCAGAAG GGCCAGGCCA ACGCCACCAG GATTCCAGCA
1621 AAAACCCCGC CCGCTCCAAA GACACCACCC AGCTCTGCGA CTAAGCAAGT CCAGAGAAGA
1681 CCACCCCCTG CAGGGCCCAG ATCTGAGAGA GGTGAACCTC CAAAATCAGG GGATCGCAGC
1741 GGCTACAGCA GCCCCGGCTC CCCAGGCACT CCCGGCAGCC GCTCCGGCAC CCCGTCCCTT
1801 CCAACCCCAC CCACCCGGGA GCCCAAGAAG GTGGCAGTGG TCCGTACTCC ACCCAAGTCG
1861 CCGTCTTCCG CCAAGAGCCG CCTGCAGACA GCCCCCGTGC CCATGCCAGA CCTGAAGAAT
1921 GTCAAGTCCA AGATCGGCTC CACTGAGAAC CTGAAGCACC AGCCGGGAGG CGGGAAGGTG
1981 CAGATAATTA ATAAGAAGCT GGATCTTAGC AACGTCCAGT CCAAGTGTGG CTCAAAGGAT
2041 AATATCAAAC ACGTCCCGGG AGGCGGCAGT GTGCAAATAG TCTACAAACC AGTTGACCTG
2101 AGCAAGGTGA CCTCCAAGTG TGGCTCATTA GGCAACATCC ATCATAAACC AGGAGGTGGC
2161 CAGGTGGAAG TAAAATCTGA GAAGCTTGAC TTCAAGGACA GAGTCCAGTC GAAGATTGGG
2221 TCCCTGGACA ATATCACCCA CGTCCCTGGC GGAGGAAATA AAAAGATTGA AACCCACAAG
2281 CTGACCTTCC GCGAGAACGC CAAAGCCAAG ACAGACCACG GGGCGGAGAT CGTGTACAAG
2341 TCGCCAGTGG TGTCTGGGGA CACGTCTCCA CGGCATCTCA GCAATGTCTC CTCCACCGGC
2401 AGCATCGACA TGGTAGACTC GCCCCAGCTC GCCACGCTAG CTGACGAGGT GTCTGCCTCC
2461 CTGGCCAAGC AGGGTTTGTG ATCAGGCCCC TGGGGCGGTC AATAATTGTG GAGAGGAGAG
2521 AATGAGAGAG TGTGGAAAAA AAAAGAATAA TGACCCGGCC CCCGCCCTCT GCCCCCAGCT
2581 GCTCCTCGCA GTTCGGTTAA TTGGTTAATC ACTTAACCTG CTTTTGTCAC TCGGCTTTGG
2641 CTCGGGACTT CAAAATCAGT GATGGGAGTA AGAGCAAATT TCATCTTTCC AAATTGATGG
2701 GTGGGCTAGT AATAAAATAT TTAAAAAAAA ACATTCAAAA ACATGGCCAC ATCCAACATT
2761 TCCTCAGGCA ATTCCTTTTG ATTCTTTTTT CTTCCCCCTC CATGTAGAAG AGGGAGAAGG
2821 AGAGGCTCTG AAAGCTGCTT CTGGGGGATT TCAAGGGACT GGGGGTGCCA ACCACCTCTG
2881 GCCCTGTTGT GGGGGTGTCA CAGAGGCAGT GGCAGCAACA AAGGATTTGA AACTTGGTGT
2941 GTTCGTGGAG CCACAGGCAG ACGATGTCAA CCTTGTGTGA GTGTGACGGG GGTTGGGGTG
3001 GGGCGGGAGG CCACGGGGGA GGCCGAGGCA GGGGCTGGGC AGAGGGGAGA GGAAGCACAA
3061 GAAGTGGGAG TGGGAGAGGA AGCCACGTGC TGGAGAGTAG ACATCCCCCT CCTTGCCGCT
3121 GGGAGAGCCA AGGCCTATGC CACCTGCAGC GTCTGAGCGG CCGCCTGTCC TTGGTGGCCG
3181 GGGGTGGGGG CCTGCTGTGG GTCAGTGTGC CACCCTCTGC AGGGCAGCCT GTGGGAGAAG
```

-continued

3241 GGACAGCGGG TAAAAAGAGA AGGCAAGCTG GCAGGAGGGT GGCACTTCGT GGATGACCTC

3301 CTTAGAAAAG ACTGACCTTG ATGTCTTGAG AGCGCTGGCC TCTTCCTCCC TCCCTGCAGG

3361 GTAGGGGGCC TGAGTTGAGG GGCTTCCCTC TGCTCCACAG AAACCCTGTT TTATTGAGTT

3421 CTGAAGGTTG GAACTGCTGC CATGATTTTG GCCACTTTGC AGACCTGGGA CTTTAGGGCT

3481 AACCAGTTCT CTTTGTAAGG ACTTGTGCCT CTTGGGAGAC GTCCACCCGT TTCCAAGCCT

3541 GGGCCACTGG CATCTCTGGA GTGTGTGGGG GTCTGGGAGG CAGGTCCCGA GCCCCCTGTC

3601 CTTCCCACGG CCACTGCAGT CACCCCGTCT GCGCCGCTGT GCTGTTGTCT GCCGTGAGAG

3661 CCCAATCACT GCCTATACCC CTCATCACAC GTCACAATGT CCCGAATTCC CAGCCTCACC

3721 ACCCCTTCTC AGTAATGACC CTGGTTGGTT GCAGGAGGTA CCTACTCCAT ACTGAGGGTG

3781 AAATTAAGGG AAGGCAAAGT CCAGGCACAA GAGTGGGACC CCAGCCTCTC ACTCTCAGTT

3841 CCACTCATCC AACTGGGACC CTCACCACGA ATCTCATGAT CTGATTCGGT TCCCTGTGTC

3901 CTCCTCCCGT CACAGATGTG AGCCAGGGCA CTGCTCAGCT GTGACCCTAG GTGTTTCTGC

3961 CTTGTTGACA TGGAGAGAGC CCTTTCCCCT GAGAAGGCCT GGCCCCTTCC TGTGCTGAGC

4021 CCACAGCAGC AGGCTGGGTG TCTTGGTTGT CAGTGGTGGC ACCAGGATGG AAGGGCAAGG

4081 CACCCAGGGC AGGCCCACAG TCCCGCTGTC CCCCACTTGC ACCCTAGCTT GTAGCTGCCA

4141 ACCTCCCAGA CAGCCCAGCC CGCTGCTCAG CTCCACATGC ATAGTATCAG CCCTCCACAC

4201 CCGACAAAGG GGAACACACC CCCTTGGAAA TGGTTCTTTT CCCCCAGTCC CAGCTGGAAG

4261 CCATGCTGTC TGTTCTGCTG GAGCAGCTGA ACATATACAT AGATGTTGCC CTGCCCTCCC

4321 CATCTGCACC CTGTTGAGTT GTAGTTGGAT TTGTCTGTTT ATGCTTGGAT TCACCAGAGT

4381 GACTATGATA GTGAAAAGAA AAAAAAAAAA AAAAAAGGAC GCATGTATCT TGAAATGCTT

4441 GTAAAGAGGT TTCTAACCCA CCCTCACGAG GTGTCTCTCA CCCCCACACT GGGACTCGTG

4501 TGGCCTGTGT GGTGCCACCC TGCTGGGGCC TCCCAAGTTT TGAAAGGCTT TCCTCAGCAC

4561 CTGGGACCCA ACAGAGACCA GCTTCTAGCA GCTAAGGAGG CCGTTCAGCT GTGACGAAGG

4621 CCTGAAGCAC AGGATTAGGA CTGAAGCGAT GATGTCCCCT TCCCTACTTC CCCTTGGGGC

4681 TCCCTGTGTC AGGGCACAGA CTAGGTCTTG TGGCTGGTCT GGCTTGCGGC GCGAGGATGG

4741 TTCTCTCTGG TCATAGCCCG AAGTCTCATG GCAGTCCCAA AGGAGGCTTA CAACTCCTGC

4801 ATCACAAGAA AAAGGAAGCC ACTGCCAGCT GGGGGGATCT GCAGCTCCCA GAAGCTCCGT

4861 GAGCCTCAGC CACCCCTCAG ACTGGGTTCC TCTCCAAGCT CGCCCTCTGG AGGGGCAGCG

4921 CAGCCTCCCA CCAAGGGCCC TGCGACCACA GCAGGGATTG GGATGAATTG CCTGTCCTGG

4981 ATCTGCTCTA GAGGCCCAAG CTGCCTGCCT GAGGAAGGAT GACTTGACAA GTCAGGAGAC

5041 ACTGTTCCCA AAGCCTTGAC CAGAGCACCT CAGCCCGCTG ACCTTGCACA AACTCCATCT

5101 GCTGCCATGA GAAAAGGGAA GCCGCCTTTG CAAAACATTG CTGCCTAAAG AAACTCAGCA

5161 GCCTCAGGCC CAATTCTGCC ACTTCTGGTT TGGGTACAGT TAAAGGCAAC CCTGAGGGAC

5221 TTGGCAGTAG AAATCCAGGG CCTCCCCTGG GGCTGGCAGC TTCGTGTGCA GCTAGAGCTT

5281 TACCTGAAAG GAAGTCTCTG GGCCCAGAAC TCTCCACCAA GAGCCTCCCT GCCGTTCGCT

5341 GAGTCCCAGC AATTCTCCTA AGTTGAAGGG ATCTGAGAAG GAGAAGGAAA TGTGGGGTAG

5401 ATTTGGTGGT GGTTAGAGAT ATGCCCCCCT CATTACTGCC AACAGTTTCG GCTGCATTTC

5461 TTCACGCACC TCGGTTCCTC TTCCTGAAGT TCTTGTGCCC TGCTCTTCAG CACCATGGGC

5521 CTTCTTATAC GGAAGGCTCT GGGATCTCCC CCTTGTGGGG CAGGCTCTTG GGGCCAGCCT

5581 AAGATCATGG TTTAGGGTGA TCAGTGCTGG CAGATAAATT GAAAAGGCAC GCTGGCTTGT

-continued

5641 GATCTTAAAT GAGGACAATC CCCCCAGGGC TGGGCACTCC TCCCCTCCCC TCACTTCTCC

5701 CACCTGCAGA GCCAGTGTCC TTGGGTGGGC TAGATAGGAT ATACTGTATG CCGGCTCCTT

5761 CAAGCTGCTG ACTCACTTTA TCAATAGTTC CATTTAAATT GACTTCAGTG GTGAGACTGT

5821 ATCCTGTTTG CTATTGCTTG TTGTGCTATG GGGGGAGGGG GGAGGAATGT GTAAGATAGT

5881 TAACATGGGC AAAGGGAGAT CTTGGGGTGC AGCACTTAAA CTGCCTCGTA ACCCTTTTCA

5941 TGATTTCAAC CACATTTGCT AGAGGGAGGG AGCAGCCACG GAGTTAGAGG CCCTTGGGGT

6001 TTCTCTTTTC CACTGACAGG CTTTCCCAGG CAGCTGGCTA GTTCATTCCC TCCCCAGCCA

6061 GGTGCAGGCG TAGGAATATG GACATCTGGT TGCTTTGGCC TGCTGCCCTC TTTCAGGGGT

6121 CCTAAGCCCA CAATCATGCC TCCCTAAGAC CTTGGCATCC TTCCCTCTAA GCCGTTGGCA

6181 CCTCTGTGCC ACCTCTCACA CTGGCTCCAG ACACACAGCC TGTGCTTTTG GAGCTGAGAT

6241 CACTCGCTTC ACCCTCCTCA TCTTTGTTCT CCAAGTAAAG CCACGAGGTC GGGGCGAGGG

6301 CAGAGGTGAT CACCTGCGTG TCCCATCTAC AGACCTGCAG CTTCATAAAA CTTCTGATTT

6361 CTCTTCAGCT TTGAAAAGGG TTACCCTGGG CACTGGCCTA GAGCCTCACC TCCTAATAGA

6421 CTTAGCCCCA TGAGTTTGCC ATGTTGAGCA GGACTATTTC TGGCACTTGC AAGTCCCATG

6481 ATTTCTTCGG TAATTCTGAG GGTGGGGGGA GGGACATGAA ATCATCTTAG CTTAGCTTTC

6541 TGTCTGTGAA TGTGTATATA GTGTATTGTG TGTTTTAACA AATGATTTAC ACTGACTGTT

6601 GCTGTAAAAG TGAATTTGGA AATAAAGTTA TTACTCTGAT TAAA.

The corresponding amino acid sequence of human Tau protein isoform 6 can be found at NP_001116538.2:

(SEQ ID NO: 50)

1 MAEPRQEFEV MEDHAGTYGL GDRKDQGGYT MHQDQEGDTD AGLKESPLQT PTEDGSEEPG

61 SETSDAKSTP TAEDVTAPLV DEGAPGKQAA AQPHTEIPEG TTAEEAGIGD TPSLEDEAAG

121 HVTQEPESGK VVQEGFLREP GPPGLSHQLM SGMPGAPLLP EGPREATRQP SGTGPEDTEG

181 GRHAPELLKH QLLGDLHQEG PPLKGAGGKE RPGSKEEVDE DRDVDESSPQ DSPPSKASPA

241 QDGRPPQTAA REATSIPGFP AEGAIPLPVD FLSKVSTEIP ASEPDGPSVG RAKGQDAPLE

301 FTFHVEITPN VQKEQAHSEE HLGRAAFPGA PGEGPEARGP SLGEDTKEAD LPEPSEKQPA

-continued

361 AAPRGKPVSR VPQLKARMVS KSKDGTGSDD KKAKTSTRSS AKTLKNRPCL SPKHPTPGSS

421 DPLIQPSSPA VCPEPPSSPK YVSSVTSRTG SSGAKEMKLK GADGKTKIAT PRGAAPPGQK

481 GQANATRIPA KTPPAPKTPP SSATKQVQRR PPPAGPRSER GEPPKSGDRS GYSSPGSPGT

541 PGSRSRTPSL PTPPTREPKK VAVVRTPPKS PSSAKSRLQT APVPMPDLKN VKSKIGSTEN

601 LKHQPGGGKV QIINKKLDLS NVQSKCGSKD NIKHVPGGGS VQIVYKPVDL SKVTSKCGSL

661 GNIHHKPGGG QVEVKSEKLD FKDRVQSKIG SLDNITHVPG GGNKKIETHK LTFRENAKAK

721 TDHGAEIVYK SPVVSGDTSP RHLSNVSSTG SIDMVDSPQL ATLADEVSAS LAKQGL.

The nucleotide sequence of a human MAPT transcript variant 5 (encoding 1N4R Tau) can be found at NM_001123067.4:

(SEQ ID NO: 51)

1 GCAGTCACCG CCACCCACCA GCTCCGGCAC CAACAGCAGC GCCGCTGCCA CCGCCCACCT

61 TCTGCCGCCG CCACCACAGC CACCTTCTCC TCCTCCGCTG TCCTCTCCCG TCCTCGCCTC

121 TGTCGACTAT CAGGTGAACT TTGAACCAGG ATGGCTGAGC CCCGCCAGGA GTTCGAAGTG

181 ATGGAAGATC ACGCTGGGAC GTACGGGTTG GGGGACAGGA AAGATCAGGG GGGCTACACC

241 ATGCACCAAG ACCAAGAGGG TGACACGGAC GCTGGCCTGA AAGAATCTCC CCTGCAGACC

-continued

```
 301 CCCACTGAGG ACGGATCTGA GGAACCGGGC TCTGAAACCT CTGATGCTAA GAGCACTCCA
 361 ACAGCGGAAG CTGAAGAAGC AGGCATTGGA GACACCCCCA GCCTGGAAGA CGAAGCTGCT
 421 GGTCACGTGA CCCAAGCTCG CATGGTCAGT AAAAGCAAAG ACGGGACTGG AAGCGATGAC
 481 AAAAAAGCCA AGGGGGCTGA TGGTAAAACG AAGATCGCCA CACCGCGGGG AGCAGCCCCT
 541 CCAGGCCAGA AGGGCCAGGC CAACGCCACC AGGATTCCAG CAAAAACCCC GCCCGCTCCA
 601 AAGACACCAC CCAGCTCTGG TGAACCTCCA AAATCAGGGG ATCGCAGCGG CTACAGCAGC
 661 CCCGGCTCCC CAGGCACTCC CGGCAGCCGC TCCCGCACCC CGTCCCTTCC AACCCCACCC
 721 ACCCGGGAGC CCAAGAAGGT GGCAGTGGTC CGTACTCCAC CCAAGTCGCC GTCTTCCGCC
 781 AAGAGCCGCC TGCAGACAGC CCCCGTGCCC ATGCCAGACC TGAAGAATGT CAAGTCCAAG
 841 ATCGGCTCCA CTGAGAACCT GAAGCACCAG CCGGGAGGCG GGAAGGTGCA GATAATTAAT
 901 AAGAAGCTGG ATCTTAGCAA CGTCCAGTCC AAGTGTGGCT CAAAGGATAA TATCAAACAC
 961 GTCCCGGGAG GCGGCAGTGT GCAAATAGTC TACAAACCAG TTGACCTGAG CAAGGTGACC
1021 TCCAAGTGTG GCTCATTAGG CAACATCCAT CATAAACCAG GAGGTGGCCA GGTGGAAGTA
1081 AAATCTGAGA AGCTTGACTT CAAGGACAGA GTCCAGTCGA AGATTGGGTC CCTGGACAAT
1141 ATCACCCACG TCCCTGGCGG AGGAAATAAA AAGATTGAAA CCCACAAGCT GACCTTCCGC
1201 GAGAACGCCA AAGCCAAGAC AGACCACGGG GCGGAGATCG TGTACAAGTC GCCAGTGGTG
1261 TCTGGGGACA CGTCTCCACG GCATCTCAGC AATGTCTCCT CCACCGGCAG CATCGACATG
1321 GTAGACTCGC CCCAGCTCGC CACGCTAGCT GACGAGGTGT CTGCCTCCCT GGCCAAGCAG
1381 GGTTTGTGAT CAGGCCCCTG GGGCGGTCAA TAATTGTGGA GAGGAGAGAA TGAGAGAGTG
1441 TGGAAAAAAA AAGAATAATG ACCCGGCCCC CGCCCTCTGC CCCCAGCTGC TCCTCGCAGT
1501 TCGGTTAATT GGTTAATCAC TTAACCTGCT TTTGTCACTC GGCTTTGGCT CGGGACTTCA
1561 AAATCAGTGA TGGGAGTAAG AGCAAATTTC ATCTTTCCAA ATTGATGGGT GGGCTAGTAA
1621 TAAAATATTT AAAAAAAAAC ATTCAAAAAC ATGGCCACAT CCAACATTTC CTCAGGCAAT
1681 TCCTTTTGAT TCTTTTTTCT TCCCCCTCCA TGTAGAAGAG GGAGAAGGAG AGGCTCTGAA
1741 AGCTGCTTCT GGGGGATTTC AAGGGACTGG GGGTGCCAAC CACCTCTGGC CCTGTTGTGG
1801 GGGTGTCACA GAGGCAGTGG CAGCAACAAA GGATTTGAAA CTTGGTGTGT TCGTGGAGCC
1861 ACAGGCAGAC GATGTCAACC TTGTGTGAGT GTGACGGGGG TTGGGGTGGG GCGGGAGGCC
1921 ACGGGGGAGG CCGAGGCAGG GGCTGGGCAG AGGGGAGAGG AAGCACAAGA AGTGGGAGTG
1981 GGAGAGGAAG CCACGTGCTG GAGAGTAGAC ATCCCCCTCC TTGCCGCTGG GAGAGCCAAG
2041 GCCTATGCCA CCTGCAGCGT CTGAGCGGCC GCCTGTCCTT GGTGGCCGGG GGTGGGGGCC
2101 TGCTGTGGGT CAGTGTGCCA CCCTCTGCAG GGCAGCCTGT GGGAGAAGGG ACAGCGGGTA
2161 AAAAGAGAAG GCAAGCTGGC AGGAGGGTGG CACTTCGTGG ATGACCTCCT TAGAAAAGAC
2221 TGACCTTGAT GTCTTGAGAG CGCTGGCCTC TTCCTCCCTC CCTGCAGGGT AGGGGGCCTG
2281 AGTTGAGGGG CTTCCCTCTG CTCCACAGAA ACCCTGTTTT ATTGAGTTCT GAAGGTTGGA
2341 ACTGCTGCCA TGATTTTGGC CACTTTGCAG ACCTGGGACT TTAGGGCTAA CCAGTTCTCT
2401 TTGTAAGGAC TTGTGCCTCT TGGGAGACGT CCACCCGTTT CCAAGCCTGG GCCACTGGCA
2461 TCTCTGGAGT GTGTGGGGGT CTGGGAGGCA GGTCCCGAGC CCCCTGTCCT TCCCACGGCC
2521 ACTGCAGTCA CCCCGTCTGC GCCGCTGTGC TGTTGTCTGC CGTGAGAGCC CAATCACTGC
2581 CTATACCCCT CATCACACGT CACAATGTCC CGAATTCCCA GCCTCACCAC CCCTTCTCAG
2641 TAATGACCCT GGTTGGTTGC AGGAGGTACC TACTCCATAC TGAGGGTGAA ATTAAGGGAA
```

-continued

2701 GGCAAAGTCC AGGCACAAGA GTGGGACCCC AGCCTCTCAC TCTCAGTTCC ACTCATCCAA

2761 CTGGGACCCT CACCACGAAT CTCATGATCT GATTCGGTTC CCTGTCTCCT CCTCCCGTCA

2821 CAGATGTGAG CCAGGGCACT GCTCAGCTGT GACCCTAGGT GTTTCTGCCT TGTTGACATG

2881 GAGAGAGCCC TTTCCCCTGA GAAGGCCTGG CCCCTTCCTG TGCTGAGCCC ACAGCAGCAG

2941 GCTGGGTGTC TTGGTTGTCA GTGGTGGCAC CAGGATGGAA GGGCAAGGCA CCCAGGGCAG

3001 GCCCACAGTC CCGCTGTCCC CCACTTGCAC CCTAGCTTGT AGCTGCCAAC CTCCCAGACA

3061 GCCCAGCCCG CTGCTCAGCT CCACATGCAT AGTATCAGCC CTCCACACCC GACAAAGGGG

3121 AACACACCCC CTTGGAAATG GTTCTTTTCC CCCAGTCCCA GCTGGAAGCC ATGCTGTCTG

3181 TTCTGCTGGA GCAGCTGAAC ATATACATAG ATGTTGCCCT GCCCTCCCCA TCTGCACCCT

3241 GTTGAGTTGT AGTTGGATTT GTCTGTTTAT GCTTGGATTC ACCAGAGTGA CTATGATAGT

3301 GAAAAGAAAA AAAAAAAAAA AAAAGGACGC ATGTATCTTG AAATGCTTGT AAAGAGGTTT

3361 CTAACCCACC CTCACGAGGT GTCTCTCACC CCCACACTGG GACTCGTGTG GCCTGTGTGG

3421 TGCCACCCTG CTGGGGCCTC CCAAGTTTTG AAAGGCTTTC CTCAGCACCT GGGACCCAAC

3481 AGAGACCAGC TTCTAGCAGC TAAGGAGGCC GTTCAGCTGT GACGAAGGCC TGAAGCACAG

3541 GATTAGGACT GAAGCGATGA TGTCCCCTTC CCTACTTCCC CTTGGGGCTC CCTGTGTCAG

3601 GGCACAGACT AGGTCTTGTG GCTGGTCTGG CTTGCGGCGC GAGGATGGTT CTCTCTGGTC

3661 ATAGCCCGAA GTCTCATGGC AGTCCCAAAG GAGGCTTACA ACTCCTGCAT CACAAGAAAA

3721 AGGAAGCCAC TGCCAGCTGG GGGGATCTGC AGCTCCCAGA AGCTCCGTGA GCCTCAGCCA

3781 CCCCTCAGAC TGGGTTCCTC TCCAAGCTCG CCCTCTGGAG GGGCAGCGCA GCCTCCCACC

3841 AAGGGCCCTG CGACCACAGC AGGGATTGGG ATGAATTGCC TGTCCTGGAT CTGCTCTAGA

3901 GGCCCAAGCT GCCTGCCTGA GGAAGGATGA CTTGACAAGT CAGGAGACAC TGTTCCCAAA

3961 GCCTTGACCA GAGCACCTCA GCCCGCTGAC CTTGCACAAA CTCCATCTGC TGCCATGAGA

4021 AAAGGGAAGC CGCCTTTGCA AAACATTGCT GCCTAAAGAA ACTCAGCAGC CTCAGGCCCA

4081 ATTCTGCCAC TTCTGGTTTG GGTACAGTTA AAGGCAACCC TGAGGGACTT GGCAGTAGAA

4141 ATCCAGGGCC TCCCCTGGGG CTGGCAGCTT CGTGTGCAGC TAGAGCTTTA CCTGAAAGGA

4201 AGTCTCTGGG CCCAGAACTC TCCACCAAGA GCCTCCCTGC CGTTCGCTGA GTCCCAGCAA

4261 TTCTCCTAAG TTGAAGGGAT CTGAGAAGGA GAAGGAAATG TGGGGTAGAT TTGGTGGTGG

4321 TTAGAGATAT GCCCCCCTCA TTACTGCCAA CAGTTTCGGC TGCATTTCTT CACGCACCTC

4381 GGTTCCTCTT CCTGAAGTTC TTGTGCCCTG CTCTTCAGCA CCATGGGCCT TCTTATACGG

4441 AAGGCTCTGG GATCTCCCCC TTGTGGGGCA GGCTCTTGGG GCCAGCCTAA GATCATGGTT

4501 TAGGGTGATC AGTGCTGGCA GATAAATTGA AAAGGCACGC TGGCTTGTGA TCTTAAATGA

4561 GGACAATCCC CCCAGGGCTG GGCACTCCTC CCCTCCCCTC ACTTCTCCCA CCTGCAGAGC

4621 CAGTGTCCTT GGGTGGGCTA GATAGGATAT ACTGTATGCC GGCTCCTTCA AGCTGCTGAC

4681 TCACTTTATC AATAGTTCCA TTTAAATTGA CTTCAGTGGT GAGACTGTAT CCTGTTTGCT

4741 ATTGCTTGTT GTGCTATGGG GGGAGGGGGG AGGAATGTGT AAGATAGTTA ACATGGGCAA

4801 AGGGAGATCT TGGGGTGCAG CACTTAAACT GCCTCGTAAC CCTTTTCATG ATTTCAACCA

4861 CATTTGCTAG AGGGAGGGAG CAGCCACGGA GTTAGAGGCC CTTGGGGTTT CTCTTTTCCA

4921 CTGACAGGCT TTCCCAGGCA GCTGGCTAGT TCATTCCCTC CCCAGCCAGG TGCAGGCGTA

4981 GGAATATGGA CATCTGGTTG CTTTGGCCTG CTGCCCTCTT TCAGGGGTCC TAAGCCCACA

5041 ATCATGCCTC CCTAAGACCT TGGCATCCTT CCCTCTAAGC CGTTGGCACC TCTGTGCCAC

5101 CTCTCACACT GGCTCCAGAC ACACAGCCTG TGCTTTTGGA GCTGAGATCA CTCGCTTCAC

-continued

5161 CCTCCTCATC TTTGTTCTCC AAGTAAAGCC ACGAGGTCGG GGCGAGGGCA GAGGTGATCA

5221 CCTGCGTGTC CCATCTACAG ACCTGCAGCT TCATAAAACT TCTGATTTCT CTTCAGCTTT

5281 GAAAAGGGTT ACCCTGGGCA CTGGCCTAGA GCCTCACCTC CTAATAGACT TAGCCCCATG

5341 AGTTTGCCAT GTTGAGCAGG ACTATTTCTG GCACTTGCAA GTCCCATGAT TTCTTCGGTA

5401 ATTCTGAGGG TGGGGGGAGG GACATGAAAT CATCTTAGCT TAGCTTTCTG TCTGTGAATG

5461 TCTATATAGT GTATTGTGTG TTTTAACAAA TGATTTAGAC TGACTGTTGC TGTAAAAGTG

5521 AATTTGGAAA TAAAGTTATT ACTCTGATTA AA.

The corresponding amino acid sequence of human Tau protein isoform 5 can be found at NP_001116539.1:

(SEQ ID NO: 52)

1 MAEPRQEFEV MEDHAGTYGL GDRKDQGGYT MHQDQEGDTD AGLKESPLQT PTEDGSEEPG

61 SETSDAKSTP TAEAEEAGIG DTPSLEDEAA GHVTQARMVS KSKDGTGSDD KKAKGADGKT

121 KIATPRGAAP PGQKGQANAT RIPAKTPPAP KTPPSSGEPP KSGDRSGYSS PGSPGTPGSR

-continued

181 SRTPSLPTPP TREPKKVAVV RTPPKSPSSA KSRLQTAPVP MPDLKNVKSK IGSTENLKHQ

241 PGGGKVQIIN KKLDLSNVQS KCGSKDNIKH VPGGGSVQIV YKPVDLSKVT SKCGSLGNIH

301 HKPGGGQVEV KSEKLDFKDR VQSKIGSLDN ITHVPGGGNK KIETHKLTER ENAKAKTDHG

361 AEIVYKSPVV SGDTSPRHLS NVSSTGSIDM VDSPQLATLA DEVSASLAKQ GL.

The nucleotide sequence of the human MAPT transcript variant 4 (encoding 0N3R Tau) can be found at NM_016841.5:

(SEQ ID NO: 53)

1 GCAGTCACCG CCACCCACCA GCTCCGGCAC CAACAGCAGC GCCGCTGCCA CCGCCCACCT

61 TCTGCCGCCG CCACCACAGC CACCTTCTCC TCCTCCGCTG TCCTCTCCCG TCCTCGCCTC

121 TGTCGACTAT CAGGTGAACT TTGAACCAGG ATGGCTGAGC CCCGCCAGGA GTTCGAAGTG

181 ATGGAAGATC ACGCTGGGAC GTACGGGTTG GGGGACAGGA AAGATCAGGG GGGCTACACC

241 ATGCACCAAG ACCAAGAGGG TGACACGGAC GCTGGCCTGA AAGCTGAAGA AGCAGGCATT

301 GGAGACACCC CCAGCCTGGA AGACGAAGCT GCTGGTCACG TGACCCAAGC TCGCATGGTC

361 AGTAAAAGCA AAGACGGGAC TGGAAGCGAT GACAAAAAAG CCAAGGGGGC TGATGGTAAA

421 ACGAAGATCG CCACACCGCG GGGAGCAGCC CCTCCAGGCC AGAAGGGCCA GGCCAACGCC

481 ACCAGGATTC CAGCAAAAAC CCCGCCCGCT CCAAAGACAC CACCCAGCTC TGGTGAACCT

541 CCAAAATCAG GGGATCGCAG CGGCTACAGC AGCCCCGGCT CCCCAGGCAC TCCCGGCAGC

601 CGCTCCCGCA CCCCGTCCCT TCCAACCCCA CCCACCCGGG AGCCCAAGAA GGTGGCAGTG

661 GTCCGTACTC CACCCAAGTC GCCGTCTTCC GCCAAGAGCC GCCTGCAGAC AGCCCCCGTG

721 CCCATGCCAG ACCTGAAGAA TGTCAAGTCC AAGATCGGCT CCACTGAGAA CCTGAAGCAC

781 CAGCCGGGAG GCGGGAAGGT GCAAATAGTC TACAAACCAG TTGACCTGAG CAAGGTGACC

841 TCCAAGTGTG GCTCATTAGG CAACATCCAT CATAAACCAG GAGGTGGCCA GGTGGAAGTA

901 AAATCTGAGA AGCTTGACTT CAAGGACAGA GTCCAGTCGA AGATTGGGTC CCTGGACAAT

961 ATCACCCACG TCCCTGGCGG AGGAAATAAA AAGATTGAAA CCCACAAGCT GACCTTCCGC

1021 GAGAACGCCA AAGCCAAGAC AGACCACGGG GCGGAGATCG TGTACAAGTC GCCAGTGGTG

1081 TCTGGGGACA CGTCTCCACG GCATCTCAGC AATGTCTCCT CCACCGGCAG CATCGACATG

1141 GTAGACTCGC CCCAGCTCGC CACGCTAGCT GACGAGGTGT CTGCCTCCCT GGCCAAGCAG

-continued

1201 GGTTTGTGAT CAGGCCCCTG GGGCGGTCAA TAATTGTGGA GAGGAGAGAA TGAGAGAGTG

1261 TGGAAAAAAA AAGAATAATG ACCCGGCCCC CGCCCTCTGC CCCCAGCTGC TCCTCGCAGT

1321 TCGGTTAATT GGTTAATCAC TTAACCTGCT TTTGTCACTC GGCTTTGGCT CGGGACTTCA

1381 AAATCAGTGA TGGGAGTAAG AGCAAATTTC ATCTTTCCAA ATTGATGGGT GGGCTAGTAA

1441 TAAAATATTT AAAAAAAAAC ATTCAAAAAC ATGGCCACAT CGAACATTTC CTCAGGCAAT

1501 TCCTTTTGAT TCTTTTTTCT TCCCCCTCCA TGTAGAAGAG GGAGAAGGAG AGGCTCTGAA

1561 AGCTGCTTCT GGGGGATTTC AAGGGACTGG GGGTGCCAAC CACCTCTGGC CCTGTTGTGG

1621 GGGTGTCACA GAGGCAGTGG CAGCAACAAA GGATTTGAAA CTTGGTGTGT TCGTGGAGCC

1681 ACAGGCAGAC GATGTCAACC TTGTGTGAGT GTGACGGGGG TTGGGGTGGG GCGGGAGGCC

1741 ACGGGGGAGG CCGAGGCAGG GGCTGGGCAG AGGGGAGAGG AAGCACAAGA AGTGGGAGTG

1801 GGAGAGGAAG CCACGTGCTG GAGAGTAGAC ATCCCCCTCC TTGCCGCTGG GAGAGCCAAG

1861 GCCTATGCCA CCTGCAGCGT CTGAGCGGCC GCCTGTCCTT GGTGGCCGGG GGTGGGGGCC

1921 TGCTGTGGGT CAGTGTGCCA CCCTCTGCAG GGCAGCCTGT GGGAGAAGGG ACAGCGGGTA

1981 AAAAGAGAAG GCAAGCTGGC AGGAGGGTGG CACTTCGTGG ATGACCTCCT TAGAAAAGAC

2041 TGACCTTGAT GTCTTGAGAG CGCTGGCCTC TTCCTCCCTC CCTGCAGGGT AGGGGGCCTG

2101 AGTTGAGGGG CTTCCCTCTG CTCCACAGAA ACCCTGTTTT ATTGAGTTCT GAAGGTTGGA

2161 ACTGCTGCCA TGATTTTGGC CACTTTGCAG ACCTGGGACT TTAGGGCTAA CCAGTTCTCT

2221 TTGTAAGGAC TTGTGCCTCT TGGGAGACGT CCACCCGTTT CCAAGCCTGG GCCACTGGCA

2281 TCTCTGGAGT GTGTGGGGGT CTGGGAGGCA GGTCCCGAGC CCCCTGTCCT TCCCACGGCC

2341 ACTGCAGTCA CCCCGTCTGC GCCGCTGTGC TGTTGTCTGC CGTGAGAGCC CAATCACTGC

2401 CTATACCCCT CATCACACGT CACAATGTCC CGAATTCCCA GCCTCACCAC CCCTTCTCAG

2461 TAATGACCCT GGTTGGTTGC AGGAGGTACC TACTCCATAC TGAGGGTGAA ATTAAGGGAA

2521 GGCAAAGTCC AGGCACAAGA GTGGGACCCC AGCCTCTCAC TCTCAGTTCC ACTCATCCAA

2581 CTGGGACCCT CACCACGAAT CTCATGATCT GATTCGGTTC CCTGTCTCCT CCTCCCGTCA

2641 CAGATGTGAG CCAGGGCACT GCTCAGCTGT GACCCTAGGT GTTTCTGCCT TGTTGACATG

2701 GAGAGAGCCC TTTCCCCTGA GAAGGCCTGG CCCCTTCCTG TGCTGAGCCC ACAGCAGCAG

2761 GCTGGGTGTC TTGGTTGTCA GTGGTGGCAC CAGGATGGAA GGGCAAGGCA CCCAGGGCAG

2821 GCCCACAGTC CCGCTGTCCC CCACTTGCAC CCTAGCTTGT AGCTGCCAAC CTCCCAGACA

2881 GCCCAGCCCG CTGCTCAGCT CCACATGCAT AGTATCAGCC CTCCACACCC GACAAAGGGG

2941 AACACACCCC CTTGGAAATG GTTCTTTTCC CCCAGTCCCA GCTGGAAGCC ATGCTGTCTG

3001 TTCTGCTGGA GCAGCTGAAC ATATACATAG ATGTTGCCCT GCCCTCCCCA TCTGCACCCT

3061 GTTGAGTTGT AGTTGGATTT GTCTGTTTAT GCTTGGATTC ACCAGAGTGA CTATGATAGT

3121 GAAAAGAAAA AAAAAAAAAA AAAAGGACGC ATGTATCTTG AAATGCTTGT AAAGAGGTTT

3181 CTAACCCACC CTCACGAGGT GTCTCTCACC CCCACACTGG GACTCGTGTG GCCTGTGTGG

3241 TGCCACCCTG CTGGGGCCTC CCAAGTTTTG AAAGGCTTTC CTCAGCACCT GGGACCCAAC

3301 AGAGACCAGC TTCTAGCAGC TAAGGAGGCC GTTCAGCTGT GACGAAGGCC TGAAGCACAG

3361 GATTAGGACT GAAGCGATGA TGTCCCCTTC CCTACTTCCC CTTGGGGCTC CCTGTGTCAG

3421 GGCACAGACT AGGTCTTGTG GCTGGTCTGG CTTGCGGCGC GAGGATGGTT CTCTCTGGTC

3481 ATAGCCCGAA GTCTCATGGC AGTCCCAAAG GAGGCTTACA ACTCCTGCAT CACAAGAAAA

3541 AGGAAGCCAC TGCCAGCTGG GGGGATCTGC AGCTCCCAGA AGCTCCGTGA GCCTCAGCCA

3601 CCCCTCAGAC TGGGTTCCTC TCCAAGCTCG CCCTCTGGAG GGGCAGCGCA GCCTCCCACC

-continued

3661 AAGGGCCCTG CGACCACAGC AGGGATTGGG ATGAATTGCC TGTCCTGGAT CTGCTCTAGA

3721 GGCCCAAGCT GCCTGCCTGA GGAAGGATGA CTTGACAAGT CAGGAGACAC TGTTCCCAAA

3781 GCCTTGACCA GAGCACCTCA GCCCGCTGAC CTTGCACAAA CTCCATCTGC TGCCATGAGA

3841 AAAGGGAAGC CGCCTTTGCA AAACATTGCT GCCTAAAGAA ACTCAGCAGC CTCAGGCCCA

3901 ATTCTGCCAC TTCTGGTTTG GGTACAGTTA AAGGCAACCC TGAGGGACTT GGCAGTAGAA

3961 ATCCAGGGCC TCCCCTGGGG CTGGCAGCTT CGTGTGCAGC TAGAGCTTTA CCTGAAAGGA

4021 AGTCTCTGGG CCCAGAACTC TCCACCAAGA GCCTCCCTGC CGTTCGCTGA GTCCCAGCAA

4081 TTCTCCTAAG TTGAAGGGAT CTGAGAAGGA GAAGGAAATG TGGGGTAGAT TTGGTGGTGG

4141 TTAGAGATAT GCCCCCCTCA TTACTGCCAA CAGTTTCGGC TGCATTTCTT CACGCACCTC

4201 GGTTCCTCTT CCTGAAGTTC TTGTGCCCTG CTCTTCAGCA CCATGGGCCT TCTTATACGG

4261 AAGGCTCTGG GATCTCCCCC TTGTGGGGCA GGCTCTTGGG GCCAGCCTAA GATCATGGTT

4321 TAGGGTGATC AGTGCTGGCA GATAAATTGA AAAGGCACGC TGGCTTGTGA TCTTAAATGA

4381 GGACAATCCC CCCAGGGCTG GGCACTCCTC CCCTCCCCTC ACTTCTCCCA CCTGCAGAGC

4441 CAGTGTCCTT GGGTGGGCTA GATAGGATAT ACTGTATGCC GGCTCCTTCA AGCTGCTGAC

4501 TCACTTTATC AATAGTTCCA TTTAAATTGA CTTCAGTGGT GAGACTGTAT CCTGTTTGCT

4561 ATTGCTTGTT GTGCTATGGG GGGAGGGGGG AGGAATGTGT AAGATAGTTA ACATGGGCAA

4621 AGGGAGATCT TGGGGTGCAG CACTTAAACT GCCTCGTAAC CCTTTTCATG ATTTCAACCA

4681 CATTTGCTAG AGGGAGGGAG CAGCCACGGA GTTAGAGGCC CTTGGGGTTT CTCTTTTCCA

4741 CTGACAGGCT TTCCCAGGCA GCTGGCTAGT TCATTCCCTC CCCAGCCAGG TGCAGGCGTA

4801 GGAATATGGA CATCTGGTTG CTTTGGCCTG CTGCCCTCTT TCAGGGGTCC TAAGCCCACA

4861 ATCATGCCTC CCTAAGACCT TGGCATCCTT CCCTCTAAGC CGTTGGCACC TCTGTGCCAC

4921 CTCTCACACT GGCTCCAGAC ACACAGCCTG TGCTTTTGGA GCTGAGATCA CTCGCTTCAC

4981 CCTCCTCATC TTTGTTCTCC AAGTAAAGCC ACGAGGTCGG GGCGAGGGCA GAGGTGATCA

5041 CCTGCGTGTC CCATCTACAG ACCTGCAGCT TCATAAAACT TCTGATTTCT CTTCAGCTTT

5101 GAAAAGGGTT ACCCTGGGCA CTGGCCTAGA GCCTCACCTC CTAATAGACT TAGCCCCATG

5161 AGTTTGCCAT GTTGAGCAGG ACTATTTCTG GCACTTGCAA GTCCCATGAT TTCTTCGGTA

5221 ATTCTGAGGG TGGGGGGAGG GACATGAAAT CATCTTAGCT TAGCTTTCTG TCTGTGAATG

5281 TCTATATAGT GTATTGTGTG TTTTAACAAA TGATTTAGAC TGACTGTTGC TGTAAAAGTG

5341 AATTTGGAAA TAAAGTTATT ACTCTGATTA AA.

The corresponding amino acid sequence of human Tau protein isoform 4 can be found at NP_058525.1:

```
                                        (SEQ ID NO: 54)
  1  MAEPRQEFEV MEDHAGTYGL GDRKDQGGYT MHQDQEGDTD

     AGLKAEEAGI GDTPSLEDEA

 61  AGHVTQARMV SKSKDGTGSD DKKAKGADGK TKIATPRGAA

     PPGQKGQANA TRIPAKTPPA

121  PKTPPSSGEP PKSGDRSGYS SPGSPGTPGS RSRTPSLPTP

     PTREPKKVAV VRTPPKSPSS

181  AKSRLQTAPV PMPDLKNVKS KIGSTENLKH QPGGGKVQIV

     YKPVDLSKVT SKCGSLGNIH

241  HKPGGGQVEV KSEKLDFKDR VQSKIGSLDN ITHVPGGGNK

     KIETHKLTFR ENAKAKTDHG

301  AEIVYKSPVV SGDTSPRHLS NVSSTGSIDM VDSPQLATLA

     DEVSASLAKQ GL.
```

As used herein, “subject” means a mammal, including cat, dog, mouse, rat, chimpanzee, ape, monkey, and human. Preferably the subject is a human.

As used herein, “treatment” or “treating” refers to all processes wherein there may be a slowing, controlling, delaying, or stopping of the progression of the disorders or disease disclosed herein, or ameliorating disorder or disease symptoms, but does not necessarily indicate a total elimination of all disorder or disease symptoms. Treatment includes administration of a protein or nucleic acid or vector or composition for treatment of a disease or condition in a patient, particularly in a human.

EXAMPLES

Example 1. Synthesis of Linker—Delivery Moiety Pairs

Certain abbreviations are defined as follows: “ACN” refers to acetonitrile; “AEX” refers to anion exchange; “C/D” refers to cleavage and deprotection; “CPG” refers to controlled pore glass; “DCM” refers to dichloromethane; “DEA” refers to diethylamine; “DIEA” refers to N,N-diisopropylethylamine; “DMAP” refers to 4-dimethylaminopyridine; “DMF” refers to dimethylformamide; “DMSO” refers to dimethyl sulfoxide; “DMTCl” refers to 4,4'-dimethoxytrityl chloride; “ES/MS” refers to electrospray mass spectrometry; “EtOAc” refers to ethyl acetate; “EtOH” refers to ethanol and ethyl alcohol; “HBTU” refers to 3-[bis(dimethylamino)methyliumyl]-3H-benzotriazol-1-oxide hexafluorophosphate; “HOBt” refers to 1-hydroxybenzotriazole; “IP-RP” refers to ion-pair reverse phase; “LCAA CPG” refers to long chain alkylamine controlled pore glass; “LC/MS” refers to liquid chromatography-mass spectrometry; “MeOH” refers to methanol and methyl alcohol; “MPA” refers to mobile phase A; “MPB” refers to mobile phase B; “MWCO” refers to molecular weight cut-off; “NMR” refers to nuclear magnetic resonance; “PBS” phosphate-buffered saline; “PEG” refers to polyethylene glycol; “PVDF” refers to polyvinylidene fluoride; “RP” refers to reverse phase; “RPM” refers to revolutions per minute; “siRNA” refers to small interfering ribonucleic acid; “TEA” refers to triethylamine; “THF” refers to tetrahydrofuran; “TLC” refers to thin line chromatography; “TMP” refers to 2,2,6,6-tetramethylpiperidine; “UPLC” refers to ultra-performance liquid chromatography; and “UV” refers to ultraviolet.

Scheme 1

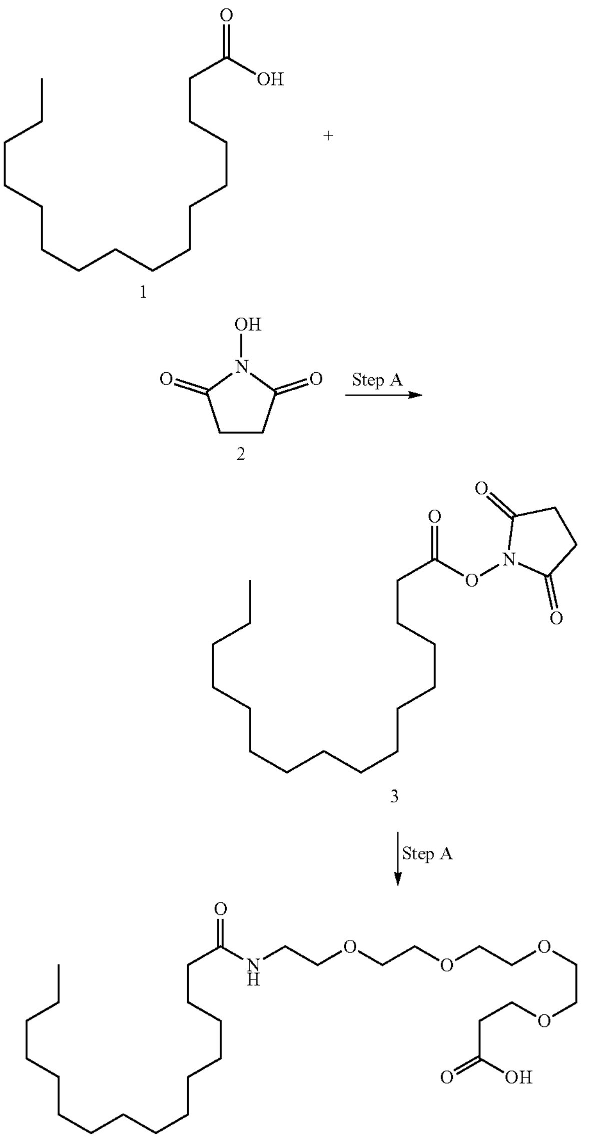

1 + 2 → 3 → 4

Scheme 1, step A depicts the coupling of compounds (1) and (2) using an appropriate base such as DMAP in a suitable solvent such as DCM to give compound (3). Step B shows the coupling of compound (3) with 1-amino-3,6,9,12-tetraoxapentadecan-15-oic acid in the presence of a base such as potassium carbonate and in a solvent system such as water and THF to give compound (4).

Scheme 2
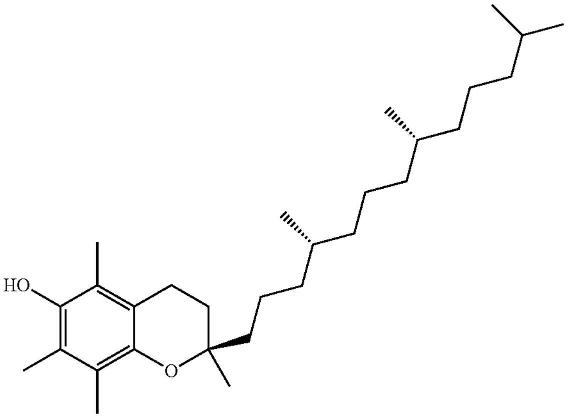
5
Step A
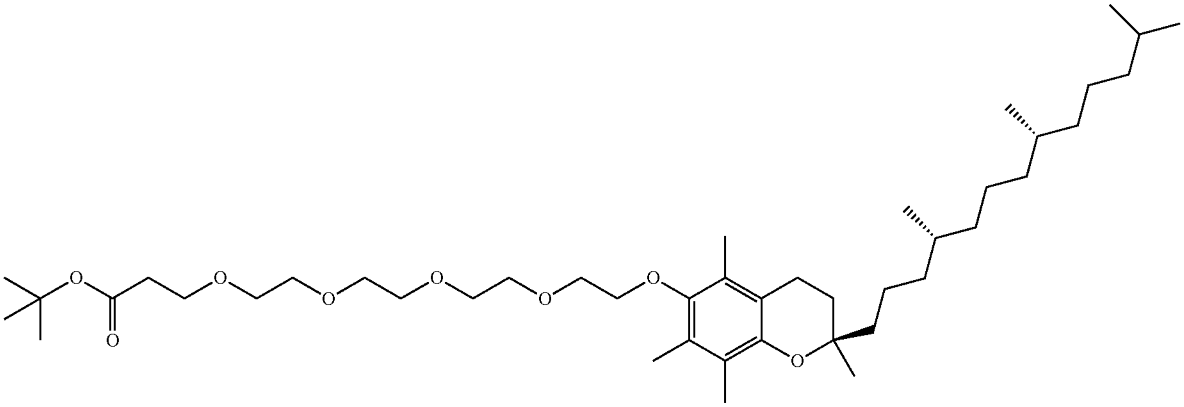
6
Step B
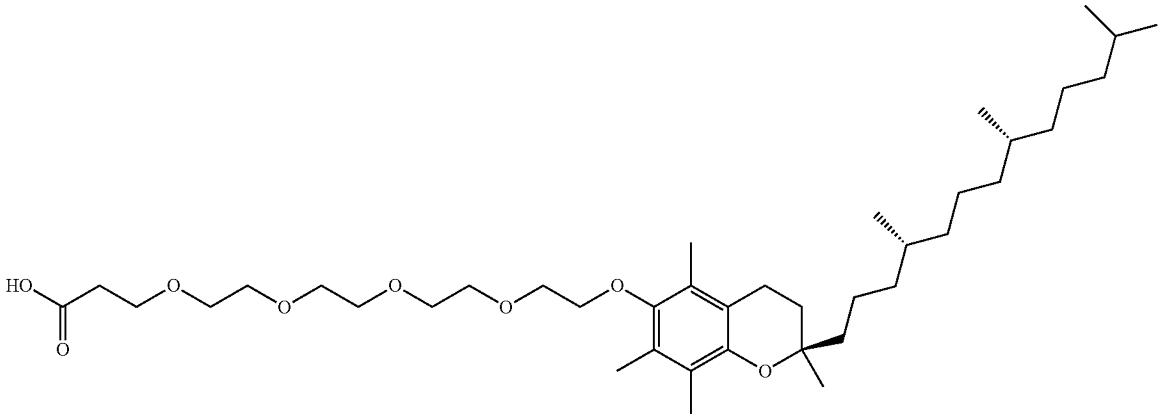
7

Scheme 2, step A depicts a Mitsunobu reaction between compound (5) and tert-butyl 1-hydroxy-3,6,9,12-tetraoxa-pentadecan-15-oate using triphenyl phosphene and diisopropyl azodicarboxylate in a solvent such as THF to give compound (6). Step B shows the acidic deprotection of compound (6) using an acid such as HCl in a solvent such as 1,4-dioxane to give compound (7).

Scheme 3

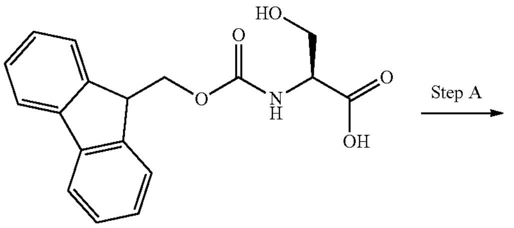

8

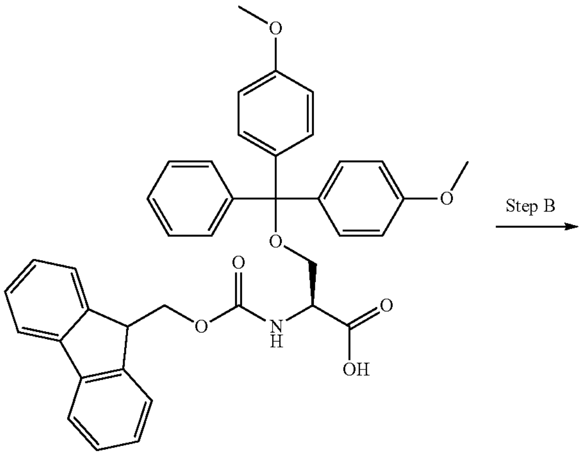

9

-continued

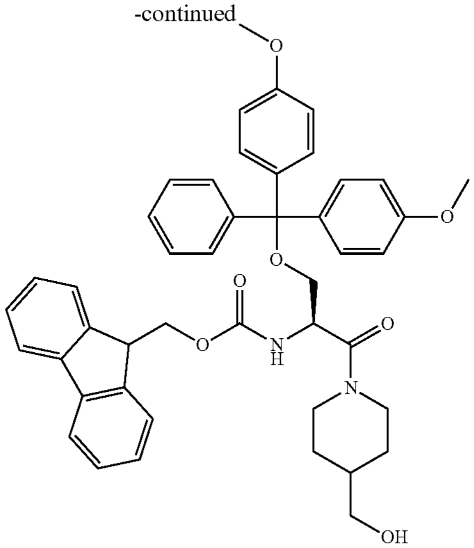

10

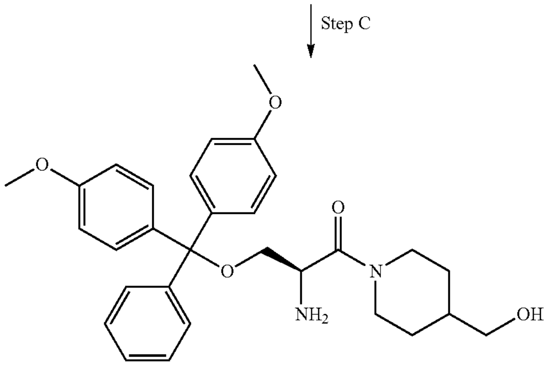

11

Scheme 3, step A depicts the protection of compound (8) using DMTCl with a suitable base such as DIEA in a solvent such as DCM to give compound (9). Step B shows an amide coupling between compound (9) and piperidin-4-yl methanol using HBTU and HOBt with TMP in a solvent such as DCM to give compound (10). The deprotection of compound (10) with 20% piperidine in DMF to give compound (11) is shown in step C.

Scheme 4

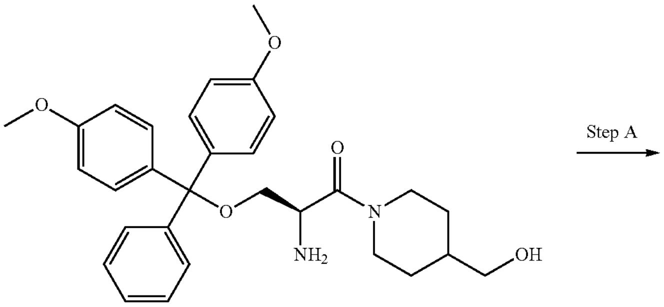

11

-continued
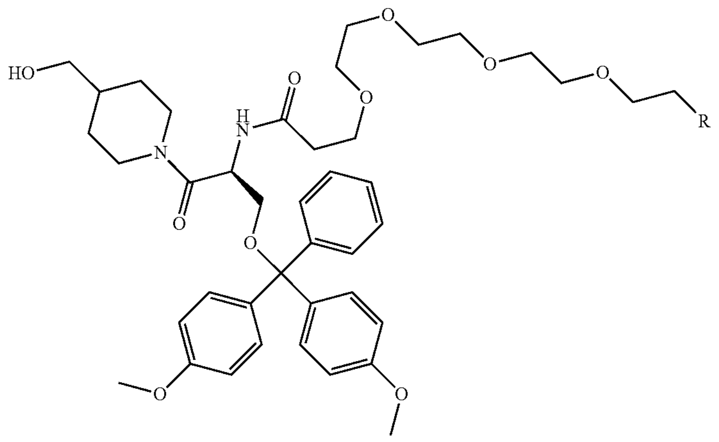
12
Step B
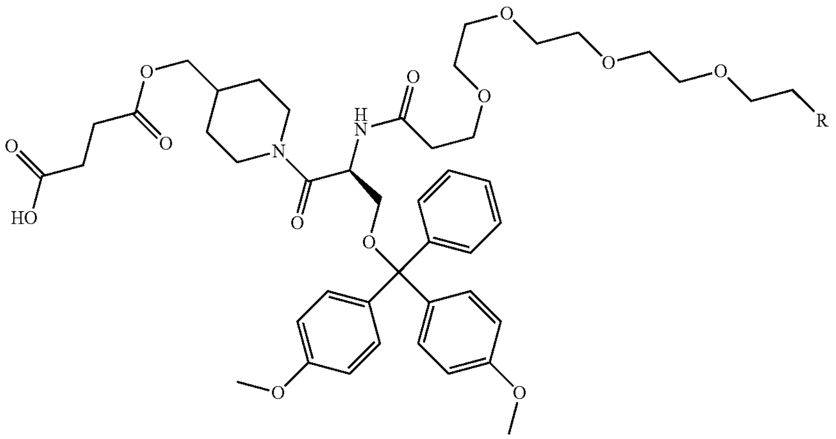
13
Step C
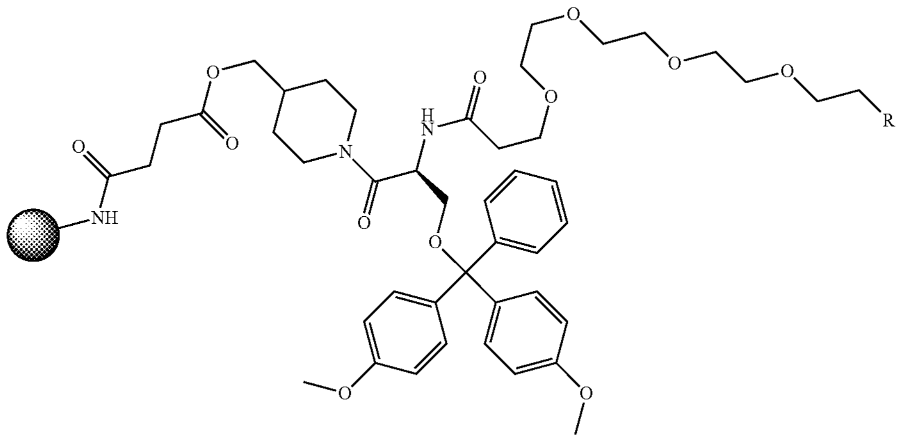
14

Scheme 4, step A depicts an amide coupling between compound (11) and either compound (4) or compound (7) using standard coupling reagents such as HBTU and HOBt with a base such as DIEA in a solvent such as DMF to give compound (12). One skilled in the art will recognize the variety of conditions which could be used to perform this amide coupling. Step B shows the coupling of compound (12) to succinic anhydride using a base such as TEA with catalytic DMAP in a solvent such as DCM to give compound (13). Step C shows the amide coupling of compound (13) to amino LCAA CPG using HBTU with a base such as DIEA in a solvent such as ACN followed by a multistep work up to give compound (14).

Preparation 1

2,5-Dioxopyrrolidin-1-yl palmitate

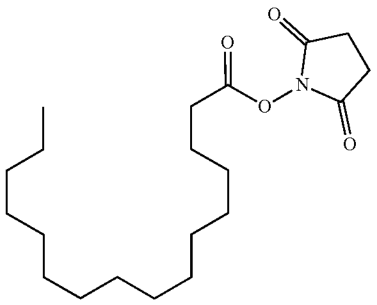 [SMILES: CCCCCCCCCCCCCCCC(=O)ON1C(=O)CCC1=O]

Added palmitic acid (2.00 g, 7.80 mmol) to a solution of 1-(3-dimethylaminopropyl)-3-ethylcarbodiimide hydrochloride (1.79 g, 9.36 mmol) and DMAP (0.19 g, 1.56 mmol) in DCM (31 mL). Stirred the mixture at ambient temperature for 5 minutes then added N-hydroxysuccinimide (0.99 g, 8.58 mmol) and stirred at ambient temperature for 18 hours. Concentrated in vacuo and purified the resulting crude material via silica gel flash chromatography eluting with a gradient of 0-80% EtOAc in hexanes to give the title compound as a white solid (2.65 g, 96%). $^1$H NMR (DMSO-$d_6$) δ 2.81 (s, 4H), 2.66 (t, 2H), 1.62 (m, 2H), 1.25 (br s, 24H), 0.87 (t, 3H).

Preparation 2

3-[2-[2-[2-[2-(Hexadecanoylamino)ethoxy]ethoxy]ethoxy]ethoxy]propanoic acid

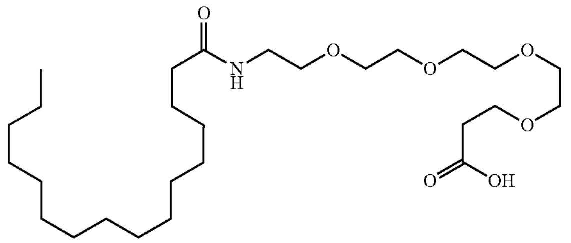 [SMILES: CCCCCCCCCCCCCCCC(=O)NCCOCCOCCOCCOCCC(=O)O]

Added 1-amino-3,6,9,12-tetraoxapentadecan-15-oic acid (0.14 g, 0.53 mmol) to a solution of potassium carbonate (0.14 g, 1.00 mmol) in THF (1 mL) and water (2 mL). Added 2,5-dioxopyrrolidin-1-yl palmitate (0.18 g, 0.51 mmol) and stirred the reaction at ambient temperature for 18 hours. Quenched the reaction with water (30 mL) and adjusted the pH to ~3 with 1N aqueous HCl. A precipitate formed and was collected by vacuum filtration to give the title compound as a white solid (0.19 g, 74%). ES/MS m/z 504 (M+H).

Preparation 3 tert-Butyl 3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoate

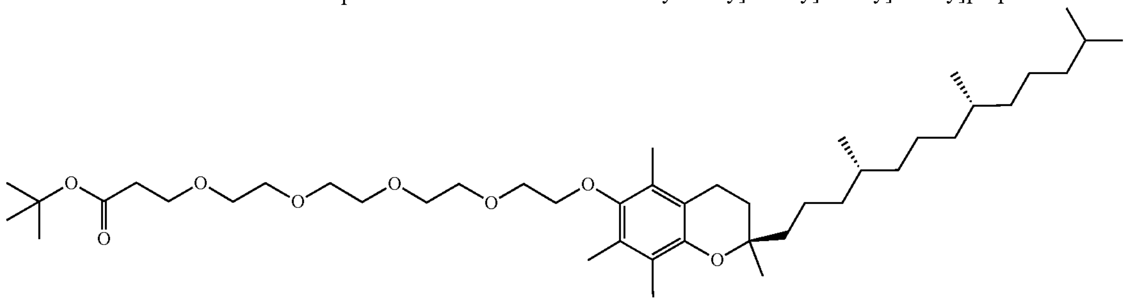

Combined (2R)-2,5,7,8-tetramethyl-2-[(4R,8R)-4,8,12-trimethyltridecyl]chroman-6-ol (3.00 g, 6.90 mmol), tert-butyl 1-hydroxy-3,6,9,12-tetraoxapentadecan-15-oate (2.50 g, 7.60 mmol), and triphenylphosphine (2.00 g, 7.60 mmol) in THF (28.0 mL) and added diisopropyl azodicarboxylate (1.50 mL, 7.60 mmol) dropwise over 5 minutes. Heated the mixture at 60° C. for 16 hours. Cooled the mixture to ambient temperature, added silica gel, and concentrated in vacuo to give an off-white solid. Purified the mixture via silica gel flash chromatography, eluting with 0-40% EtOAc/hexanes, to give the title compound as an oil (3.33 g, 66%). $^1$H NMR ($CDCl_3$): 3.84 (s, 4H), 3.77-3.71 (m, 13H), 2.59 (t, J=6.8 Hz, 2H), 2.52 (t, J=6.6 Hz, 2H), 2.20-2.20 (m, 3H), 2.15-2.12 (m, 3H), 2.10 (s, 3H), 1.87-1.73 (m, 2H), 1.58-1.51 (m, 4H), 1.47 (s, 9H), 1.35-1.27 (m, 21H), 0.90-0.86 (m, 12H).

Preparation 4

3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoic acid

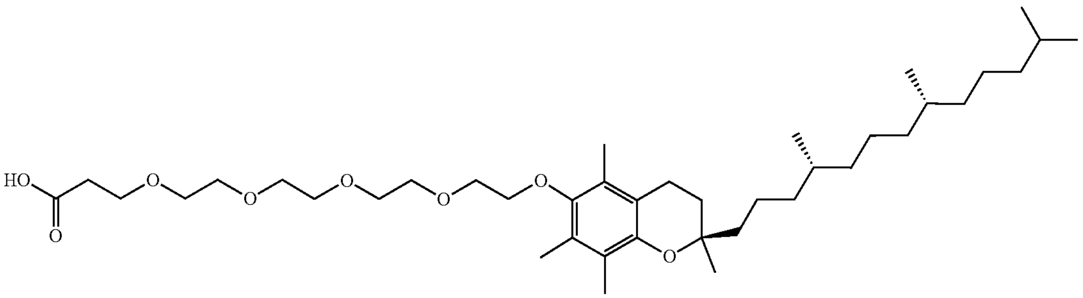 [SMILES: Cc1c(C)c2c(c(C)c1OCCOCCOCCOCCOCCC(=O)O)CC[C@@](C)(CCC[C@H](C)CCC[C@H](C)CCCC(C)C)O2]

Dissolved tert-butyl 3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoate (3.33 g, 4.53 mmol) in 4M HCl in dioxane (22.6 mL, 90.6 mmol) and stirred for 16 hours at ambient temperature. Removed the solvent under reduced pressure to give the title compound as an off-white solid (3.08 g, 100%). ES/MS m/z 678.0 (M−H).

Preparation 5

(2 S)-3-[Bis(4-methoxyphenyl)-phenyl-methoxy]-2-(9H-fluoren-9ylmethoxycarbonylamino) propanoic acid

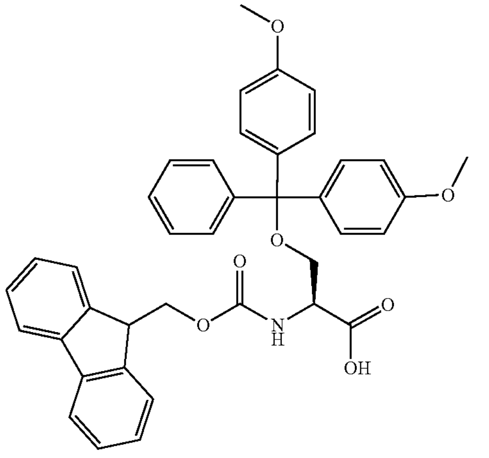 [SMILES: COc1ccc(C(OC[C@H](NC(=O)OCC2c3ccccc3-c3ccccc32)C(=O)O)(c2ccccc2)c2ccc(OC)cc2)cc1]

Added DIEA (64 mL, 0.366 mol) to a stirring solution of (25)-2-(9H-fluoren-9-ylmethoxycarbonylamino)-3-hydroxy-propanoic acid (40 g, 0.122 mol) in dry DCM (400 mL) at 0° C. under an inert atmosphere. To this mixture, slowly added a solution of DMTCl (49.6 g, 0.146 mol) in DCM (200 mL). Allowed to warm to ambient temperature and stirred for 16 hours. After this time, diluted the reaction mixture with water and extracted with DCM. Dried organics over anhydrous sodium sulphate, filtered, and concentrated in vacuo. Washed the crude residue with 10% EtOAc/hexane and dried under vacuum to give the crude title compound as a pale brown solid (62 g, crude). TLC: 5% $MeOH/CH_2Cl_2$ ($R_f$: 0.5) UV, 254 nM.

Preparation 6

9H-Fluoren-9-ylmethyl N-[(1S)-1-[[bis(4-methoxyphenyl)-phenyl-methoxy]methyl]-2-[4-(hydroxymethyl)-1-piperidyl]-2-oxo-ethyl]carbamate

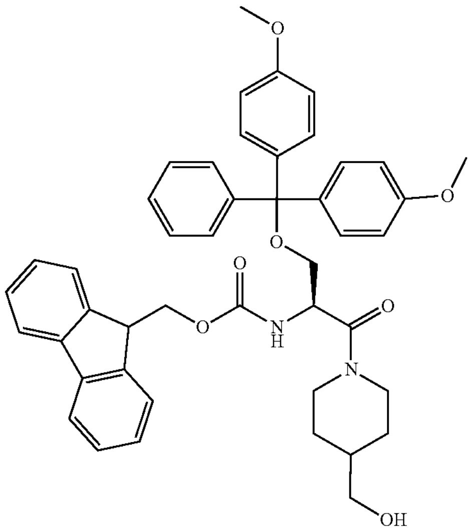 [SMILES: COc1ccc(C(OC[C@H](NC(=O)OCC2c3ccccc3-c3ccccc32)C(=O)N2CCC(CO)CC2)(c2ccccc2)c2ccc(OC)cc2)cc1]

Slowly added HBTU (78.3 g, 0.206 mol), HOBt (27.9 g, 0.206 mol), and piperidin-4-yl methanol (15.4 g, 0.134 mol) followed by TMP (15 mL, 0.113 mol) to a stirring solution of (2S)-3-[bis(4-methoxyphenyl)-phenyl-methoxy]-2-(9H-fluoren-9-ylmethoxycarbonylamino) propanoic acid (62 g, 0.103 mol) in DCM (750 mL) at 0° C. under inert atmosphere. Allowed the resulting reaction mixture to reach ambient temperature and stirred for 4 hours. After this time, diluted the mixture with water and extracted with DCM. Dried the organics over anhydrous sodium sulphate, filtered, and concentrated in vacuo. Purified the resulting residue via silica gel flash chromatography eluting with 20-40% EtOAc/hexane and 1% MeOH/DCM to give the title compound (40 g, 52% over two steps). $^1H$ NMR (DMSO-$d_6$) δ 7.88 (br d, J=7.5 Hz, 2H), 7.79-7.59 (m, 3H), 7.45-7.12 (m, 13H), 6.92-6.76 (m, 4H), 4.79-4.44 (m, 2H), 4.32 (br d, J=11.4 Hz, 2H), 4.20 (br s, 2H), 3.71 (s, 6H), 3.21 (br s, 4H), 2.99-2.79 (m, 1H), 2.69 (br s, 2H), 1.81-1.43 (m, 3H), 1.08-0.73 (m, 2H).

Preparation 7

(2 S)-2-Amino-3-[bis(4-methoxyphenyl)-phenyl-methoxy]-1-[4-(hydroxymethyl) piperidyl]propan-1-one

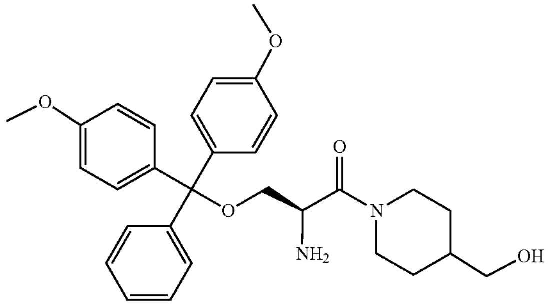 [SMILES: COc1ccc(C(OC[C@H](N)C(=O)N2CCC(CO)CC2)(c2ccccc2)c2ccc(OC)cc2)cc1]

Slowly added a solution of 20% piperidine in DMF (400 mL) to 9H-fluoren-9-ylmethyl N-[(1S)-1-[[bis(4-methoxy-phenyl)-phenyl-methoxy]methyl]-2-[4-(hydroxymethyl)-1-piperidyl]-2-oxo-ethyl]carbamate (40 g, 0.055 mol) at 0° C. under inert atmosphere. Allowed the mixture to warm to ambient temperature and stirred for 1 hour. After this time, diluted the mixture with water and extracted with EtOAc. Dried organics over anhydrous sodium sulphate, filtered, and concentrated in vacuo. Purified the resulting residue via silica gel flash chromatography eluting with 1-8% MeOH/DCM to give the title compound as an off-white solid (13 g, 47%). ES/MS m/z 1009.5 (2M+H).

Preparation 8

N-[2-[2-[2-[2-[3-[[(1 S)-1-[[Bis(4-methoxyphenyl)-phenyl-methoxy]methyl]-2-[4-(hydroxymethyl)-1-piperidyl]-2-oxo-ethyl]amino]-3-oxo-propoxy] ethoxy]ethoxy]ethoxy]ethyl]hexadecanamide

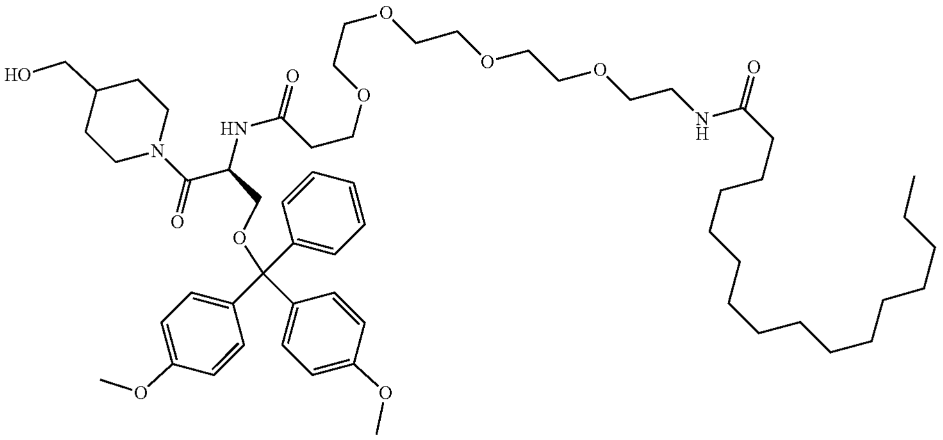 [SMILES: CCCCCCCCCCCCCCCC(=O)NCCOCCOCCOCCOCCC(=O)N[C@@H](COC(c1ccccc1)(c1ccc(OC)cc1)c1ccc(OC)cc1)C(=O)N1CCC(CO)CC1]

Combined 3-[2-[2-[2-[2-(hexadecanoylamino)ethoxy] ethoxy]ethoxy]ethoxy]propanoic acid (496 mg, 0.984 mmol), HOBt (146 mg, 1.08 mmol), HBTU (410 mg, 1.08 mmol), and DIEA (1.03 mL, 5.90 mmol) in DMF (9.84 mL) and stirred at ambient temperature for 10 minutes. Added (2S)-2-amino-3-[bis(4-methoxyphenyl)-phenyl-methoxy]-1-[4-(hydroxymethyl)-1-piperidyl]propan-1-one (546 mg, 1.08 mmol) to the mixture and stirred at ambient temperature for 16 hours. Partitioned the mixture between EtOAc and saturated aqueous sodium chloride solution. Separated the layers and washed the organics with saturated aqueous sodium chloride solution. Dried the organics over sodium sulfate, filtered, and concentrated in vacuo. Purified the resulting residue by silica gel flash chromatography eluting with 0-10% MeOH/DCM to give the title compound as an oil (327 mg, 34%). 1H NMR (DMSO-$d_6$) 8.21 (d, J=8.5 Hz, 1H), 7.80 (t, J=5.6 Hz, 1H), 7.37-7.28 (m, 4H), 7.23-7.20 (m, 5H), 6.88 (d, J=8.3 Hz, 4H), 5.06-5.02 (m, 1H), 4.51-4.49 (m, 1H), 4.45-4.40 (m, 1H), 3.97-3.93 (m, 1H), 3.74 (s, 5H), 3.63-3.56 (m, 2H), 3.49-3.48 (m, 4H), 3.47-3.45 (m, 7H), 3.40-3.35 (m, 2H), 3.30 (s, 1H), 3.23-3.13 (m, 7H), 2.41-2.33 (m, 2H), 2.04 (t, J=7.4 Hz, 2H), 1.74-1.69 (m, 3H), 1.51-1.44 (m, 2H), 1.26-1.24 (m, 24H), 1.00-0.97 (m, 1H), 0.88-0.82 (m, 5H).

Preparation 9

4-[[1-[(2S)-3-[Bis(4-methoxyphenyl)-phenyl-methoxy]-2-[3-[2-[2-[2-[2-(hexadecanoylamino)ethoxy]ethoxy]ethoxy]ethoxy]propanoylamino]propanoyl]-4-piperidyl]methoxy]-4-oxo-butanoic acid

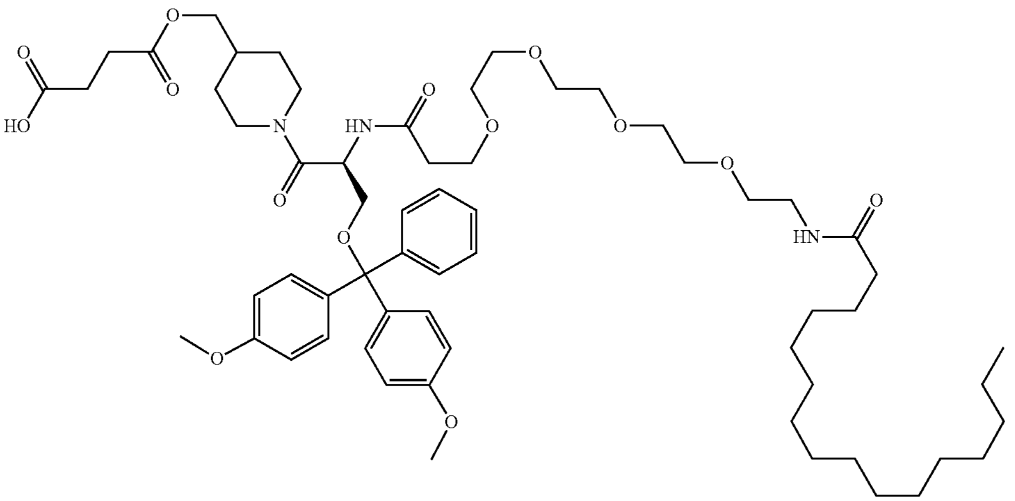 [SMILES: CCCCCCCCCCCCCCCC(=O)NCCOCCOCCOCCOCCC(=O)N[C@@H](COC(c1ccccc1)(c1ccc(OC)cc1)c1ccc(OC)cc1)C(=O)N1CCC(COC(=O)CCC(=O)O)CC1]

Combined N-[2-[2-[2-[2-[3-[[(1S)-1-[[bis(4-methoxyphenyl)-phenyl-methoxy]methyl]-2-[4-(hydroxymethyl)-1-piperidyl]-2-oxo-ethyl]amino]-3-oxo-propoxy]ethoxy]ethoxy]ethoxy]ethyl]hexadecanamide (320 mg, 0.323 mmol), DMAP (120 mg, 0.969 mmol), TEA (225 μL, 1.62 mmol), and succinic anhydride (64.7 mg, 0.646 mmol) in DCM (6.46 mL) and stirred the mixture for 16 hours at ambient temperature. Purified the mixture directly via silica gel flash chromatography, eluting with 0% to 40% MeOH/DCM, to give the title compound as a colorless oil (279 mg, 79%). $^1$H NMR (DMSO-$d_6$) 12.65-12.64 (m, 1H), 8.24-8.19 (m, 1H), 7.80 (t, J=5.6 Hz, 1H), 7.37-7.28 (m, 4H), 7.24-7.20 (m, 5H), 6.88 (d, J=8.6 Hz, 4H), 5.05-5.01 (m, 1H), 4.44-4.40 (m, 1H), 3.97-3.95 (m, 3H), 3.74 (s, 6H), 3.61-3.56 (m, 2H), 3.49-3.45 (m, 11H), 3.38 (t, J=5.9 Hz, 3H), 3.22-3.14 (m, 6H), 2.48-2.31 (m, 7H), 2.04 (t, J=7.4 Hz, 2H), 1.90-1.87 (m, 5H), 1.24 (s, 23H), 0.98-0.96 (m, 1H), 0.87-0.82 (m, 4H).

Preparation 10

4-[[1-[(2S)-3-[Bis(4-methoxyphenyl)-phenyl-methoxy]-2-[3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoylamino]propanoyl]-4-piperidyl]methoxy]-4-oxo-butanoic acid

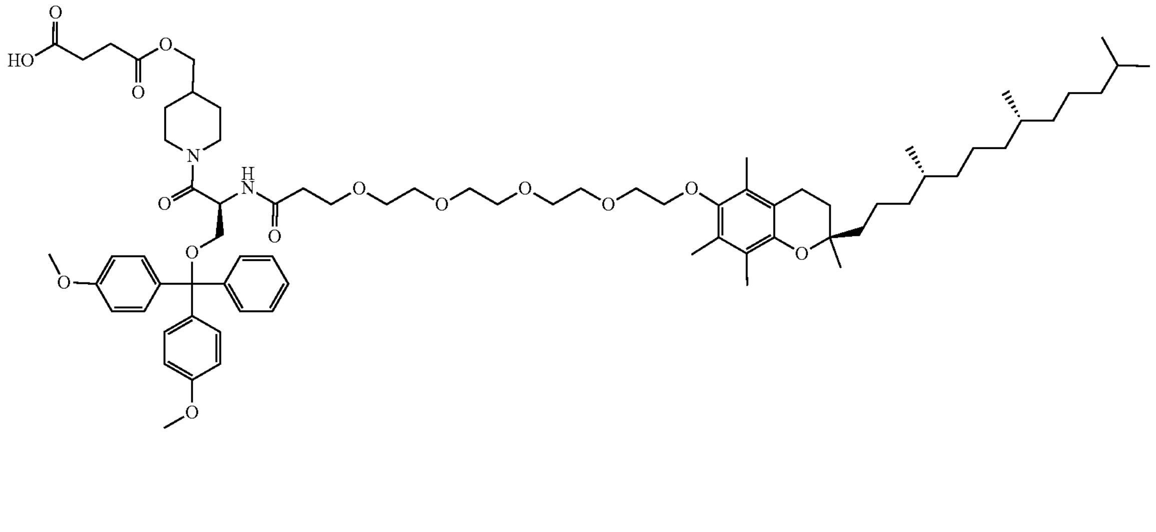 [SMILES: COc1ccc(C(OC[C@H](NC(=O)CCOCCOCCOCCOCCOc2c(C)c(C)c3c(c2C)CC[C@@](C)(CCC[C@H](C)CCC[C@H](C)CCCC(C)C)O3)C(=O)N2CCC(COC(=O)CCC(=O)O)CC2)(c2ccccc2)c2ccc(OC)cc2)cc1]

Combined 3-[2-[2-[2-[2-[(2R)-2,5,7,8-tetramethyl-2-[(4R,8R)-4,8,12-trimethyltridecyl]chroman-6-yl]oxy-ethoxy]ethoxy]ethoxy]ethoxy]propanoic acid (1.20 g, 1.80 mmol), HOBt (260 mg, 1.90 mmol), HBTU (740 mg, 1.90 mmol), and DIEA (1.80 mL, 11.0 mmol) in DMF (18.0 mL) and stirred at ambient temperature for 10 minutes. Added (2S)-2-amino-3-[bis(4-methoxyphenyl)-phenyl-methoxy]-1-[4-(hydroxymethyl)-1-piperidyl]propan-1-one (980 mg, 1.90 mmol) to the mixture and stirred at ambient temperature for 16 hours. Partitioned the mixture between EtOAc and saturated aqueous sodium chloride solution. Separated the layers and washed the organics with saturated aqueous sodium chloride solution. Dried the organic layer over sodium sulfate, filtered, and concentrated in vacuo. Purified the resulting residue by silica gel flash chromatography, eluting with 0-10% MeOH/DCM, to give N-[(1S)-1-[[bis(4-methoxyphenyl)-phenyl-methoxy]methyl]-2-[4-(hydroxymethyl)-1-piperidyl]-2-oxo-ethyl]-3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propenamide as a yellow oil.

Combined N-[(1S)-1-[[bis(4-methoxyphenyl)-phenyl-methoxy]methyl]-2-[4-(hydroxymethyl)-1-piperidyl]-2-oxo-ethyl]-3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propenamide (1.45 g, 1.24 mmol), DMAP (456 mg, 3.73 mmol), TEA (867 μL, 6.22 mmol), and succinic anhydride (249 mg, 2.49 mmol) in DCM (24.9 mL) and stirred for 16 hours at ambient temperature. Concentrated in vacuo and purified the resulting residue via silica gel flash chromatography, eluting with 0-40% MeOH/DCM, to give the title compound as an oil (1.36 g, 60%). ES/MS m/z 1264.4 (M−H).

Preparation 11

[[4-[[1-[(2S)-3-[Bis(4-methoxyphenyl)-phenyl-methoxy]-2-[3-[2-[2-[2-[2-(hexadecanoylamino)ethoxy]ethoxy]ethoxy]ethoxy]propanoylamino]propanoyl]-4-piperidyl]methoxy]-4-oxo-butanoyl]amino] on CPG

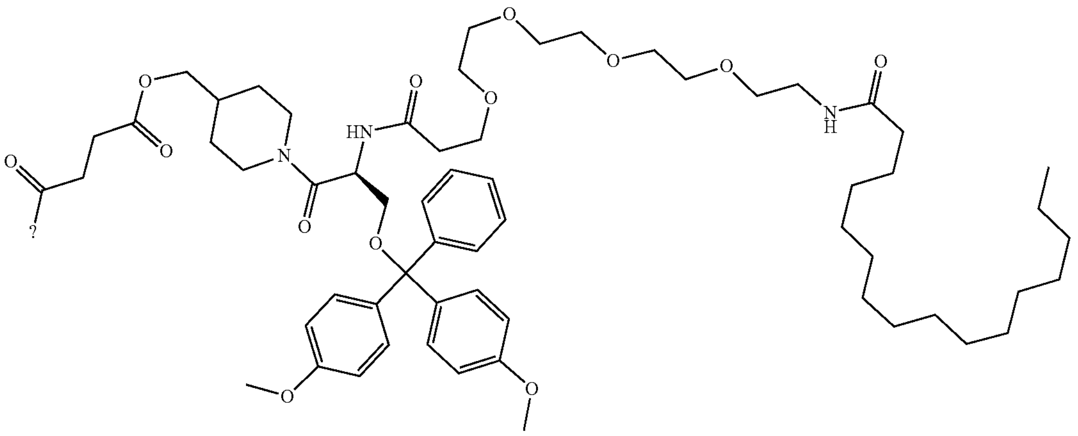

Dissolved 4-[[1-[(2S)-3-[bis(4-methoxyphenyl)-phenyl-methoxy]-2-[3-[2-[2-[2-[2-(hexadecanoylamino)ethoxy]ethoxy]ethoxy]ethoxy]propanoylamino]propanoyl]-4-piperidyl]methoxy]-4-oxo-butanoic acid (270 mg, 0.248 mmol) in ACN (12.5 mL) and transferred the solution to a fritted glass dropping funnel. Added DIEA (150 μL, 0.860 mmol) and HBTU (190 mg, 0.500 mmol) to the solution and shook the mixture at ambient temperature for 10 minutes. Added native amino LCAA CPG 500 Å (1.92 g, 129 μmol/g,) to the solution and shook the mixture at 500 RPM for 16 hours at ambient temperature. Drained the CPG and dried under nitrogen for 5 minutes. Washed the CPG with DCM (50 mL), 10% MeOH/DCM (50 mL), and then diethyl ether (50 mL). Dried the CPG for 30 minutes under nitrogen and then resuspended in pyridine (15 mL). Added acetic anhydride (3.30 mL, 35.0 mmol) and TEA (0.50 mL) and shook the mixture at 500 RPM for 2 hours at ambient temperature. Drained the CPG and dried for 5 minutes under nitrogen. Washed the CPG with DCM (50 mL), 10% MeOH/DCM (50 mL), and then diethyl ether (50 mL). Dried the CPG for 45 minutes under nitrogen and determined the ligand loading at 505 nm to give the title compound (1.92 g, 75.5 μmol/g).

Preparation 12

[[4-[[1-[(2S)-3-[Bis(4-methoxyphenyl)-phenyl-methoxy]-2-[3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoylamino]propanoyl]-4-piperidyl]methoxy]-4-oxo-butanoyl]amino] on CPG

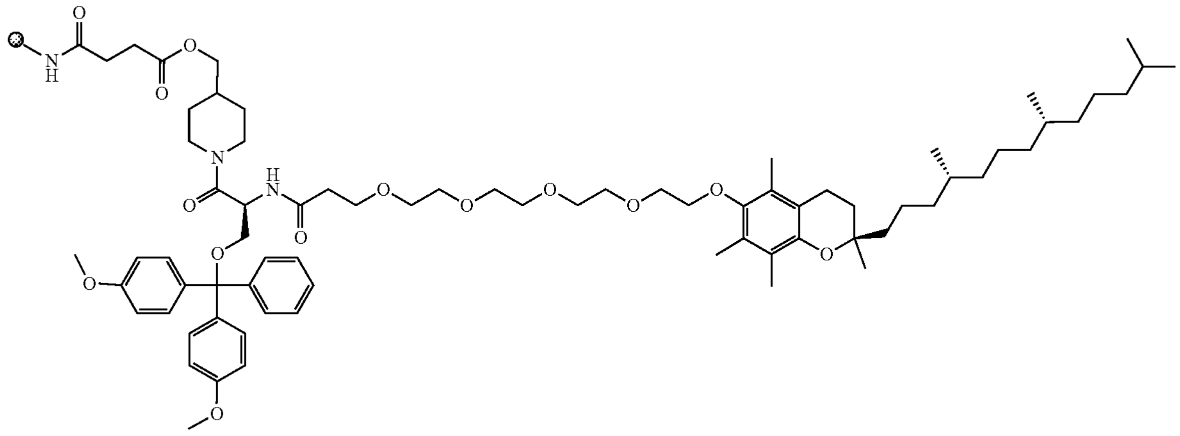 [SMILES: CNC(=O)CCC(=O)OCC1CCN(C(=O)[C@H](COC(c2ccccc2)(c2ccc(OC)cc2)c2ccc(OC)cc2)NC(=O)CCOCCOCCOCCOCCOc2c(C)c(C)c3c(c2C)CC[C@@](C)(CCC[C@H](C)CCC[C@H](C)CCCC(C)C)O3)CC1]

Prepared the title compound from 4-[[1-[(2S)-3-[bis(4-methoxyphenyl)-phenyl-methoxy]-2-[3-[2-[2-[2-[2-[(2R)-2,5,7,8-tetramethyl-2-[(4R,8R)-4,8,12-trimethyltridecyl]chroman-6-yl]oxyethoxy]ethoxy]ethoxy]ethoxy]propanoylamino]propanoyl]-4-piperidyl]methoxy]-4-oxo-butanoic acid in a manner essentially analogous to Preparation 11. Determined the ligand loading at 505 nm to give the title compound (4.01 g, 66.9 μmol/g).

Preparation 13

3-[[(2R,3R,4R,5R)-2-[[Bis(4-methoxyphenyl)-phenyl-methoxy]methyl]-4-hexadecoxy-5-(2-hydroxy-4-oxo-pyrimidin-1-yl)THF-3-yl]oxy-(diisopropylamino)phosphanyl]oxypropanenitrile

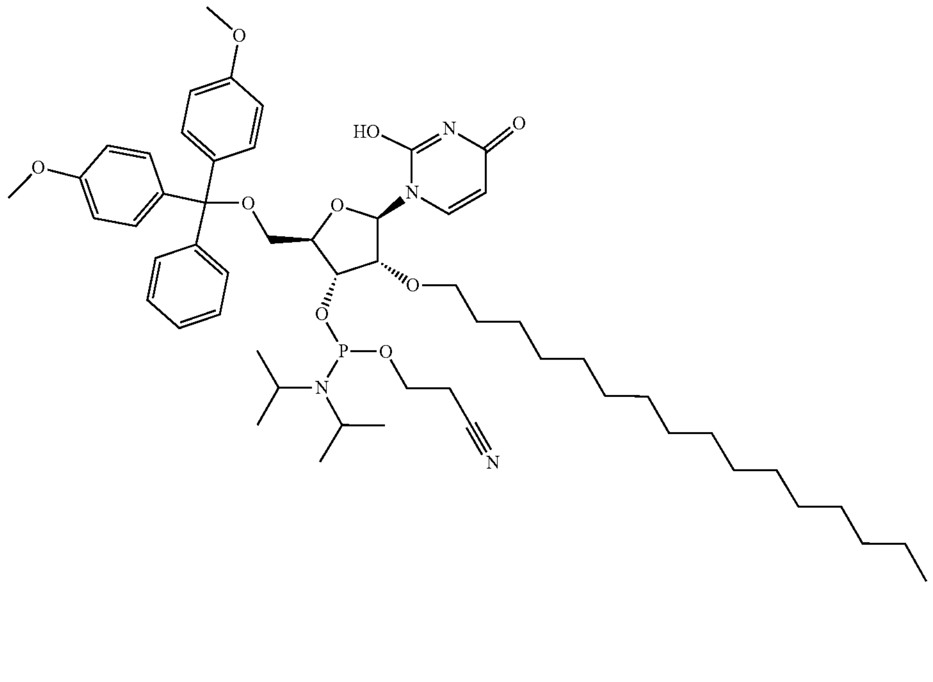 [SMILES: CCCCCCCCCCCCCCCCO[C@@H]1[C@H](OP(OCCC#N)N(C(C)C)C(C)C)[C@@H](COC(c2ccccc2)(c2ccc(OC)cc2)c2ccc(OC)cc2)O[C@H]1n1ccc(=O)nc1O]

Prepared the title compound according to the protocols described in WO2019217459. $^1$H NMR ($CD_3CN$): 7.86-7.73 (m, 1H), 7.51-7.43 (m, 2H), 7.40-7.23 (m, 7H), 6.95-6.87 (m, 4H), 5.90-5.84 (m, 1H), 5.29-5.21 (m, 1H), 4.54-4.40 (m, 1H), 4.21-4.13 (m, 1H), 4.10-3.56 (m, 13H), 3.50-3.34 (m, 2H), 2.75-2.62 (m, 1H), 2.55 (t, J=6.0 Hz, 1H), 1.66-1.51 (m, 2H), 1.40-1.14 (m, 35H), 1.08 (d, J=6.8 Hz, 3H), 0.91 (t, J=6.8 Hz, 3H). $^{31}$P NMR ($CD_3CN$): 149.6, 149.2.

Preparation 14

N-[9-[(2R,3R,4R,5R)-5-[[Bis(4-methoxyphenyl)-phenyl-methoxy]methyl]-4-[2-cyanoethoxy-(diisopropylamino)phosphanyl]oxy-3-hexadecoxy-tetrahydrofuran-2-yl]purin-6-yl]benzamide

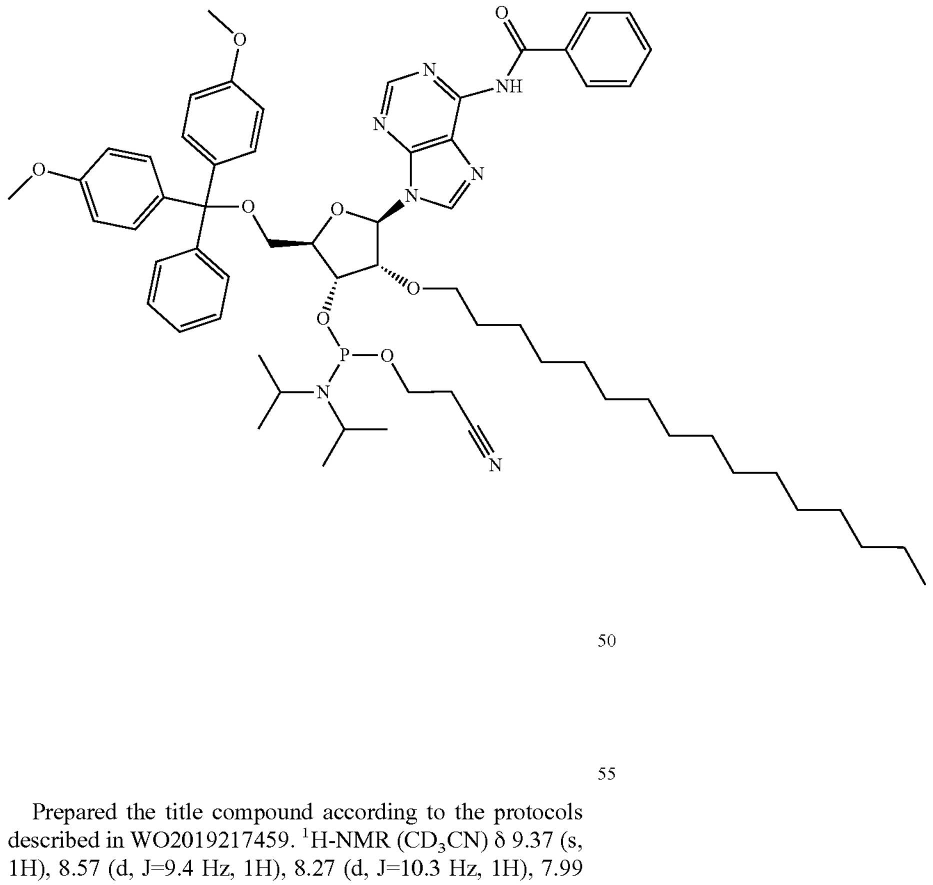

Prepared the title compound according to the protocols described in WO2019217459. $^1$H-NMR ($CD_3CN$) δ 9.37 (s, 1H), 8.57 (d, J=9.4 Hz, 1H), 8.27 (d, J=10.3 Hz, 1H), 7.99 (d, J=7.6 Hz, 2H), 7.61 (d, J=7.4 Hz, 1H), 7.52 (t, J=7.6 Hz, 2H), 7.42 (t, J=7.3 Hz, 2H), 7.34-7.16 (m, 7H), 6.85-6.77 (m, 4H), 6.11 (dd, J=5.0, 2.5 Hz, 1H), 4.80 (m, 1H), 4.69 (m, 1H), 4.32 (m, 1H), 3.97-3.78 (m, 1H), 3.74 (d, J=3.1 Hz, 7H), 3.64 (m, 4H), 3.56-3.40 (m, 2H), 3.33 (m, 1H), 2.73-2.59 (m, 1H), 2.50 (t, J=6.0 Hz, 1H), 1.52-1.45 (m, 2H), 1.33-1.12 (m, 37H), 1.09 (d, J=6.8 Hz, 3H), 0.87 (t, J=6.8 Hz, 3H). $^{31}$P NMR ($CD_3CN$) δ 151.19, 150.78.

Preparation 15

N-[1-[(2R,3R,4R,5R)-5-[[Bis(4-methoxyphenyl)-phenyl-methoxy]methyl]-4-[2-cyanoethoxy-(diisopropylamino)phosphanyl]oxy-3-hexadecoxy-tetrahydrofuran-2-yl]-2-oxo-pyrimidin-4-yl]acetamide

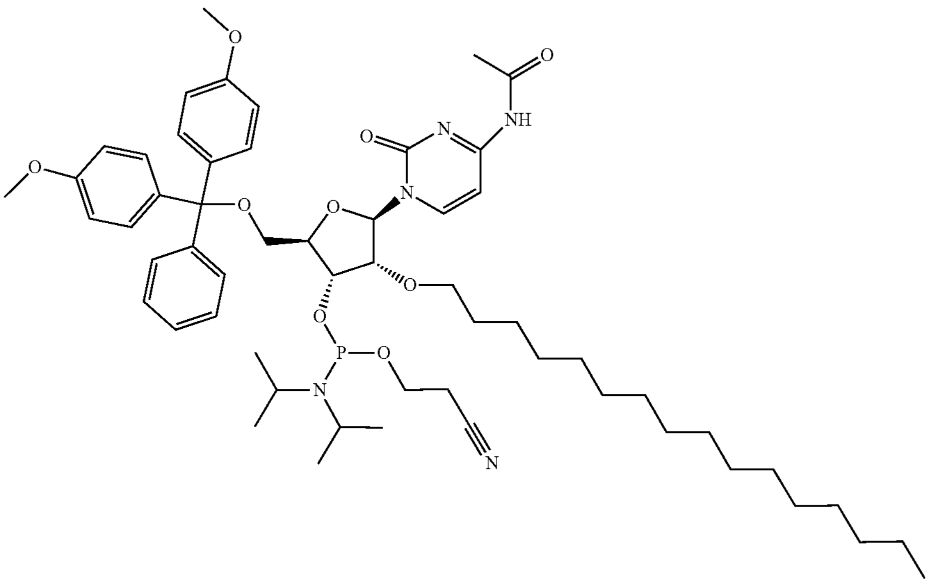 [SMILES: CCCCCCCCCCCCCCCCO[C@@H]1[C@H](OP(OCCC#N)N(C(C)C)C(C)C)[C@@H](COC(c2ccccc2)(c2ccc(OC)cc2)c2ccc(OC)cc2)O[C@H]1n1ccc(NC(C)=O)nc1=O]

Prepared the title compound according to the protocols described in WO2019217459. $^{1}$H-NMR ($CD_3CN$) 9.15 (s, 1H), 8.46 (dd, J=7.5 Hz, 1H), 7.95 (d, J=7.6 Hz, 2H), 7.63 (t, J=7.5 Hz, 1H), 7.57-7.41 (m, 5H), 7.41-7.31 (m, 6H), 7.28 (m, 1H), 7.04 (d, J=15.8 Hz, 1H), 6.90 (t, J=7.9 Hz, 4H), 5.90 (d, J=7.8 Hz, 1H), 4.51 (m, 1H), 4.20 (dd, J=10.6, 8.1 Hz, 1H), 4.04 (dd, J=31.3, 4.6 Hz, 1H), 3.91-3.81 (m, 2H), 3.79 (d, J=3.1 Hz, 6H), 3.74 (m, 2H), 3.69-3.41 (m, 6H), 2.67-2.59 (m, 1H), 2.54-2.48 (m, 1H), 1.58 (m, 2H), 1.36 (m, 2H), 1.25 (d, J=4.7 Hz, 26H), 1.21-1.09 (m, 10H), 1.04 (d, J=6.8 Hz, 3H), 0.87 (t, J=6.8 Hz, 3H). $^{31}$P NMR ($CD_3CN$) δ 151.10, 150.19.

Preparation 16

N-9-[(2R,3R,4R,5R)-5-[[Bis(4-methoxyphenyl)-phenyl-methoxy]methyl]-4-[2-cyanoethoxy-(diisopropylamino)phosphanyl]oxy-3-hexadecoxy-tetrahydrofuran-2-yl]-6-oxo-1H-purin-2-yl]-2-methyl-propanamide

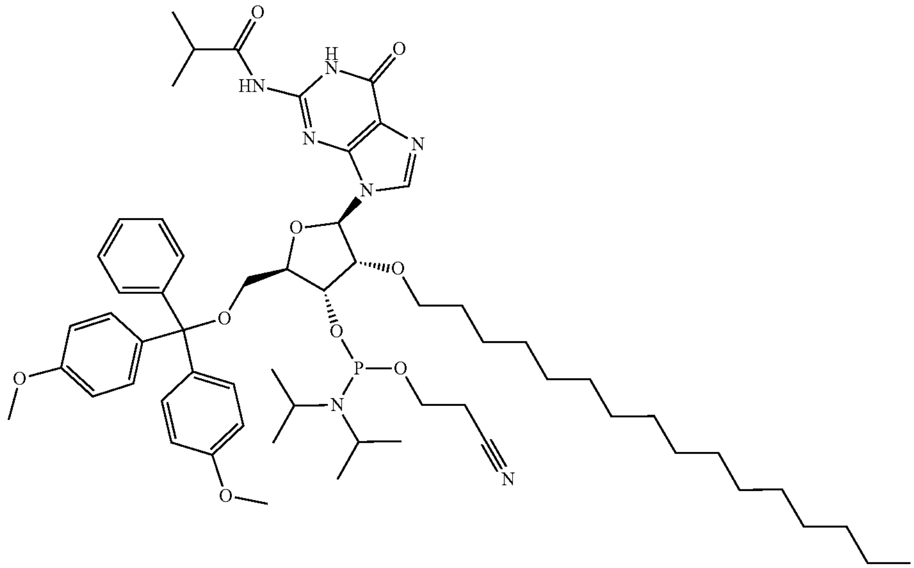 [SMILES: CCCCCCCCCCCCCCCCO[C@@H]1[C@H](OP(OCCC#N)N(C(C)C)C(C)C)[C@@H](COC(c2ccccc2)(c2ccc(OC)cc2)c2ccc(OC)cc2)O[C@H]1n1cnc2c(=O)[nH]c(NC(=O)C(C)C)nc21]

Prepared the title compound according to the protocols described in WO2019217459. $^{1}$H-NMR ($CDCl_3$) δ 12.01-11.96 (m, 1H), 7.82-7.78 (m, 1H), 7.59-7.53 (m, 1H), 7.47-7.42 (m, 1H), 7.41-7.37 (m, 2H), 7.34-7.29 (m, 2H), 7.27-7.22 (m, 3H), 6.85-6.80 (m, 4H), 5.99-5.82 (m, 1H), 4.40-4.36 (m, 1H), 4.17-4.11 (m, 1H), 3.80-3.77 (m, 6H), 3.76-3.68 (m, 6H), 3.22-3.17 (m, 1H), 2.84-2.79 (m, 1H), 1.60-1.54 (m, 4H), 1.35-1.30 (m, 6H), 1.27 (s, 19H), 1.24-1.15 (m, 13H), 1.06-1.03 (m, 5H), 0.93-0.88 (m, 6H), 0.74-0.70 (m, 1H). $^{31}$P NMR ($CDCl_3$) δ 150.20, 149.92.

Example 2. Synthesis of MAPT RNAi Agents

Single strands (sense and antisense) of the RNA duplexes were synthesized on solid support via a MerMade™ 12 (LGC Biosearch Technologies). The sequences of the sense and antisense strands were shown in Table 2. The oligonucleotides were synthesized via phosphoramidite chemistry at either 5, 10, 25 or 50 μmol scales.

For the sense strands, the types of solid supports were universal CPG: (3'-Piperidinol-PEG-Palmitate) and (3'-Piperidinol-PEG-Tocopherol) were synthesized in house (see Example 1) while the Universal UnyLinker (Chemgenes, Catalog No. AT273-27) and 3'Teg-Tocopherol (LGC Biosearch Technologies, Catalog No. BG7-1190) were purchased commercially. For all the antisense strands, commercially available standard support mA was utilized. Standard reagents were used in the oligo synthesis (Table 7), where 0.1M xanthane hydride in pyridine was used as the sulfurization reagent and 20% DEA in ACN was used as an auxiliary wash post synthesis. All monomers (Table 8) were made at 0.1M in ACN and contained a molecular sieves trap bag.

The oligonucleotides were cleaved and deprotected (C/D) at 45° C. for 20 hours. The sense strands were C/D from the CPG using ammonia hydroxide (28-30%, cold), whereas 3% DEA in ammonia hydroxide (28-30%, cold) was used for the antisense strands. C/D was determined complete by IP-RP LCMS when the resulting mass data confirmed the identity of sequence. Dependent on scale, the CPG was filtered via 0.45 um PVDF syringeless filter, 0.22 um PVDF Steriflip® vacuum filtration or 0.22 um PVDF Stericup® Quick release. The CPG was back washed/rinsed with either 30% ACN/RNAse free water or 30% EtOH/RNAse free water then filtered through the same filtering device and combined with the first filtrate. This was repeated twice. The material was then divided evenly into 50 mL falcon tubes to remove organics via Genevac™. After concentration, the crude oligonucleotides were diluted back to synthesized scale with RNAse free water and filtered either by 0.45 μm PVDF syringeless filter, 0.22 μm PVDF Steriflip® vacuum filtration or 0.22 μm PVDF Stericup® Quick release.

The crude oligonucleotides were purified via AKTA™ Pure purification system using either anion-exchange (AEX) or reverse phase (RP) a source 15Q-RP column. For AEX, an ES Industry Source™ 15Q column maintaining column temperature at 65° C. with MPA: 20 mM $NaH_2PO_4$, 15% ACN, pH 7.4 and MPB: 20 mM $NaH_2PO_4$, 1M NaBr, 15% ACN, pH 7.4. For RP, a Source™ 15Q-RP column with MPA: 50 mM NaOAc with 10% ACN and MPB: 50 mM NaOAc with 80% ACN. In all cases, fractions which contained a mass purity greater than 85% without impurities >5% where combined.

The purified oligonucleotides were desalted using 15 mL 3K MWCO centrifugal spin tubes at 3500×g for ~30 min. The oligonucleotides were rinsed with RNAse free water until the eluent conductivity reached <100 usemi/cm. After desalting was complete, 2-3 mL of RNAse free water was added then aspirated 10x, the retainment was transferred to a 50 mL falcon tube, this was repeated until complete transfer of oligo by measuring concentration of compound on filter via nanodrop. The final oligonucleotide was then nano filtered 2× via 15 mL 100K MWCO centrifugal spin tubes at 3500×g for 2 min. The final desalted oligonucleotides were analyzed for concentration (nano drop at A260), characterized by IP-RP LCMS for mass purity and UPLC for UV-purity.

For the preparation of duplexes, equimolar amounts of sense and antisense strand were combined and heated at 65° C. for 10 minutes then slowly cooled to ambient temperature over 40 minutes. Integrity of the duplex was confirmed by UPLC analysis and characterized by LCMS using IP-RP. All duplexes were nano filtered then endotoxin levels measured via Charles River Endosafe® Cartridge Device to give the final compounds of conjugated RNAi (Table 9). For in vivo analysis, the appropriate amount of duplex was lyophilized then reconstituted in 1×PBS for rodent studies and a CSF for non-human primate studies.

TABLE 7

| Oligonucleotide Synthesis Reagents<br>Reagents |
|---|
| Activator Solution (0.5M ETT in ACN) |
| Cap A (Acetic Anhydride, Pyridine in THF, 1:1:8) |
| Cap B (1-Methylimidazole in THF, 16:84) |
| Oxidation Solution (0.02M Iodine in THF/Pyridine/Water, 70:20:10) |
| Deblock Solution, 3% TCA in DCM (w/v) |
| Acetonitrile (Anhydrosolv, Water max. 10 ppm) |
| Xanthane Hydride (0.1M in Pyridine) |
| Diethylamine (20% in Acetonitrile) |

TABLE 8

| Phosphoramidites | | | | |
|---|---|---|---|---|
| Phosphoramidite | Abbreviation | Supplier | Catalog # | CAS |
| DMT-2'-F—A(Bz)—CE Phosphoamidite | fA | Hongene | PD1-001 | 136834-22-5 |
| DMT-2'-F—C(Ac)—CE Phosphoamidite | fC | Hongene | PD3-001 | 159414-99-0 |
| DMT-2'-F—G(iBu)—CE Phosphoamidite | fG | Hongene | PD2-002 | 144089-97-4 |
| DMT-2'-F—U—CE Phosphoamidite | fU | Hongene | PD5-001 | 146954-75-8 |
| DMT-2'-O—Me—A(Bz)—CE Phosphoamidite | mA | Hongene | PR1-001 | 110782-31-5 |

TABLE 8-continued

| Phosphoramidites | | | | |
|---|---|---|---|---|
| Phosphoramidite | Abbreviation | Supplier | Catalog # | CAS |
| DMT-2'-O—Me—C(Ac)—CE Phosphoamidite | mC | Hongene | PR3-001 | 199593-09-4 |
| DMT-2'-O—Me—G(iBu)—CE Phosphoamidite | mG | Hongene | PR2-002 | 150780-67-9 |
| DMT-2'-O—Me—U—CE Phosphoamidite | mU | Hongene | PR5-001 | 110764-79-9 |
| 5'bis(POM) vinyl phosphate-2'-Ome—U3'CE phosphoroamidite | POM-VPmU | Hongene | PR5-032 | BVPMUP23B2A1 |
| Reverse Abasic phosphoroamidite | iAb | Chemgenes | ANP-1422 | 401813-16-9 |
| Uhd | Uhd | Lilly | | |
| Chd | Chd | Lilly | | |
| Ahd | Ahd | Lilly | | |
| Ghd | Ghd | Lilly | | |

TABLE 9

| Conjugated MAPT RNAi Agents | | | | | |
|---|---|---|---|---|---|
| Conjugated MAPT RNAi Agent No. | RNAi Agent No. | Strand | LDP | MW Cal. (g/mol) | MW Obs. (g/mol) |
| 1 | 13 | S: SEQ ID NO: 25 | 1 | 7703.75 | 7704.3 |
| | | AS: SEQ ID NO: 26 | | 7810.25 | 7810.7 |
| 2 | 14 | S: SEQ ID NO: 27 | 1 | 7735.81 | 7736.4 |
| | | AS: SEQ ID NO: 28 | | 7655.08 | 7656.1 |
| 3 | 15 | S: SEQ ID NO: 29 | 1 | 7751.87 | 7752.7 |
| | | AS: SEQ ID NO: 30 | | 7577.99 | 7579.0 |
| 4 | 16 | S: SEQ ID NO: 31 | 1 | 7831.93 | 7832.4 |
| | | AS: SEQ ID NO: 32 | | 7497.93 | 7498.5 |
| 5 | 17 | S: SEQ ID NO: 33 | 1 | 7902.97 | 7903.1 |
| | | AS: SEQ ID NO: 34 | | 7534.99 | 7535.3 |
| 6 | 18 | S: SEQ ID NO: 35 | 1 | 7800.86 | 7801.2 |
| | | AS: SEQ ID NO: 36 | | 7582.06 | 7582.6 |
| 7 | 19 | S: SEQ ID NO: 37 | 1 | 7839.9 | 7840.1 |
| | | AS: SEQ ID NO: 38 | | 7558.03 | 7558.5 |
| 8 | 20 | S: SEQ ID NO: 39 | 1 | 7840.89 | 7841.5 |
| | | AS: SEQ ID NO: 40 | | 7518.99 | 7520.0 |
| 9 | 21 | S: SEQ ID NO: 41 | 1 | 7792.83 | 7793.2 |
| | | AS: SEQ ID NO: 42 | | 7596.08 | 7596.9 |
| 10 | 22 | S: SEQ ID NO: 43 | 1 | 7687.75 | 7688.7 |
| | | AS: SEQ ID NO: 44 | | 7755.21 | 7756.2 |
| 11 | 23 | S: SEQ ID NO: 45 | 1 | 7649.7 | 7650.3 |
| | | AS: SEQ ID NO: 46 | | 7779.24 | 7779.3 |
| 12 | 24 | S: SEQ ID NO: 47 | 1 | 7816.86 | 7817.6 |
| | | AS: SEQ ID NO: 48 | | 7597.07 | 7597.7 |
| / | 31 | S: SEQ ID NO: 63 | 4 | 7352.24 | 7352.5 |
| | | AS: SEQ ID NO: 40 | | 7518.87 | 7519.1 |
| / | 32 | S: SEQ ID NO: 64 | 4 | 7364.27 | 7364.7 |
| | | AS: SEQ ID NO: 65 | | 7506.84 | 7507.4 |
| / | 33 | S: SEQ ID NO: 66 | 5 | 7364.27 | 7364.0 |
| | | AS: SEQ ID NO: 65 | | 7506.84 | 7507.4 |
| / | 34 | S: SEQ ID NO: 67 | 4 | 7213.17 | 7213.7 |
| | | AS: SEQ ID NO: 65 | | 7506.84 | 7507.4 |
| / | 35 | S: SEQ ID NO: 68 | 4 | 7199.15 | 7199.6 |
| | | AS: SEQ ID NO: 65 | | 7506.84 | 7507.4 |
| / | 36 | S: SEQ ID NO: 69 | 4 | 7213.17 | 7213.5 |
| | | AS: SEQ ID NO: 65 | | 7506.84 | 7507.4 |
| / | 37 | S: SEQ ID NO: 64 | 4 | 7364.27 | 7364.8 |
| | | AS: SEQ ID NO: 70 | | 7482.76 | 7482.9 |
| / | 38 | S: SEQ ID NO: 71 | 4 | 7352.24 | 7352.7 |
| | | AS: SEQ ID NO: 65 | | 7506.84 | 7507.5 |
| / | 39 | S: SEQ ID NO: 64 | 4 | 7364.27 | 7364.8 |
| | | AS: SEQ ID NO: 72 | | 7506.84 | 7507.5 |
| / | 40 | S: SEQ ID NO: 64 | 4 | 7364.27 | 7365.0 |
| | | AS: SEQ ID NO: 73 | | 7506.84 | 7507.4 |
| / | 41 | S: SEQ ID NO: 64 | 4 | 7364.27 | 7364.9 |
| | | AS: SEQ ID NO: 74 | | 7530.91 | 7531.6 |

TABLE 9-continued

| Conjugated MAPT RNAi Agents | | | | | |
|---|---|---|---|---|---|
| Conjugated MAPT RNAi Agent No. | RNAi Agent No. | Strand | LDP | MW Cal. (g/mol) | MW Obs. (g/mol) |
| / | 42 | S: SEQ ID NO: 75 | 4 | 7340.20 | 7340.7 |
| | | AS: SEQ ID NO: 65 | | 7506.84 | 7507.5 |
| / | 43 | S: SEQ ID NO: 76 | 7 | 7364.27 | 7365.4 |
| | | AS: SEQ ID NO: 65 | | 7506.84 | 7508.0 |
| / | 44 | S: SEQ ID NO: 77 | 4 | 7364.27 | 7365.5 |
| | | AS: SEQ ID NO: 65 | | 7506.84 | 7507.9 |
| / | 45 | S: SEQ ID NO: 78 | 7 | 7364.27 | 7365.5 |
| | | AS: SEQ ID NO: 65 | | 7506.84 | 7508.1 |
| / | 46 | S: SEQ ID NO: 79 | 5 | 7364.27 | 7365.5 |
| | | AS: SEQ ID NO: 65 | | 7506.84 | 7508.1 |
| / | 47 | S: SEQ ID NO: 80 | 4 | 7364.27 | 7365.6 |
| | | AS: SEQ ID NO: 65 | | 7506.84 | 7508.0 |
| / | 48 | S: SEQ ID NO: 81 | 5 | 7376.31 | 7377.7 |
| | | AS: SEQ ID NO: 65 | | 7506.84 | 7508.1 |
| / | 49 | S: SEQ ID NO: 82 | 5 | 7376.31 | 7377.7 |
| | | AS: SEQ ID NO: 65 | | 7506.84 | 7508.2 |
| / | 50 | S: SEQ ID NO: 83 | 4 | 7364.27 | 7365.5 |
| | | AS: SEQ ID NO: 65 | | 7506.84 | 7508.2 |
| / | 51 | S: SEQ ID NO: 84 | 5 | 7364.27 | 7365.9 |
| | | AS: SEQ ID NO: 65 | | 7506.84 | 7508.2 |
| / | 52 | S: SEQ ID NO: 85 | 5 | 7364.27 | 7365.7 |
| | | AS: SEQ ID NO: 65 | | 7506.84 | 7508.0 |
| / | 53 | S: SEQ ID NO: 86 | 5 | 7364.27 | 7365.6 |
| | | AS: SEQ ID NO: 65 | | 7506.84 | 7508.0 |
| / | 54 | S: SEQ ID NO: 87 | 6 | 7245.13 | 7245.7 |
| | | AS: SEQ ID NO: 88 | | 7749.10 | 7749.5 |
| / | 55 | S: SEQ ID NO: 89 | 6 | 7078.03 | 7079.3 |
| | | AS: SEQ ID NO: 88 | | 7749.10 | 7750.7 |
| / | 56 | S: SEQ ID NO: 90 | 5 | 7037.08 | 7038.6 |
| | | AS: SEQ ID NO: 91 | | 7665.95 | 7667.5 |
| / | 57 | S: SEQ ID NO: 92 | 5 | 7204.18 | 7204.2 |
| | | AS: SEQ ID NO: 91 | | 7665.95 | 7665.9 |
| / | 58 | S: SEQ ID NO: 93 | 7 | 7364.27 | 7365.5 |
| | | AS: SEQ ID NO: 65 | | 7506.84 | 7508.1 |
| / | 59 | S: SEQ ID NO: 94 | 5 | 7364.27 | 7365.4 |
| | | AS: SEQ ID NO: 65 | | 7506.84 | 7508.1 |
| / | 60 | S: SEQ ID NO: 95 | 7 | 7364.27 | 7365.5 |
| | | AS: SEQ ID NO: 65 | | 7506.84 | 7508.1 |
| / | 61 | S: SEQ ID NO: 96 | 5 | 7376.31 | 7377.6 |
| | | AS: SEQ ID NO: 65 | | 7506.84 | 7508.1 |
| / | 62 | S: SEQ ID NO: 97 | 6 | 7364.27 | 7365.4 |
| | | AS: SEQ ID NO: 65 | | 7506.84 | 7508.1 |
| / | 63 | S: SEQ ID NO: 98 | 7 | 7364.27 | 7365.4 |
| | | AS: SEQ ID NO: 65 | | 7506.84 | 7508.1 |
| / | 64 | S: SEQ ID NO: 99 | 5 | 7364.27 | 7365.5 |
| | | AS: SEQ ID NO: 65 | | 7506.84 | 7508.1 |

TABLE 9-continued

Conjugated MAPT RNAi Agents

| Conjugated MAPT RNAi Agent No. | RNAi Agent No. | Strand | LDP | MW Cal. (g/mol) | MW Obs. (g/mol) |
|---|---|---|---|---|---|
| / | 65 | S: SEQ ID NO: 100 | 7 | 7364.27 | 7365.4 |
| | | AS: SEQ ID NO: 65 | | 7506.84 | 7508.1 |
| / | 66 | S: SEQ ID NO: 101 | 5 | 7316.22 | 7315.2 |
| | | AS: SEQ ID NO: 102 | | 7583.93 | 7582.9 |
| / | 67 | S: SEQ ID NO: 103 | 4 | 7363.29 | 7362.5 |
| | | AS: SEQ ID NO: 104 | | 7545.87 | 7544.8 |
| 13 | 68 | S: SEQ ID NO: 105 | 1 | 7840.74 | 7841.4 |
| | | AS: SEQ ID NO: 106 | | 7530.90 | 7532.0 |
| 14 | 69 | S: SEQ ID NO: 105 | 1 | 7840.74 | 7841.5 |
| | | AS: SEQ ID NO: 107 | | 7482.76 | 7483.6 |
| 15 | 70 | S: SEQ ID NO: 105 | 1 | 7840.74 | 7841.4 |
| | | AS: SEQ ID NO: 65 | | 7506.83 | 7507.5 |
| 16 | 71 | S: SEQ ID NO: 105 | 1 | 7840.74 | 7841.4 |
| | | AS: SEQ ID NO: 108 | | 7482.76 | 7483.6 |
| 17 | 72 | S: SEQ ID NO: 109 | 1 | 7689.64 | 7690.6 |
| | | AS: SEQ ID NO: 65 | | 7506.83 | 7507.6 |
| 18 | 73 | S: SEQ ID NO: 110 | 1 | 7856.74 | 7857.3 |
| | | AS: SEQ ID NO: 40 | | 7518.87 | 7520.0 |
| 19 | 74 | S: SEQ ID NO: 111 | 1 | 6442.86 | 6443.5 |
| | | AS: SEQ ID NO: 112 | | 7583.13 | 7584.1 |
| 20 | 75 | S: SEQ ID NO: 113 | 1 | 8433.06 | 8434.3 |
| | | AS: SEQ ID NO: 114 | | 7487.86 | 7488.9 |
| 21 | 76 | S: SEQ ID NO: 115 | 1 | 7852.78 | 7854.4 |
| | | AS: SEQ ID NO: 116 | | 7534.93 | 7535.9 |

"S" means the sense strand; "AS" means the antisense strand.

* LDP 1 is linked to the 3' of the sense strand.

** LDPs 4-7 are Uhd, Ahd, Chd, Ghd respectively linked to a nucleotide in the sense strand.

Example 3. Characterization of MAPT RNAi Agents

Selected MAPT RNAi agents were tested in vitro for MAPT inhibition in cultured cells, including SH-SY5Y cells, mouse cortical neurons (MCN) and/or human induced pluripotent stem cells (hiPSC). A subset of the selected MAPT RNAi agents were tested in vivo in transgenic human Tau mouse.

Materials and Methods

SH-SY5Y Cell Culture and RNAi Treatment and Analysis: SH-SY5Y cells (ATCC CRL-2266) were derived from the SK-N-SH neuroblastoma cell line (Ross, R. A., et al., 1983. J Natl Cancer Inst 71, 741-747). The base medium was composed of a 1:1 mixture of ATCC-formulated Eagle's Minimum Essential Medium, (Cat No. 30-2003), and F12 Medium. The complete growth medium was supplemented with 10% fetal bovine serum, 1× amino acids, 1× sodium bicarbonate, and 1× penicillin-streptomycin (Gibco) and cells incubated at 37° C. in a humidified atmosphere of 5% $CO_2$. On Day One, SH-SY5Y cells were plated in 96 well fibronectin coated tissue culture plates and allowed to attach overnight. On Day Two, complete media was removed and replaced with RNAi agent in serum free media. Cells were incubated with RNAi agent for 72 hours before analysis of gene expression. Analysis of changes in gene expression in RNAi treated SH-SY5Y cells was measured using Cells-to-CT Kits following the manufacturer's protocol (ThermoFisher A35377). Predesigned gene expression assays (supplied as 20× mixtures) were selected from Applied Bio-systems (Foster City, CA, USA). The efficiencies of these assays (ThermoFisher Hs00902194_m1 MAPT and ThermoFisher Hs99999905_m1 GAPDH) were characterized with a dilution series of cDNA. RT-QPCR was performed in MicroAmp Optical 384-well reaction plates using QuantStudio 7 Flex system. The delta-delta CT method of normalizing to the housekeeping gene GAPDH was used to determine relative amounts of gene expression. GraphPad Prism v9.0 was used to determine IC50 with a four parameter logistic fit.

Mouse Primary Cortical Neuron (MCN) Culture and RNAi Treatment and Analysis: Mouse primary cortical neurons were isolated from hTau C57BL6 transgenic mouse embryos expressing human tau transgene at E18. Cells were plated in poly-D-lysine coated 96-well plates at a density of 40 k cells/well and cultured in NbActiv1 (BrainBits, LLC) containing 1% Antibiotic/Antimycotic (Corning) for 7 days at 37° C. in a tissue culture incubator in a humidified chamber with 5% $CO_2$. On Day 7, half of the medium was removed from each well and 2× concentration of RNAi in culture media with 2% FBS was added for treatment as CRC and incubated with cells for additional 7, 14 or 21 days. Half media change was done every 7 days with fresh culture media. At the end of RNAi treatment, RT-qPCR was performed to quantify MAPT mRNA levels using TaqMan Fast Advanced Cell-to-CT kit. Specifically, cells were lysed, cDNA was generated on Mastercycler X50a (Eppendorf), and qPCR was carried out on QuantStudio 7 Flex Real-Time PCR System (Applied Biosystems). Human MAPT (ThermoFisher, Hs00902194_m1) gene expression levels were normalized by β-actin (ThermoFisher, Mm02619580_g1) using respective probes.

Human Induced Pluripotent Stem Cell-derived Neuron (hiPSC Neuron) Culture and RNAi Treatment and Analysis: Doxycycline-inducible Neurogenin2 (NGN2) human induced Pluripotent Stem Cells (hiPSC) were developed by Bioneer for Eli Lilly. The hiPSC were doxycycline-induced for three days (DIV3) to initiate neuronal differentiation and plated on 96-well PDL and laminin coated plates at 30 k/well and grown in Neuronal Differentiation Media (NDM) consisting of DMFM/F12 (Life Technologies 11330-057), Neurobasal media (Gibco 15240062), antibiotics, supplements, growth factors and doxycycline in an incubator (37° C./5% $CO_2$). Cells were half-fed every seven days, and on DIV21, RNAi agent was serially diluted in NDM, and cells were treated with RNAi by aspirating 75 μL and adding 75 μL of 2×RNAi concentration for a final of 1×RNAi according to dilutions. Cells were half-fed every seven days after treatment by removing half of media and adding back fresh NDM. Cell lysates were harvested at DIV35 (14 days later) or DIV42 (21 days later) and RT-qPCR was performed using TaqMan Fast Advanced Cells-to-CT Kit (ThermoFisher, A35377) and to determine mRNA knock down using MAPT probe as the gene of interest (ThermoFisher, Hs00902194_m1) and ACTb probe as the housekeeping gene (ThermoFisher, Hs99999903_m1).

In Vivo Characterization of Selected RNAi Agents in Transgenic Mice

The efficacy of selected RNAi agents was also studied in hTau transgenic mice expressing human MAPT RNA and lacking murine MAPT RNA (Andorfer et al., J Neurochem 2003, 86, 582-590). Six mice received intracerebroventricular (ICV) injection of 100 μg of the RNAi agent or PBS (phosphate buffered saline) and were sacrificed on Day 14 after the injection. MAPT mRNA expression in the brain was measured and analyzed by quantitative PCR (qPCR).

Results

Table 10A summarizes the in vitro and in vivo activities of selected MAPT RNAi agents. As shown in Table 10A, the tested RNAi agents knock down MAPT expression in vitro and in vivo.

TABLE 10A

In vitro and in vivo activities of selected MAPT RNAi agents

| MAPT RNAi Agent | SHSY5Y, 3 d IC50 (nM) | SHSY5Y, 3 d % KD (knockdown) of MAPT at 1 μM | Mouse ICV, 14 d % KD Brain stem | Mouse ICV, 14 d % KD Frontal Cortex |
|---|---|---|---|---|
| Conjugated RNAi Agent NO. 1 | 204.2 | 77.3 | 37.8 | 32.6 |
| Conjugated RNAi Agent NO. 2 | 231.7 | 74.8 | 36.3 | 36.0 |
| Conjugated RNAi Agent NO. 3 | 210.1 | 84.1 | 48.0 | 36.0 |
| Conjugated RNAi Agent NO. 4 | 11051 | 69.6 | 54.4 | 33.7 |
| Conjugated RNAi Agent NO. 5 | 60503 | 59.4 | 53.7 | NE* |
| Conjugated RNAi Agent NO. 6 | 275.6 | 66.7 | 47.9 | 26.6 |
| Conjugated RNAi Agent NO. 7 | 431.3 | 65.4 | 68.0 | 34.4 |
| Conjugated RNAi Agent NO. 8 | 286.2 | 72.9 | 65.9 | 46.1 |
| Conjugated RNAi Agent NO. 9 | 124.9 | 86 | 64.9 | 44.9 |
| Conjugated RNAi Agent NO. 10 | 516.1 | 70.7 | 52.1 | 22.4 |
| Conjugated RNAi Agent NO. 11 | 424.3 | 60.1 | 41.4 | 29.1 |
| Conjugated RNAi Agent No. 12 | 309.3 | 73.4 | 54.7 | 22.5 |

*NE means no observed effect.

Additional RNAi agents with different modification patterns were also tested. Table 10B shows the in vitro and in vivo activities of additional MAPT RNAi agents with different modification patterns.

TABLE 10B

In vitro and in vivo activities of additional MAPT RNAi agents with different modification patterns

| MAPT RNAi Agent No. or Conjugate No. | SHSY5Y, 3d IC50 (nM) | SHSY5Y, 3d % KD (knockdown) of MAPT at 1 μM | MCN, 7d IC50 (nM) | MCN, 7d % KD (knockdown) of SNCA at 1 uM | Mouse ICV, 14d % KD Brain stem | Mouse ICV, 14d % KD Frontal Cortex |
|---|---|---|---|---|---|---|
| 31 | ND* | ND | 7.24 | 85.6 | 67 | 58 |
| 32 | ND | ND | 5.648 | 86.8 | 66 | 57 |
| 33 | ND | ND | 12.38 | 83.2 | 48 | 45 |
| 34 | ND | ND | 28.32 | 79.3 | 48 | 52 |
| 35 | ND | ND | 64.94 | 73 | 56 | 56 |
| 36 | ND | ND | 16.01 | 83 | 71 | 70 |
| 37 | ND | ND | 9.5 | 86.5 | 68 | 68 |
| 38 | ND | ND | 9.01 | 87.8 | 72 | 46 |
| 39 | ND | ND | 8.58 | 88.5 | 78 | 61 |
| 40 | ND | ND | 7.3 | 88.3 | 79 | 59 |
| 41 | ND | ND | 57.6 | 84.3 | 61 | 38 |
| 42 | ND | ND | 16.16 | 86.1 | 69 | 45 |
| 43 | ND | ND | 71.82 | 89.4 | ND | ND |
| 44 | ND | ND | 64.11 | 87.3 | ND | ND |
| 45 | ND | ND | 89.05 | 85.5 | ND | ND |
| 46 | ND | ND | 25.06 | 87.2 | ND | ND |
| 47 | ND | ND | 68.9 | 86.3 | ND | ND |
| 48 | ND | ND | 45.8 | 59.9 | ND | ND |
| 49 | ND | ND | 333.7 | 84 | ND | ND |
| 50 | ND | ND | 15.02 | 81.6 | ND | ND |
| 51 | ND | ND | 72.72 | 81.4 | ND | ND |
| 52 | ND | ND | 99.63 | 86.2 | ND | ND |
| 53 | ND | ND | 157.9 | 88.1 | ND | ND |
| 54 | ND | ND | 2.01 | 88.3 | 81 | 54 |
| 55 | ND | ND | 10.33 | 82.5 | ND | ND |
| 56 | ND | ND | 25.05 | 77.8 | ND | ND |
| 57 | ND | ND | 1.12 | 87.2 | ND | ND |
| 58 | ND | ND | 22.8 | 87.2 | ND | ND |
| 59 | ND | ND | 18.1 | 88.4 | ND | ND |
| 60 | ND | ND | 20.6 | 89.7 | ND | ND |
| 61 | ND | ND | 99.1 | 66.8 | ND | ND |
| 62 | ND | ND | 23.2 | 89.0 | ND | ND |
| 63 | ND | ND | 36.7 | 89.3 | ND | ND |
| 64 | ND | ND | 39.5 | 90.6 | ND | ND |

TABLE 10B-continued

In vitro and in vivo activities of additional MAPT RNAi agents with different modification patterns

| MAPT RNAi Agent No. or Conjugate No. | SHSY5Y, 3d IC50 (nM) | SHSY5Y, 3d % KD (knockdown) of MAPT at 1 μM | MCN, 7d IC50 (nM) | MCN, 7d % KD (knockdown) of SNCA at 1 uM | Mouse ICV, 14d % KD Brain stem | Mouse ICV, 14d % KD Frontal Cortex |
|---|---|---|---|---|---|---|
| 65 | ND | ND | 76.0 | 89.1 | ND | ND |
| 66 | ND | ND | 22.3 | 87.9 | ND | ND |
| 67 | ND | ND | 39.2 | 84.5 | ND | ND |
| Conjugated RNAi Agent No. 13 | 384.56 | 71.02 | ND | ND | 68 | 42 |
| Conjugated RNAi Agent No. 14 | 320.53 | 79.53 | ND | ND | 67 | 41 |
| Conjugated RNAi Agent No. 15 | 630.91 | 64.37 | ND | ND | 68 | 48 |
| Conjugated RNAi Agent No. 16 | 232.42 | 77.03 | ND | ND | 71 | 41 |
| Conjugated RNAi Agent No. 17 | >1000 | 24.79 | ND | ND | 68 | 51 |
| Conjugated RNAi Agent No. 18 | >1000 | 54.08 | ND | ND | ND | ND |
| Conjugated RNAi Agent No. 19 | 625.79 | 60.91 | ND | ND | ND | ND |
| Conjugated RNAi Agent No. 20 | 406.76 | 66.69 | ND | ND | ND | ND |
| Conjugated RNAi Agent No. 21 | 683.09 | 58.54 | ND | ND | ND | ND |

*ND means not determined.

Example 4. Knockdown of MAPT mRNA in Cynomolgus Monkey Following a Single Administration of MAPT siRNA by Intrathecal Injection In vivo testing of MAPT RNAi agent No. 31 (sense strand of SEQ ID NO: 63 and antisense strand of SEQ ID NO: 40) in Cynomolgus monkey (*Macaca fascicularis*) was conducted to assess the efficacy of MAPT siRNA. In order to elucidate the efficacy of the siRNA in silencing the target gene; n=4/group cynomolgus monkeys were ported with indwelling catheters intrathecally in the lumbar region. The monkeys were infused with either aCSF or MAPT RNAi agent No. 31 (2.4 mg/ml in aCSF) over 15 minutes and were perfused 78 days later. Tissues collected at necropsy included spinal cord (lumbar) and brain (prefrontal cortex, motor cortex, parietal cortex, hippocampus and thalamus). qPCR and ELISA was performed to determine MAPT mRNA and protein knockdown respectively in the CNS regions. Tables 11 and 12 below show MAPT mRNA and protein knockdown observed in all the regions, 78 days after a single administration of the siRNA.

TABLE 11

Mean MAPT mRNA knockdown following a single intrathecal administration of MAPT RNAi agent No. 31.

| Route of administration | Dose [mg] | Lumbar Spinal Cord | Prefrontal Cortex | Motor Cortex | Parietal Cortex | Hippo-campus | Thalamus |
|---|---|---|---|---|---|---|---|
| Intrathecal-Catheter | 6 | 80% | 73% | 62% | 72% | 61% | 34% |

TABLE 12

Mean MAPT protein knockdown following a single intrathecal administration of MAPT RNAi agent No. 31.

| Route of administration | Dose [mg] | Lumbar Spinal Cord | Prefrontal Cortex | Motor Cortex | Parietal Cortex | Hippo-campus | Thalamus |
|---|---|---|---|---|---|---|---|
| Intrathecal-Catheter | 6 | 75% | 70% | 72% | 77% | 63% | 67% |

SEQUENCE LISTING

| SEQ ID NO | Sequence |
|---|---|
| 1 | ACAAGCUGACCUUCCGCGAGA |
| 2 | UCUCGCGGAAGGUCAGCUUGUGG |
| 3 | AGAUUGAAACCCACAAGCUGA |
| 4 | UCAGCUUGUGGGUUUCAAUCUUU |
| 5 | AAUAAAAAGAUUGAAACCCAA |
| 6 | UUGGGUUUCAAUCUUUUUAUUUC |
| 7 | GGAAAUAAAAAGAUUGAAACA |
| 8 | UGUUUCAAUCUUUUUAUUUCCUC |
| 9 | GGCGGAGGAAAUAAAAAGAUA |
| 10 | UAUCUUUUUAUUUCCUCCGCCAG |
| 11 | GAAGUAAAAUCUGAGAAGCUA |
| 12 | UAGCUUCUCAGAUUUUACUUCCA |
| 13 | GGAAGUAAAAUCUGAGAAGCA |
| 14 | UGCUUCUCAGAUUUUACUUCCAC |
| 15 | GUGGAAGUAAAAUCUGAGAAA |
| 16 | UUUCUCAGAUUUUACUUCCACCU |
| 17 | CCAGGUGGAAGUAAAAUCUGA |
| 18 | UCAGAUUUUACUUCCACCUGGCC |
| 19 | CAAGUCCAAGAUCGGCUCCAA |
| 20 | UUGGAGCCGAUCUUGGACUUGAC |
| 21 | UCUGGUGAACCUCCAAAAUCA |
| 22 | UGAUUUUGGAGGUUCACCAGAGC |
| 23 | CAGGUGGAAGUAAAAUCUGAA |
| 24 | UUCAGAUUUUACUUCCACCUGGC |
| 25 | mA*mC*mAmAmGmCfUmGfAfCfCmUmUmCmCmGmCmGmA*mG*mA |
| 26 | VPmU*fC*mUmCmGfCmGmGmAmAmGmGmUfCmAfGmCmUmUmGmU*mG*mG |
| 27 | mA*mG*mAmUmUmGfAmAfAfCfCmCmAmCmAmAmGmCmU*mG*mA |
| 28 | VPmU*fC*mAmGmCfUmUmGmUmGmGmGmUfUmUfCmAmAmUmCmU*mU*mU |
| 29 | mA*mA*mUmAmAmAfAmAfGfAfUmUmGmAmAmAmCmCmC*mA*mA |
| 30 | VPmU*fU*mGmGmGfUmUmUmCmAmAmUmCfUmUfUmUmUmAmUmU*mU*mC |
| 31 | mG*mG*mAmAmAmUfAmAfAfAfAmGmAmUmUmGmAmAmA*mC*mA |

-continued

SEQUENCE LISTING

| SEQ ID NO | Sequence |
|---|---|
| 32 | VPmU*fG*mUmUmUfCmAmAmUmCmUmUmUfUmUfAmUmUmUmCmC*mU*mC |
| 33 | mG*mG*mCmGmGmAfGmGfAfAfAmUmAmAmAmAmAmGmA*mU*mA |
| 34 | VPmU*fA*mUmCmUfUmUmUmUmAmUmUmUfCmCfUmCmCmGmCmC*mA*mG |
| 35 | mG*mA*mAmGmUmAfAmAfAfUfCmUmGmAmGmAmAmGmC*mU*mA |
| 36 | VPmU*fA*mGmCmUfUmCmUmCmAmGmAmUfUmUfUmAmCmUmUmC*mC*mA |
| 37 | mG*mG*mAmAmGmUfAmAfAfAfUmCmUmGmAmGmAmAmG*mC*mA |
| 38 | VPmU*fG*mCmUmUfCmUmCmAmGmAmUmUfUmUfAmCmUmUmCmC*mA*mC |
| 39 | mG*mU*mGmGmAmAfGmUfAfAfAmAmUmCmUmGmAmGmA*mA*mA |
| 40 | VPmU*fU*mUmCmUfCmAmGmAmUmUmUmUfAmCfUmUmCmCmAmC*mC*mU |
| 41 | mC*mC*mAmGmGmUfGmGfAfAfGmUmAmAmAmAmUmCmU*mG*mA |
| 42 | VPmU*fC*mAmGmAfUmUmUmUmAmCmUmUfCmCfAmCmCmUmGmG*mC*mC |
| 43 | mC*mA*mAmGmUmCfCmAfAfGfAmUmCmGmGmCmUmCmC*mA*mA |
| 44 | VPmU*fU*mGmGmAfGmCmCmGmAmUmCmUfUmGfGmAmCmUmUmG*mA*mC |
| 45 | mU*mC*mUmGmGmUfGmAfAfCfCmUmCmCmAmAmAmAmU*mC*mA |
| 46 | VPmU*fG*mAmUmUfUmUmGmGmAmGmGmUfUmCfAmCmCmAmGmA*mG*mC |
| 47 | mC*mA*mGmGmUmGfGmAfAfGfUmAmAmAmAmUmCmUmG*mA*mA |
| 48 | VPmU*fU*mCmAmGfAmUmUmUmUmAmCmUfUmCfCmAmCmCmUmG*mG*mC |
| 49 | GCAGTCACCG CCACCCACCA GCTCCGGCAC CAACAGCAGC GCCGCTGCCA CCGCCCACCT<br>TCTGCCGCCG CCACCACAGC CACCTTCTCC TCCTCCGCTG TCCTCTCCCG TCCTCGCCTC<br>TGTCGACTAT CAGGTGAACT TTGAACCAGG ATGGCTGAGC CCCGCCAGGA GTTCGAAGTG<br>ATGGAAGATC ACGCTGGGAC GTACGGGTTG GGGGACAGGA AAGATCAGGG GGGCTACACC<br>ATGCACCAAG ACCAAGAGGG TGACACGGAC GCTGGCCTGA AAGAATCTCC CCTGCAGACC<br>CCCACTGAGG ACGGATCTGA GGAACCGGGC TCTGAAACCT CTGATGCTAA GAGCACTCCA<br>ACAGCGGAAG ATGTGACAGC ACCCTTAGTG GATGAGGGAG CTCCCGGCAA GCAGGCTGCC<br>GCGCAGCCCC ACACGGAGAT CCCAGAAGGA ACCACAGCTG AAGAAGCAGG CATTGGAGAC<br>ACCCCCAGCC TGGAAGACGA AGCTGCTGGT CACGTGACCC AAGAGCCTGA AAGTGGTAAG<br>GTGGTCCAGG AAGGCTTCCT CCGAGAGCCA GGCCCCCCAG GTCTGAGCCA CCAGCTCATG<br>TCCGGCATGC CTGGGGCTCC CCTCCTGCCT GAGGGCCCCA GAGAGGCCAC ACGCCAACCT<br>TCGGGGACAG GACCTGAGGA CACAGAGGGC GGCCGCCACG CCCCTGAGCT GCTCAAGCAC<br>CAGCTTCTAG GAGACCTGCA CCAGGAGGGG CCGCCGCTGA AGGGGGCAGG GGGCAAAGAG<br>AGGCCGGGGA GCAAGGAGGA GGTGGATGAA GACCGCGACG TCGATGAGTC CTCCCCCCAA<br>GACTCCCCTC CCTCCAAGGC CTCCCCAGCC CAAGATGGGC GGCCTCCCCA GACAGCCGCC<br>AGAGAAGCCA CCAGCATCCC AGGCTTCCCA GCGGAGGGTG CCATCCCCCT CCCTGTGGAT<br>TTCCTCTCCA AAGTTTCCAC AGAGATCCCA GCCTCAGAGC CCGACGGGCC CAGTGTAGGG<br>CGGGCCAAAG GGCAGGATGC CCCCCTGGAG TTCACGTTTC ACGTGGAAAT CACACCCAAC<br>GTGCAGAAGG AGCAGGCGCA CTCGGAGGAG CATTTGGGAA GGGCTGCATT TCCAGGGGCC<br>CCTGGAGAGG GGCCAGAGGC CCGGGGCCCC TCTTTGGGAG AGGACACAAA AGAGGCTGAC<br>CTTCCAGAGC CCTCTGAAAA GCAGCCTGCT GCTGCTCCGC GGGGGAAGCC CGTCAGCCGG<br>GTCCCTCAAC TCAAAGCTCG CATGGTCAGT AAAAGCAAAG ACGGGACTGG AAGCGATGAC<br>AAAAAAGCCA AGACATCCAC ACGTTCCTCT GCTAAAACCT TGAAAAATAG GCCTTGCCTT<br>AGCCCCAAAC ACCCCACTCC TGGTAGCTCA GACCCTCTGA TCCAACCCTC CAGCCCTGCT<br>GTGTGCCCAG AGCCACCTTC CTCTCCTAAA TACGTCTCTT CTGTCACTTC CCGAACTGGC<br>AGTTCTGGAG CAAAGGAGAT GAAACTCAAG GGGGCTGATG GTAAAACGAA GATCGCCACA<br>CCGCGGGGAG CAGCCCCTCC AGGCCAGAAG GGCCAGGCCA ACGCCACCAG GATTCCAGGA<br>AAAACCCCGC CCGCTCCAAA GACACCACCC AGCTCTGCGA CTAAGCAAGT CCAGAGAAGA<br>CCACCCCCTG CAGGGCCCAG ATCTGAGAGA GGTGAACCTC CAAAATCAGG GGATCGCAGC<br>GGCTACAGCA GCCCCGGCTC CCCAGGCACT CCCGGCAGCC GCTCCGGCAC CCCGTCCCTT<br>CCAACCCCAC CCACCCGGGA GCCCAAGAAG GTGGCAGTGG TCCGTACTCC ACCCAAGTCG<br>CCGTCTTCCG CCAAGAGCCG CCTGCAGACA GCCCCCGTGC CCATGCCAGA CCTGAAGAAT<br>GTCAAGTCCA AGATCGGCTC CACTGAGAAC CTGAAGCACC AGCCGGGAGG CGGGAAGGTG<br>CAGATAATTA ATAAGAAGCT GGATCTTAGC AACGTCCAGT CCAAGTGTGG CTCAAAGGAT<br>AATATCAAAC ACGTCCCGGG AGGCGGCAGT GTGCAAATAG TCTACAAACC AGTTGACCTG<br>AGCAAGGTGA CCTCCAAGTG TGGCTCATTA GGCAACATCC ATCATAAACC AGGAGGTGGC<br>CAGGTGGAAG TAAAATCTGA GAAGCTTGAC TTCAAGGACA GAGTCCAGTC GAAGATTGGG<br>TCCCTGGACA ATATCACCCA CGTCCCTGGC GGAGGAAATA AAAAGATTGA AACCCACAAG<br>CTGACCTTCC GCGAGAACGC CAAAGCCAAG ACAGACCACG GGGCGGAGAT CGTGTACAAG<br>TCGCCAGTGG TGTCTGGGGA CACGTCTCCA CGGCATCTCA GCAATGTCTC CTCCACCGGC<br>AGCATCGACA TGGTAGACTC GCCCCAGCTC GCCACGCTAG CTGACGAGGT GTCTGCCTCC |

-continued

SEQUENCE LISTING

| SEQ ID NO | Sequence |
|---|---|
| | CTGGCCAAGC AGGGTTTGTG ATCAGGCCCC TGGGGCGGTC AATAATTGTG GAGAGGAGAG |
| | AATGAGAGAG TGTGGAAAAA AAAAGAATAA TGACCCGGCC CCCGCCCTCT GCCCCCAGCT |
| | GCTCCTCGCA GTTCGGTTAA TTGGTTAATC ACTTAACCTG CTTTTGTCAC TCGGCTTTGG |
| | CTCGGGACTT CAAAATCAGT GATGGGAGTA AGAGCAAATT TCATCTTTCC AAATTGATGG |
| | GTGGGCTAGT AATAAAATAT TTAAAAAAAA ACATTCAAAA ACATGGCCAC ATCCAACATT |
| | TCCTCAGGCA ATTCCTTTTG ATTCTTTTTT CTTCCCCCTC CATGTAGAAG AGGGAGAAGG |
| | AGAGGCTCTG AAAGCTGCTT CTGGGGGATT TCAAGGGACT GGGGGTGCCA ACCACCTCTG |
| | GCCCTGTTGT GGGGGTGTCA CAGAGGCAGT GGCAGCAACA AAGGATTTGA AACTTGGTGT |
| | GTTCGTGGAG CCACAGGCAG ACGATGTCAA CCTTGTGTGA GTGTGACGGG GGTTGGGGTG |
| | GGGCGGGAGG CCACGGGGGA GGCCGAGGCA GGGGCTGGGC AGAGGGGAGA GGAAGCACAA |
| | GAAGTGGGAG TGGGAGAGGA AGCCACGTGC TGGAGAGTAG ACATCCCCCT CCTTGCCGCT |
| | GGGAGAGCCA AGGCCTATGC CACCTGCAGC GTCTGAGCGG CCGCCTGTCC TTGGTGGCCG |
| | GGGGTGGGGG CCTGCTGTGG GTCAGTGTGC CACCCTCTGC AGGGCAGCCT GTGGGAGAAG |
| | GGACAGCGGG TAAAAAGAGA AGGCAAGCTG GCAGGAGGGT GGCACTTCGT GGATGACCTC |
| | CTTAGAAAAG ACTGACCTTG ATGTCTTGAG AGCGCTGGCC TCTTCCTCCC TCCCTGCAGG |
| | GTAGGGGGCC TGAGTTGAGG GGCTTCCCTC TGCTCCACAG AAACCCTGTT TTATTGAGTT |
| | CTGAAGGTTG GAACTGCTGC CATGATTTTG GCCACTTTGC AGACCTGGGA CTTTAGGGCT |
| | AACCAGTTCT CTTTGTAAGG ACTTGTGCCT CTTGGGAGAC GTCCACCCGT TTCCAAGCCT |
| | GGGCCACTGG CATCTCTGGA GTGTGTGGGG GTCTGGGAGG CAGGTCCCGA GCCCCCTGTC |
| | CTTCCCACGG CCACTGCAGT CACCCCGTCT GCGCCGCTGT GCTGTTGTCT GCCGTGAGAG |
| | CCCAATCACT GCCTATACCC CTCATCACAC GTCACAATGT CCCGAATTCC CAGCCTCACC |
| | ACCCCTTCTC AGTAATGACC CTGGTTGGTT GCAGGAGGTA CCTACTCCAT ACTGAGGGTG |
| | AAATTAAGGG AAGGCAAAGT CCAGGCACAA GAGTGGGACC CCAGCCTCTC ACTCTCAGTT |
| | CCACTCATCC AACTGGGACC CTCACCACGA ATCTCATGAT CTGATTCGGT TCCCTGTCTC |
| | CTCCTCCCGT CACAGATGTG AGCCAGGGCA CTGCTCAGCT GTGACCCTAG GTGTTTCTGC |
| | CTTGTTGACA TGGAGAGAGC CCTTTCCCCT GAGAAGGCCT GGCCCCTTCC TGTGCTGAGC |
| | CCACAGCAGC AGGCTGGGTG TCTTGGTTGT CAGTGGTGGC ACCAGGATGG AAGGGCAAGG |
| | CACCCAGGGC AGGCCCACAG TCCCGCTGTC CCCCACTTGC ACCCTAGCTT GTAGCTGCCA |
| | ACCTCCCAGA CAGCCCAGCC CGCTGCTCAG CTCCACATGC ATAGTATCAG CCCTCCACAC |
| | CCGACAAAGG GGAACACACC CCCTTGGAAA TGGTTCTTTT CCCCCAGTCC CAGGTGGAAG |
| | CCATGCTGTC TGTTCTGCTG GAGCAGCTGA ACATATACAT AGATGTTGCC CTGCCCTCCC |
| | CATCTGCACC CTGTTGAGTT GTAGTTGGAT TTGTCTGTTT ATGCTTGGAT TCACCAGAGT |
| | GACTATGATA GTGAAAAGAA AAAAAAAAAA AAAAAAGGAC GCATGTATCT TGAAATGCTT |
| | GTAAAGAGGT TTCTAACCCA CCCTCACGAG GTGTCTCTCA CCCCCACACT GGGACTCGTG |
| | TGGCCTGTGT GGTGCCACCC TGCTGGGGCC TCCCAAGTTT TGAAAGGCTT TCCTCAGCAC |
| | CTGGGACCCA ACAGAGACCA GCTTCTAGCA GCTAAGGAGG CCGTTCAGCT GTGACGAAGG |
| | CCTGAAGCAC AGGATTAGGA CTGAAGCGAT GATGTCCCCT TCCCTACTTC CCCTTGGGGC |
| | TCCCTGTGTC AGGGCACAGA CTAGGTCTTG TGGCTGGTCT GGCTTGCGGC GCGAGGATGG |
| | TTCTCTCTGG TCATAGCCCG AAGTCTCATG GCAGTCCCAA AGGAGGCTTA CAACTCCTGC |
| | ATCACAAGAA AAAGGAAGCC ACTGCCAGCT GGGGGGATCT GCAGCTCCCA GAAGCTCCGT |
| | GAGCCTCAGC CACCCCTCAG ACTGGGTTCC TCTCCAAGCT CGCCCTCTGG AGGGGCAGCG |
| | CAGCCTCCCA CCAAGGGCCC TGCGACCACA GCAGGGATTG GGATGAATTG CCTGTCCTGG |
| | ATCTGCTCTA GAGGCCCAAG CTGCCTGCCT GAGGAAGGAT GACTTGACAA GTCAGGAGAC |
| | ACTGTTCCCA AAGCCTTGAC CAGAGCACCT CAGCCCGCTG ACCTTGCACA AACTCCATCT |
| | GCTGCCATGA GAAAAGGGAA GCCGCCTTTG CAAAACATTG CTGCCTAAAG AAACTCAGCA |
| | GCCTCAGGCC CAATTCTGCC ACTTCTGGTT TGGGTACAGT TAAAGGCAAC CCTGAGGGAC |
| | TTGGCAGTAG AAATCCAGGG CCTCCCCTGG GGCTGGCAGC TTCGTGTGCA GCTAGAGCTT |
| | TACCTGAAAG GAAGTCTCTG GGCCCAGAAC TCTCCACCAA GAGCCTCCCT GCCGTTCGCT |
| | GAGTCCCAGC AATTCTCCTA AGTTGAAGGG ATCTGAGAAG GAGAAGGAAA TGTGGGGTAG |
| | ATTTGGTGGT GGTTAGAGAT ATGCCCCCCT CATTACTGCC AACAGTTTCG GCTGCATTTC |
| | TTCACGCACC TCGGTTCCTC TTCCTGAAGT TCTTGTGCCC TGCTCTTCAG CACCATGGGC |
| | CTTCTTATAC GGAAGGCTCT GGGATCTCCC CCTTGTGGGG CAGGCTCTTG GGGCCAGCCT |
| | AAGATCATGG TTTAGGGTGA TCAGTGCTGG CAGATAAATT GAAAAGGCAC GCTGGCTTGT |
| | GATCTTAAAT GAGGACAATC CCCCCAGGGC TGGGCACTCC TCCCCTCCCC TCACTTCTCC |
| | CACCTGCAGA GCCAGTGTCC TTGGGTGGGC TAGATAGGAT ATACTGTATG CCGGCTCCTT |
| | CAAGCTGCTG ACTCACTTTA TCAATAGTTC CATTTAAATT GACTTCAGTG GTGAGACTGT |
| | ATCCTGTTTG CTATTGCTTG TTGTGCTATG GGGGGAGGGG GGAGGAATGT GTAAGATAGT |
| | TAACATGGGC AAAGGGAGAT CTTGGGGTGC AGCACTTAAA CTGCCTCGTA ACCCTTTTCA |
| | TGATTTCAAC CACATTTGCT AGAGGGAGGG AGCAGCCACG GAGTTAGAGG CCCTTGGGGT |
| | TTCTCTTTTC CACTGACAGG CTTTCCCAGG CAGCTGGCTA GTTCATTCCC TCCCCAGCCA |
| | GGTGCAGGCG TAGGAATATG GACATCTGGT TGCTTTGGCC TGCTGCCCTC TTTCAGGGGT |
| | CCTAAGCCCA CAATCATGCC TCCCTAAGAC CTTGGCATCC TTCCCTCTAA GCCGTTGGCA |
| | CCTCTGTGCC ACCTCTCACA CTGGCTCCAG ACACACAGCC TGTGCTTTTG GAGCTGAGAT |
| | CACTCGCTTC ACCCTCCTCA TCTTTGTTCT CCAAGTAAAG CCACGAGGTC GGGGCGAGGG |
| | CAGAGGTGAT CACCTGCGTG TCCCATCTAC AGACCTGCAG CTTCATAAAA CTTCTGATTT |
| | CTCTTCAGCT TTGAAAAGGG TTACCCTGGG CACTGGCCTA GAGCCTCACC TCCTAATAGA |
| | CTTAGCCCCA TGAGTTTGCC ATGTTGAGCA GGACTATTTC TGGCACTTGC AAGTCCCATG |
| | ATTTCTTCGG TAATTCTGAG GGTGGGGGGA GGGACATGAA ATCATCTTAG CTTAGCTTTC |
| | TGTCTGTGAA TGTCTATATA GTGTATTGTG TGTTTTAACA AATGATTTAC ACTGACTGTT |
| | GCTGTAAAAG TGAATTTGGA AATAAAGTTA TTACTCTGAT TAAA |
| 50 | MAEPRQEFEV MEDHAGTYGL GDRKDQGGYT MHQDQEGDTD AGLKESPLQT PTEDGSEEPG |
| | SETSDAKSTP TAEDVTAPLV DEGAPGKQAA AQPHTEIPEG TTAEEAGIGD TPSLEDEAAG |
| | HVTQEPESGK VVQEGFLREP GPPGLSHQLM SGMPGAPLLP EGPREATRQP SGTGPEDTEG |
| | GRHAPELLKH QLLGDLHQEG PPLKGAGGKE RPGSKEEVDE DRDVDESSPQ DSPPSKASPA |

-continued

SEQUENCE LISTING

| SEQ ID NO | Sequence |
|---|---|
| | QDGRPPQTAA REATSIPGFP AEGAIPLPVD FLSKVSTEIP ASEPDGPSVG RAKGQDAPLE |
| | FTFHVEITPN VQKEQAHSEE HLGRAAFPGA PGEGPEARGP SLGEDTKEAD LPEPSEKQPA |
| | AAPRGKPVSR VPQLKARMVS KSKDGTGSDD KKAKTSTRSS AKTLKNRPCL SPKHPTPGSS |
| | DPLIQPSSPA VCPEPPSSPK YVSSVTSRTG SSGAKEMKLK GADGKTKIAT PRGAAPPGQK |
| | GQANATRIPA KTPPAPKTPP SSATKQVQRR PPPAGPRSER GEPPKSGDRS GYSSPGSPGT |
| | PGSRSRTPSL PTPPTREPKK VAVVRTPPKS PSSAKSRLQT APVPMPDLKN VKSKIGSTEN |
| | LKHQPGGGKV QIINKKLDLS NVQSKCGSKD NIKHVPGGGS VQIVYKPVDL SKVTSKCGSL |
| | GNIHHKPGGG QVEVKSEKLD FKDRVQSKIG SLDNITHVPG GGNKKIETHK LTFRENAKAK |
| | TDHGAEIVYK SPVVSGDTSP RHLSNVSSTG SIDMVDSPQL ATLADEVSAS LAKQGL |
| 51 | GCAGTCACCG CCACCCACCA GCTCCGGCAC CAACAGCAGC GCCGCTGCCA CCGCCCACCT |
| | TCTGCCGCCG CCACCACAGC CACCTTCTCC TCCTCCGCTG TCCTCTCCCG TCCTCGCCTC |
| | TGTCGACTAT CAGGTGAACT TTGAACCAGG ATGGCTGAGC CCCGCCAGGA GTTCGAAGTG |
| | ATGGAAGATC ACGCTGGGAC GTACGGGTTG GGGGACAGGA AAGATCAGGG GGGCTACACC |
| | ATGCACCAAG ACCAAGAGGG TGACACGGAC GCTGGCCTGA AAGAATCTCC CCTGCAGACC |
| | CCCACTGAGG ACGGATCTGA GGAACCGGGC TCTGAAACCT CTGATGCTAA GAGCACTCCA |
| | ACAGCGGAAG CTGAAGAAGC AGGCATTGGA GACACCCCCA GCCTGGAAGA CGAAGCTGCT |
| | GGTCACGTGA CCCAAGCTCG CATGGTCAGT AAAAGCAAAG ACGGGACTGG AAGCGATGAC |
| | AAAAAAGCCA AGGGGGCTGA TGGTAAAACG AAGATCGCCA CACCGCGGGG AGCAGCCCCT |
| | CCAGGCCAGA AGGGCCAGGC CAACGCCACC AGGATTCCAG CAAAAACCCC GCCCGCTCCA |
| | AAGACACCAC CCAGCTCTGG TGAACCTCCA AAATCAGGGG ATCGCAGCGG CTACAGCAGC |
| | CCCGGCTCCC CAGGCACTCC CGGCAGCCGC TCCCGCACCC CGTCCCTTCC AACCCCACCC |
| | ACCCGGGAGC CCAAGAAGGT GGCAGTGGTC CGTACTCCAC CCAAGTCGCC GTCTTCCGCC |
| | AAGAGCCGCC TGCAGACAGC CCCCGTGCCC ATGCCAGACC TGAAGAATGT CAAGTCCAAG |
| | ATCGGCTCCA CTGAGAACCT GAAGCACCAG CCGGGAGGCG GGAAGGTGCA GATAATTAAT |
| | AAGAAGCTGG ATCTTAGCAA CGTCCAGTCC AAGTGTGGCT CAAAGGATAA TATCAAACAC |
| | GTCCCGGGAG GCGGCAGTGT GCAAATAGTC TACAAACCAG TTGACCTGAG CAAGGTGACC |
| | TCCAAGTGTG GCTCATTAGG CAACATCCAT CATAAACCAG GAGGTGGCCA GGTGGAAGTA |
| | AAATCTGAGA AGCTTGACTT CAAGGACAGA GTCCAGTCGA AGATTGGGTC CCTGGACAAT |
| | ATCACCCACG TCCCTGGCGG AGGAAATAAA AAGATTGAAA CCCACAAGCT GACCTTCCGC |
| | GAGAACGCCA AAGCCAAGAC AGACCACGGG GCGGAGATCG TGTACAAGTC GCCAGTGGTG |
| | TCTGGGGACA CGTCTCCACG GCATCTCAGC AATGTCTCCT CCACCGGCAG CATCGACATG |
| | GTAGACTCGC CCCAGCTCGC CACGCTAGCT GACGAGGTGT CTGCCTCCCT GGCCAAGCAG |
| | GGTTTGTGAT CAGGCCCCTG GGGCGGTCAA TAATTGTGGA GAGGAGAGAA TGAGAGAGTG |
| | TGGAAAAAAA AAGAATAATG ACCCGGCCCC CGCCCTCTGC CCCCAGCTGC TCCTCGCAGT |
| | TCGGTTAATT GGTTAATCAC TTAACCTGCT TTTGTCACTC GGCTTTGGCT CGGGACTTCA |
| | AAATCAGTGA TGGGAGTAAG AGCAAATTTC ATCTTTCCAA ATTGATGGGT GGGCTAGTAA |
| | TAAAATATTT AAAAAAAAAC ATTCAAAAAC ATGGCCACAT CCAACATTTC CTCAGGCAAT |
| | TCCTTTTGAT TCTTTTTTCT TCCCCCTCCA TGTAGAAGAG GGAGAAGGAG AGGCTCTGAA |
| | AGCTGCTTCT GGGGGATTTC AAGGGACTGG GGGTGCCAAC CACCTCTGGC CCTGTTGTGG |
| | GGGTGTCACA GAGGCAGTGG CAGCAACAAA GGATTTGAAA CTTGGTGTGT TCGTGGAGCC |
| | ACAGGCAGAC GATGTCAACC TTGTGTGAGT GTGACGGGGG TTGGGGTGGG GCGGGAGGCC |
| | ACGGGGGAGG CCGAGGCAGG GGCTGGGCAG AGGGGAGAGG AAGCACAAGA AGTGGGAGTG |
| | GGAGAGGAAG CCACGTGCTG GAGAGTAGAC ATCCCCCTCC TTGCCGCTGG GAGAGCCAAG |
| | GCCTATGCCA CCTGCAGCGT CTGAGCGGCC GCCTGTCCTT GGTGGCCGGG GGTGGGGGCC |
| | TGCTGTGGGT CAGTGTGCCA CCCTCTGCAG GGCAGCCTGT GGGAGAAGGG ACAGCGGGTA |
| | AAAAGAGAAG GCAAGCTGGC AGGAGGGTGG CACTTCGTGG ATGACCTCCT TAGAAAAGAC |
| | TGACCTTGAT GTCTTGAGAG CGCTGGCCTC TTCCTCCCTC CCTGCAGGGT AGGGGGCCTG |
| | AGTTGAGGGG CTTCCCTCTG CTCCACAGAA ACCCTGTTTT ATTGAGTTCT GAAGGTTGGA |
| | ACTGCTGCCA TGATTTTGGC CACTTTGCAG ACCTGGGACT TTAGGGCTAA CCAGTTCTCT |
| | TTGTAAGGAC TTGTGCCTCT TGGGAGACGT CCACCCGTTT CCAAGCCTGG GCCACTGGCA |
| | TCTCTGGAGT GTGTGGGGGT CTGGGAGGCA GGTCCCGAGC CCCCTGTCCT TCCCACGGCC |
| | ACTGCAGTCA CCCCGTCTGC GCCGCTGTGC TGTTGTCTGC CGTGAGAGCC CAATCACTGC |
| | CTATACCCCT CATCACACGT CACAATGTCC CGAATTCCCA GCCTCACCAC CCCTTCTCAG |
| | TAATGACCCT GGTTGGTTGC AGGAGGTACC TACTCCATAC TGAGGGTGAA ATTAAGGGAA |
| | GGCAAAGTCC AGGCACAAGA GTGGGACCCC AGCCTCTCAC TCTCAGTTCC ACTCATCCAA |
| | CTGGGACCCT CACCACGAAT CTCATGATCT GATTCGGTTC CCTGTCTCCT CCTCCCGTCA |
| | CAGATGTGAG CCAGGGCACT GCTCAGCTGT GACCCTAGGT GTTTCTGCCT TGTTGACATG |
| | GAGAGAGCCC TTTCCCCTGA GAAGGCCTGG CCCCTTCCTG TGCTGAGCCC ACAGCAGCAG |
| | GCTGGGTGTC TTGGTTGTCA GTGGTGGCAC CAGGATGGAA GGGCAAGGCA CCCAGGGCAG |
| | GCCCACAGTC CCGCTGTCCC CCACTTGCAC CCTAGCTTGT AGCTGCCAAC CTCCCAGACA |
| | GCCCAGCCCG CTGCTCAGCT CCACATGCAT AGTATCAGCC CTCCACACCC GACAAAGGGG |
| | AACACACCCC CTTGGAAATG GTTCTTTTCC CCCAGTCCCA GCTGGAAGCC ATGCTGTCTG |
| | TTCTGCTGGA GCAGCTGAAC ATATACATAG ATGTTGCCCT GCCCTCCCCA TCTGCACCCT |
| | GTTGAGTTGT AGTTGGATTT GTCTGTTTAT GCTTGGATTC ACCAGAGTGA CTATGATAGT |
| | GAAAAGAAAA AAAAAAAAAA AAAAGGACGC ATGTATCTTG AAATGCTTGT AAAGAGGTTT |
| | CTAACCCACC CTCACGAGGT GTCTCTCACC CCCACACTGG GACTCGTGTG GCCTGTGTGG |
| | TGCCACCCTG CTGGGGCCTC CCAAGTTTTG AAAGGCTTTC CTCAGCACCT GGGACCCAAC |
| | AGAGACCAGC TTCTAGCAGC TAAGGAGGCC GTTCAGCTGT GACGAAGGCC TGAAGCACAG |
| | GATTAGGACT GAAGCGATGA TGTCCCCTTC CCTACTTCCC CTTGGGGCTC CCTGTGTCAG |
| | GGCACAGACT AGGTCTTGTG GCTGGTCTGG CTTGCGGCGC GAGGATGGTT CTCTCTGGTC |
| | ATAGCCCGAA GTCTCATGGC AGTCCCAAAG GAGGCTTACA ACTCCTGCAT CACAAGAAAA |
| | AGGAAGCCAC TGCCAGCTGG GGGGATCTGC AGCTCCCAGA AGCTCCGTGA GCCTCAGCCA |
| | CCCCTCAGAC TGGGTTCCTC TCCAAGCTCG CCCTCTGGAG GGCAGCGCA GCCTCCCACC |
| | AAGGGCCCTG CGACCACAGC AGGGATTGGG ATGAATTGCC TGTCCTGGAT CTGCTCTAGA |

-continued

SEQUENCE LISTING

| SEQ ID NO | Sequence |
|---|---|
| | GGCCCAAGCT GCCTGCCTGA GGAAGGATGA CTTGACAAGT CAGGAGACAC TGTTCCCAAA<br>GCCTTGACCA GAGCACCTCA GCCCGCTGAC CTTGCACAAA CTCCATCTGC TGCCATGAGA<br>AAAGGGAAGC CGCCTTTGCA AAACATTGCT GCCTAAAGAA ACTCAGCAGC CTCAGGCCCA<br>ATTCTGCCAC TTCTGGTTTG GGTACAGTTA AAGGCAACCC TGAGGGACTT GGCAGTAGAA<br>ATCCAGGGCC TCCCCTGGGG CTGGCAGCTT CGTGTGCAGC TAGAGCTTTA CCTGAAAGGA<br>AGTCTCTGGG CCCAGAACTC TCCACCAAGA GCCTCCCTGC CGTTCGCTGA GTCCCAGCAA<br>TTCTCCTAAG TTGAAGGGAT CTGAGAAGGA GAAGGAAATG TGGGGTAGAT TTGGTGGTGG<br>TTAGAGATAT GCCCCCCTCA TTACTGCCAA CAGTTTCGGC TGCATTTCTT CACGCACCTC<br>GGTTCCTCTT CCTGAAGTTC TTGTGCCCTG CTCTTCAGCA CCATGGGCCT TCTTATACGG<br>AAGGCTCTGG GATCTCCCCC TTGTGGGGCA GGCTCTTGGG GCCAGCCTAA GATCATGGTT<br>TAGGGTGATC AGTGCTGGCA GATAAATTGA AAAGGCACGC TGGCTTGTGA TCTTAAATGA<br>GGACAATCCC CCCAGGGCTG GGCACTCCTC CCCTCCCCTC ACTTCTCCCA CCTGCAGAGC<br>CAGTGTCCTT GGGTGGGCTA GATAGGATAT ACTGTATGCC GGCTCCTTCA AGCTGCTGAC<br>TCACTTTATC AATAGTTCCA TTTAAATTGA CTTCAGTGGT GAGACTGTAT CCTGTTTGCT<br>ATTGCTTGTT GTGCTATGGG GGGAGGGGGG AGGAATGTGT AAGATAGTTA ACATGGGCAA<br>AGGGAGATCT TGGGGTGCAG CACTTAAACT GCCTCGTAAC CCTTTTCATG ATTTCAACCA<br>CATTTGCTAG AGGGAGGGAG CAGCCACGGA GTTAGAGGCC CTTGGGGTTT CTCTTTTCCA<br>CTGACAGGCT TTCCCAGGCA GCTGGCTAGT TCATTCCCTC CCCAGCCAGG TGCAGGCGTA<br>GGAATATGGA CATCTGGTTG CTTTGGCCTG CTGCCCTCTT TCAGGGGTCC TAAGCCCACA<br>ATCATGCCTC CCTAAGACCT TGGCATCCTT CCCTCTAAGC CGTTGGCACC TCTGTGCCAC<br>CTCTCACACT GGCTCCAGAC ACACAGCCTG TGCTTTTGGA GCTGAGATCA CTCGCTTCAC<br>CCTCCTCATC TTTGTTCTCC AAGTAAAGCC ACGAGGTCGG GGCGAGGGCA GAGGTGATCA<br>CCTGCGTGTC CCATCTACAG ACCTGCAGCT TCATAAAACT TCTGATTTCT CTTCAGCTTT<br>GAAAAGGGTT ACCCTGGGCA CTGGCCTAGA GCCTCACCTC CTAATAGACT TAGCCCCATG<br>AGTTTGCCAT GTTGAGCAGG ACTATTTCTG GCACTTGCAA GTCCCATGAT TTCTTCGGTA<br>ATTCTGAGGG TGGGGGGAGG GACATGAAAT CATCTTAGCT TAGCTTTCTG TCTGTGAATG<br>TCTATATAGT GTATTGTGTG TTTTAACAAA TGATTTACAC TGACTGTTGC TGTAAAAGTG<br>AATTTGGAAA TAAAGTTATT ACTCTGATTA AA |
| 52 | MAEPRQEFEV MEDHAGTYGL GDRKDQGGYT MHQDQEGDTD AGLKESPLQT PTEDGSEEPG<br>SETSDAKSTP TAEAEEAGIG DTPSLEDEAA GHVTQARMVS KSKDGTGSDD KKAKGADGKT<br>KIATPRGAAP PGQKGQANAT RIPAKTPPAP KTPPSSGEPP KSGDRSGYSS PGSPGTPGSR<br>SRTPSLPTPP TREPKKVAVV RTPPKSPSSA KSRLQTAPVP MPDLKNVKSK IGSTENLKHQ<br>PGGGKVQIIN KKLDLSNVQS KCGSKDNIKH VPGGGSVQIV YKPVDLSKVT SKCGSLGNIH<br>HKPGGGQVEV KSEKLDFKDR VQSKIGSLDN ITHVPGGGNK KIETHKLTFR ENAKAKTDHG<br>AEIVYKSPVV SGDTSPRHLS NVSSTGSIDM VDSPQLATLA DEVSASLAKQ GL |
| 53 | GCAGTCACCG CCACCCACCA GCTCCGGCAC CAACAGCAGC GCCGCTGCCA CCGCCCACCT<br>TCTGCCGCCG CCACCACAGC CACCTTCTCC TCCTCCGCTG TCCTCTCCCG TCCTCGCCTC<br>TGTCGACTAT CAGGTGAACT TTGAACCAGG ATGGCTGAGC CCCGCCAGGA GTTCGAAGTG<br>ATGGAAGATC ACGCTGGGAC GTACGGGTTG GGGGACAGGA AAGATCAGGG GGGCTACACC<br>ATGCACCAAG ACCAAGAGGG TGACACGGAC GCTGGCCTGA AAGCTGAAGA AGCAGGCATT<br>GGAGACACCC CCAGCCTGGA AGACGAAGCT GCTGGTCACG TGACCCAAGC TCGCATGGTC<br>AGTAAAAGCA AAGACGGGAC TGGAAGCGAT GACAAAAAAG CCAAGGGGGC TGATGGTAAA<br>ACGAAGATCG CCACACCGCG GGGAGCAGCC CCTCCAGGCC AGAAGGGCCA GGCCAACGCC<br>ACCAGGATTC CAGCAAAAAC CCCGCCCGCT CCAAAGACAC CACCCAGCTC TGGTGAACCT<br>CCAAAATCAG GGGATCGCAG CGGCTACAGC AGCCCCGGCT CCCCAGGCAC TCCCGGCAGC<br>CGCTCCCGCA CCCCGTCCCT TCCAACCCCA CCCACCCGGG AGCCCAAGAA GGTGGCAGTG<br>GTCCGTACTC CACCCAAGTC GCCGTCTTCC GCCAAGAGCC GCCTGCAGAC AGCCCCCGTG<br>CCCATGCCAG ACCTGAAGAA TGTCAAGTCC AAGATCGGCT CCACTGAGAA CCTGAAGCAC<br>CAGCCGGGAG GCGGGAAGGT GCAAATAGTC TACAAACCAG TTGACCTGAG CAAGGTGACC<br>TCCAAGTGTG GCTCATTAGG CAACATCCAT CATAAACCAG GAGGTGGCCA GGTGGAAGTA<br>AAATCTGAGA AGCTTGACTT CAAGGACAGA GTCCAGTCGA AGATTGGGTC CCTGGACAAT<br>ATCACCCACG TCCCTGGCGG AGGAAATAAA AAGATTGAAA CCCACAAGCT GACCTTCCGC<br>GAGAACGCCA AAGCCAAGAC AGACCACGGG GCGGAGATCG TGTACAAGTC GCCAGTGGTG<br>TCTGGGGACA CGTCTCCACG GCATCTCAGC AATGTCTCCT CCACCGGCAG CATCGACATG<br>GTAGACTCGC CCCAGCTCGC CACGCTAGCT GACGAGGTGT CTGCCTCCCT GGCCAAGCAG<br>GGTTTGTGAT CAGGCCCCTG GGGCGGTCAA TAATTGTGGA GAGGAGAGAA TGAGAGAGTG<br>TGGAAAAAAA AAGAATAATG ACCCGGCCCC CGCCCTCTGC CCCCAGCTGC TCCTCGCAGT<br>TCGGTTAATT GGTTAATCAC TTAACCTGCT TTTGTCACTC GGCTTTGGCT CGGGACTTCA<br>AAATCAGTGA TGGGAGTAAG AGCAAATTTC ATCTTTCCAA ATTGATGGGT GGGCTAGTAA<br>TAAAATATTT AAAAAAAAAC ATTCAAAAAC ATGGCCACAT CCAACATTTC CTCAGGCAAT<br>TCCTTTTGAT TCTTTTTTCT TCCCCCTCCA TGTAGAAGAG GGAGAAGGAG AGGCTCTGAA<br>AGCTGCTTCT GGGGGATTTC AAGGGACTGG GGGTGCCAAC CACCTCTGGC CCTGTTGTGG<br>GGGTGTCACA GAGGCAGTGG CAGCAACAAA GGATTTGAAA CTTGGTGTGT TCGTGGAGCC<br>ACAGGCAGAC GATGTCAACC TTGTGTGAGT GTGACGGGGG TTGGGGTGGG GCGGGAGGCC<br>ACGGGGGAGG CCGAGGCAGG GGCTGGGCAG AGGGGAGAGG AAGCACAAGA AGTGGGAGTG<br>GGAGAGGAAG CCACGTGCTG GAGAGTAGAC ATCCCCCTCC TTGCCGCTGG GAGAGCCAAG<br>GCCTATGCCA CCTGCAGCGT CTGAGCGGCC GCCTGTCCTT GGTGGCCGGG GGTGGGGGCC<br>TGCTGTGGGT CAGTGTGCCA CCCTCTGCAG GGCAGCCTGT GGGAGAAGGG ACAGCGGGTA<br>AAAAGAGAAG GCAAGCTGGC AGGAGGGTGG CACTTCGTGG ATGACCTCCT TAGAAAAGAC<br>TGACCTTGAT GTCTTGAGAG CGCTGGCCTC TTCCTCCCTC CCTGCAGGGT AGGGGGCCTG<br>AGTTGAGGGG CTTCCCTCTG CTCCACAGAA ACCCTGTTTT ATTGAGTTCT GAAGGTTGGA<br>ACTGCTGCCA TGATTTTGGC CACTTTGCAG ACCTGGGACT TTAGGGCTAA CCAGTTCTCT<br>TTGTAAGGAC TTGTGCCTCT TGGGAGACGT CCACCCGTTT CCAAGCCTGG GCCACTGGCA |

-continued

SEQUENCE LISTING

| SEQ ID NO | Sequence |
|---|---|
| | TCTCTGGAGT GTGTGGGGGT CTGGGAGGCA GGTCCCGAGC CCCCTGTCCT TCCCACGGCC<br>ACTGCAGTCA CCCCGTCTGC GCCGCTGTGC TGTTGTCTGC CGTGAGAGCC CAATCACTGC<br>CTATACCCCT CATCACACGT CACAATGTCC CGAATTCCCA GCCTCACCAC CCCTTCTCAG<br>TAATGACCCT GGTTGGTTGC AGGAGGTACC TACTCCATAC TGAGGGTGAA ATTAAGGGAA<br>GGCAAAGTCC AGGCACAAGA GTGGGACCCC AGCCTCTCAC TCTCAGTTCC ACTCATCCAA<br>CTGGGACCCT CACCACGAAT CTCATGATCT GATTCGGTTC CCTGTCTCCT CCTCCCGTCA<br>CAGATGTGAG CCAGGGCACT GCTCAGCTGT GACCCTAGGT GTTTCTGCCT TGTTGACATG<br>GAGAGAGCCC TTTCCCCTGA GAAGGCCTGG CCCCTTCCTG TGCTGAGCCC ACAGCAGCAG<br>GCTGGGTGTC TTGGTTGTCA GTGGTGGCAC CAGGATGGAA GGGCAAGGCA CCCAGGGCAG<br>GCCCACAGTC CCGCTGTCCC CCACTTGCAC CCTAGCTTGT AGCTGCCAAC CTCCCAGACA<br>GCCCAGCCCG CTGCTCAGCT CCACATGCAT AGTATCAGCC CTCCACACCC GACAAAGGGG<br>AACACACCCC CTTGGAAATG GTTCTTTTCC CCCAGTCCCA GCTGGAAGCC ATGCTGTCTG<br>TTCTGCTGGA GCAGCTGAAC ATATACATAG ATGTTGCCCT GCCCTCCCCA TCTGCACCCT<br>GTTGAGTTGT AGTTGGATTT GTCTGTTTAT GCTTGGATTC ACCAGAGTGA CTATGATAGT<br>GAAAAGAAAA AAAAAAAAAA AAAAGGACGC ATGTATCTTG AAATGCTTGT AAAGAGGTTT<br>CTAACCCACC CTCACGAGGT GTCTCTCACC CCCACACTGG GACTCGTGTG GCCTGTGTGG<br>TGCCACCCTG CTGGGGCCTC CCAAGTTTTG AAAGGCTTTC CTCAGCACCT GGGACCCAAC<br>AGAGACCAGC TTCTAGCAGC TAAGGAGGCC GTTCAGCTGT GACGAAGGCC TGAAGCACAG<br>GATTAGGACT GAAGCGATGA TGTCCCCTTC CCTACTTCCC CTTGGGGCTC CCTGTGTCAG<br>GGCACAGACT AGGTCTTGTG GCTGGTCTGG CTTGCGGCGC GAGGATGGTT CTCTCTGGTC<br>ATAGCCCGAA GTCTCATGGC AGTCCCAAAG GAGGCTTACA ACTCCTGCAT CACAAGAAAA<br>AGGAAGCCAC TGCCAGCTGG GGGGATCTGC AGCTCCCAGA AGCTCCGTGA GCCTCAGCCA<br>CCCCTCAGAC TGGGTTCCTC TCCAAGCTCG CCCTCTGGAG GGGCAGCGCA GCCTCCCACC<br>AAGGGCCCTG CGACCACAGC AGGGATTGGG ATGAATTGCC TGTCCTGGAT CTGCTCTAGA<br>GGCCCAAGCT GCCTGCCTGA GGAAGGATGA CTTGACAAGT CAGGAGACAC TGTTCCCAAA<br>GCCTTGACCA GAGCACCTCA GCCCGCTGAC CTTGCACAAA CTCCATCTGC TGCCATGAGA<br>AAAGGGAAGC CGCCTTTGCA AAACATTGCT GCCTAAAGAA ACTCAGCAGC CTCAGGCCCA<br>ATTCTGCCAC TTCTGGTTTG GGTACAGTTA AAGGCAACCC TGAGGGACTT GGCAGTAGAA<br>ATCCAGGGCC TCCCCTGGGG CTGGCAGCTT CGTGTGCAGC TAGAGCTTTA CCTGAAAGGA<br>AGTCTCTGGG CCCAGAACTC TCCACCAAGA GCCTCCCTGC CGTTCGCTGA GTCCCAGCAA<br>TTCTCCTAAG TTGAAGGGAT CTGAGAAGGA GAAGGAAATG TGGGGTAGAT TTGGTGGTGG<br>TTAGAGATAT GCCCCCCTCA TTACTGCCAA CAGTTTCGGC TGCATTTCTT CACGCACCTC<br>GGTTCCTCTT CCTGAAGTTC TTGTGCCCTG CTCTTCAGCA CCATGGGCCT TCTTATACGG<br>AAGGCTCTGG GATCTCCCCC TTGTGGGGCA GGCTCTTGGG GCCAGCCTAA GATCATGGTT<br>TAGGGTGATC AGTGCTGGCA GATAAATTGA AAAGGCACGC TGGCTTGTGA TCTTAAATGA<br>GGACAATCCC CCCAGGGCTG GGCACTCCTC CCCTCCCCTC ACTTCTCCCA CCTGCAGAGC<br>CAGTGTCCTT GGGTGGGCTA GATAGGATAT ACTGTATGCC GGCTCCTTCA AGCTGCTGAC<br>TCACTTTATC AATAGTTCCA TTTAAATTGA CTTCAGTGGT GAGACTGTAT CCTGTTTGCT<br>ATTGCTTGTT GTGCTATGGG GGGAGGGGGG AGGAATGTGT AAGATAGTTA ACATGGGCAA<br>AGGGAGATCT TGGGGTGCAG CACTTAAACT GCCTCGTAAC CCTTTTCATG ATTTCAACCA<br>CATTTGCTAG AGGGAGGGAG CAGCCACGGA GTTAGAGGCC CTTGGGGTTT CTCTTTTCCA<br>CTGACAGGCT TTCCCAGGCA GCTGGCTAGT TCATTCCCTC CCCAGCCAGG TGCAGGCGTA<br>GGAATATGGA CATCTGGTTG CTTTGGCCTG CTGCCCTCTT TCAGGGGTCC TAAGCCCACA<br>ATCATGCCTC CCTAAGACCT TGGCATCCTT CCCTCTAAGC CGTTGGCACC TCTGTGCCAC<br>CTCTCACACT GGCTCCAGAC ACACAGCCTG TGCTTTTGGA GCTGAGATCA CTCGCTTCAC<br>CCTCCTCATC TTTGTTCTCC AAGTAAAGCC ACGAGGTCGG GGCGAGGGCA GAGGTGATCA<br>CCTGCGTGTC CCATCTACAG ACCTGCAGCT TCATAAAACT TCTGATTTCT CTTCAGCTTT<br>GAAAAGGGTT ACCCTGGGCA CTGGCCTAGA GCCTCACCTC CTAATAGACT TAGCCCCATG<br>AGTTTGCCAT GTTGAGCAGG ACTATTTCTG GCACTTGCAA GTCCCATGAT TTCTTCGGTA<br>ATTCTGAGGG TGGGGGGAGG GACATGAAAT CATCTTAGCT TAGCTTTCTG TCTGTGAATG<br>TCTATATAGT GTATTGTGTG TTTTAACAAA TGATTTACAC TGACTGTTGC TGTAAAAGTG<br>AATTTGGAAA TAAAGTTATT ACTCTGATTA AA |
| 54 | MAEPRQEFEV MEDHAGTYGL GDRKDQGGYT MHQDQEGDTD AGLKAEEAGI GDTPSLEDEA<br>AGHVTQARMV SKSKDGTGSD DKKAKGADGK TKIATPRGAA PPGQKGQANA TRIPAKTPPA<br>PKTPPSSGEP PKSGDRSGYS SPGSPGTPGS RSRTPSLPTP PTREPKKVAV VRTPPKSPSS<br>AKSRLQTAPV PMPDLKNVKS KIGSTENLKH QPGGGKVQIV YKPVDLSKVT SKCGSLGNIH<br>HKPGGGQVEV KSEKLDFKDR VQSKIGSLDN ITHVPGGGNK KIETHKLTFR ENAKAKTDHG<br>AEIVYKSPVV SGDTSPRHLS NVSSTGSIDM VDSPQLATLA DEVSASLAKQ GL |
| 55 | GUGGAAGUA(n)AAUCUGAGAAA, wherein (n) indicates an abasic moiety. |
| 56 | GUGGAAGU(n)AAAUCUGAGAAA, wherein (n) indicates an abasic moiety. |
| 57 | CCAAGUGUGGCUCAUUAGGCA |
| 58 | UGCCUAAUGAGCCACACUUGGAG |
| 59 | CCAAGUGU(n)GCUCAUUAGGCA, wherein (n) indicates an abasic moiety. |
| 60 | UGCAAAUA(n)UCUACAAACCAA, wherein (n) indicates an abasic moiety. |
| 61 | UUGGUUUGUAGACUAUUUGCACC |
| 62 | UGCAAAUAGUCUACAAACCAA |

-continued

SEQUENCE LISTING

| SEQ ID NO | Sequence |
|---|---|
| 63 | mG*mU*mGmGmAmAfGmUfAfAfAmA(Uhd)mCmUmGmAmGmA*mA*mA |
| 64 | mG*mU*mGmGmAmAmGmUfAfAfAmA(Uhd)mCmUmGmAmGmA*mA*mA |
| 65 | VPmU*fU*mUmCfUmCmAfGmAmUmUmUfAmCfUmUmCmCmAmC*mC*mU |
| 66 | mG*mU*mGmGmAmAmGmUfAfAfA(Ahd)mUmCmUmGmAmGmA*mA*mA |
| 67 | mG*mU*mGmGmAmAmGmUfA(n)fAmA(Uhd)mCmUmGmAmGmA*mA*mA |
| 68 | mG*mU*mGmGmAmAGmUfA(n)fAmA(Uhd)mCmUmGmAmGmA*mA*mA |
| 69 | mG*mU*mGmGmAmAmGmU(n)fAfAmA(Uhd)mCmUmGmAmGmA*mA*mA |
| 70 | VPmU*fU*mUmCmUfCmAmGmAfUmUmUfAmCfUmUfCmCfAmC*mC*mU |
| 71 | mG*mU*mGmGmAmAmGmUfAfAfAmA(Uhd)mCfUmGmAmGmA*mA*mA |
| 72 | VPmU*fU*mUmCfUmCfAmGmAmUmUmUfAmCfUmUmCmCmAmC*mC*mU |
| 73 | VPmU*fU*fUmCmUmCfAmGmAmUmUmUfAmCfUmUmCmCmAmC*mC*mU |
| 74 | VPmU*fU*mUmCfUmCmAmGmAmUmUmUfAmCmUmUmCmCmAmC*mC*mU |
| 75 | mG*mU*mGmGmAmAmGmUfAfAfA(Uhd)fUmCfUmGmAmGmA*mA*mA |
| 76 | (Ghd)*mU*mGmGmAmAmGmUfAfAfAmAmUmCmUmGmAmGmA*mA*mA |
| 77 | mG*(Uhd)*mGmGmAmAmGmUfAfAfAmAmUmCmUmGmAmGmA*mA*mA |
| 78 | mG*mU*(Ghd)mGmAmAmGmUfAfAfAmAmUmCmUmGmAmGmA*mA*mA |
| 79 | mG*mU*mGmGmA(Ahd)mGmUfAfAfAmAmUmCmUmGmAmGmA*mA*mA |
| 80 | mG*mU*mGmGmAmAmG(Uhd)fAfAfAmAmUmCmUmGmAmGmA*mA*mA |
| 81 | mG*mU*mGmGmAmAmGmU(Ahd)fAfAmAmUmCmUmGmAmGmA*mA*mA |
| 82 | mG*mU*mGmGmAmAmGmUfA(Ahd)fAmAmUmCmUmGmAmGmA*mA*mA |
| 83 | mG*mU*mGmGmAmAmGmUfAfAfAmAmUmC(Uhd)mGmAmGmA*mA*mA |
| 84 | mG*mU*mGmGmAmAmGmUfAfAfAmAmUmCmUmGmAmG(Ahd)*mA*mA |
| 85 | mG*mU*mGmGmAmAmGmUfAfAfAmAmUmCmUmGmAmGmA*(Ahd)*mA |
| 86 | mG*mU*mGmGmAmAmGmUfAfAfAmAmUmCmUmGmAmGmA*mA*(Ahd) |
| 87 | mC*mC*mAmAmGmUmGmUfGfGfCmU(Chd)mAmUmUmAmGmG*mC*mA |
| 88 | VPmU*fG*mCmCfUmAmAfUmGmAmGmCmCfAmCfAmCmUmUmGmG*mA*mG |
| 89 | mC*mC*mAmAmGmUmGmU(n)fGfCmU(Chd)mAmUmUmAmGmG*mC*mA |
| 90 | mU*mG*mCmAmAmAmUmA(n)fUfCmU(Ahd)mCmAmAmAmCmC*mA*mA |
| 91 | VPmU*fU*mGmGfUmUmUfGmUmAmGmAmCfUmAfUmUmUmGmCmA*mC*mC |
| 92 | mU*mG*mCmAmAmAmUmAfGfUfCmU(Ahd)mCmAmAmAmCmC*mA*mA |
| 93 | mG*mU*mG(Ghd)mAmAmGmUfAfAfAmAmUmCmUmGmAmGmA*mA*mA |
| 94 | mG*mU*mGmG(Ahd)mAmGmUfAfAfAmAmUmCmUmGmAmGmA*mA*mA |
| 95 | mG*mU*mGmGmAmA(Ghd)mUfAfAfAmAmUmCmUmGmAmGmA*mA*mA |
| 96 | mG*mU*mGmGmAmAmGmUfAfA(Ahd)mAmUmCmUmGmAmGmA*mA*mA |
| 97 | mG*mU*mGmGmAmAmGmUfAfAfAmAmU(Chd)mUmGmAmGmA*mA*mA |
| 98 | mG*mU*mGmGmAmAmGmUfAfAfAmAmUmCmU(Ghd)mAmGmA*mA*mA |
| 99 | mG*mU*mGmGmAmAmGmUfAfAfAmAmUmCmUmG(Ahd)mGmA*mA*mA |

-continued

SEQUENCE LISTING

| SEQ ID NO | Sequence |
|---|---|
| 100 | mG*mU*mGmGmAmAmGmUfAfAfAmAmUmCmUmGmA(Ghd)mA*mA*mA |
| 101 | mC*mC*mAmGmGmUmGmGfAfAfGmU(Ahd)mAmAmAmUmCmU*mG*mA |
| 102 | VPmU*fC*mAmGfAmUmUfUmUmAmCmUmUfCmCfAmCmCmUmGmG*mC*mC |
| 103 | mG*mG*mAmAmGmUmAmAfAfAfUmC(Uhd)mGmAmGmAmAmG*mC*mA |
| 104 | VPmU*fG*mCmUfUmCmUfCmAmGmAmUmUfUmUfAmCmUmUmCmC*mA*mC |
| 105 | mG*mU*mGmGmAmAfGmUfAfAfAmAmUmCmUmGmAmGmAmA*mA* |
| 106 | VPmU*fU*mUmCmUmCmAmGmAmUmUmUmUfAmCfUmUmCmCmAmC*mC*mU |
| 107 | VPmU*fU*mUfCmUfCfAmGfAmUmUmUmUfAmCfUmUmCmCmAmC*mC*mU |
| 108 | VPmU*fU*mUmCfUfCfAfGmAmUmUmUmUfAmCfUmUmCmCmAmC*mC*mU |
| 109 | mG*mU*mGmGmAmAfGmUfA(n)fAmAmUmCmUmGmAmGmAmA*mA* |
| 110 | mG*mU*mGmGmAmAfGmUfAfAfAmAmUmCmUmGmAmGmA*mA*mG |
| 111 | mA*mA*fGmUfAfAfAmAmUmCmUmGmAmGmA*mA*mA |
| 112 | VPmU*fU*mUmCmUfCmAmGmAmUmUmUmUfAmCfUmU*mC*mC*mA*mC*mC*mU |
| 113 | mG*mU*mGmGmAmAfGmUfAfAfAmAmUmCmUmGmAmGmAmAmAdTdT* |
| 114 | VPmU*fU*mUmCmUfCmAmGmAmUmUmUmUfAmCfUmUmCmC*mA*mCdTdT |
| 115 | mG*mU*mGmGmAmAmGmUfAfAfAmAmUmCmUmGmAmGmAmA*mA* |
| 116 | VPmU*fU*mUmCmUfCmAmGmAmUmUmUmUfAmCfUmUmCmCmA*mC*mC*mU |
| 117 | GUGGAAGUAAAAUCUGAGAAATT |
| 118 | UUUCUCAGAUUUUACUUCCACTT |
| 119 | GUGGAAGUAAAAUCUGAGAAG |

The invention claimed is:

1. A MAPT RNAi agent having a sense strand and an antisense strand, wherein the sense strand and the antisense strand form a duplex, and wherein the sense strand comprises the nucleic acid sequence of SEQ ID NO:17, and the antisense strand comprises the nucleic acid sequence of SEQ ID NO: 18;

wherein optionally one or more nucleotides of the sense strand and the antisense strand are independently modified nucleotides, and wherein optionally one or more internucleotide linkages of the sense strand and the antisense strand are modified internucleotide linkages.

2. The MAPT RNAi agent of claim 1, wherein one or more nucleotides of the sense strand are modified nucleotides.

3. The MAPT RNAi agent of claim 1, wherein each nucleotide of the sense strand is a modified nucleotide.

4. The MAPT RNAi agent of claim 1, wherein one or more nucleotides of the antisense strand are modified nucleotides.

5. The MAPT RNAi agent of claim 1, wherein each nucleotide of the antisense strand is a modified nucleotide.

6. The MAPT RNAi agent of claim 1, wherein the modified nucleotide is a 2'-fluoro modified nucleotide, 2'-O-methyl modified nucleotide or 2'-O—C16 alkyl modified nucleotide.

7. The MAPT RNAi agent of claim 1, wherein the sense strand has four 2'-fluoro modified nucleotides at positions 7, 9, 10, 11 from the 5' end of the sense strand.

8. The MAPT RNAi agent of claim 7, wherein nucleotides at positions other than positions 7, 9, 10, and 11 of the sense strand are 2'-O-methyl modified nucleotides or 2'-O—C16 alkyl modified nucleotides.

9. The MAPT RNAi agent of claim 1, wherein the antisense strand has four 2'-fluoro modified nucleotides at positions 2, 6, 14, 16 from the 5' end of the antisense strand.

10. The MAPT RNAi agent of claim 9, wherein nucleotides at positions other than positions 2, 6, 14 and 16 of the antisense strand are 2'-O-methyl modified nucleotides or 2'-O—C16 alkyl modified nucleotides.

11. The MAPT RNAi agent of claim 1, wherein the sense strand has three 2'-fluoro modified nucleotides at positions 9, 10, and 11 from the 5' end of the sense strand.

12. The MAPT RNAi agent of claim 11, wherein nucleotides at positions other than positions 9, 10, and 11 of the sense strand are 2'-O-methyl modified nucleotides or 2'-O—C16 alkyl modified nucleotides.

13. The MAPT RNAi agent of claim 1, wherein the antisense strand has five 2'-fluoro modified nucleotides at positions 2, 5, 7, 14, and 16 from the 5' end of the antisense strand.

14. The MAPT RNAi agent of claim 13, wherein nucleotides at positions other than positions 2, 5, 7, 14, and 16 of the antisense strand are 2'-O-methyl modified nucleotides or 2'-O—C16 alkyl modified nucleotides.

15. The MAPT RNAi agent of claim 1, wherein the antisense strand has five 2'-fluoro modified nucleotides at positions 2, 5, 8, 14, and 16 from the 5' end of the antisense strand.

16. The MAPT RNAi agent of claim 15, wherein nucleotides at positions other than positions 2, 5, 8, 14, and 16 of the antisense strand are 2'-O-methyl modified nucleotides or 2'-O—C16 alkyl modified nucleotides.

17. The MAPT RNAi agent of claim 1, wherein the sense strand and the antisense strand have one or more modified internucleotide linkages.

18. The MAPT RNAi agent of claim 17, wherein the modified internucleotide linkage is phosphorothioate linkage.

19. The MAPT RNAi agent of claim 18, wherein the sense strand has four or five phosphorothioate linkages.

20. The MAPT RNAi agent of claim 18, wherein the antisense strand has four or five phosphorothioate linkages.

21. The MAPT RNAi agent of claim 1, wherein the first nucleotide from the 5' end of the antisense strand is a modified nucleotide that has a phosphate analog.

22. The MAPT RNAi agent of claim 21, wherein the phosphate analog is 5'-vinylphosphonate.

23. The MAPT RNAi agent of claim 1, wherein the sense strand comprises an abasic moiety or inverted abasic moiety.

24. The MAPT RNAi agent of claim 1, wherein the sense strand and the antisense strand comprise a pair of nucleic acid sequences selected from:

(a) the sense strand comprises the nucleic acid sequence of SEQ ID NO: 41, and the antisense strand comprises the nucleic acid sequence of SEQ ID NO: 42;

(b) the sense strand comprises the nucleic acid sequence of SEQ ID NO: 101, and the antisense strand comprises the nucleic acid sequence of SEQ ID NO: 102.

25. The MAPT RNAi agent of claim 1, wherein the sense strand and the antisense strand have a pair of nucleic acid sequences selected from the group consisting of:

(a) the sense strand consists of the nucleic acid sequence of SEQ ID NO: 41, and the antisense strand consists of the nucleic acid sequence of SEQ ID NO: 42;

(b) the sense strand consists of the nucleic acid sequence of SEQ ID NO: 101, and the antisense strand consists of the nucleic acid sequence of SEQ ID NO: 102.

26. A pharmaceutical composition comprising the MAPT RNAi agent of claim 1 and a pharmaceutically acceptable carrier.

27. A pharmaceutical composition comprising the MAPT RNAi agent of claim 24 and a pharmaceutically acceptable carrier.

28. The MAPT RNAi agent of claim 1, wherein the sense strand is 21 nucleotides in length.

29. The MAPT RNAi agent of claim 1, wherein the antisense strand is 23 nucleotides in length.

30. The MAPT RNAi agent of claim 1, wherein the duplex region is 21 nucleotides in length.

31. The MAPT RNAi agent of claim 1, wherein the sense strand and the antisense strand each have four phosphorothioate linkages.

32. The MAPT RNAi agent of claim 1, wherein the sense strand has four phosphorothioate linkages and the antisense strand has five phosphorothioate linkages.

33. A pharmaceutical composition comprising the MAPT RNAi agent of claim 25 and a pharmaceutically acceptable carrier.

* * * * *